(12) United States Patent
Craighead et al.

(10) Patent No.: US 8,946,224 B2
(45) Date of Patent: Feb. 3, 2015

(54) SUBSTITUTED [1,2,4]TRIAZOLO[4,3-A]PYRAZINES FOR MEDICAMENTS AND PHARMACEUTICAL COMPOSITIONS

(75) Inventors: Mark Craighead, Manchester (GB); Ronald Palin, Manchester (GB); Neil Murray, Manchester (GB); Derek Lindsay, Manchester (GB)

(73) Assignee: Redx Pharma Limited, Liverpool (GB)

( * ) Notice: Subject to any disclaimer, the term of this patent is extended or adjusted under 35 U.S.C. 154(b) by 0 days.

(21) Appl. No.: 13/883,713

(22) PCT Filed: Nov. 11, 2011

(86) PCT No.: PCT/GB2011/052211
§ 371 (c)(1),
(2), (4) Date: May 6, 2013

(87) PCT Pub. No.: WO2012/063085
PCT Pub. Date: May 18, 2012

(65) Prior Publication Data
US 2013/0225594 A1    Aug. 29, 2013

(30) Foreign Application Priority Data

Nov. 11, 2010   (GB) .................................. 1019078.3
Nov. 18, 2010   (GB) .................................. 1019527.9

(51) Int. Cl.
*A61K 31/4985*   (2006.01)
*C07D 487/04*   (2006.01)
(Continued)

(52) U.S. Cl.
CPC ............ *C07D 487/04* (2013.01); *C07D 498/06* (2013.01); *C07D 413/12* (2013.01); *C07C 63/64* (2013.01); *C07D 213/60* (2013.01); *C07C 217/58* (2013.01); *C07D 403/06* (2013.01); *C07C 69/12* (2013.01); *C07C 235/16* (2013.01); *C07D 257/04* (2013.01); *C07D 313/04* (2013.01); *C07D 407/06* (2013.01); *C07C 2102/10* (2013.01); *C07C 43/205* (2013.01); *C07C 215/46* (2013.01); *C07C 255/25* (2013.01); *C07D 205/08* (2013.01); *C07D 281/06* (2013.01); *C07D 417/06* (2013.01); *C07D 413/04* (2013.01); *C07D 401/04* (2013.01); *C07C 63/66* (2013.01); *C07D 499/88* (2013.01); *C07D 401/12* (2013.01); *C07C 2101/16* (2013.01); *C07D 519/00* (2013.01); *C07D 209/18* (2013.01); *C07D 307/00* (2013.01); *C07D 501/00* (2013.01); *C07C 233/22* (2013.01); *C07D 473/00* (2013.01); *C07H 19/052* (2013.01); *C07C 251/40* (2013.01); *C07D 403/12* (2013.01); *C07D 513/06* (2013.01); *C07C 2103/74* (2013.01); *C07C 251/54* (2013.01); *C07C 257/14* (2013.01); *C07C 251/48* (2013.01); *C07C 57/00* (2013.01); *C07C 233/36* (2013.01); *C07H 19/173* (2013.01); *C07D 411/10* (2013.01); *C07C 229/18* (2013.01); *C07D 295/02* (2013.01); *C07H 19/06* (2013.01);
(Continued)

(58) Field of Classification Search
CPC .......................... A61K 31/4985; C07D 487/04
USPC ........................................... 514/249; 544/350
See application file for complete search history.

(56) References Cited

U.S. PATENT DOCUMENTS 7,326,708 B2 * 2/2008 Cypes et al. .................. 514/249

FOREIGN PATENT DOCUMENTS

CN    101429115 A    5/2009
EP    2397141 A1    12/2011
(Continued)

OTHER PUBLICATIONS

International Search Report mailed Jun. 21, 2012 for International Application No. PCT/GB2011/052211 (20 pages).
(Continued)

*Primary Examiner* — Douglas M Willis
(74) *Attorney, Agent, or Firm* — Morgan, Lewis & Bockius LLP

(57) ABSTRACT

The present invention relates to derivatives of known active pharmaceutical compounds. These derivatives are differentiated from the parent active compound by virtue of being redox derivatives of the active compound. This means that one or more of the functional groups in the active compound has been converted to another group in one or more reactions which may be considered to represent a change of oxidation state. We refer to these compounds generally as redox derivatives. The derivatives of the invention may be related to the original parent active pharmaceutical compound by only a single step transformation, or may be related via several synthetic steps including one or more changes of oxidation state. Exemplary derivatives have the formula

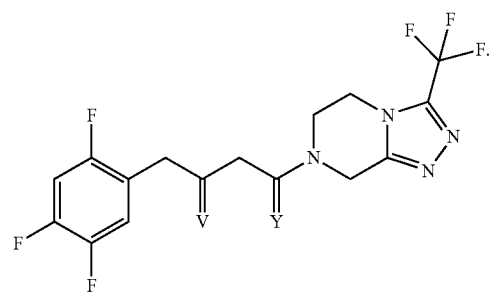

10 Claims, 1 Drawing Sheet

(51) Int. Cl.

| | | |
|---|---|---|
| C07D 498/06 | (2006.01) | |
| C07D 413/12 | (2006.01) | |
| C07C 63/64 | (2006.01) | |
| C07D 213/60 | (2006.01) | |
| C07C 217/58 | (2006.01) | |
| C07D 403/06 | (2006.01) | |
| C07C 69/12 | (2006.01) | |
| C07C 235/16 | (2006.01) | |
| C07D 257/04 | (2006.01) | |
| C07D 313/04 | (2006.01) | |
| C07D 407/06 | (2006.01) | |
| C07C 43/205 | (2006.01) | |
| C07C 215/46 | (2006.01) | |
| C07C 255/25 | (2006.01) | |
| C07D 205/08 | (2006.01) | |
| C07D 281/06 | (2006.01) | |
| C07D 417/06 | (2006.01) | |
| C07D 413/04 | (2006.01) | |
| C07D 401/04 | (2006.01) | |
| C07C 63/66 | (2006.01) | |
| C07D 499/88 | (2006.01) | |
| C07D 401/12 | (2006.01) | |
| C07D 519/00 | (2006.01) | |
| C07D 209/18 | (2006.01) | |
| C07D 307/00 | (2006.01) | |
| C07D 501/00 | (2006.01) | |
| C07C 233/22 | (2006.01) | |
| C07D 473/00 | (2006.01) | |
| C07H 19/052 | (2006.01) | |
| C07C 251/40 | (2006.01) | |
| C07D 403/12 | (2006.01) | |
| C07D 513/06 | (2006.01) | |
| C07C 251/54 | (2006.01) | |
| C07C 257/14 | (2006.01) | |
| C07C 251/48 | (2006.01) | |
| C07C 57/00 | (2006.01) | |
| C07C 233/36 | (2006.01) | |
| C07H 19/173 | (2006.01) | |
| C07D 411/10 | (2006.01) | |
| C07C 229/18 | (2006.01) | |
| C07D 295/02 | (2006.01) | |
| C07H 19/06 | (2006.01) | |
| C07C 235/28 | (2006.01) | |
| C07D 233/54 | (2006.01) | |
| C07J 5/00 | (2006.01) | |
| C07D 471/04 | (2006.01) | |
| C07D 241/04 | (2006.01) | |
| C07D 235/16 | (2006.01) | |
| C07D 277/40 | (2006.01) | |
| C07D 417/12 | (2006.01) | |
| C07D 309/32 | (2006.01) | |
| C07C 237/20 | (2006.01) | |
| C07C 251/58 | (2006.01) | |
| C07D 401/14 | (2006.01) | |
| C07D 491/04 | (2006.01) | |

(52) U.S. Cl.
CPC ............ *C07C 235/28* (2013.01); *C07D 233/54* (2013.01); *C07J 5/00* (2013.01); *C07D 471/04* (2013.01); *C07D 241/04* (2013.01); *C07D 235/16* (2013.01); *C07D 277/40* (2013.01); *C07D 417/12* (2013.01); *C07D 309/32* (2013.01); *C07C 237/20* (2013.01); *C07C 251/58* (2013.01); *C07D 401/14* (2013.01); *C07D 491/04* (2013.01)
USPC .......................................... 514/249; 544/350

(56) References Cited

FOREIGN PATENT DOCUMENTS

| WO | WO-2004087650 A2 | 10/2004 |
| WO | WO-2009084024 A2 | 7/2009 |
| WO | WO-2010078440 A1 | 7/2010 |
| WO | WO 2010/122578 | * 10/2010 |

OTHER PUBLICATIONS

International Written Opinion mailed Jun. 21, 2012 for International Application No. PCT/GB2011/052211 (29 pages).
English translation of Chinese Office Action mailed May 29, 2014 for corresponding Chinese Patent Application No. 201180053804.2. (5 pages).
International Search Report mailed May 9, 2014 for Singapore Application No. 2013035365 (7 pages).
International Written Opinion mailed Sep. 9, 2014 for Singapore Application No. 2013035365 (13 pages).

* cited by examiner

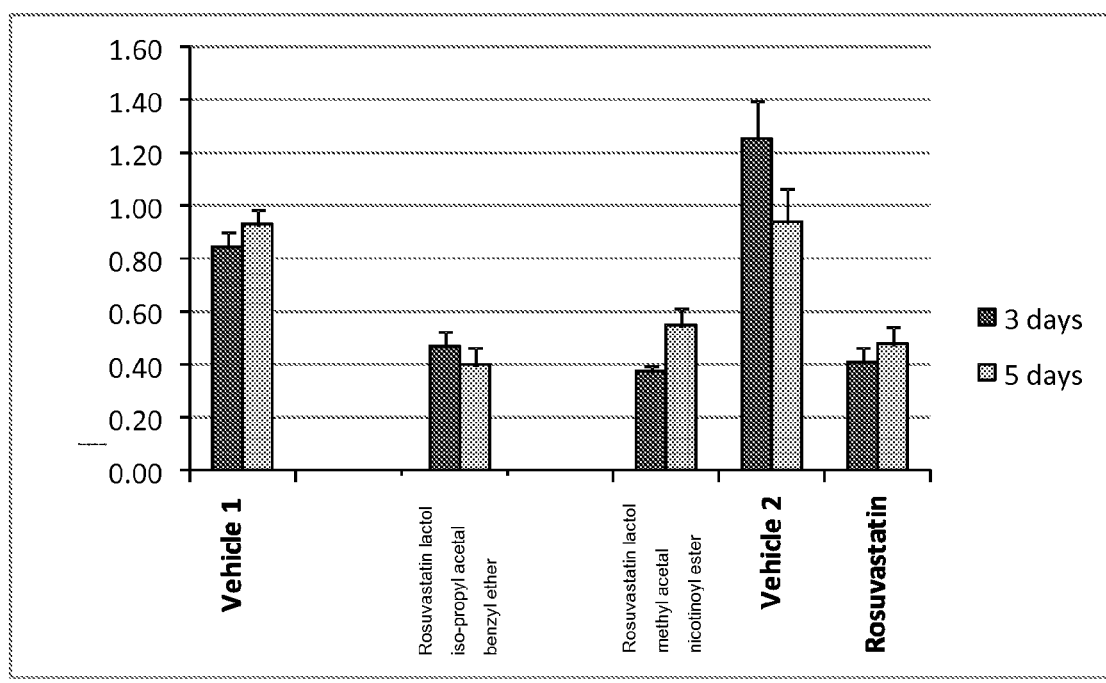

SUBSTITUTED [1,2,4]TRIAZOLO[4,3-A]PYRAZINES FOR MEDICAMENTS AND PHARMACEUTICAL COMPOSITIONS

CROSS-REFERENCE TO RELATED APPLICATIONS

This application is the U.S. national stage application of International (PCT) Patent Application Serial No. PCT/GB2011/052211, filed Nov. 11, 2011, which claims the benefit of GB Application No. 1019078.3, filed Nov. 11, 2010, and GB Application No. 1019527.9, filed Nov. 18, 2010. The entire disclosure of each of these applications is hereby incorporated by reference.

SUMMARY

The present invention relates to derivatives of known active pharmaceutical compounds. These derivatives are differentiated from the parent active compound by virtue of being redox derivatives of the active compound. This means that one or more of the functional groups in the active compound has been converted to another group in one or more reactions which may be considered to represent a change of oxidation state. We refer to these compounds generally as redox derivatives.

Many known drugs are less stable than the ideal. For example, drug molecules containing carboxylic acids may undergo decarboxylation of the terminal acid. This represents a significant problem during manufacture of an active principal or during extended storage of the same in a pharmacy. Similarly, amides can be subject to hydrolysis to the carboxylic acid derivatives. The resulting decomposition products may have reduced activity and potentially increased toxicity when compared with the parent active.

It is therefore an aim of the present invention to provide reduced or oxidised derivatives of active compounds which are able to demonstrate similar to or better longevity than the parent active compound. It is also an aim of the present invention to provide compounds which have an IC50 value comparable to or better than that of the parent active. Ideally, these reduced or oxidised derivatives will have good stability and/or bioavailability relative to the parent active compound. It is thus an aim to provide reduced or oxidised derivatives having improved stability. Another aim of the present invention is to provide compounds having improved bioavailability. Ideally, the reduced or oxidised derivatives will have an extended shelf-life.

The derivatives of the invention may be related to the original parent active pharmaceutical compound by only a single step transformation, or may be related via several synthetic steps including one or more changes of oxidation state. In certain cases, the functional group obtained after two or more transformations may be in the same oxidation state as the parent active compound (and we include these compounds in our definition of redox derivatives). In other cases, the oxidation state of the derivative of the invention may be regarded as being different from that of the parent compound.

In many cases, the compounds of the invention have inherent therapeutic activity on their own account. In some cases, this activity relative to the same target or targets of the parent compound is as good as or better than the activity which the parent compound has against the target or targets. However, the present invention also concerns such redox derivatives of active compounds which have only a low level activity relative to that of the parent compound but which are easily capable of metabolising in vivo to active pharmaceutical compounds, including the parent active compound itself. These compounds perform a useful function as prodrugs of the active compound.

Generally, the present invention thus relates to redox derivatives which have the same type of activity i.e. against the same targets as the parent known active pharmaceutical compound itself does. In some instances, the compounds may have new activity against a different target also in addition to that of the parent, or may have activity against a different target in preference to that of the parent. It is generally intended however that the activity of the compounds of the invention is the same in terms of its type as that of its respective ultimate parent compound i.e. the known pharmaceutically active compound upon which the redox compound of the invention is ultimately based.

This invention provides compounds that achieve one or more of the above aims. The compounds may be active in their own right or may metabolise or react in aqueous media to yield a parent active compound. Ultimately, the overall skeleton i.e. gross structure of the parent active molecule is retained but the various functional groups have been modified and we have identified "islands of activity" in these new compounds. The activity of these compounds of the present invention cannot be predicted empirically based on knowledge of the respective parent compounds because the change of potency of an inhibitor depends on the binding of the inhibitor to the protein. Generally, only molecules having the correct shape and electronic properties will be suitable for binding at the relevant site on the protein. However, we have identified a small group of compounds related to each parent for which we have evidence of activity. This evidence shows that in the case of each of our "islands of compounds" i.e. for each of the individual genera represented by formulae 1 to 159 there is activity across the group of compounds. This is so despite each of these genera having a different shape, due to changes in substitution, and having a different electron distribution, due to different electronic properties in the new substituents, relative to the relevant parent compound. This activity across the small but diverse range of compounds within each formula is quite surprising but can be seen from the various examples provided later below which all show activity. In addition, conventional wisdom in the pharmaceutical field specifically aims to avoid having substituent groups such as those utilised in the present invention, for example such as aldehydes and oximes etc, present in active molecules on account of expected instability or unwanted reactivity. The compounds of the invention have surprisingly been found to be active and stable.

According to a first aspect, the present invention provides a compound or compounds according to any one of the formulae below taken alone or any combination of more than one of the formulae 1-161 taken together:

| Formula number | Name of Parent Active Compound | Formula |
|---|---|---|
| 1. | Metronidazole | 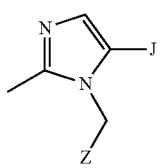 |

-continued
| Formula number | Name of Parent Active Compound | Formula |
|---|---|---|
| 2. | PD 0332991 | 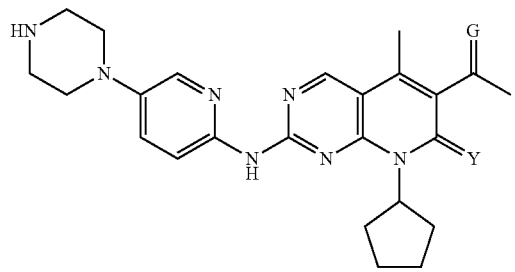 |
| 3. | Sitagliptin | 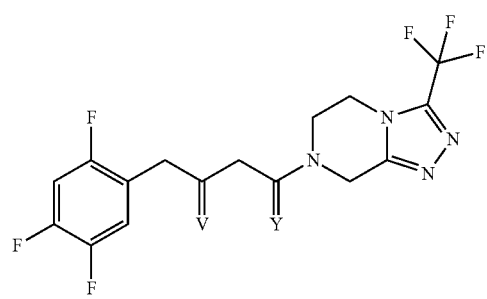 |
| 4. | Cefadroxil | 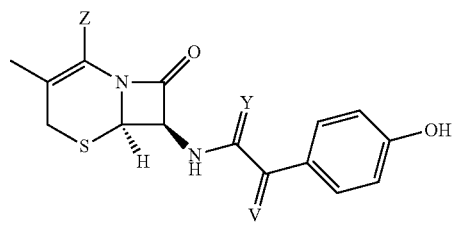 |
| 5. | Cefazolin | 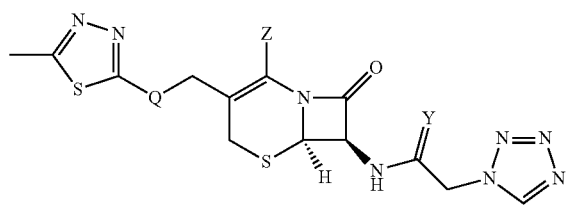 |
| 6. | Cefacetrile | 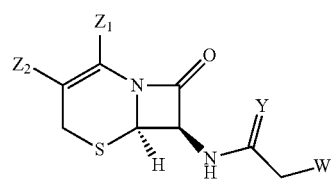 |
| 7. | Cefaloglycin | 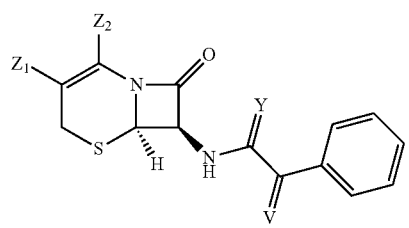 |

-continued

| Formula number | Name of Parent Active Compound | Formula |
|---|---|---|
| 8. | Cefalonium | |
| 9. | Cefaloridine | |
| 10. | Cefalotin | |
| 11. | Cefapirin | |
| 12. | Cefatrizine | |
| 13. | Cefazedone | |

| Formula number | Name of Parent Active Compound | Formula |
|---|---|---|
| 14. | Cefazaflur | |
| 15. | Cefradine | |
| 16. | Cefroxadine | |
| 17. | Ceftezole | |
| 18. | Cefaclor | |
| 19. | Cefamandole | |

-continued
| Formula number | Name of Parent Active Compound | Formula |
|---|---|---|
| 20. | Cefminox | 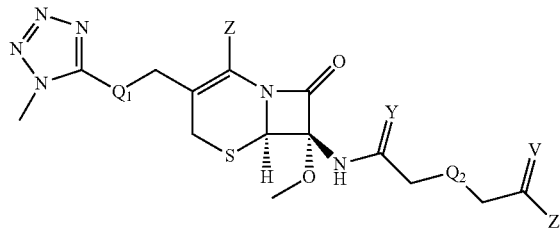 |
| 21. | Cefonicid | 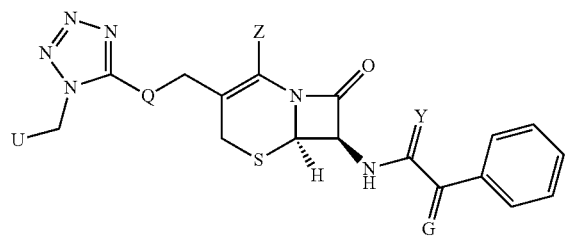 |
| 22. | Ceforanide | 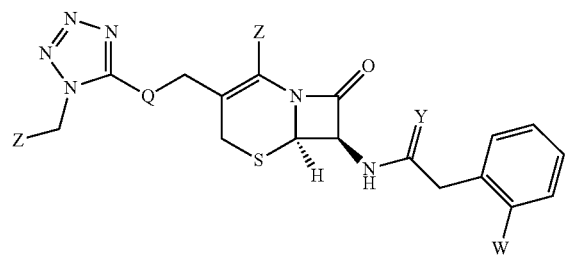 |
| 23. | Cefotiam | 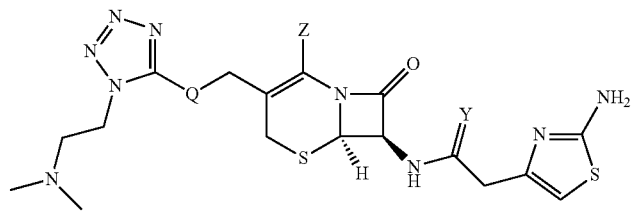 |
| 24. | Cefbuperazone | 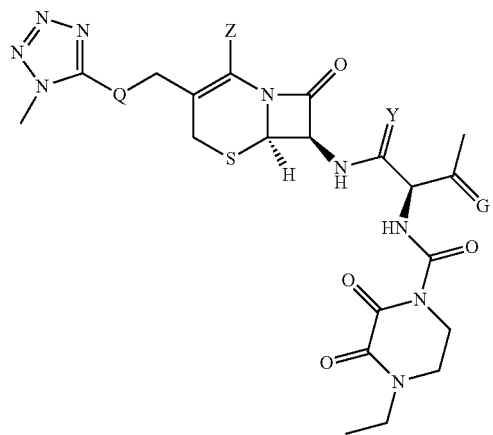 |

-continued
| Formula number | Name of Parent Active Compound | Formula |
|---|---|---|
| 25. | Cefuroxime | 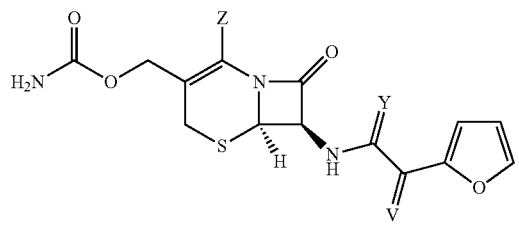 |
| 26. | Cefuzonam | 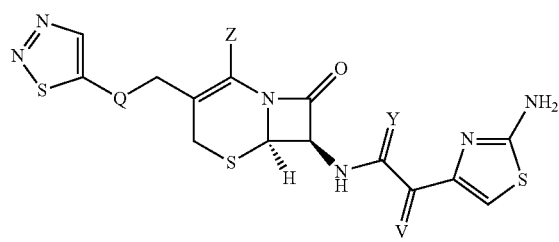 |
| 27. | Cefoxitin | 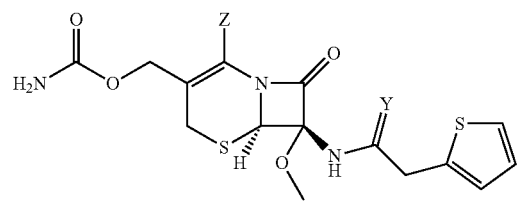 |
| 28. | Cefotetan | 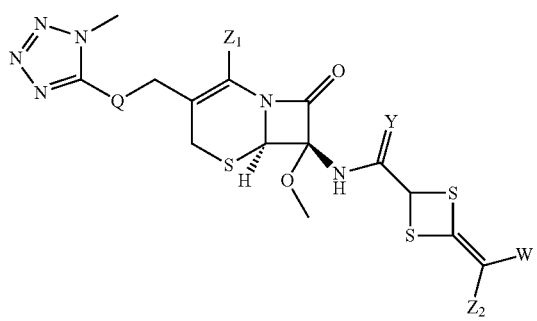 |
| 29. | Cefmetazole | 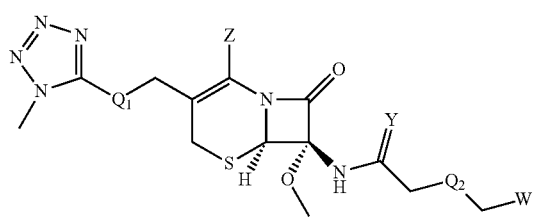 |
| 30. | Flomoxef | 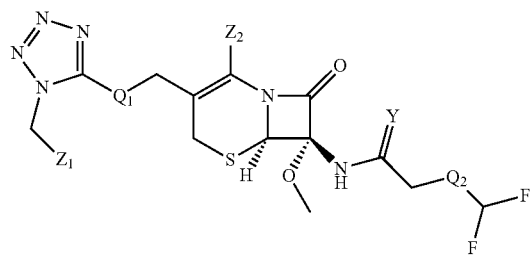 |

| Formula number | Name of Parent Active Compound | Formula |
|---|---|---|
| 31. | Loracarbef | 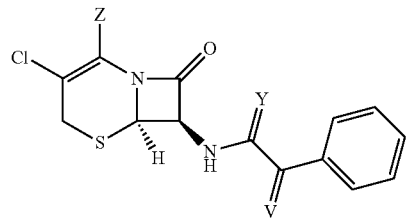 |
| 32. | Cefixime | 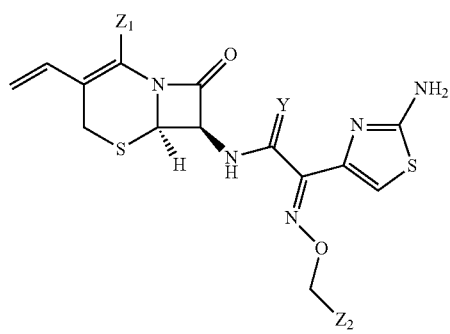 |
| 33. | Ceftazidime | 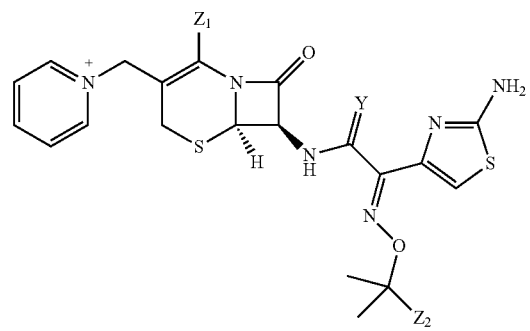 |
| 34. | Ceftriaxone | 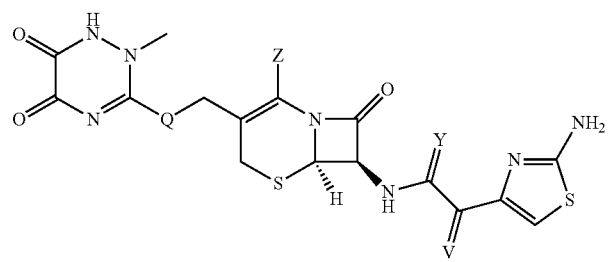 |
| 35. | Cefcapene | 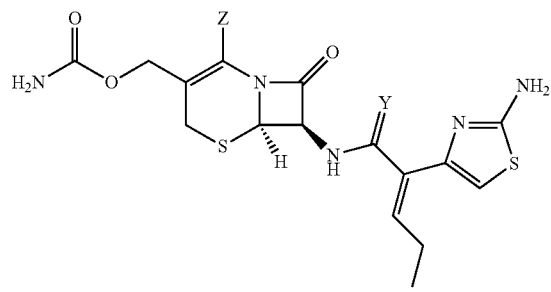 |

-continued
| Formula number | Name of Parent Active Compound | Formula |
|---|---|---|
| 36. | Cefdaloxime | 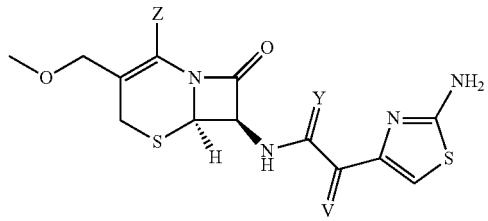 |
| 37. | Cefetamet | 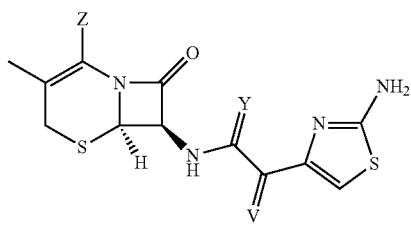 |
| 38. | Cefmenoxime | 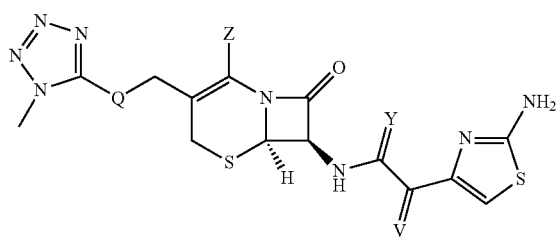 |
| 39. | Cefodizime | 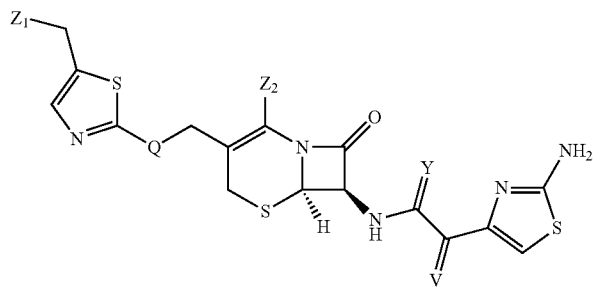 |
| 40. | Cefoperazone | 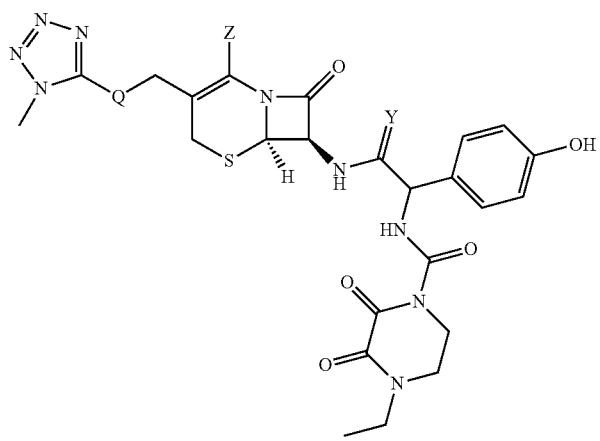 |

-continued
| Formula number | Name of Parent Active Compound | Formula |
|---|---|---|
| 41. | Cefotaxime | 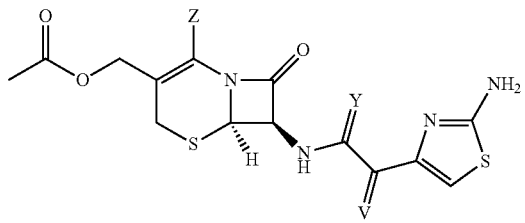 |
| 42. | Cefpimizole | 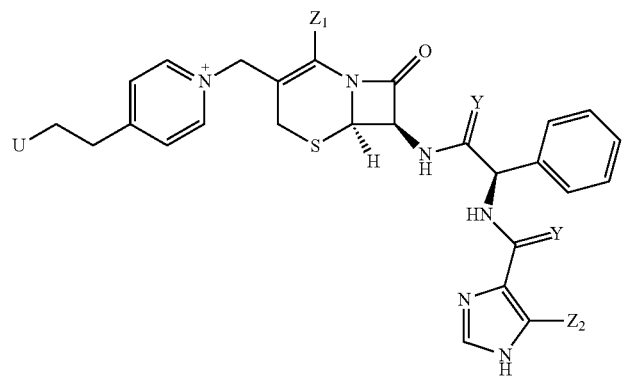 |
| 43. | Cefpiramide | 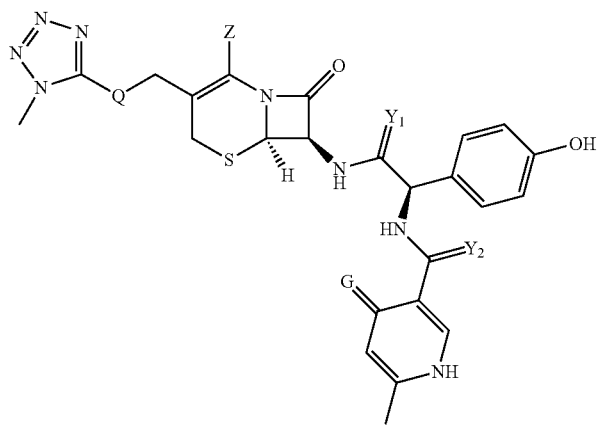 |
| 44. | Cefpodoxime | 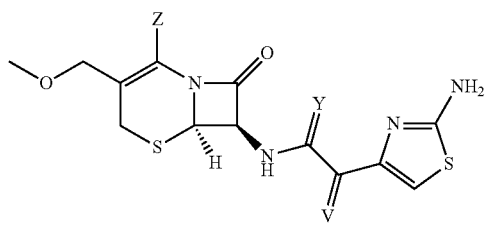 |
| 45. | Cefsulodin | 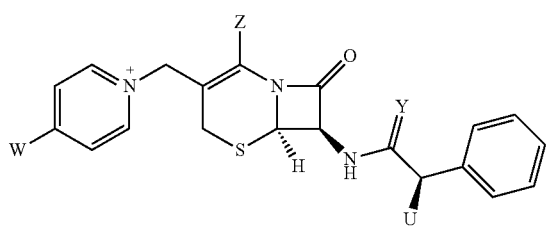 |

| Formula number | Name of Parent Active Compound | Formula |
|---|---|---|
| 46. | Cefteram | |
| 47. | Ceftibuten | |
| 48. | Ceftiolene | |
| 49. | Ceftizoxime | |
| 50. | Moxalactam | |
| 51. | Cefepime | |

-continued

| Formula number | Name of Parent Active Compound | Formula |
|---|---|---|
| 52. | Cefozopran | |
| 53. | Cefpirome | |
| 54. | Cefquinome | |
| 55. | Ceftobiprole | |
| 56. | Ceftaroline | |
| 57. | Neratinib | |

-continued
| Formula number | Name of Parent Active Compound | Formula |
|---|---|---|
| 58. | Sutinib | 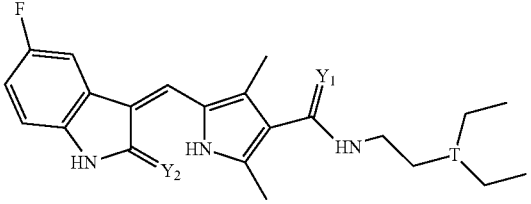 |
| 59. | Imatinib | 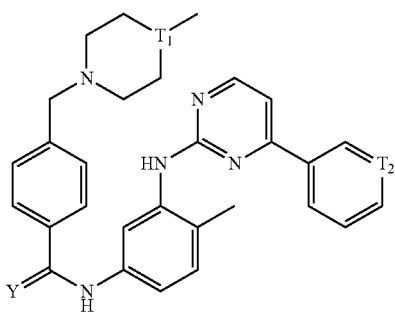 |
| 60. | Faropenem | 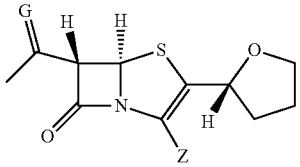 |
| 61. | Biapenem | 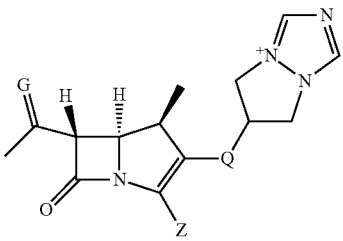 |
| 62. | Doripenem | 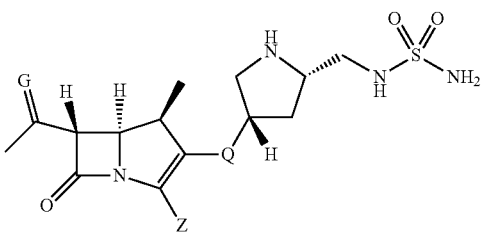 |
| 63. | Ertapenem | 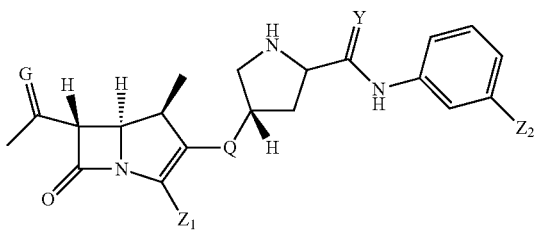 |

-continued

| Formula number | Name of Parent Active Compound | Formula |
|---|---|---|
| 64. | Imipenem | |
| 65. | Meropenem | |
| 66. | Panipenem | |
| 67. | Cefdinir | |
| 68. | Cefprozil | |
| 69. | Cefalexin | |
| 70. | Enoxacin | |

-continued

| Formula number | Name of Parent Active Compound | Formula |
|---|---|---|
| 71. | Fleroxacin | |
| 72. | Lomefloxacin | |
| 73. | Nadifloxacin | |
| 74. | Norfloxacin | |
| 75. | Rufloxacin | |
| 76. | Balofloxacin | |

-continued
| Formula number | Name of Parent Active Compound | Formula |
|---|---|---|
| 77. | Grepafloxacin | 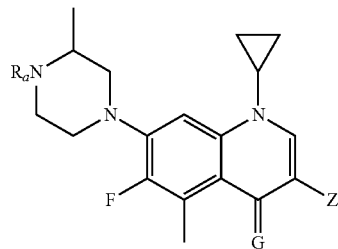 |
| 78. | Pazufloxacin | 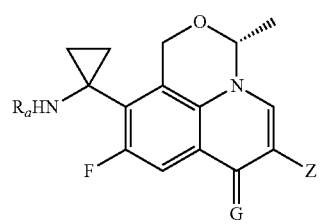 |
| 79. | Sparfloxacin | 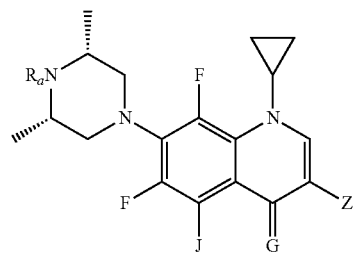 |
| 80. | Temafloxacin | 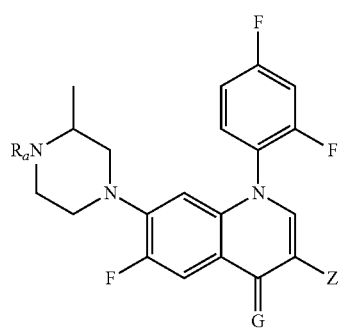 |
| 81. | Tosufloxacin | 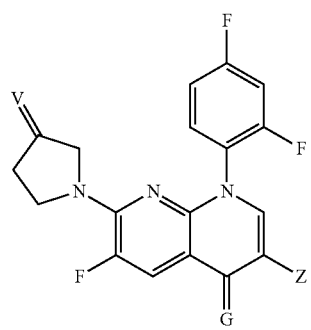 |

-continued
| Formula number | Name of Parent Active Compound | Formula |
|---|---|---|
| 82. | Besifloxacin | 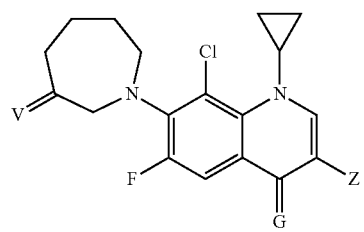 |
| 83. | Clinafloxacin | 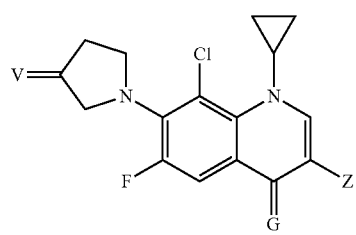 |
| 84. | Garenoxacin | 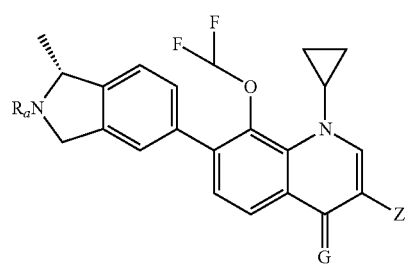 |
| 85. | Gemifloxacin | 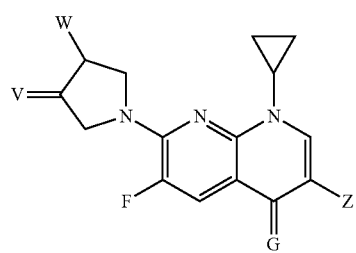 |
| 86. | Gatifloxacin | 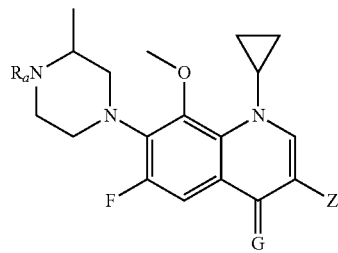 |
| 87. | Sitafloxacin | 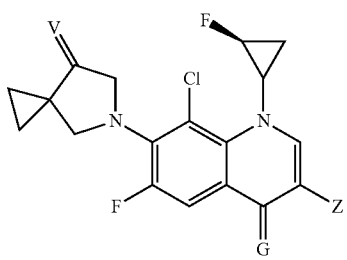 |

-continued

| Formula number | Name of Parent Active Compound | Formula |
|---|---|---|
| 88. | Trovafloxacin | |
| 89. | Prulifloxacin | |
| 90. | Ciprofloxacin | |
| 91. | Clindamycin | |
| 92. | Mupirocin | |
| 93. | Verapamil | |

| Formula number | Name of Parent Active Compound | Formula |
|---|---|---|
| 94. | Alitretinoin | |
| 95. | Aliskiren | |
| 96. | Eprosartan | |
| 97. | Doxorubicin | |
| 98. | Etoposide | |

-continued

| Formula number | Name of Parent Active Compound | Formula |
|---|---|---|
| 99. | Gemcitabine | |
| 100. | Chlorambucil | |
| 101. | Megestrol | |
| 102. | Bexarotene | |
| 103. | BIBF-1120 | |
| 104. | Eprotirome | |

| Formula number | Name of Parent Active Compound | Formula |
|---|---|---|
| 105. | Remikiren | 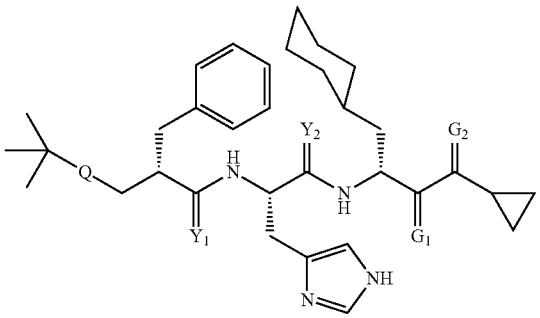 |
| 106. | Acadesine | 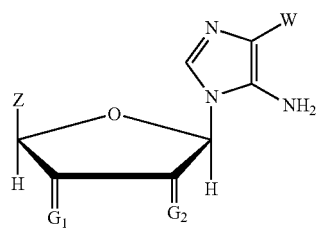 |
| 107. | Aleglitazar | 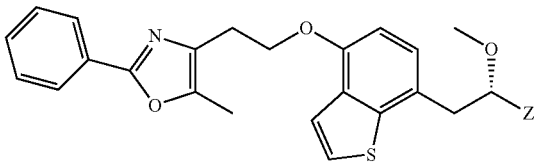 |
| 108. | Nifedipine | 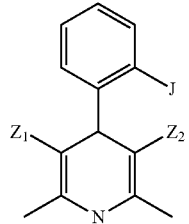 |
| 109. | Alvocidib | 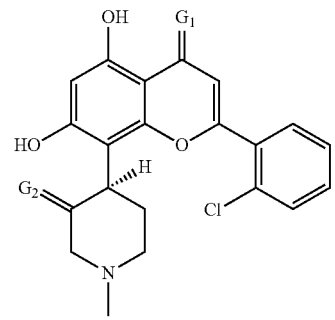 |
| 110. | Amrubicin | 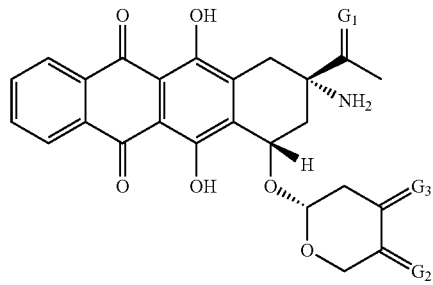 |

-continued
| Formula number | Name of Parent Active Compound | Formula |
|---|---|---|
| 111. | Apaziquone | 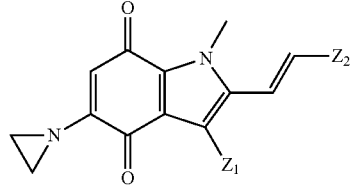 |
| 112. | Azilsartan | 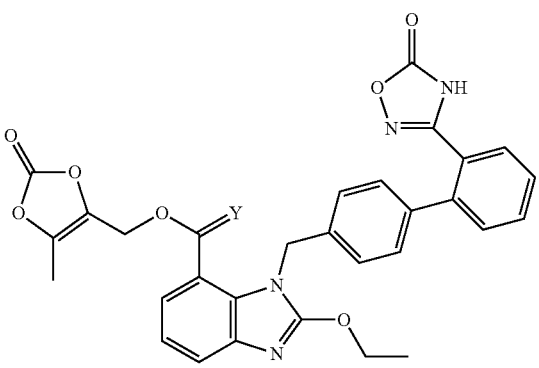 |
| 113. | Bendamustine | 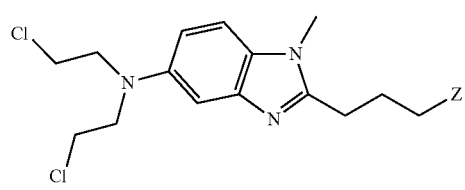 |
| 114. | Canagliflozin | 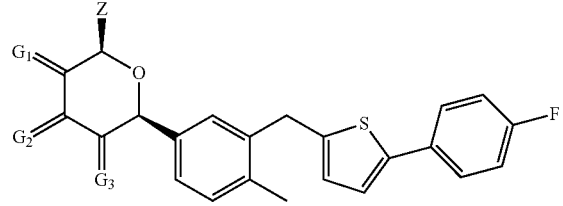 |
| 115. | Cladribine | 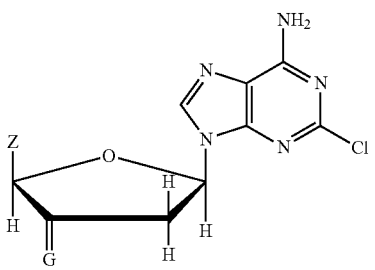 |
| 116. | Dabigatran etexilate | 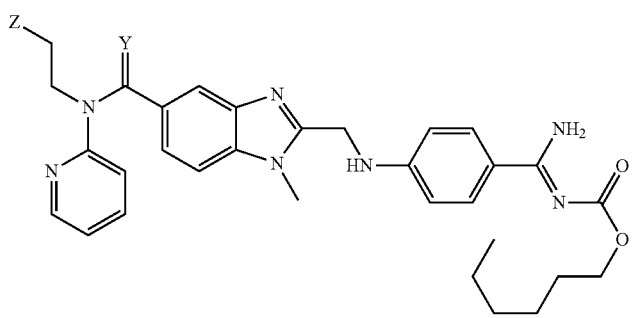 |

-continued
| Formula number | Name of Parent Active Compound | Formula |
|---|---|---|
| 117. | Fluocinolone Acetonide | 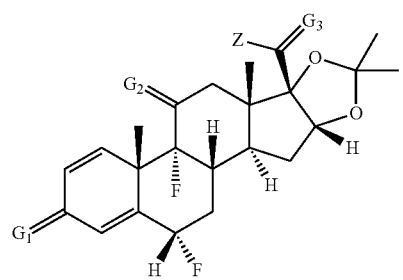 |
| 118. | Forodesine | 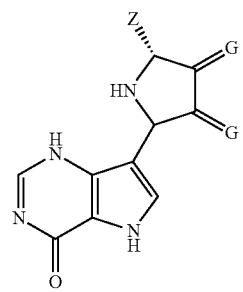 |
| 119. | Nabumetone | 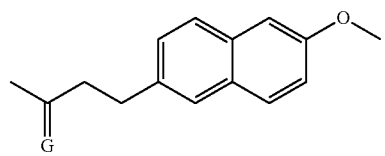 |
| 120. | Laninamivir | 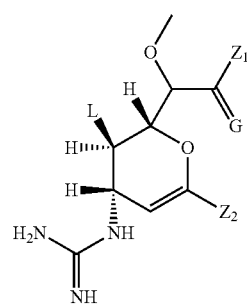 |
| 121. | Lixivaptan | 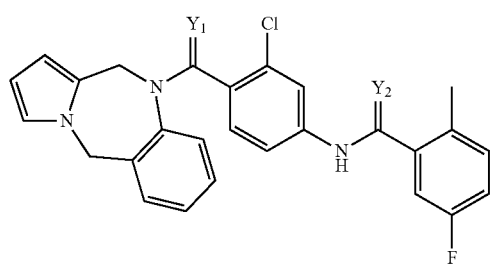 |

-continued

| Formula number | Name of Parent Active Compound | Formula |
|---|---|---|
| 122. | Mirabegron | |
| 123. | Motesanib | |
| 124. | Otamixaban | |
| 125. | Pemetrexed | |
| 126. | Rivaroxaban | |

-continued

| Formula number | Name of Parent Active Compound | Formula |
|---|---|---|
| 127. | Safinamide | |
| 128. | Sapacitabine | |
| 129. | Saredutant | |
| 130. | Semagacestat | |
| 131. | Teriflunomide | |
| 132. | Trabectedin | |

| Formula number | Name of Parent Active Compound | Formula |
|---|---|---|
| 133. | Ramelteon | 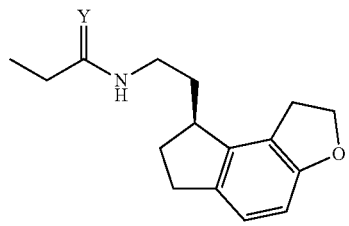 |
| 134. | Ombrabulin (AVE8062) | 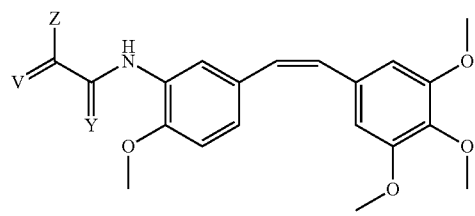 |
| 135. | Adapalene | 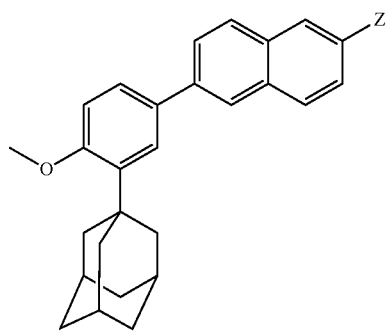 |
| 136. | Bimatoprost | 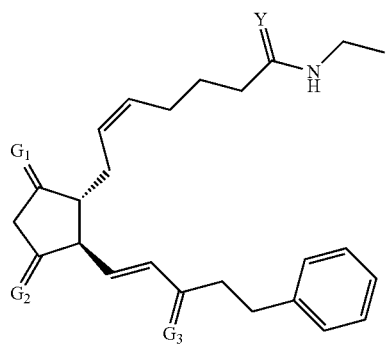 |
| 137. | Candesartan Cilexetil | 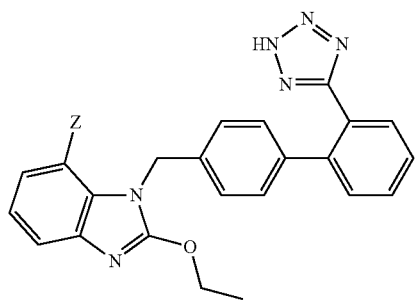 |

-continued

| Formula number | Name of Parent Active Compound | Formula |
|---|---|---|
| 138. | Ezetimibe | |
| 139. | Fenofibrate | |
| 140. | Latanoprost | |
| 141. | Losartan | |
| 142. | Olopatadine | |
| 143. | Quetiapine | |

-continued

| Formula number | Name of Parent Active Compound | Formula |
|---|---|---|
| 144. | Telmisartan | |
| 145. | Valaciclovir | |
| 146. | Valsartan | |
| 147. | Amlodipine Besylate | |
| 148. | Omacetaxine Mepesuccinate | |

| Formula number | Name of Parent Active Compound | Formula |
|---|---|---|
| 149. | Voreloxin | 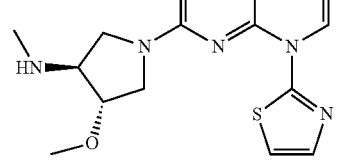 |
| 150. | ABT-263 | 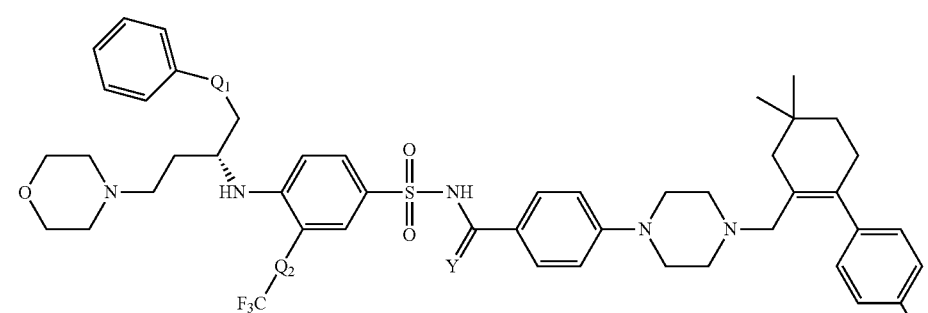 |
| 151. | Clopidogrel | 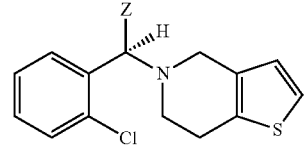 |
| 152. | Dilitazem | 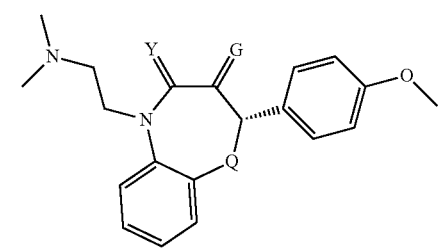 |
| 153. | Etodolac | 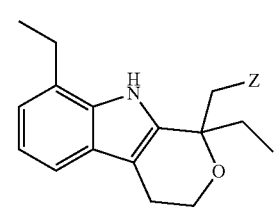 |
| 154. | Felodipine | 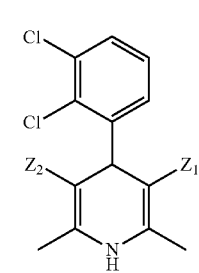 |

-continued
| Formula number | Name of Parent Active Compound | Formula |
|---|---|---|
| 155. | Fexofenadine | 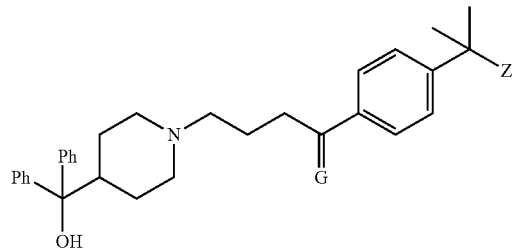 |
| 156. | Gemfibrozil | 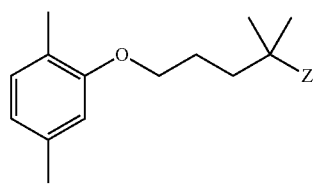 |
| 157. | Hydroxyzine | 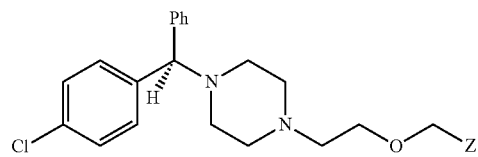 |
| 158. | Indometacin | 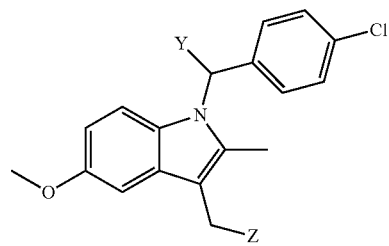 |
| 159. | Acyclovir | 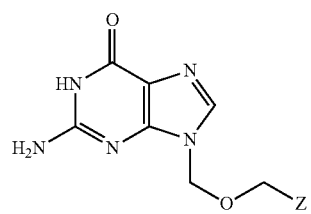 |
| 160. | Aztreonam | 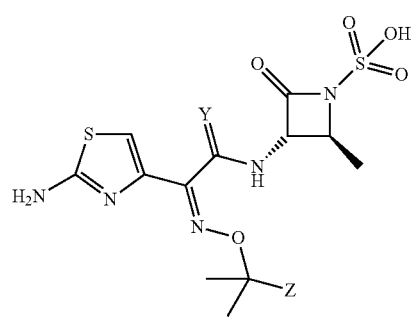 |

| Formula number | Name of Parent Active Compound | Formula |
|---|---|---|
| 161. | Apixaban | | wherein:

Z, $Z_1$ and $Z_2$ are independently, at each occurrence, selected from the group comprising:

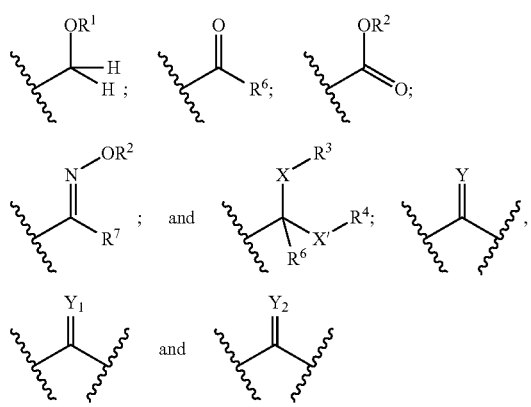

are independently, at each occurrence, selected from the group comprising:

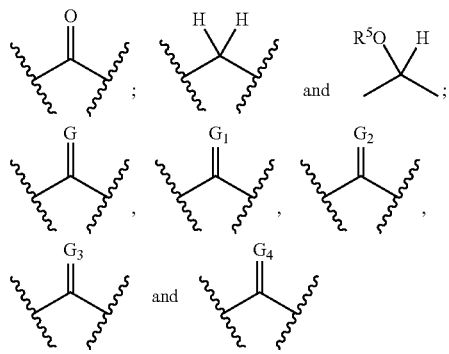

are independently, at each occurrence, selected from the group comprising:

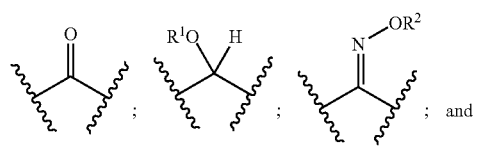

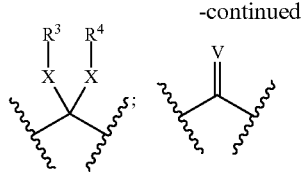

is independently, at each occurrence, selected from the group comprising:

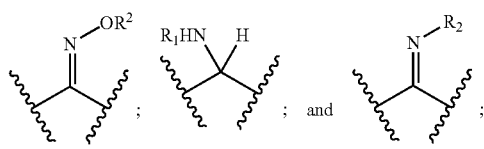

W is independently, at each occurrence, selected from the group comprising

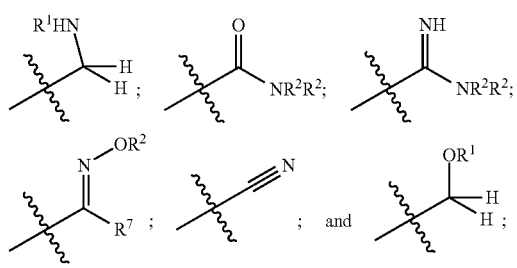

J is independently, at each occurrence, selected from the group comprising: —$NO_2$; and —$NHR^1$;

Q, $Q_1$ and $Q_2$ are independently at each occurrence selected from the group comprising:

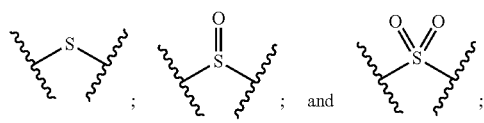

U is independently at each occurrence selected from the group comprising:

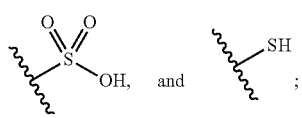

T, $T_1$ and $T_2$ is independently at each occurrence selected from the group comprising: N and NO;

L is independently at each occurrence selected from the group comprising:

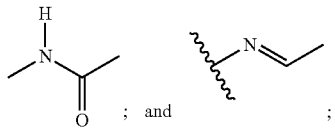

$R_a$ is H or Ac;
$R^1$ is independently at each occurrence H or Ac;
$R^2$ is independently at each occurrence H, $C_1$ alkyl, $C_2$ alkyl, $C_3$ alkyl or $C_4$ alkyl;
$R^3$ and $R^4$ are independently, at each occurrence, selected from the group comprising: H and $C_{1-4}$ alkyl, or alternatively $R^3$ and $R^4$, together with the X atoms to which they are attached and the carbon atom bearing the X atoms, form a 5-, 6- or 7-membered ring which is saturated or unsaturated;
$R^5$ is independently at each occurrence selected from the group comprising: H, Ac, and $C_1$ alkyl, C2 alkyl, $C_3$ alkyl or $C_4$ alkyl;
$R^6$ is independently at each occurrence selected from the group comprising: H, $C_1$ alkyl, $C_2$ alkyl, $C_1$ haloalkyl and $C^2$ haloalkyl;
$R^7$ is independently at each occurrence selected from the group comprising: H, $C_1$ alkyl, $C_2$ alkyl, $C_1$ haloalkyl, $C^2$ haloalkyl and $NR^6R^6$; and
X is independently, at each occurrence, —O— or —S—;
provided that the compound is not selected from the group comprising:
Cafedroxil, Cefazolin, Cefacetrile, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefbuperazone, Cefuroxime, Cefuzonam, Cefoxitin, Cefotetan, Cefmetazole, Flomoxef, Loracarbef, Cefixime, Ceftazidime, Ceftriaxone, Cefcapene, Cefdaloxime, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Moxalactam, Cefepime, Cefozopran, Cefpirome, Cefquinome, Ceftobiprole, Ceftaroline, Faropenem, Biapenem, Doripenem, Ertapenem, Imipenem, Meropenem, Panipenem, Cefdinir, Cefprozil, Cefalexin, Enoxacin, Fleroxacin, Lomefloxacin, Nadifloxacin, Norfloxacin, Rufloxacin, Balofloxacin, Grepafloxacin, Pazufloxacin, Sparfloxacin, Temafloxacin, Tosufloxacin, Besifloxacin, Clinafloxacin, Garenoxacin, Gemifloxacin, Gatifloxacin, Sitafloxacin, Trovafloxacin, Prulifloxacin, Ciprofloxacin, Clindamycin, Metronidazole, Mupirocin, Verapamil, Alitretinoin, Aliskiren, Eprosartan, Doxorubicin, Etoposide, Raloxifene, Fulvestrant, Gemcitabine, Imatinib, Chlorambucil, Megestrol, Bexarotene, BIBF-1120, Eprotirome, Remikiren, Acadesine, Aleglitazar, Nifedipine, Alvocidib, Amrubicin, Apaziquone, Azilsartan, Bendamustine, Canagliflozin, Cladribine, Dabigatran etexilate, Fluocinolone Acetonide, Forodesine, Nabumetone, Laninamivir, Lixivaptan, Mirabegron, Motesanib, Neratinib, Otamixaban, Pemetrexed, Rivaroxaban, Safinamide, Sapacitabine, Saredutant, Semagacestat, Teriflunomide, Trabectedin, Ramelteon, Ombrabulin (AVE8062), PD 0332991, Sunitinib, Adapalene, Aripiprazole, Bimatoprost, Candesartan, Cilexetil, Ezetimibe, Fenofibrate, Latanoprost, Losartan, Clopidogrel, Olopatadine, Quetiapine, Sitagliptin, Telmisartan, Valaciclovir, Valsartan, Acyclovir, Amlodipine, Besylate, Omacetaxine Mepesuccinate, Voreloxin, ABT-263, Diltiazem, Etodolac, Felodipine, Fexofenadine, Gemfibrozil, Hydroxyzine, aztreonam, apixaban and Indometacin.

The compound may be selected from the group of compounds defined by all of the formulae 161, or it may be selected from a smaller group such as that defined by a single formula from within the formulae 1 to 161, or from a group of compounds defined by a combination of from two to twenty of any of the above formulae.

In an embodiment, W is independently at each occurrence selected from the group comprising

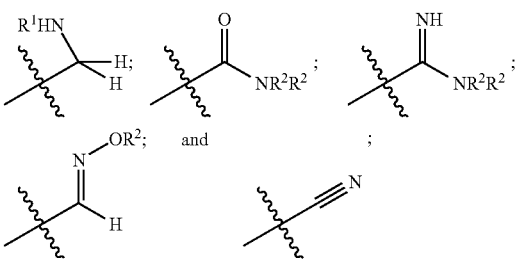

wherein $R^1$ and $R^2$ are as described above;
In an embodiment $R_a$ is H.
In an embodiment, $R_6$ is H.
In an embodiment $R_7$ is H.

The compounds of the invention are based on the parent approved pharmaceutically active compounds disclosed below. The synthetic routes to each of the compounds are available in the literature and in the relevant EMA and FDA regulatory files and accordingly are not reproduced here. These disclosures insofar as the synthetic procedures are concerned form part of the disclosure of the present invention. In the interests of brevity, the details of these synthetic procedures are not reproduced here but it is intended that this subject matter is specifically incorporated into the disclosure of these documents by reference.

Equally, the compounds can be prepared by total or partial synthesis. Thus, conveniently, the derivatives of each parent active may be prepared directly from the respective parent active itself by reactions known to the skilled person. However, in practice the skilled person will design a suitable synthetic procedure, including convergent synthesis, to prepare a given derivative depending on its particular functionality and oxidation state. The skilled person is familiar with such procedures and these represent common general knowledge as set out in text books such as Warren "Organic Synthesis: The disconnection" Approach; Mackie and Smith "Guidebook to Organic Chemistry"; and Clayden, Greeves, Warren and Wothers "Organic Chemistry".

For convenience only, the derivatives of the invention may be obtained by effecting oxidation or reduction of the target functional group at an intermediate stage in the synthesis rather than as a final stage in the synthesis of the derivatives of the present invention. Where necessary, the skilled person will be aware of the need to use suitable protecting groups to protect other functionalities in the molecule from unwanted oxidation or reduction during transformation of the target functional group.

The skilled man will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", RC Larock, Wiley-VCH (1999 or later editions), "March's Advanced Organic Chemistry—Reactions, Mechanisms and Structure", M B Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

The skilled chemist will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

Each of the compounds of the present invention may be used as a medicament.

The compounds of the present invention can be used in the treatment of the human body. They may be used in the treatment of the animal body. In particular, the compounds of the present invention can be used to treat commercial animals such as livestock. Alternatively, the compounds of the present invention can be used to treat companion animals such as cats, dogs, etc.

The compounds and formulations of the present invention may be used in the treatment of diabetes, bacterial infections and viral infections. They may be used in the fields of oncology, urology, immunology and ophthalmology. They may be used to treat diseases and disorders of the gastrointestinal system, the central nervous system, the bones and joints, and the cardiovascular system.

The compounds and formulations of the present invention can be used to treat type II diabetes including non-insulin-dependent diabetes mellitus (adult onset) diabetes, or as an adjunct therapy to hyperglycaemia.

The compounds and formulations of the present invention can be used to treat both Gram positive and Gram negative bacterial infections such as infections of the urinary tract, the respiratory tract, the ear, the skin, the throat, soft tissue, bone and joints (including infections caused by Staph Aureus). The compounds can be used to treat pneumonia, sinusitis, acute bacterial sinusitis, bronchitis, acute bacterial exacerbation of chronic bronchitis, anthrax, chronic bacterial prostatitis, acute pyelonephritis, pharyngitis, tonsillitis, eColi, prophylaxis before dental surgery, cellulitis, acnes, cystitis, infectious diarrhoea, typhoid fever, infections caused by anaerobic bacteria, peritonitis, malaria, babesiosis bacterial vaginosis, pelvic inflammatory disease, pseudomembranous colitis, helicobacter pylori, amoebiasis, giardasis, acute gingivitis, Crohn's Disease, rosacea, fungating Tumours, MRSA, impetigo.

The compounds and formulations of the present invention can be used to treat viral infections including HIV, influenza virus A & B, hepatitis B, herpes simplex and herpes zoster.

The compounds and formulations of the present invention can be used to treat cancers such as colon cancer, breast cancer (hormone-receptor positive, postmenopausal, metastatic breast cancer), prostate cancer, chronic myelogenous leukaemia, GI stromal tumours (including imatinib resistant GI stromal tumours), endometrium cancer, cutaneous T cell lymphoma, ovarian cancer (including platinum resistant ovarian cancer), acute lymphoblastic leukaemia, chronic lymphocytic leukaemia, lung cancer (including both small cell and non small cell lung cancers), superficial non-muscle invasive bladder cancer, hairy cell leukaemia, relapsed B-cell chronic lymphocytic leukaemia, pleural mesothelioma, solid & haematological tumours, acute myeloid leukaemia, advanced soft tissue sarcoma, refractory advance soft tissue sarcoma, ovarian & peritoneal neoplasms, head & neck cancers, glioma, multiple myeloma, renal cell carcinoma, non Hodgkins lymphoma, stage III or IV melanoma, HER2 negative metastatic breast cancer, neoplastic disorders and B-Cell malignancies.

The compounds of the present invention can be used to treat incontinence and overactive bladder disorder.

The compounds and formulations of the present invention can be used to treat cutaneous lesions in patients with AIDS-related Kaposi's sarcoma, chronic hand eczema, asthma, nasal polyposis, allergic rhinitis, Crohn's disease, prevention of rejection in organ transplants, lupus, acne, keratosis, pilaris, allergies, hay fever, angioedema, chronic obstructive pulmonary disease, idiopathic thrombocytopenic purpura, allergic conjunctivities & other eye allergies (eg. from contact lenses), bronchospasms, idiopathic urticaria, itching, hyperalgesia.

The compounds and formulations of the present invention can be used to treat diabetic macular edema, open angle glaucoma and ocular hypertension.

The compounds and formulations of the present invention can be used to treat stomach ulcers, Zollinger Ellison syndrome, gastroesophageal reflux disease, erosive oesophagitis, H Pylori, functional dyspepsia, ulcerative colitis and Crohn's disease.

The compounds and formulations of the present invention can be used to treat bipolar depression, schizophrenia including acute relapsed schizophrenia), narcolepsy, Parkinson's disease (both early stage and advanced Parkinson's disease), Alzheimer's Disease, restless leg syndrome, epilepsy, relapsing/remitting multiple sclerosis, insomnia, delayed sleep phase disorder, bipolar I and II disorders, clinical depression, ADHD, postural orthostatis, tachycardia syndrome, nausea, vomiting (in chemotherapy regimens), gastric emptying in patients with gastroparesis, gastroesophageal reflux disease, migraine, mania, major depressive disorder, generalised anxiety disorder, obsessive compulsive disorder, social anxiety disorder, panic disorder, menopausal hot flushes, acute psychosis, parasomnia, rapid eye movement disorder, spinal chord injury, spastic diplegia, amyotrophic lateral sclerosis, peripheral neuropathy, trigeminal and glossopharyngeal neuralgias, alcohol withdrawal, smoking cessation, sexual dysfunction, obesity, seasonal affected disorder, prolactinomas, hyperprolactinaemia and psychoneurosis, neuropathic pain from diabetic neuropathy, post herpetic neuralgia, partial seizures, fibromyalgia.

The compounds and formulations of the present invention can be used to treat osteoporosis in menopause, rheumatoid arthritis, osteoarthritis, arthritic gout, reactive arthritis, Pagets disease of bone, Barter syndrome, and pseudogout and tendonitis.

The compounds and formulations of the present invention can be used to treat orthostatic hypotension, hypertension, congestive heart failure, MI, renal and retinal complications of diabetes, tachycardia, Angina, heart failure, migraine prophylaxis, vasovagal syncope, adjunctive treatment of hyperthyroidism, long QT syndrome (in patients with Asthma), hypertension of pheochromocytoma, supraventricular tachyarrhythmias, cluster headaches, migraine, non-surgical treatment of gall stones, hypercholesterolaemia, biliary cirrhosis, benign prostatic hyperplasia (BPH), cardiac arrythmia, congestive heart failure, coronary artery disease, acute coronary syndrome chest pain, statin-treated dyslipidaemia, hyponatremia (with liver cirrhosis or congestive heart failure, venous thrombo embolism, phytosterolemiaypercholesterolaemia, hypertriglyceridaemia, combined dyslipidaemias, diabetic nephropathy, essential hypertension, ventricular fibrillation, ventricular tachycardia, atrial fibrillation, peripheral vascular disease, cerebrovascular disease, prevention of ischaemic events in patients with atherosclerosis, Graves disease, pre-eclampsia, oesophageal spasm, mild achalasia, oedema associated with heart failure, hepatic cirrhosis, renal impairment and hyperlipidaemia.

In an embodiment, the parent of the derivative of the invention is selected from one of the compounds identified in the table below. In each case, the therapeutic class and target indication is identified for the derivatives of the invention. This can be seen in the second and third columns respectively.

TABLE

| Name of parent active compound | Therapeutic class | Target indication |
| --- | --- | --- |
| Cefadroxil | Antibacterial | Gram Positive & Gram Negative infections (Skin, UTI, ENT), Pharyngitis, Tonsilitis, *e Coli*, Prophylaxis before dental surgery |
| Cefazolin | Antibacterial | Bacterial infections |
| Cefacetrile | Antibacterial | Bacterial infections |
| Cefaloglycin | Antibacterial | Bacterial infections |
| Cefalonium | Antibacterial | Bacterial infections |
| Cefaloridine | Antibacterial | Bacterial infections |
| Cefalotin | Antibacterial | Bacterial infections |
| Cefapirin | Antibacterial | Bacterial infections |
| Cefatrizine | Antibacterial | Bacterial infections |
| Cefazedone | Antibacterial | Bacterial infections |
| Cefazaflur | Antibacterial | Bacterial infections |
| Cefradine | Antibacterial | Bacterial infections |
| Cefroxadine | Antibacterial | Bacterial infections |
| Ceftezole | Antibacterial | Bacterial infections |
| Cefaclor | Antibacterial | Bacterial infections |
| Cefamandole | Antibacterial | Bacterial infections |
| Cefminox | Antibacterial | Bacterial infections |
| Cefonicid | Antibacterial | Bacterial infections |
| Ceforanide | Antibacterial | Bacterial infections |
| Cefotiam | Antibacterial | Bacterial infections |
| Cefbuperazone | Antibacterial | Bacterial infections |
| Cefuroxime | Antibacterial | Bacterial infections |
| Cefuzonam | Antibacterial | Bacterial infections |
| Cefoxitin | Antibacterial | Bacterial infections |
| Cefotetan | Antibacterial | Bacterial infections |
| Cefmetazole | Antibacterial | Bacterial infections |
| Flomoxef | Antibacterial | Bacterial infections |
| Loracarbef | Antibacterial | Bacterial infections |
| Cefixime | Antibacterial | Bacterial infections |
| Ceftazidime | Antibacterial | Bacterial infections |
| Ceftriaxone | Antibacterial | Bacterial infections |
| Cefcapene | Antibacterial | Bacterial infections |
| Cefdaloxime | Antibacterial | Bacterial infections |
| Cefetamet | Antibacterial | Bacterial infections |
| Cefmenoxime | Antibacterial | Bacterial infections |
| Cefodizime | Antibacterial | Bacterial infections |
| Cefoperazone | Antibacterial | Bacterial infections |
| Cefotaxime | Antibacterial | Bacterial infections |
| Cefpimizole | Antibacterial | Bacterial infections |
| Cefpiramide | Antibacterial | Bacterial infections |
| Cefpodoxime | Antibacterial | Bacterial infections |
| Cefsulodin | Antibacterial | Bacterial infections |
| Cefteram | Antibacterial | Bacterial infections |
| Ceftibuten | Antibacterial | Bacterial infections |
| Ceftiolene | Antibacterial | Bacterial infections |
| Ceftizoxime | Antibacterial | Bacterial infections |
| Moxalactam | Antibacterial | Bacterial infections |
| Cefepime | Antibacterial | Bacterial infections |
| Cefozopran | Antibacterial | Bacterial infections |
| Cefpirome | Antibacterial | Bacterial infections |
| Cefquinome | Antibacterial | Bacterial infections |

TABLE-continued

| Name of parent active compound | Therapeutic class | Target indication |
| --- | --- | --- |
| Ceftobiprole | Antibacterial | Bacterial infections |
| Ceftaroline | Antibacterial | Bacterial infections |
| Faropenem | Antibacterial | Bacterial infections |
| Biapenem | Antibacterial | Bacterial infections |
| Doripenem | Antibacterial | Bacterial infections |
| Ertapenem | Antibacterial | Bacterial infections |
| Imipenem | Antibacterial | Bacterial infections |
| Meropenem | Antibacterial | Bacterial infections |
| Panipenem | Antibacterial | Bacterial infections |
| Cefdinir | Antibacterial | Bacterial infections of ear, sinus, throat & skin, CAP, Bronchitis |
| Cefprozil | Antibacterial | Bronchitis, ear & skin infections |
| Cefalexin | Antibacterial | UTIs, respiratory tract infections, skin & soft tissue infections, cellulitis, acne |
| Enoxacin | Antibacterial | Bacterial infections |
| Fleroxacin | Antibacterial | Bacterial infections |
| Lomefloxacin | Antibacterial | Bacterial infections |
| Nadifloxacin | Antibacterial | Bacterial infections |
| Norfloxacin | Antibacterial | Bacterial infections |
| Rufloxacin | Antibacterial | Bacterial infections |
| Balofloxacin | Antibacterial | Bacterial infections |
| Grepafloxacin | Antibacterial | Bacterial infections |
| Pazufloxacin | Antibacterial | Bacterial infections |
| Sparfloxacin | Antibacterial | Bacterial infections |
| Temafloxacin | Antibacterial | Bacterial infections |
| Tosufloxacin | Antibacterial | Bacterial infections |
| Besifloxacin | Antibacterial | Bacterial infections |
| Clinafloxacin | Antibacterial | Bacterial infections |
| Garenoxacin | Antibacterial | Bacterial infections |
| Gemifloxacin | Antibacterial | Bacterial infections |
| Gatifloxacin | Antibacterial | Bacterial infections |
| Sitafloxacin | Antibacterial | Bacterial infections |
| Trovafloxacin | Antibacterial | Bacterial infections |
| Prulifloxacin | Antibacterial | Bacterial infections |
| Aztreonam | Antibacterial | Bacterial infections |
| Ciprofloxacin | Antibacterial | UTIs, Cystitis, Chronic Bacterial Prostatits, Lower Respiratory Tract Infections, Sinusitis, skin infections, bone & joint infections, Infectious Diarrhoea, Typhoid Fever |
| Clindamycin | Antibacterial | Combination therapy in Acne, infections caused by anaerobic bacteria: respiratory tract, skin and soft tissue infections, Peritonitis, Bone & Joint infections caused by *Staph Aureus*, Combination treatment for Malaria & Babesiosis |
| Metronidazole | Antibacterial | Bacterial Vaginosis, Pelvic Inflammatory Disease, Anaerobic Bacterial Infections, Pseudomembranous Colitis, *Helicobacter Pylori*, Amoebiasis, Giardasis, Acute Gingivitis, Crohn's Disease, Rosacea, Fungating Tumours |
| Mupirocin | Antibacterial | Gram-Positive Bacteria, including MRSA, Skin infections, Impetigo, *Staph Aureus* infections which are resistent to other anibiotics |
| Verapamil | Cardiovascular | Angina, Hypertension, Supraventricular Tachyarrhythmias, Cluster Headaches, Migraine prevention, Potential combined use in treatment of Malaria |
| Alitretinoin | Immunology | Cutaneous Lesions in patients with AIDS-related Kaposi's Sarcoma, Chronic Hand Eczema |
| Aliskiren | Cardiovascular | Hypertension |
| Eprosartan | Cardiovascular | Hypertension |
| Doxorubicin | Oncology | Oncology (Chemotherapy) |
| Etoposide | Oncology | Oncology (Chemotherapy) |
| Gemcitabine | Oncology | Oncology (Chemotherapy) |
| Imatinib | Oncology | Chronic Myelogenous Leukaemia & GI Stromal Tumours |
| Chlorambucil | Oncology | Oncology (Chemotherapy) |
| Megestrol | Oncology | Breast & Endometrium Cancer |
| Bexarotene | Oncology | Cutaneous T Cell Lympoma |
| BIBF-1120 | Oncology | Ovarian Cancer |
| Eprotirome | Cardiovascular | Statin-Treated Dyslipidaemia |
| Remikiren | Cardiovascular | Hypertension |

TABLE-continued

| Name of parent active compound | Therapeutic class | Target indication |
|---|---|---|
| Acadesine | Oncology | Acute Lymphoblastic Leukaemia |
| Aleglitazar | Diabetes | Type II Diabetes |
| Nifedipine | Cardiovascular | Anti-anginal (Prinzmetal's Angina) & Hypertension, Raynaud's, Premature Labor, Oesophageal Spasm (in cancer and tetanus patients) |
| Alvocidib | Oncology | Chronic Lymphocytic Leukaemia |
| Amrubicin | Oncology | Lung Cancer |
| Apaziquone | Oncology | Superficial non-muscle invasive Bladder Cancer |
| Azilsartan | Cardiovascular | Hypertension |
| Bendamustine | Oncology | Chronic Lymphocytic Leukaemia |
| Canagliflozin | Diabetes | Type II Diabetes |
| Cladribine | CNS/Oncology | Hairy Cell Leukaemia & Multiple Sclerosis |
| Dabigatran Etexilate | | |
| Fluocinolone Acetonide | Ophthamology | Diabetic Macular Edema & Dermatitis/Eczema/Psoriasis |
| Forodesine | Oncology | Cutaneous T-Cell Lymphoma & Relapsed B-Cell Chronic Lymphocytic Leukaemia |
| Nabumetone | Bones and joints | Rheumatoid Arthritis, Osteoarthritis |
| Laninamivir | Antiviral | Influenza virus A & B |
| Lixivaptan | Cardiovascular | Hyponatremia (with Liver Cirrhosis or Congestive Heart Failure) |
| Mirabegron | Urology | Incontinence - Overactive Bladder |
| Motesanib | Oncology | Non Small Cell Lung Cancer |
| Neratinib | Oncology | Breast Cancer |
| Otamixaban | Cardiovascular | Acute Coronary Syndrome |
| Apixaban | Cardiovascular | Acute Coronary Syndrome |
| Pemetrexed | Oncology | Non Small Cell Lung Cancer & Pleural Mesothelioma |
| Rivaroxaban | Cardiovascular | Venous Thrombo Embolism/ACS following hip or knee replacements |
| Safinamide | CNS | Alzheimer's Disease, Restless Leg Syndrome, Epilepsy |
| Sapacitabine | Oncology | Solid & Haematological Tumours & Cutaneous T-Cell Lymphoma & Acute Myeloid Leukaemia in elderly) |
| Saredutant | CNS | Anti-depressant & Anxiolytic |
| Semagacestat | CNS | Alzheimer's Disease |
| Teriflunomide | CNS | Rheumatoid Arthritis & relapsing/remitting Multiple Sclerosis |
| Trabectedin | Oncology | Advanced Soft Tissue Sarcoma & Ovarian Cancer |
| Ramelteon | CNS | Insomnia & Delayed Sleep Phase Disorder |
| Ombrabulin (AVE8062) | Oncology | Refractory Advance Soft Tissue Sarcoma & Non Small Cell Lung Cancer |
| PD 0332991 | Oncology | Multiple Myeloma |
| Sunitinib | Oncology | Renal Cell Carcinoma & Imatinib-resistant GI Stromal Tumour |
| Adapalene | Immunology | Acne & Keratosis Pilaris |
| Aripiprazole | CNS | Acute Relapsed Schizophrenia, Bipolar Disorder & Clinical Depression |
| Bimatoprost | Ophthamology | Open Angle Glaucoma & Ocular Hypertension |
| Candesartan Cilexetil | Cardiovascular | Hypertension & in heart failure where ACE Inhibitors not tolerated |
| Ezetimibe | Cardiovascular | Hypercholesterolaemia, Phytosterolemia |
| Fenofibrate | Cardiovascular | Hypercholesterolaemia & Hypertriglyceridaemia or Combined Dyslipidaemias |
| Latanoprost | Ophthamology | Glaucoma & Ocular Hypertension |
| Losartan | Cardiovascular | Hypertension, Diabetic Nephropathy |
| Olopatadine | Immunology | Allergic Conjunctivities & other eye allergies (eg. from contact lenses) |
| Quetiapine | CNS | Schizophrenia, Bipolar I & II mania & depression. insomnia & anxiety disorders |
| Sitagliptin | Diabetes | Type II Diabetes |
| Telmisartan | Cardiovascular | Essential Hypertension |
| Valaciclovir | Antiviral | Herpes Simplex & Herpes Zoster |
| Valsartan | Cardiovascular | Hypertension, Congestive Heart Failure, post-MMI |

TABLE-continued

| Name of parent active compound | Therapeutic class | Target indication |
|---|---|---|
| Acyclovir | Antiviral | Herpes Simplex & Herpes Zoster |
| Amlodipine Besylate | Cardiovascular | Hypertension, Angina |
| Omacetaxine Mepesuccinate | Cardiovascular | Acute coronary syndrome |
| Voreloxin | Oncology | Acute Myeloid Leukaemia & Platinum-Resistant Ovarian Cancer |
| ABT-263 | Oncology | Small Cell Lung Cancer & B-Cell Malignancies |
| Clopidogrel | Cardiovascular | Coronary Artery Disease, Peripheral Vascular Disease, Cerebrovascular Disease, prevention of ischaemic events in patients with atherosclerosis, Acute Coronary syndrome without NSTEMI, |
| Diltiazem | Cardiovascular | Hypertension, Angina, Arrhythmia, Prevention of Migraine |
| Etodolac | Bones and joints | Osteoarthritis & Rheumatoid Arthritis |
| Felodipine | Cardiovascular | Hypertension, Pre-Eclampsia, Angina, Oesophageal Spasm, Mild Achalasia |
| Fexofenadine | Immunology | Hay Fever, Allergies, Allergic Rhinitis, Chronic Idiopathic Urticaria |
| Gemfibrozil | Cardiovascular | Hyperlipidaemia, Hypertriglyceridaemia |
| Hydroxyzine | Immunology/CNS | Itching, Allergies, Hyperalgesia, Motion Sickness-induced Nausea, Insomnia, Mild Anxiety, Psychoneurosis |
| Indometacin | CNS/bones and joints | Patent Ductus Arteriosus, Retinopathy of Prematurity, Ankylating Spondylitis, Rheumatoid Arthritis, Arthritic Gout, Osteoarthritis, Reactive Arthritis (ReA), Pagets Disease of Bone, Bartter Syndrome, Pseudogout, Dysmenorrhoea, Pericarditis, Bursitis, Tendonitis, Nephrogenic Diabetes Insipidus, Renal Colic, Migraine |
| Perfloxacin | Antibacterial | Pneumonia, UTIs, anthrax, acutebacterial sinusitis, chronic bacterial prosttitis, acute pyelonephritis, skin infections |
| Moxifloxacin | Antibacterial | Pneumonia, UTIs, anthrax, acutebacterial sinusitis, chronic bacterial prosttitis, acute pyelonephritis, skin infections |
| Ofloxacin | Antibacterial | Pneumonia, UTIs, anthrax, acutebacterial sinusitis, chronic bacterial prosttitis, acute pyelonephritis, skin infections |
| Oseltamivir | Antiviral | Influenza virus |
| Pregabalin | CNS | Neuropathic pain from Diabetic Neuropathy & Post Herpetic Neuralgia, Partial Seizures, Fibromyalgia, Generalised Anxiety Disorder |
| Darifenacin | Urology | Urinary Incontinence, Over Active Bladder |
| Peramivir | Antiviral | Influenza virus |
| Zanamivir | Antiviral | Influenza virus |

The compounds of the present invention may also be used in treating other conditions treatable by modulating the appropriate receptor.

In a second aspect of the present invention, there is provided a method of preparing a formulation of an oxidised or reduced derivative of a pharmaceutically active compound, the method comprising:
  (i) either synthesising a derivative of a pharmaceutically active compound as defined in the first aspect of the invention; or
    oxidising the pharmaceutically active compound to provide an oxidised derivative which is in an oxidation state one or more oxidation states higher than the pharmaceutically active compound; or
    reducing the pharmaceutically active compound to provide an reduced derivative which is in an oxidation state one or more oxidation states lower than the pharmaceutically active compound;
  (ii) isolating the oxidised or reduced derivative; and
  (iii) mixing the oxidised or reduced derivative with one or more pharmaceutically acceptable excipients to produce the pharmaceutical formulation.

In an embodiment, step (i) of the method comprises oxidising the pharmaceutically active compound to provide an oxidised derivative.

In an embodiment, step (i) of the method comprises reducing the pharmaceutically active compound to provide a reduced derivative.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The above in silico methods have been demonstrated in predicting activity against target receptors. The more promising candidates are then taken forwards into in vitro assays.

In another aspect the present invention provides a pharmaceutical formulation comprising a compound selected from the compounds of formulae 1-161 and a pharmaceutically acceptable excipient.

In another aspect the present invention provides a pharmaceutical formulation comprising a compound selected from the compounds of formula 162-169 and a pharmaceutically acceptable excipient:

| Formula number | Name of Parent Active Compound | Formula |
|---|---|---|
| 162. | oseltamivir | 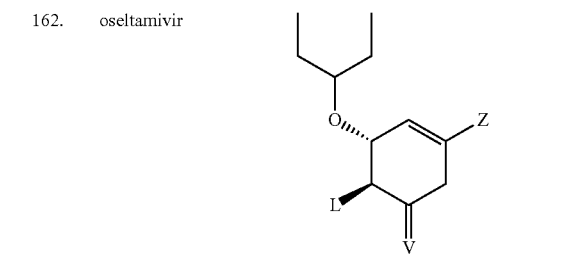 |
| 163. | pregabalin | 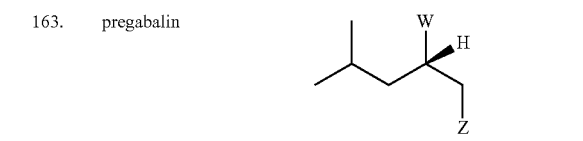 |
| 164. | darifenacin | 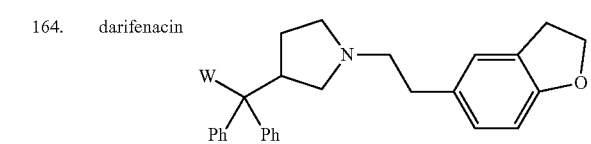 |
| 165. | peramivir | 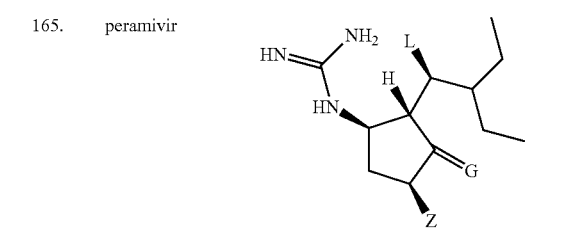 |
| 166. | zanamivir | 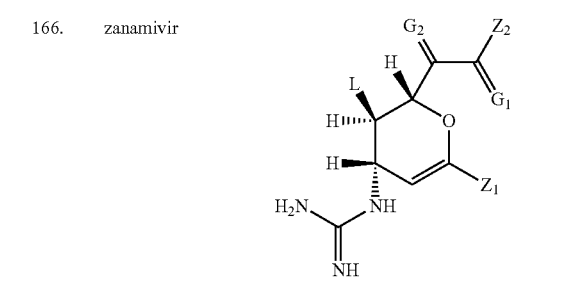 |

-continued

| Formula number | Name of Parent Active Compound | Formula |
|---|---|---|
| 167. | pefloxacin | |
| 168. | moxifloxacin | |
| 169. | ofloxacin | | wherein $R_a$, Z, L, G, W and V are as defined above; provided that the compound is not selected from the group comprising: pefloxacin, moxifloxacin, ofloxacin, oseltamivir, pregabalin, darifenacin, peramivir and zanamivir.

Compounds of the invention containing one or more asymmetric carbon atoms can exist as two or more stereoisomers. Where a compound of the invention contains a double bond such as a C=C or C=N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity, which is illustrated in the Examples below.

The activity of the compounds of the present invention may be predicted using one or more of the in silico techniques mentioned below as a precursor to in vitro testing.

Structure-based drug design works by positioning compounds or fragments of compounds from a database into a selected region of a target structure. These compounds or fragments of compounds are scored and ranked based on their steric and electrostatic interactions with the target site. The best scoring and ranking compounds are then tested with biochemical assays (Anderson, A. C., Chemistry & Biology, Vol. 10, 787-797).

The target structure is first chosen on the basis of biological and biochemical properties. Ideally, a target structure is one that is (i) linked to a human disease, (ii) binds a small in order to carry out a function and (iii) has a well-defined binding pocket. Once a target structure has been identified, it is necessary to obtain accurate structural information. This can be achieved using x-ray crystallography, NMR and/or homology modelling. Once the structural information has been obtained through these techniques, the structure of target can then be prepared for the drug design computer program by e.g. adding hydrogen atoms which may be absent and correctly defining tautomeric structures. Alternatively, structural information of target structures may also be available commercially.

After the structural information of the target structure has been obtained, a potential ligand binding site on the target structure must then be identified. The target site is ideally a pocket or a protrusion having a number of possible hydrogen bond donors and acceptors and particular hydrophobic/hydrophilic characteristics. Again, information relating to ligand binding sites on target structures may be readily available commercially.

After identification of the target structure binding site, databases of small molecules can be virtually screened for docking into the target site of interest in silico. Each small molecule of the database can be scored based on the predicted interaction with the target site.

Examples of algorithms for docking small molecules and/or fragments against the target binding site include:

| Name | Description | Reference |
| --- | --- | --- |
| DOCK | Docks either small molecules or fragments and can include solvent effects; | Kuntz, I., Blaney, J., Oatley, S., Langridge, R., and Ferrin, T. (1982). A geometric approach to macromolecular-ligand interactions. J. Mol. Biol. 161, 269-288.<br>Lorber, D., and Shoichet, B. (1998). Flexible ligand docking using conformational ensembles. Protein Sci. 7, 938-950.<br>Ewing, T., Makino, S., Skillman, G., and Kuntz, I. (2001). DOCK 4.0: search strategies for automated molecular docking of flexible molecule databases. J. Comput. Aided Mol. Des. 15, 411-428.<br>Shoichet, B., Leach, A., and Kuntz, I. (1999). Ligand salvation in molecular docking. Proteins 34, 4-16. |
| FlexX | Utilises incremental construction; | Kramer, B., Metz, G., Rarey, M., and Lengauer, T. (1999). Ligand docking and screening with FlexX. Med. Chem. Res. 9, 463-478. |
| FlexE | Utilises incremental construction and can sample ensembles of receptor structures; | Claussen, H., Buning, C., Rarey, M., and Lengauer, T. (2001). FlexE. Efficientmolecular docking considering protein structure variations. J. Mol. Biol. 308, 377-395. |
| SLIDE | Operates by firstly anchoring fragments and then subsequently adding the remainder of the ligand; | Schnecke, V., Swanson, C., Getzoff, E., Tainer, J., and Kuhn, L.(1998). Screening a peptidyl database for potential ligands to proteins with side-chain flexibility. Proteins 33, 74-87. |

-continued

| Name | Description | Reference |
| --- | --- | --- |
| Flo98 | Rapidly dock a large number of ligand molecules and enables the user to graphically view results; | McMartin, C., and Bohacek, R. (1997). QXP: Powerful, rapid computer algorithms for structure-based drug design. J. Comput. Aided Mol. Des. 11, 333-344. |
| ADAM | Aligns fragments based on hydrogen bonding; | Mitzutani, M., Tomioka, N., and Itai, A. (1994). Rational automatic search method for stable docking models of protein and ligand. J. Mol. Biol. 243, 310-326. |
| AUTODOCK | Uses averaged interaction energy grid to account for receptor conformations and simulated annealing for ligand conformations; | Goodsell, D., Morris, G., and Olson, A. (1996). Automated docking of flexible ligands: applications of AutoDock. J. Mol. Recognit. 9, 1-5. |
| MCDOCK | Uses Monte Carlo to sample ligand placement; | Liu, M., and Wang, S. (1999). MCDOCK: A Monte Carlo simulation approach to the molecular docking problem. J. Comput. Aided Mol. Des. 13, 435-451. |
| ProDOCK | Uses Monte Carlo minimization for flexible ligands; | Trosset, J., and Scheraga, H. (1999). Prodock: software package for protein modeling and docking. J. Comput. Chem. 20, 412-427. |
| ICM | Uses Monte Carlo minimization for protein-ligand docking; and | Abagyan, R., Totrov, M., and Kuznetsov, D. (1994). ICM-a new method for protein modeling and design-applications to docking and structure prediction from the distorted native conformation. J. Comput. Chem. 15, 488-506. |
| DockVision | Uses Monte Carlo minimization. | Hart, T., and Read, R. (1992). Proteins 13, 206-222. |

Once a small molecule has been identified as potentially binding to the target molecule, it must be evaluated before proceeding to further stages. Usually, several molecules which scored well during the docking run are evaluated in further tests e.g. visually with computer graphics or their likelihood to be orally bioavailable using the so-called "rule of 5" which states that good leads generally have less than five hydrogen bond donors and less than 10 hydrogen bond acceptors, a molecular weight less than 500 and the calculated log of the partition coefficient less than 5.

In many cases, the docked and experimental confirmations are within 2 Å root mean standard deviation (rmsd) using structure-based drug design methods.

Alternative methods to structure-based design methods include three-dimensional quantitative structure-activity relationship (3D-QSAR) methods for deriving ligand-based models to estimate the activities of new compounds. Some methods also provide a graphical output indicating regions where increases in affinity might be expected from modifying physical properties such as steric book, partial charge, hydrophobicity, or hydrogen-bond donor/except ability. Comparative molecular field analysis (CoMFA) and comparative molecular similarity indices analysis (CoMSIA) are well-known examples of these techniques. These methods compare molecules in terms of grid-based field energies or similarity indices and use partial least-squares statistics to generate models that have been widely applied to medicinal chemistry problems. However, specific receptor antagonists may encompass a wide range of structures. For example, cholecystokinin 2 receptor antagonists include molecules of varying structure (C. M. R., J. Med. Chem., 2008, 51, 565-573). This can make certain receptor antagonists unsuitable candidates for 3D-QSAR.

An alternative to the QSAR methods includes molecular field-based similarity analysis. These methods rely on the fact that similar field patterns will bind at the same target site regardless of their underlying structure. In fact, it has been reported that there may be a linear correlation between ligand similarity and biological activity.

Molecules interact via their electronic properties: electrostatic and van der Waals forces. If two molecules with diverse structures interact with an enzyme or receptor in a similar way, their bound conformations will have similar properties, although this might not be immediately apparent from a consideration of their structures alone. The idea of a field pattern around a ligand is intuitively appealing as the main criterion for binding recognition and has been acknowledged for many years. There exist in silico methods for defining molecular fields in a form that enables similarity comparisons across molecules in three dimensions and defining how molecular fields can be used as non-structural templates for defining similar biological behaviour.

Field Templating and Field Screening rely on the assumption that those molecules whose field patterns are most similar to those of an active search molecule will be the ones most likely to show the same patterns of biological activity and should be chosen for further investigation.

It is reported in C. M. R., J. Med. Chem., 2008, 51, 565-573 that the field patterns of three potent and selective CCK2 antagonists can be amalgamated to give a ligand based view of the active site of the receptor in field point terms. A test set of compounds can then be selected from a very diverse collection of CCK2 receptor-ligands and each compared to the "receptor template". The field overlay scores for the model system can then be compared to experimentally determined affinity estimates (pKB values) for the compounds in a functional in vitro CCK2 bioassay.

The above in silico methods have been demonstrated in predicting activity against target receptors. The more promising candidates are then taken forwards into in vitro assays.

The following embodiments apply independently to compounds according to any one, or any combination of more than one, of formulae 1-169.

In an embodiment, when Z is $CO_2H$, G is not $=O$.
In an embodiment, when G is $=O$, Z is not $CO_2H$.
In an embodiment, Z, $Z_1$ or $Z_2$ are independently at each occurrence

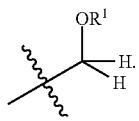

Thus, Z, $Z_1$ or $Z_2$ may independently at each occurrence be

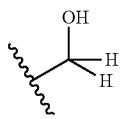

or, alternatively, Z, $Z_1$ or $Z_2$ may independently at each occurrence be

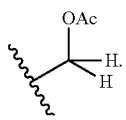

In an alternative embodiment, Z, $Z_1$ or $Z_2$ are independently at each occurrence

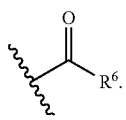

Preferably, Z, $Z_1$ or $Z_2$ are independently at each occurrence

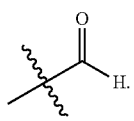

In a further alternative embodiment, Z, $Z_1$ or $Z_2$ are independently

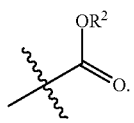

In this embodiment, $R^2$ may be H. Alternatively, $R^2$ may be selected from $C_1$ alkyl, $C_2$ alkyl, $C_3$ alkyl or $C_4$ alkyl. For example, $R^2$ may be methyl, ethyl, propyl, isopropyl, butyl or tert-butyl. In particular embodiments, $R^2$ is methyl.

In a further alternative embodiment, Z, $Z_1$ or $Z_2$ are independently at each occurrence

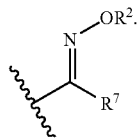

Preferably, Z, $Z_1$ and $Z_2$ are independently at each occurrence

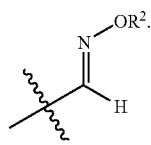

In these embodiments, $R^2$ may be H. Alternatively, $R^2$ may be selected from $C_1$ alkyl, $C_2$ alkyl, $C_3$ alkyl or $C_4$ alkyl. For example, $R^2$ may be methyl, ethyl, propyl, isopropyl, butyl or tert-butyl. In particular embodiments, $R^2$ is methyl.

In a further alternative embodiment, Z, $Z_1$ or $Z_2$ are independently at each occurrence

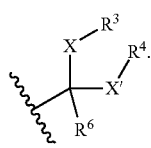

In a preferred embodiment, Z, $Z_1$ or $Z_2$ are independently at each occurrence

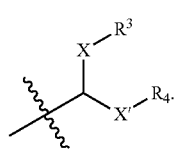

Preferably X is O. In these embodiment, $R^3$ and $R^4$ may both be $C_1$ alkyl, $C_2$ alkyl, $C_3$ alkyl or $C_4$ alkyl. $R_3$ and $R_4$ may be the same or different. For example, $R^3$ and $R^4$ may both be methyl or may both be ethyl. Alternatively, $R^3$ and $R^4$, together with the X atoms to which they are attached and the carbon atom bearing the X atoms, form a 5 membered ring. For example, Z, $Z_1$ and $Z_2$ may independently at each occurrence be CH-ethylene glycol acetal, i.e. Z, $Z_1$ or $Z_2$ are independently

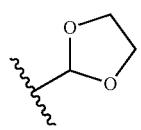

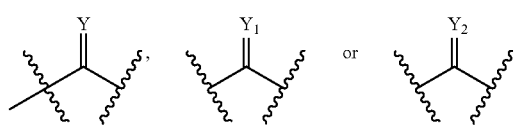

are independently, wherever they occur, selected from the group comprising:

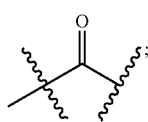 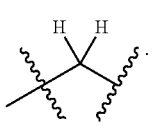 Thus,

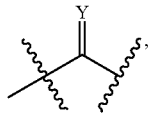 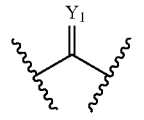 or 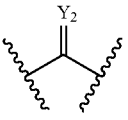

may independently at each occurrence be

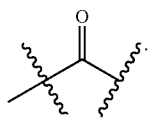 [SMILES: *C(*)=O]

Alternatively,

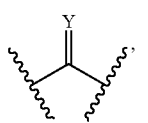 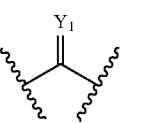 or 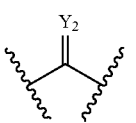

may independently at each occurrence be

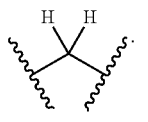

In an embodiment,

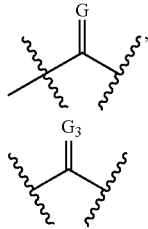 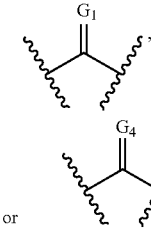 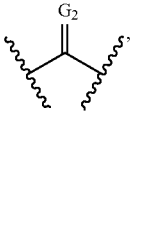

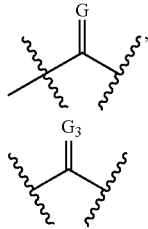 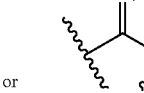

or are independently

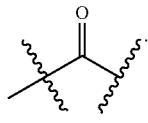 [SMILES: *C(*)=O]

Alternatively,

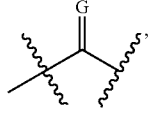 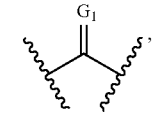 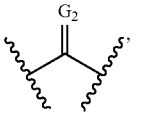

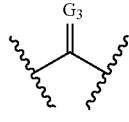 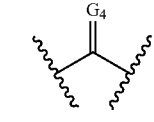

or are independently at each occurrence

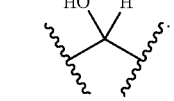

In an alternate embodiment,

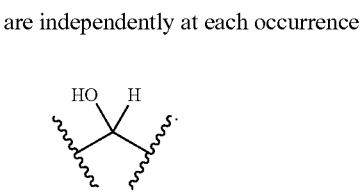

or are

In this embodiment, $R^2$ may be H. Alternatively, $R^2$ may be selected from $C_1$ alkyl, $C_2$ alkyl, $C_3$ alkyl or $C_4$ alkyl. For example, $R^2$ may be methyl, ethyl, propyl, isopropyl, butyl or tert-butyl. In particular embodiments, $R^2$ is methyl.

In a further alternate embodiment

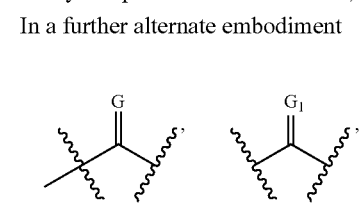

or are

Preferably X is O. In an embodiment, $R^3$ and $R^4$ may both be $C_1$ alkyl, $C_2$ alkyl, $C_3$ alkyl or $C_4$ alkyl. $R_3$ and $R_4$ may be the same or different. For example, $R^3$ and $R^4$ may both be methyl or may both be ethyl. Alternatively, $R^3$ and $R^4$, together with the X atoms to which they are attached and the carbon atom bearing the X atoms, form a 5 membered ring. For example, G, $G^1$, $G^2$, $G^3$ and $G^4$ may independently at each occurrence be ethylene glycol acetal, i.e.

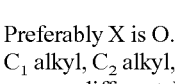 

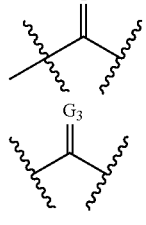 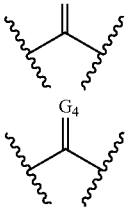 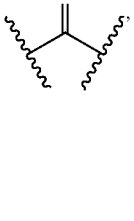

or may independently at each occurrence be

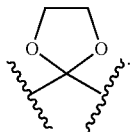

In an embodiment,

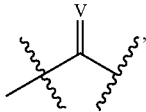

is independently at each occurrence

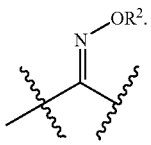

In this embodiment, $R^2$ may be H. Alternatively, $R^2$ may be selected from $C_1$ alkyl, $C_2$ alkyl, $C_3$ alkyl or C4 alkyl. For example, $R^2$ may be methyl, ethyl, propyl, isopropyl, butyl or tert-butyl. In particular embodiments, $R^2$ is methyl.

In an alternative embodiment,

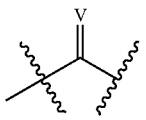

may be

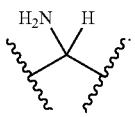

In an embodiment, Q, $Q_1$ or $Q_2$ may independently at each occurrence be

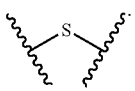

In an alternative embodiment, Q, $Q_1$ or $Q_2$ may independently at each occurrence be

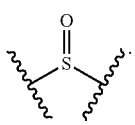

In a further alternative embodiment, Q, $Q_1$ or $Q_2$ may independently at each occurrence be

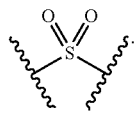 [SMILES: *S(*)(=O)=O]

In an embodiment, W is

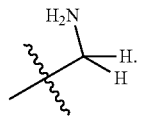

Alternatively, W may be

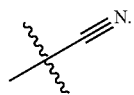

In an alternative embodiment, W is

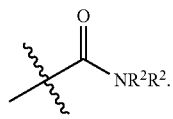

In this embodiment, W may be selected from

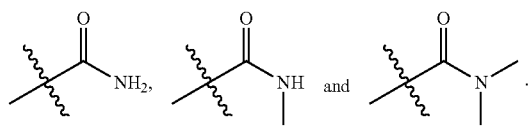

In a further alternative embodiment, W is

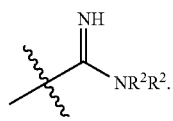

In this embodiment, W may be selected from

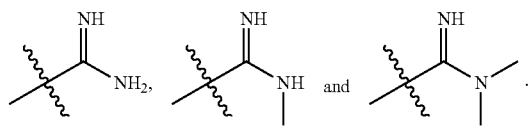

In a further alternative embodiment, W is

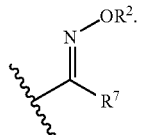

In a preferred alternative embodiment, W is

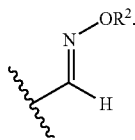

In these embodiments, $R^2$ may be H. Alternatively, $R^2$ may be selected from $C_1$ alkyl, $C_2$ alkyl, $C_3$ alkyl or $C_4$ alkyl. For example, $R^2$ may be methyl, ethyl, propyl, isopropyl, butyl or tert-butyl. In particular embodiments, $R^2$ is methyl.

In an embodiment, T, $T_1$ or $T_2$ may independently at each occurrence be N. Alternatively, T, $T_1$ or $T_2$ may independently at each occurrence be NO.

In an embodiment, L is

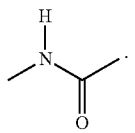

Alternatively, L is

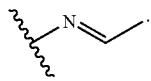 [SMILES: */N=C/C]

In an embodiment, two adjacent G, V or Y groups when present in a vicinal arrangement may form a 5- or 6-membered ring, optionally substituted with an oxo group. In a preferred embodiment, two adjacent G, V or Y groups when present in a vicinal arrangement may form a 5-membered ring, optionally substituted with an oxo group.

The present invention also includes the synthesis of all pharmaceutically acceptable isotopically-labelled compounds of formulae (I) to (VI) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWING

FIG. 1 illustrates the efficacy of particular rosuvastatin compounds in vivo as described in example 1.

DETAILED DESCRIPTION

Example 1

This example serves to illustrate that the activity of the compounds of the present invention derived by in silico methods can be predictive of ultimate in vitro and even in vivo activity.

In Silico

The structures of a number of rosuvastatin analogues were screened in silico to determine whether or not these compounds are active against the enzyme 3-hydroxy-3-methyl-glutaryl-coenzyme A reductase (HMG-CoA). The results are given as the binding free energy (kcal/mol) when each compound is docked with the 1HWL structure (i.e. the complex of the catalytic portion of human HMG CoA reductase with rosuvastatin) in silico. Two different conformations of the binding site were also modelled for comparison. It can be deduced that all compounds listed in the table below have a binding energy comparable to rosuvastatin and therefore can be expected to have an activity comparable to rosuvastatin.

In Vitro

The following procedure was followed using a HMG-CoA Reductase assay kit obtained from Sigma-Aldrich (catalogue number CS1090). The assay is based on the spectrophotometric measurement of the decrease in absorbance at 340 nm of NADPH in solution. A decrease in absorbance is caused by the oxidation of NADPH by the catalytic subunit of HMGR in the presence of the substrate HMG-CoA. Effective inhibition of the HMG-CoA leads to a reduction in oxidation of NADPH which in turn leads to a smaller reduction in the absorbance at 340 nm over time. This is illustrated in the following reaction scheme:

$$HMG\text{-}CoA + 2NADPH + 2H^+ \rightarrow mevalonate + 2NADP^+ + CoA\text{-}SH$$

Compounds showing the best inhibitory action are those which reduce the absorbance least.

Preparation of the Assay Solution

Ultrapure water (17 MΩ-cm or equivalent was used for the preparation of reagents and throughout the procedure.

First, an assay buffer solution was prepared using the following method: 0.2 ml of assay buffer, 5× (catalogue number A5981) was diluted with 0.8 ml of ultrapure water. The resulting buffer solution was kept on ice or stored at −20° C. for further use.

Next, 25 mg of NADPH (catalogue number N6505) was reconstituted with 1.5 ml of the buffer solution. The reconstituted NADPH was stored in working aliquots at −20° C.

The HMG-CoA substrate solution (catalogue number S7447), HMG-CoA reductase (catalogue number H8789) and inhibitor solution (e.g. pravastatin, catalogue number 15909) were kept on ice throughout the procedure.

1. Before beginning, the spectrophotometer was set at 37° C. and 340 nm, with a kinetic programme: 1 ml sample, read every 20 seconds for up to 10 minutes.
2. The appropriate volumes of the reaction solutions were added according to Table 1 (1 ml assay).

TABLE 1

Reaction volumes for 1 ml samples

| Sample | 1× Assay buffer | Test compound/ Pravastatin | NADPH | HMG-CoA | HGMG |
|---|---|---|---|---|---|
| Blank | 920 μl | — | 20 μl | 60 μl | — |
| Activity | 915 μl | — | 20 μl | 60 μl | 5 μl |
| Inhibition | 910 μl | 5 μl | 20 μl | 60 μl | 5 μl |

The reagents were added to the reaction in the following order:
a. Add a buffer to all samples.
b. Add the inhibitor (test compound/Pravastatin) to the inhibition sample.
c. Add the reconstituted NADPH to all samples.
d. Add Substrate Solution (HMG-CoA) to all samples.
e. Add HMG-CoA Reductase (HMGR) to the Activity and Inhibition samples.
f. Mix the samples thoroughly.

3. The kinetics programme was started immediately. The activity of the product was calculated according to the following equation:

$$\text{Units/mgP} = \frac{(\Delta A_{340}/\min_{sample} - \Delta A_{340}/\min_{control}) \times TV}{12.44 \times V \times 0.6 \times LP}$$

where:

$12.44 = \epsilon_{mM}$—the extinction coefficient for NADPH at 340 nm is $6.22 \text{ mM}^{-1}\text{cm}^{-1}$. 12.44 represents the 2 NADPH consumed in the reaction.

TV=total volume of the reaction in ml (1 ml for cuvettes)
V=volume of enzyme used in the assay (ml)
0.6=enzyme concentration in mg-protein (mgP0/ml (0.55-0.65 mgP/ml)
LP=light path in cm (1 for cuvettes).

The $IC_{50}$ values for particular rosuvastatin analogues are provided in the table below. It can be seen that the rosuvastatin analogues have a comparable $IC_{50}$ value to rosuvastatin itself. This confirms the conclusion derived from the in silico data.

In Vivo

The efficacy of particular rosuvastatin compounds was then determined in vivo. The Example demonstrates the effect of 3 or 5 days BID treatment with rosuvastatin analogues and rosuvastatin (all at 25 mg/kg po) on rat plasma triglyceride levels 16 hours after the last treatment dose. The measurement of the change in rat plasma triglyceride levels is considered to be a fair test for determining HMG CoA reductase activity.

112 male SD rats (Harlan) were housed in groups of 6 under a 12 h light dark cycle (lights on 07.00 h) with free access to food (normal laboratory chow) and water. Animals between 148-183 g were allocated to treatment groups of 8 balanced by body weight and treatments were balanced across cages.

The rosuvastatin analogues were made up in 10% PEG300/10% cremophor/80% methyl cellulose (0.5%) (vehicle 1) to make a 5 mg/mL solution. The rosuvastatin compounds used were:

Rosuvastatin lactol iso-propyl acetal benzyl ether; and
Rosuvastatin lactol methyl acetal nicotinoyl ester (diastereomeric ratio 2/1).

Rosuvastatin was formulated in 0.5% Tween in 0.5% methyl cellulose (vehicle 2) at 5 mg/kg as a suspension.

Rats were orally dosed with vehicle 1, one of the rosuvastatin analogues in vehicle 1 (25 mg/kg), vehicle 2 or rosuvastatin in vehicle 2 (25 mg/kg po), BID for 3 or 5 days.

Sixteen hours after the last treatment, terminal plasma samples were taken, stored at −20° C., and transported on dry ice for analysis of triglyceride levels.

Data for each time-point were analysed by 1-way ANOVA and post-hoc Dunnett's test.

The results are provided in FIG. 1 from which it can be deduced that administration of rosuvastatin (25 mg/kg po) BID for 3 or 5 days causes a marked reduction in plasma triglycerides. All rosuvastatin analogues also significantly reduced plasma triglycerides after both 3 and 5 days BID treatment. All animals tolerated the rosuvastatin treatments well and there was no evidence of any adverse events.

The magnitude of the effect of the rosuvastatin analogues was equivalent to that of rosuvastatin.

| Structure | Binding free energy (kcal/mol) | | | $IC_{50}$ (nm) | In vivo |
|---|---|---|---|---|---|
| | 1HWL | 1HWL (configuration 2) | 1HWL (configuration 3) | | |
| Rosuvastatin | −9.37 | −8.78 | −8.83 | 4 | Reduction in plasma triglycerides |

-continued

| Structure | Binding free energy (kcal/mol) | | | IC$_{50}$ (nm) | In vivo |
|---|---|---|---|---|---|
| | 1HWL | 1HWL (configuration 2) | 1HWL (configuration 3) | | |
| (structure) | −8.56 | −8.98 | N/A | 3 | N/A |
| (structure) | −8.20 | −9.08 | N/A | 22 | N/A |
| (structure) | −8.00 | −8.70 | −8.81 | <1 | Reduction in plasma triglycerides |
| (structure) | N/A | −8.52 | −8.63 | 1 | Reduction in plasma triglycerides |

-continued

| Structure | Binding free energy (kcal/mol) | | | $IC_{50}$ (nm) | In vivo |
|---|---|---|---|---|---|
| | 1HWL | 1HWL (configuration 2) | 1HWL (configuration 3) | | |
| 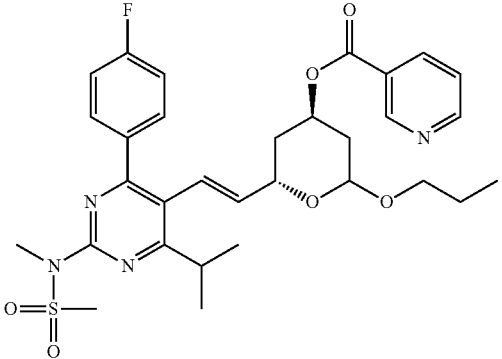 | N/A | N/A | −8.75 | 8 | N/A |

Example 2

This example serves to illustrate that the activity of the compounds of the present invention derived by in silico methods can be predictive of ultimate in vitro and even in vivo activity.

In Silico

The structures of a number of rosuvastatin and atorvastatin analogues were screened in silico to determine whether or not these compounds are active against the enzyme 3-hydroxy-3-methylglutaryl-coenzyme A reductase (HMG-CoA). The results are given as the binding free energy (kcal/mol) when each compound is docked with the 1HWL structure (i.e. the complex of the catalytic portion of human HMG CoA reductase with rosuvastatin) or the 1HWK structure (i.e. the complex of the catalytic portion of human HMG CoA reductase with atorvastatin) in silico. It can be deduced that all compounds listed in the table below have a binding energy comparable to either rosuvastatin or atorvastatin and therefore can be expected to have an activity comparable to rosuvastatin or atorvastatin.

In Vitro

The above assay procedure described in example 1 was followed.

The $IC_{50}$ values for particular rosuvastatin and atorvastatin analogues are provided in the table below. It can be seen that the analogues have a comparable $IC_{50}$ value to rosuvastatin and atorvastatin themselves. This confirms the conclusion derived from the in silico data.

| Structure | Docking energy (kcal/mol) | $IC_{50}$ (nm) |
|---|---|---|
| Rosuvastatin | −9.83 | 4 |
| 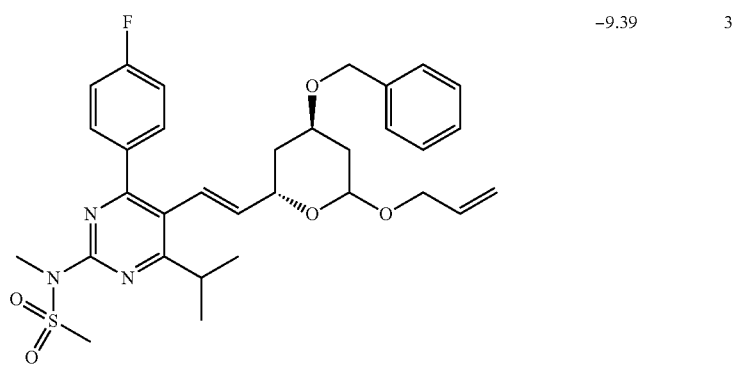 | −9.39 | 3 |

| Structure | Docking energy (kcal/mol) | IC$_{50}$ (nm) |
|---|---|---|
| [structure] | −9.73 | 4 |
| Atorvastatin | −11.07 | 7 |
| [structure] | −10.07 | 3 |
| [structure] | −10.49 | 1 |

Synthetic Examples

Materials and Methods

Equipment:

$^1$H NMR Spectra were recorded at 400 MHz using a Bruker AVANCE 400 MHz spectrometer. LC-MS equipment and conditions are as follows:

LC-MS (Agilent):

1. LC: Agilent Technologies 1200 series, Binary Pump, Diode Array Detector. Ultimate AQ-C18, 3 μm, 2.1×50 mm column. Mobile phase: B (MeOH) and A (0.07% HCOOH aqueous solution). Flow Rate: 0.4 mL/min at 25° C. Detector: 214 nm, 254 nm. Gradient stop time, 5 min. Timetable:

| T (min) | B(%) | A(%) |
|---|---|---|
| 0 | 10 | 90 |
| 0.2 | 10 | 90 |
| 1.2 | 95 | 5 |
| 2.8 | 95 | 5 |
| 3 | 10 | 90 |
| 5 | 10 | 90 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.

3. Sample preparation: samples were dissolved in methanol at 1~10 μg/mL, then filtered through a 0.22 μm filter membrane. Injection volume: 1~10 μL.

LC-MS (Waters):
1. LC: Waters 2695, Quaterary Pump, Waters 2996 Photo-diode Array Detector. Xbridge-C18, 3.5 μm, 2.1×50 mm column. Mobile Phase: B (MeOH) and A (0.07% HCOOH aqueous solution). Flow Rate: 0.3 mL/min at 30° C. Detector: 214 nm, 254 nm. Gradient stop time, 10 min. Timetable:

| T (min) | B(%) | A(%) |
| --- | --- | --- |
| 0 | 10 | 90 |
| 2.5 | 75 | 25 |
| 5.0 | 95 | 5 |
| 7.5 | 95 | 5 |
| 7.6 | 10 | 90 |
| 10 | 10 | 90 |

2. MS: Micromass QZ, TIC: 100~900 m/z, Ion Source: ES, Capillary: 3 kV, Cone: 3V, Extractor: 3V, Drying gas flow: 600 L/hr, cone: 50 L/hr, Desolvation temperature: 300° C., Source temperature: 100° C.
3. Sample preparation: samples were dissolved in methanol at 1~10 μg/mL, then filtered through a 0.22 μm filter membrane. Injection volume: 1~10 μL.

Compound Synthesis:

The compounds of the invention may be prepared by methods well known to those skilled in the art, and as described in the synthetic experimental procedures shown below.

DEFINITIONS

Ac$_2$O (acetic anhydride); AcOK (potassium acetate); Boc (tert-butoxycarbonyl); Boc$_2$O (di-tert-butyl dicarbonate); cat (catalytic); Cbz-OSu (N-(benzyloxycarbonyloxy)succinimide); CDCl$_3$ (deuterated chloroform); CD$_3$OD (deuterated methanol); conc (concentrated); DIBAl-H (diisobutylaluminium hydride); DIPEA (N,N-diisopropylethylamine); DMAP (4-dimethylaminopyridine); DMF (N,N-dimethylformamide); DMP (Dess-Martin Periodinane); DMSO (dimethylsulfoxide); DMSO-d$_6$ (deuterated dimethylsulfoxide); EDCl (1-ethyl-3-(3-dimethylaminopropyl) carbodiimide); eq (equivalent); ES-API (electrospray atmospheric pressure ionization); Et$_3$N (triethylamine); Et$_2$O (diethyl ether); EtOAc (ethyl acetate); EtOH (ethanol); g (gram); h (hour); HATU (2-(7-aza-1H-benzotriazole-1-yl)-1,1,3,3-tetramethyluronium hexafluorophosphate); HBTU (2-(1H-benzotriazole-1-yl)-1,1,3,3-tetramethyluronium hexafluorophosphate); $^1$H NMR (proton nuclear magnetic resonance); HOBt (hydroxybenzotriazole); HPLC (high-performance liquid chromatography); Hz (hertz); IBX (2-iodoxybenzoic acid); i-PrOH (isopropanol); L (liter); LAH (lithium aluminium hydride); LC-MS (liquid chromatography-mass spectrometry); M (molar); m-CPBA (meta-chloroperoxybenzoic acid); MeCN (acetonitrile); MeOH (methanol); mg (milligrams); MHz (megahertz); min (minutes); mL (milliliters); mmol (millimoles); MTBE (methyl tert-butyl ether); NaOMe (sodium methoxide); PCC (pyridinium chlorochromate); Pet. ether (petroleum ether); ppm (parts per million); PPTS (pyridinium p-toluenesulfonate); psi (pounds per square inch); R$_t$ (retention time); RT (room temperature); TBAF (tetra-n-butylammonium fluoride); TBS-Cl (tert-butyldimethylsilyl chloride); t-BuOH (tert-butanol); TFA (trifluoroacetic acid); THF (tetrahydrofuran); TLC (thin layer chromatography); Tol (toluene); Ts-OH (p-toluene sulfonic acid); v/v (volume/volume).

Example 3

Formula 1—Compounds 3a & 3b

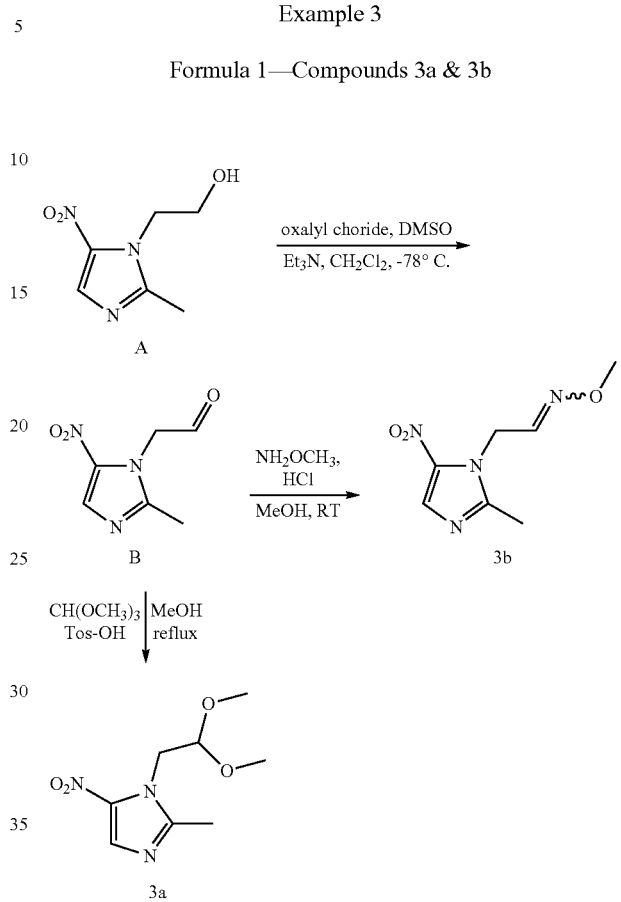

2-(2-Methyl-5-nitro-1H-imidazol-1-yl)acetaldehyde

To a solution of anhydrous DMSO (10 mL) in CH$_2$Cl$_2$ (120 mL) at −78° C. was added a 2 M solution of oxalyl chloride in CH$_2$Cl$_2$ (10 mL, 20 mmol) slowly dropwise. The reaction mixture was allowed to stir for 20 min and a solution of compound A (2.00 g, 11.7 mmol) in DMSO (15 mL) and CH$_2$Cl$_2$ (25 mL) was added at −78° C. The mixture was stirred at −78° C. for 1 h then triethylamine (14.2 g 140.3 mmol) was added and stirring was continued at −78° C. for another 1 h. The mixture was allowed to warm to room temperature then poured into water (70 mL) and extracted with CH$_2$Cl$_2$ (50 mL×3). The combined organic layers were washed with brine then dried (MgSO$_4$) and concentrated under reduced pressure. The residue was purified by flash chromatography (CH$_2$Cl$_2$/MeOH, 100~40/1, v/v) to give 2-(2-methyl-5-nitro-1H-imidazol-1-yl)acetaldehyde (1.30 g, 66%) as a yellow oil.

LC-MS (Agilent): R$_t$ 2.61 min; m/z calculated for C$_6$H$_7$N$_3$O [M+MeOH+H]$^+$ 202.2. found 202.1.

Compound 3a: 1-(2,2-Dimethoxyethyl)-2-methyl-5-nitro-1H-imidazole

A solution of intermediate B (200 mg, 1.18 mmol, 1.0 eq), CH(OCH$_3$)$_3$ (376 mg, 3.55 mmol, 3 eq) and Tos-OH (10 mg)

in MeOH (4 mL) was heated at reflux overnight. The reaction mixture was allowed to cool to room temperature and concentrated under reduced pressure. The residue was diluted with EtOAc and washed with water, brine then dried over $Na_2SO_4$ and concentrated under reduced pressure. The residue was purified by flash chromatography (Pet. ether/$CH_2Cl_2$, 1/2 to $CH_2Cl_2$, v/v) to give 1-(2,2-dimethoxyethyl)-2-methyl-5-nitro-1H-imidazole (120 mg, 47%) as a light brown oil.

LC-MS (Agilent): $R_t$ 2.86 min; m/z calculated for $C_8H_{13}N_3O_4$ $[M+H]^+$ 216.2. found 216.1.

$^1$H NMR: (400 MHz, $CDCl_3$) δ (ppm): 7.97 (s, 1H), 4.57 (t, J=5.2 Hz, 1H), 4.39 (d, J=5.2 Hz, 2H), 3.45 (s, 6H), 2.53 (s, 3H).

Compound 3b: 2-(2-Methyl-5-nitro-1H-imidazol-1-yl)acetaldehyde O-methyl oxime

A solution of intermediate B (200 mg, 1.18 mmol, 1.0 eq) and O-methylhydroxylamine hydrochloride (197 mg, 2.36 mmol, 2.0 eq) in MeOH (3 mL) was stirred at room temperature for 16 h. The mixture was concentrated under reduced pressure and the residue was diluted with water (5 mL) and brine (5 mL) and extracted with EtOAc (10 mL×3). The combined organic layers were washed with brine, dried over $Na_2SO_4$ and concentrated under reduce pressure to give 2-(2-methyl-5-nitro-1H-imidazol-1-yl)acetaldehyde O-methyl oxime (120 mg, 53%) as a light brown oil, $^1$H-NMR spectroscopy revealed a 2:3 mixture of isomers.

LC-MS (Agilent): $R_t$ 2.87 min; m/z calculated for $C_7H_{10}N_4O_3$ $[M+H]^+$ 199.2. found 199.1.

$^1$H NMR: (400 MHz, $CDCl_3$) δ (ppm): 7.98 (s, 0.4H), 7.97 (s, 0.6H), 7.52 (t, J=4.8 Hz, 0.6H), 6.75 (t, J=4.4 Hz, 0.4H), 5.16 (d, J=4.4 Hz, 0.8H), 5.05 (d, J=4.8 Hz, 1.2H), 4.0 (s, 1.2H), 3.85 (s, 1.8H), 2.53 (s, 1.8H), 2.50 (s, 1.2H).

Example 4

Formula 141—Compounds 4a & 4b

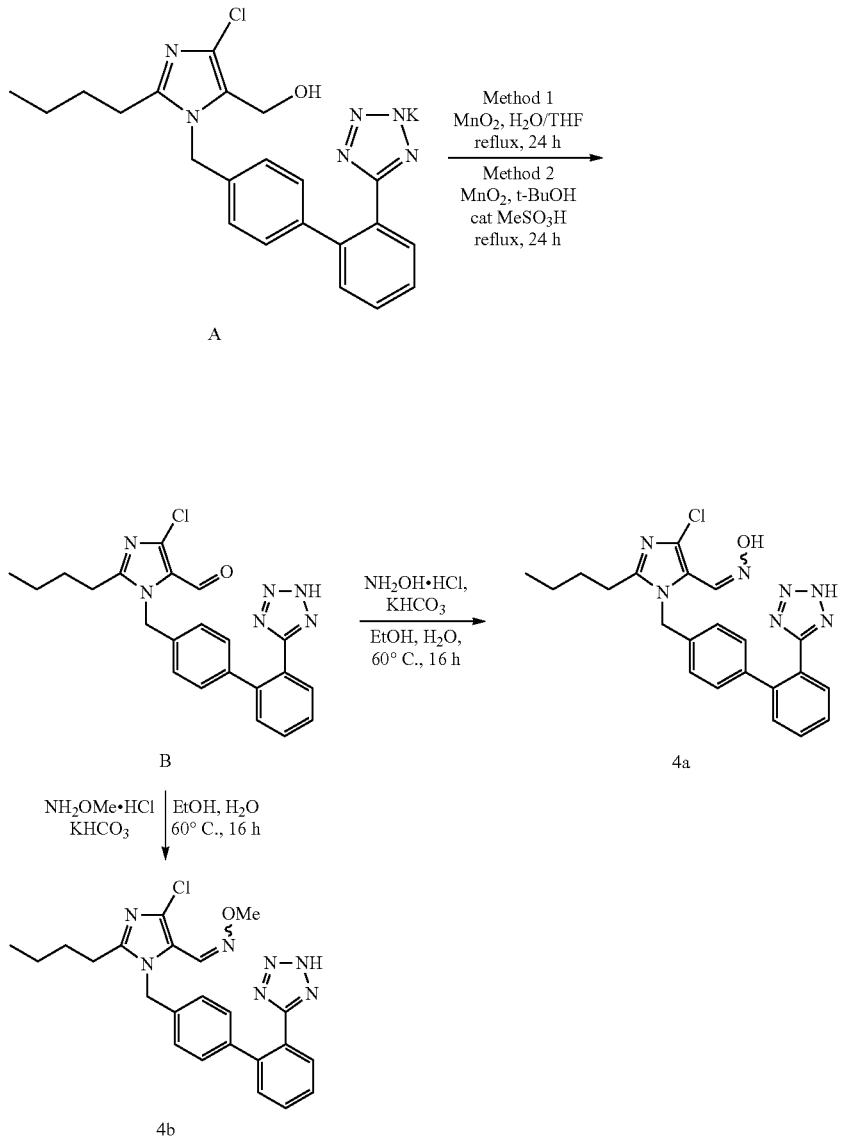

Intermediate B: 1-((2'-(2H-Tetrazol-5-yl)-[1,1'-biphenyl]-4-yl)methyl)-2-butyl-4-chloro-1H-imidazole-5-carbaldehyde Method 1: To a solution of compound A (922 mg, 2.0 mmol) in water (15 mL) and THF (10 mL) was added $MnO_2$ (522 mg, 6.0 mmol, 3.0 eq) and the resulting mixture was heated at reflux for 24 h. The $MnO_2$ was removed by suction filtration and the filtrate was concentrated under reduced pressure. The residue was dissolved in EtOH (30 mL) and the solvent was removed by rotary evaporation to remove residual water before purification by silica gel column chromatography (MeOH/$CH_2Cl_2$, 0~1/50, v/v) to give 1-((2'-(2H-tetrazol-5-yl)-[1,1'-biphenyl]-4-yl)methyl)-2-butyl-4-chloro-1H-imidazole-5-carbaldehyde (280 mg, 33%) as a brown solid.

LC-MS (Agilent): $R_t$ 3.23 min; m/z calculated for $C_{22}H_{21}ClN_6O$ [M+H]$^+$ 420.9, [M+Na]$^+$ 442.9, found 421.1, 443.1.

$^1$H NMR: (400 MHz, $CD_3OD$) δ (ppm): 9.77 (s, 1H), 7.71-7.67 (m, 2H), 7.60-7.55 (m, 2H), 5.65 (s, 2H), 2.53 (s, 3H), 2.69 (t, J=7.8 Hz, 2H), 1.64-1.56 (m, 2H), 1.31-1.39 (m, 2H), 0.90 (t, J=7.4 Hz, 3H).

Method 2: To a solution of compound A (2.31 g, 5.0 mmol) in t-BuOH (20 mL) was added $MnO_2$ (2.17 mg, 25.0 mmol, 5.0 eq) and $MeSO_3H$ (238 mg, 2.5 mmol, 0.5 eq) and the resulting mixture was heated at reflux for 16 hours. The mixture was allowed to cool to room temperature and MeOH (50 mL) was added. The $MnO_2$ was removed by suction filtration and the filtrate was concentrated under reduced pressure. The residue was purified by silica gel column chromatography (MeOH/$CH_2Cl_2$, 0~1/50, v/v) to give 1-((2'-(2H-tetrazol-5-yl)-[1,1'-biphenyl]-4-yl)methyl)-2-butyl-4-chloro-1H-imidazole-5-carbaldehyde (1.27 g, 60%) as a brown solid.

LC-MS (Agilent): $R_t$ 3.23 min; m/z calculated for $C_{22}H_{21}ClN_6O$ [M+H]$^+$ 420.9, [M+Na]$^+$ 442.9, found 421.1, 443.1.

Compound 4a: 1-((2'-(2H-Tetrazol-5-yl)-[1,1'-biphenyl]-4-yl)methyl)-2-butyl-4-chloro-1H-imidazole-5-carbaldehyde oxime To a solution of intermediate B (250 mg, 0.545 mmol) in EtOH (5 mL) and water (10 mL) was added hydroxylamine hydrochloride (189 mg, 2.72 mmol, 5.0 eq) and $KHCO_3$ (327 mg, 3.27 mmol, 6.0 eq). The resulting mixture was heated at 60° C. for 16 h then poured into water (20 mL) and extracted with EtOAc (20 mL×3). The combined organic layers were washed with brine, dried over $Na_2SO_4$ and concentrated under reduced pressure and the residue was purified by silica gel column chromatography (MeOH/$CH_2Cl_2$, 0~1/20, v/v) to give 1-((2'-(2H-tetrazol-5-yl)-[1,1'-biphenyl]-4-yl)methyl)-2-butyl-4-chloro-1H-imidazole-5-carbaldehyde oxime (100 mg, 39%) as a light yellow solid.

LC-MS (Agilent): $R_t$ 3.20 min; m/z calculated for $C_{22}H_{22}ClN_7O$ [M+H]$^+$ 435.9. found 436.

$^1$H NMR: (400 MHz, DMSO-$d_6$) δ (ppm): 11.39 (s, 1H), 8.01 (s, 1H), 7.66-7.50 (m, 2H), 7.09 (d, J=8.0 Hz, 2H), 6.97 (d, J=8.4 Hz, 2H), 5.56 (s, 2H), 2.50 (t, J=7.6 Hz, 2H), 1.48 (quint, 2H), 1.28-1.19 (m, 2H), 0.80 (t, J=7.4 Hz, 3H).

Compound 4b: 1-((2'-(2H-Tetrazol-5-yl)-[1',1'-biphenyl]-4-yl)methyl)-2-butyl-4-chloro-1H-imidazole-5-carbaldehyde O-methyl oxime To a solution of intermediate B (300 mg, 0.713 mmol) in EtOH (10 mL) and water (15 mL) was added O-methylhydroxylamine hydrochloride (298 mg, 3.57 mmol, 5.0 eq) and $KHCO_3$ (428 mg, 4.28 mmol, 6.0 eq). The resulting mixture was heated at 60° C. for 16 h then poured into water (15 mL) and extracted with EtOAc (20 mL×3). The combined organic layers were washed with brine, dried over $Na_2SO_4$ and concentrated under reduced pressure and the residue was purified by silica gel column chromatography (MeOH/$CH_2Cl_2$, 0~1/50, v/v) to give 1-((2'-(2H-tetrazol-5-yl)-[1,1'-biphenyl]-4-yl)methyl)-2-butyl-4-chloro-1H-imidazole-5-carbaldehyde O-methyl oxime (100 mg, 31%) as a white solid, $^1$H-NMR spectroscopy revealed a 8:92 mixture of isomers.

LC-MS (Agilent): $R_t$ 3.34 min; m/z calculated for $C_{23}H_{24}ClN_7O$ [M+H]$^+$ 449.9. found 450.1.

$^1$H NMR: (400 MHz, DMSO-$d_6$) δ (ppm): 8.02 (s, 0.92H), 7.70-7.52 (m, 4H), 7.46 (s, 0.08H), 7.09 (d, J=8.4 Hz, 2H), 6.97 (d, J=8.0 Hz, 2H), 5.51 (s, 1.84H), 5.23 (s, 0.16H), 3.80 (s, 0.24H), 3.76 (s, 2.76H), 2.60 (t, J=7.6 Hz, 2H), 1.52 (quint, 2H), 1.33-1.24 (m, 2H), 0.83 (t, J=7.2 Hz, 3H).

Example 5

Formula 135—Examples 5a & 5b

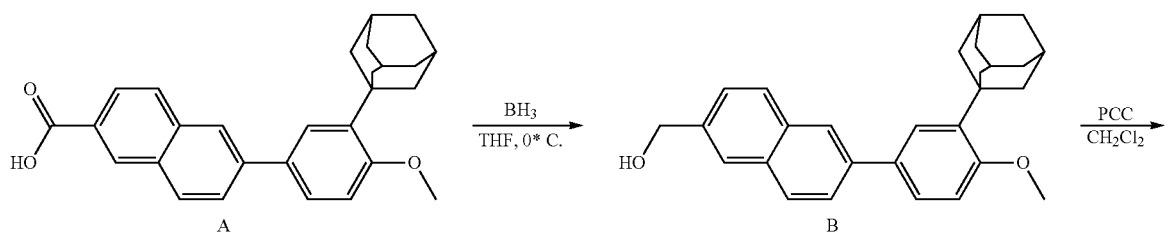

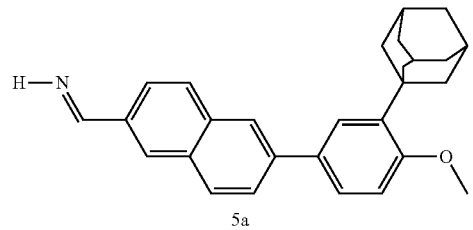

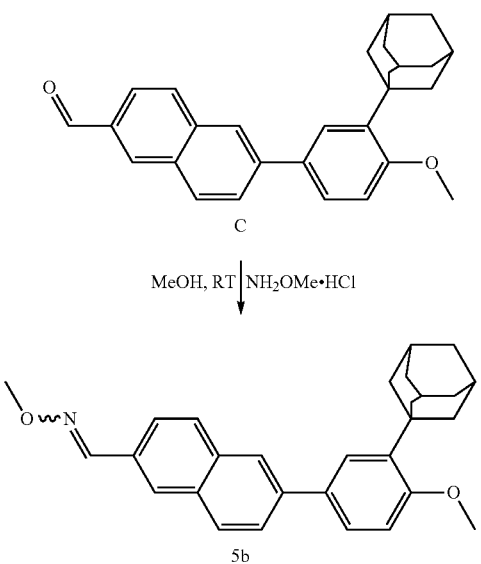

Intermediate B: (6-(3-(Adamantan-1-yl)-4-methoxyphenyl)naphthalen-2-yl)methanol A solution of compound A (2.00 g, 4.85 mmol, 1 eq) in THF (180 mL) was cooled to 0° C. before adding BH$_3$.THF (1M solution in THF, 14.6 mL, 14.6 mmol, 3 eq) dropwise. The reaction mixture was warmed to room temperature and stirred for 3 h then diluted with water and extracted with CH$_2$Cl$_2$ (30 mL×3). The organic layers were combined, washed with brine and dried over anhydrous MgSO$_4$. The solvent was removed under reduced pressure and the residue was purified by silica gel column chromatography (CH$_2$Cl$_2$/Pet. ether, 1/2, v/v) to give (6-(3-(adamantan-1-yl)-4-methoxyphenyl)naphthalen-2-yl)methanol (1.90 g, 98%) as a white solid.

LC-MS (Agilent): R$_t$ 4.11 min; m/z calculated for C$_{28}$H$_{30}$O$_2$ [M+Na]$^+$ 421.5. found [M+Na]$^+$ 421.2

$^1$H NMR: (400 MHz, CDCl$_3$) δ (ppm): 8.00 (s, 1H), 7.92-7.75 (m, 4H), 7.62 (d, J=2.4 Hz, 1H), 7.57-7.51 (m, 2H), 7.01 (d, J=8.4 Hz, 1H), 4.90 (s, 2H), 3.93 (s, 3H), 2.21 (s, 6H), 2.13 (s, 3H), 1.83 (m, 6H).

Intermediate C: 6-(3-(Adamantan-1-yl)-4-methoxyphenyl)-2-naphthaldehyde

A solution of intermediate B (1.00 g, 2.51 mmol) and PCC (1.62 g, 7.53 mmol) in dry CH$_2$Cl$_2$ (80 mL) was stirred at room temperature for 3 h. The solids were removed by filtration and rinsed with CH$_2$Cl$_2$. The filtrate was concentrated under reduced pressure and the residue was purified by silica gel column chromatography (CH$_2$Cl$_2$/Pet. ether, 1/10~1/2, v/v) to give 6-(3-(adamantan-1-yl)-4-methoxyphenyl)-2-naphthaldehyde (800 mg, 80%) as a light red solid.

$^1$H NMR: (400 MHz, CDCl$_3$) δ (ppm): 10.18 (s, 1H), 8.37 (s, 1H), 8.07 (m, 2H), 7.99 (s, 1H), 7.87 (dd, J=7.2, 1.6 Hz, 1H), 7.63 (d, J=2.0 Hz, 1H), 7.58 (dd, J=6.0, 2.0 Hz, 1H), 7.03 (d, J=8.8 Hz, 1H), 3.94 (s, 3H), 2.21 (d, J=2.8 Hz, 6H), 2.13 (s, 3H), 1.83 (s, 6H).

5a: 6-(3-(Adamantan-1-yl)-4-methoxyphenyl)-2-naphthaldehyde oxime

A solution of intermediate C (200 mg, 0.25 mmol) and hydroxylamine hydrochloride (42 mg, 0.5 mmol) in CH$_2$Cl$_2$ (5 mL) and MeOH (5 mL) was stirred at room temperature overnight. The reaction mixture was concentrated under reduced pressure and the residue was purified by silica gel column chromatography (CH$_2$Cl$_2$/Pet. ether, 1/10~1/2, v/v) to give 6-(3-(adamantan-1-yl)-4-methoxyphenyl)-2-naphthaldehyde oxime (180 mg, 80%) as an off-white solid.

$^1$H NMR: (400 MHz, CDCl$_3$) δ (ppm): 8.32 (s, 1H), 8.00 (s, 1H), 7.92-7.84 (m, 4H), 7.77 (dd, J=6.8, 2.0 Hz, 1H), 7.67 (s, 1H), 7.61 (d, J=2.4 Hz, 1H), 7.55 (dd, J=6.4, 2.0 Hz, 1H), 7.01 (d, J=8.4 Hz, 1H), 3.93 (s, 3H), 2.21 (d, J=2.8 Hz, 6H), 2.13 (br s, 3H), 1.82 (s, 6H).

5b: 6-(3-(Adamantan-1-yl)-4-methoxyphenyl)-2-naphthaldehyde O-methyl oxime

A solution of intermediate C (100 mg, 0.25 mmol) and O-methylhydroxylamine hydrochloride (42 mg, 0.5 mmol) in CH$_2$Cl$_2$ (5 mL) and MeOH (5 mL) was stirred at room temperature overnight. The reaction mixture was concentrated under reduced pressure and the residue was purified by silica gel column chromatography (CH$_2$Cl$_2$/Pet. ether, 1/10~1/2, v/v) to give 6-(3-(adamantan-1-yl)-4-methoxyphenyl)-2-naphthaldehyde O-methyl oxime (67 mg, 62%) as an off-white solid.

$^1$H NMR: (400 MHz, CDCl$_3$) δ (ppm): 8.24 (s, 1H), 7.99 (d, J=1.6 Hz, 1H), 7.89 (m, 4H), 7.77 (dd, J=6.8, 2.0 Hz, 1H), 7.61 (d, J=2.4 Hz, 1H), 7.55 (dd, J=6.0, 2.4 Hz, 1H), 7.01 (d, J=8.4 Hz, 1H), 4.05 (s, 3H), 3.92 (s, 3H), 2.21 (d, J=2.8 Hz, 6H), 2.12 (s, 3H), 1.82 (s, 6H).

Example 6

Formula 113—Compounds 6a & 6b

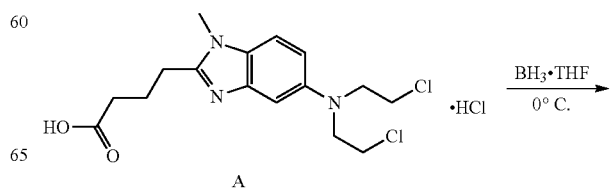

103
-continued

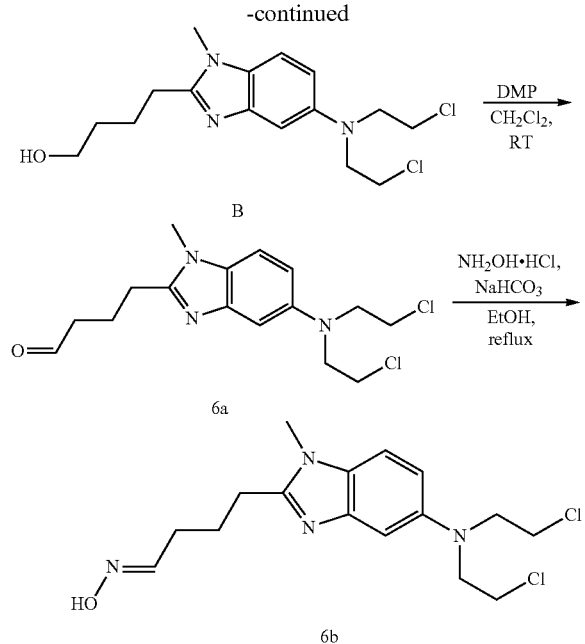

Intermediate B: 4-(5-(Bis(2-chloroethyl)amino)-1-methyl-1H-benzo[d]imidazol-2-yl)butan-1-ol To a stirred solution of compound A (393 mg, 1 mmol) in dry THF (20 mL) was added borane in THF (1M, 3.0 mL, 3 mmol) dropwise at 0° C. under nitrogen. The resulting mixture was allowed to warm to room temperature and stirred overnight. The reaction was quenched with water at 0° C., extracted with CH$_2$Cl$_2$ (20 mL×3) and the combined organic layers were washed with brine then dried over anhydrous Na$_2$SO$_4$. The solvent was removed under reduced pressure and the residue was purified by flash chromatography (CH$_2$Cl$_2$/MeOH, 50/1 to 25/1, v/v) to give 4-(5-(bis(2-chloroethyl)amino)-1-methyl-1H-benzo[d]imidazol-2-yl)butan-1-ol (300 mg, 86%) as a white solid.

LC-MS (Agilent): R$_t$ 2.84 min; m/z calculated for C$_{16}$H$_{23}$Cl$_2$N$_3$O [M+H]$^+$ 344.28. found [M+H]$^+$ 344.1

104

Example 6a 4-(5-(Bis(2-chloroethyl)amino)-1-methyl-1H-benzo[d]imidazol-2-yl)butanal To a stirred solution of intermediate B (1.03 g, 3.0 mmol) in dry CH$_2$Cl$_2$ (50 mL) was added Dess-Martin Periodinane (1.90 g, 4.5 mmol) at room temperature and the mixture was allowed to stir overnight. The reaction was quenched with water and extracted with CH$_2$Cl$_2$ (30 mL×3). The combined organic layers were washed with brine, dried over Na$_2$SO$_4$ and the solvent was removed under reduced pressure. The residue was purified by flash chromatography (CH$_2$Cl$_2$/MeOH, 100/1 to 25/1, v/v) to give 4-(5-(bis(2-chloroethyl)amino)-1-methyl-1H-benzo[d]imidazol-2-yl)butanal (590 mg, 59%) as a white solid.

LC-MS (Agilent): R$_t$ 2.74 min; m/z calculated for C$_{16}$H$_{21}$Cl$_2$N$_3$O [M+H]$^+$ 342.26. found [M+H]$^+$ 342.1

$^1$H NMR: (400 MHz, CDCl$_3$) δ (ppm): 8.46 (br s, 1H), 7.94 (br s, 1H), 7.35 (d, J=1.6 Hz, 1H), 6.93 (dd, J=7.6, 1.6 Hz, 1H), 3.98 (m, 4H), 3.89 (s, 3H), 3.82 (t, J=6.0 Hz, 4H), 3.33 (m, 1H), 2.89 (m, 1H), 1.96-2.10 (m, 4H).

Example 6b 4-(5-(Bis(2-chloroethyl)amino)-1-methyl-1H-benzo[d]imidazol-2-yl)butanal oxime A stirred solution of example 4a (171 mg, 0.5 mmol), hydroxylamine hydrochloride (208 mg, 3 mmol) and NaHCO$_3$ (252 mg, 3 mmol) in EtOH (20 mL) was heated at reflux overnight. The reaction mixture was allowed to cool to room temperature and concentrated under reduced pressure. The residue was purified by flash chromatography (CH$_2$Cl$_2$/MeOH, 50/1 to 25/1, v/v) to give 4-(5-(bis(2-chloroethyl)amino)-1-methyl-1H-benzo[d]imidazol-2-yl)butanal oxime (130 mg, 73%) as a white solid, $^1$H-NMR spectroscopy revealed a ~2:1 mixture of isomers.

LC-MS (Agilent): R$_t$ 2.79 min; m/z calculated for C$_{16}$H$_{22}$Cl$_2$N$_4$O [M+H]$^+$ 357.28. found [M+H]$^+$ 357.1

$^1$H NMR: (400 MHz, CDCl$_3$) δ (ppm): 7.48 (t, J=6.0 Hz, 0.65H), 7.20 (dd, J=8.8, 1.6 Hz, 1H), 7.11 (t, J=1.6 Hz, 1H), 6.79 (m, 1.35H), 3.76-3.64 (m, 11H), 2.89 (t, J=7.6 Hz, 2H), 2.55 (m, 1H), 2.40 (m, 1H), 2.11 (m, 2H).

Example 7

Formula 99-7a & 7b

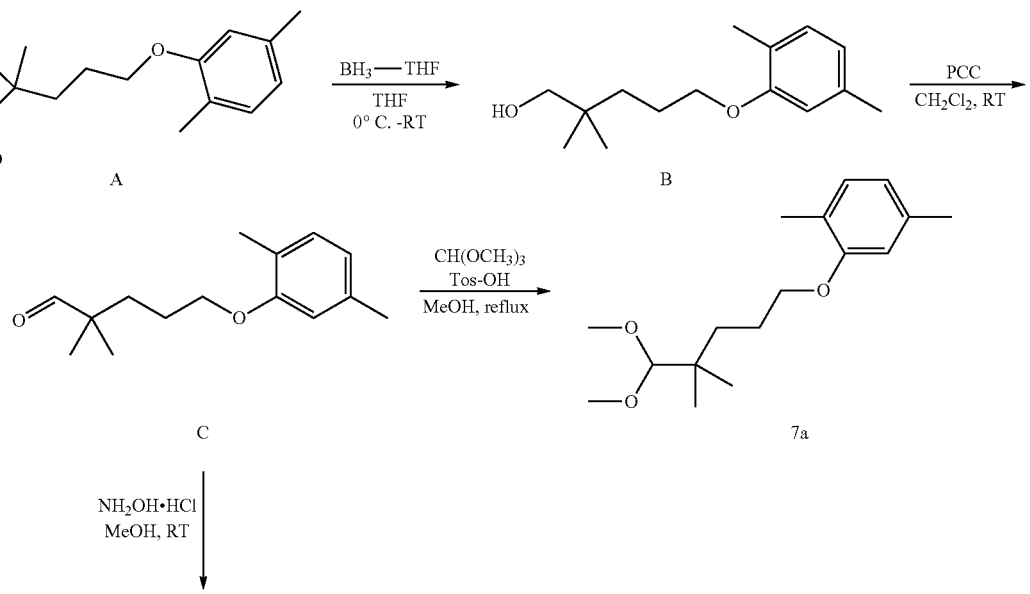

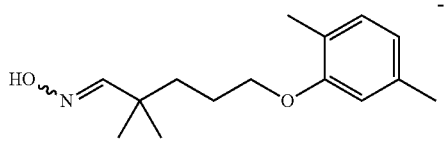

7b

Intermediate B: 5-(2,5-Dimethylphenoxy)-2,2-dimethylpentan-1-ol

To a stirred solution of compound A (250 mg, 1.0 mmol, 1.0 eq) in dry THF (25 mL) was added $BH_3$.THF (1M solution in THF, 3 mL, 3 mmol, 3 eq) dropwise at 0° C. and the mixture was stirred at 0° C. for 1 h. The mixture was allowed to warm to room temperature and stirred for 16 h then diluted with water and extracted with EtOAc (20 mL×3). The combined organic layers were washed with a saturated aqueous solution of $NaHCO_3$ then brine and dried over $Na_2SO_4$. The solvent was removed under reduced pressure to give 5-(2,5-dimethylphenoxy)-2,2-dimethylpentan-1-ol (229 mg, 97%) as a colourless oil.

LC-MS (Agilent): $R_t$ 3.51 min; m/z calculated for $C_{15}H_{24}O_2$ [M+H]$^+$ 237.35. found 237.2.

Intermediate C: 5-(2,5-Dimethylphenoxy)-2,2-dimethylpentanal

To a solution of intermediate B (400 mg, 1.69 mmol, 1 eq) in $CH_2Cl_2$ (5 mL) was added PCC (1.09 g, 5.09 mmol, 3 eq) and the mixture was stirred at room temperature for 16 h. The solids were removed by filtration and washed with $CH_2Cl_2$. The filtrate was concentrated under reduced pressure and the residue was purified by chromatography (Pet. ether/EtOAc, 50/1, v/v) to give 5-(2,5-dimethylphenoxy)-2,2-dimethylpentanal (215 mg, 54%) as a brown oil.

LC-MS (Agilent): $R_t$ 3.51 min; m/z calculated for $C_{15}H_2O_2$ [M+Na]$^+$ 257.33, [M+MeOH+Na]$^+$ 30 289.33. found [M+Na]$^+$ 257.2, [M+MeOH+Na]$^+$ 289.2.

Example 7a

2-((5,5-Dimethoxy-4,4-dimethylpentyl)oxy)-1,4-dimethylbenzene

To a solution of intermediate C (200 mg, 0.85 mmol, 1 eq) in MeOH (10 mL) was added $CH(OCH_3)_3$ (271 mg, 2.57 mmol, 3 eq) and Tos-OH (5 mg). The mixture was heated at reflux for 5 h then allowed to cool to rt and concentrated under vacuum. The residue was diluted with a saturated aqueous solution of $NaHCO_3$ and extracted with EtOAc (20 mL×3). The combined organic layers were washed with brine, dried over $Na_2SO_4$ and the solvent was removed under reduced pressure. The residue was purified by chromatography (Pet. ether/EtOAc, 100/1 to 50/1, v/v) to give 2-((5,5-dimethoxy-4,4-dimethylpentyl)oxy)-1,4-dimethylbenzene (150 mg, 63%) as a colourless oil.

LC-MS (Agilent): $R_t$ 3.70 min; m/z calculated for $C_{17}H_{28}O_3$ [M+Na]$^+$ 303.4. found 303.2.

$^1$H NMR: (400 MHz, $CDCl_3$) δ (ppm): 7.02 (d, J=7.6 Hz, 1H), 6.67 (d, J=7.6 Hz, 1H), 6.64 (s, 1H), 3.94 (t, J=6.4 Hz, 2H), 3.89 (s, 1H), 3.54 (s, 6H), 2.33 (s, 3H), 2.22 (s, 3H), 1.81-1.76 (m, 2H), 1.50-1.46 (m, 2H), 0.94 (s, 6H).

Example 7b

5-(2,5-Dimethylphenoxy)-2,2-dimethylpentanal oxime

To a solution of intermediate C (90 mg, 0.384 mmol, 1 eq) in MeOH (5 mL) was added hydroxylamine hydrochloride (54 mg, 0.768 mmol, 2 eq) and the mixture was stirred at room temperature for 16 h. The solvent was removed under reduced pressure and the residue was purified by chromatography (Pet. ether/EtOAc, 50/1, v/v) to give 5-(2,5-dimethylphenoxy)-2,2-dimethylpentanal oxime (65 mg, 68%) as a colourless oil.

LC-MS (Agilent): $R_t$ 3.45 min; m/z calculated for $C_{15}H_{23}NO_2$ [M+H]$^+$ 250.35, [M+Na]$^+$ 272.35, found [M+H]$^+$ 250.2, [M+Na]$^+$ 272.2.

$^1$H NMR: (400 MHz, $CDCl_3$) δ (ppm): 7.45 (br s, 1H), 7.36 (s, 1H), 7.02 (d, J=7.6 Hz, 1H), 6.89 (d, J=7.6 Hz, 1H), 6.63 (s, 1H), 3.94 (t, J=6.4 Hz, 2H), 2.33 (s, 3H), 2.20 (s, 3H), 1.81-1.77 (m, 2H), 1.63-1.59 (m, 2H), 1.15 (s, 6H).

Example 8

Formula 138—Compounds 8a & 8b

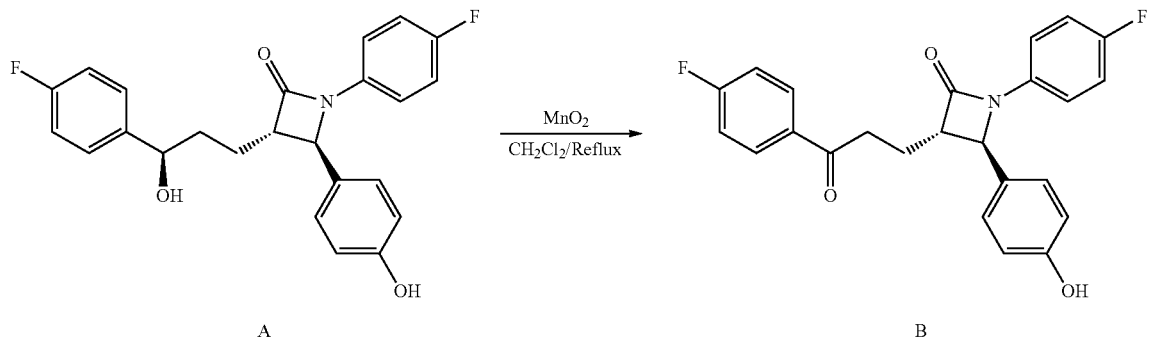

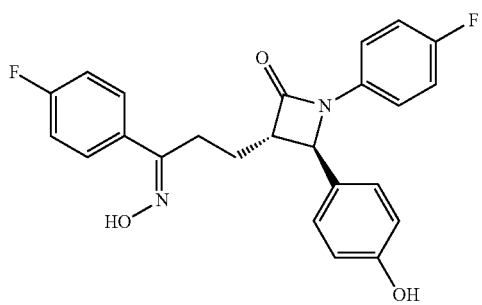

8a

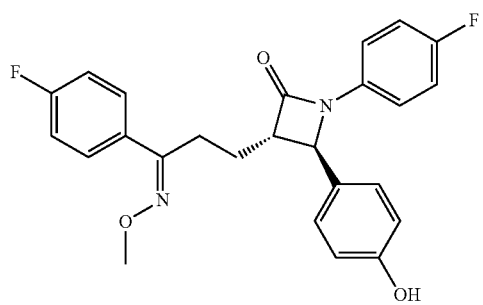

8b

Intermediate B: (3S,4R)-1-(4-Fluorophenyl)-3-(3-(4-fluorophenyl)-3-oxopropyl)-4-(4-hydroxyphenyl)azetidin-2-one To a rapidly stirred solution of compound A (1.0 g, 2.4 mmol) in $CH_2Cl_2$ (50 mL) was added activated manganese (IV) oxide (1.0 g, 12 mmol) in small portions over 15 min. The mixture was heated at reflux for 18 h then additional activated manganese (IV) oxide (0.5 g, 6.0 mmol) was added in portions. The mixture was heated at reflux for another 24 h then cooled to room temperature. The solids were removed by filtration and washed with $CH_2Cl_2$ (3×50 mL). The filtrate was concentrated under reduced pressure and the residue was purified by silica gel chromatography (Pet. ether/EtOAc, 5/1, v/v) to give (3S,4R)-1-(4-fluorophenyl)-3-(3-(4-fluorophenyl)-3-oxopropyl)-4-(4-hydroxyphenyl)azetidin-2-one (410 mg, 41%) as a white solid.

LC-MS (Agilent): $R_t$ 3.21 min; m/z calculated for $C_{24}H_{19}F_2NO_3$ $[M+H]^+$ 408.41, $[M+Na]^+$ 430.41, found $[M+H]^+$ 408.0, $[M+Na]^+$ 430.1.

8a: (3S,4R)-1-(4-Fluorophenyl)-3-(3-(4-fluorophenyl)-3-(hydroxyimino)propyl)-4-(4-hydroxyphenyl)azetidin-2-one A solution of intermediate B (180 mg, 0.44 mmol) and hydroxylamine hydrochloride (92 mg, 1.33 mmol) in EtOH (50 mL) was heated at reflux for 5 h. The mixture was cooled to room temperature, poured into water and extracted with EtOAc (3×50 mL). The organic layers were combined, dried over $Na_2SO_4$ and concentrated under reduced pressure. The residue was purified by silica gel chromatography (Pet. ether/EtOAc, 5/1, v/v) to afford (3S,4R)-1-(4-fluorophenyl)-3-(3-(4-fluorophenyl)-3-(hydroxyimino)propyl)-4-(4-hydroxyphenyl)azetidin-2-one (108 mg, 60%) as a white solid.

LC-MS (Agilent): $R_t$ 2.70 min; m/z calculated for $C_{24}H_{20}F_2N_2O_3$ $[M+H]^+$ 423.14, $[M+Na]^+$ 445.14, found $[M+H]^+$ 423.1, $[M+Na]^+$ 445.1.

$^1$H NMR: (400 MHz, DMSO-$d_6$) δ (ppm): 11.3 (s, 1H), 9.55 (s, 1H), 7.69 (dd, J=8.8, 5.6 Hz, 2H), 7.21 (m, 8H), 6.76 (d, J=8.4 Hz, 2H), 4.89 (d, J=2.0 Hz, 1H), 3.15 (m, 1H), 2.87 (m, 2H), 2.22 (m, 2H).

8b: (3S,4R)-1-(4-Fluorophenyl)-3-(3-(4-fluorophenyl)-3-(methoxyimino)propyl)-4-(4-hydroxyphenyl)azetidin-2-one A solution of intermediate B (200 mg, 0.49 mmol) and O-methylhydroxylamine hydrochloride (123 mg, 1.47 mmol) in EtOH (50 mL) was heated at reflux for 5 h. The mixture was cooled to room temperature and poured into water and extracted with EtOAc (3×50 mL). The combined organic layers were concentrated under reduced pressure and the residue was purified by silica gel chromatography (Pet. ether/EtOAc, 5/1, v/v) to give (3S,4R)-1-(4-fluorophenyl)-3-(3-(4-fluorophenyl)-3-(methoxyimino)propyl)-4-(4-hydroxyphenyl)azetidin-2-one (120 mg, 56%) as a white solid.

LC-MS (Agilent): $R_t$ 3.33 min; m/z calculated for $C_{25}H_{22}F_2N_2O_3$ $[M+H]^+$ 437.16, $[M+Na]^+$ 459.15, found $[M+H]^+$ 437.2, $[M+Na]^+$ 459.1.

$^1$H NMR: (400 MHz, $CDCl_3$) δ (ppm): 7.63 (m, 2H), 7.25 (m, 4H), 7.05 (app t, J=8.8 Hz, 2H), 6.93 (app t, J=8.8 Hz, 2H), 6.86 (d, J=8.4 Hz, 2H), 5.85 (s, 1H), 4.62 (d, J=2.4 Hz, 1H), 3.89 (s, 3H), 3.14 (m, 1H), 2.93 (m, 2H), 2.13 (m, 2H).

Example 9

Formula 133—Compound 9a

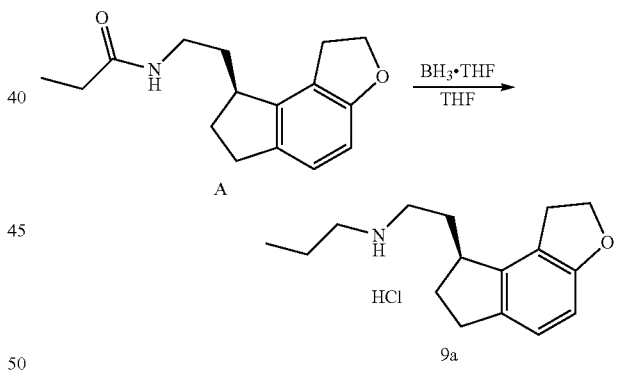

9a: (S)—N-(2-(2,6,7,8-Tetrahydro-1H-indeno[5,4-b]furan-8-yl)ethyl)propan-1-amine hydrochloride To a solution of compound A (200 mg, 0.77 mmol) in anhydrous THF (50 ml) was added $BH_3$.THF (1M solution in THF, 2.3 mL, 2.3 mmol) and the mixture was stirred at room temperature for 2 h. A 1M aqueous HCl solution was then added dropwise into the reaction mixture until pH 7. The solution was extracted with EtOAc (3×50 mL) and the organic layers were combined, dried over $Na_2SO_4$ and concentrated under reduced pressure. The residue was purified by silica gel column chromatography (Pet. ether/EtOAc, 5/1, v/v) to give (S)—N-(2-(2,6,7,8-tetrahydro-1H-indeno[5,4-b]furan-8-yl)ethyl)propan-1-amine hydrochloride (105 mg, 56%) as a white solid.

LC-MS (Agilent): $R_t$ 2.84 min; m/z calculated for $C_{16}H_{23}NO$ [M+H]$^+$ 246.36. found 246.2.

$^1$H NMR: (400 MHz, CDCl$_3$) δ (ppm): 9.56 (br s, 2H), 6.94 (d, J=8.0 Hz, 1H), 6.62 (d, J=8.0 Hz, 1H), 4.62-4.50 (m, 2H), 3.36 (m, 1H), 3.24-3.16 (m, 2H), 3.13-2.75 (m, 6H), 2.48 (m, 1H), 2.29 (m, 1H), 2.12 (m, 1H), 1.89 (m, 2H), 1.81-1.71 (m, 1H), 0.92 (t, J=7.6 Hz, 3H).

Example 10

Formula 137—Compounds 10a & 10b

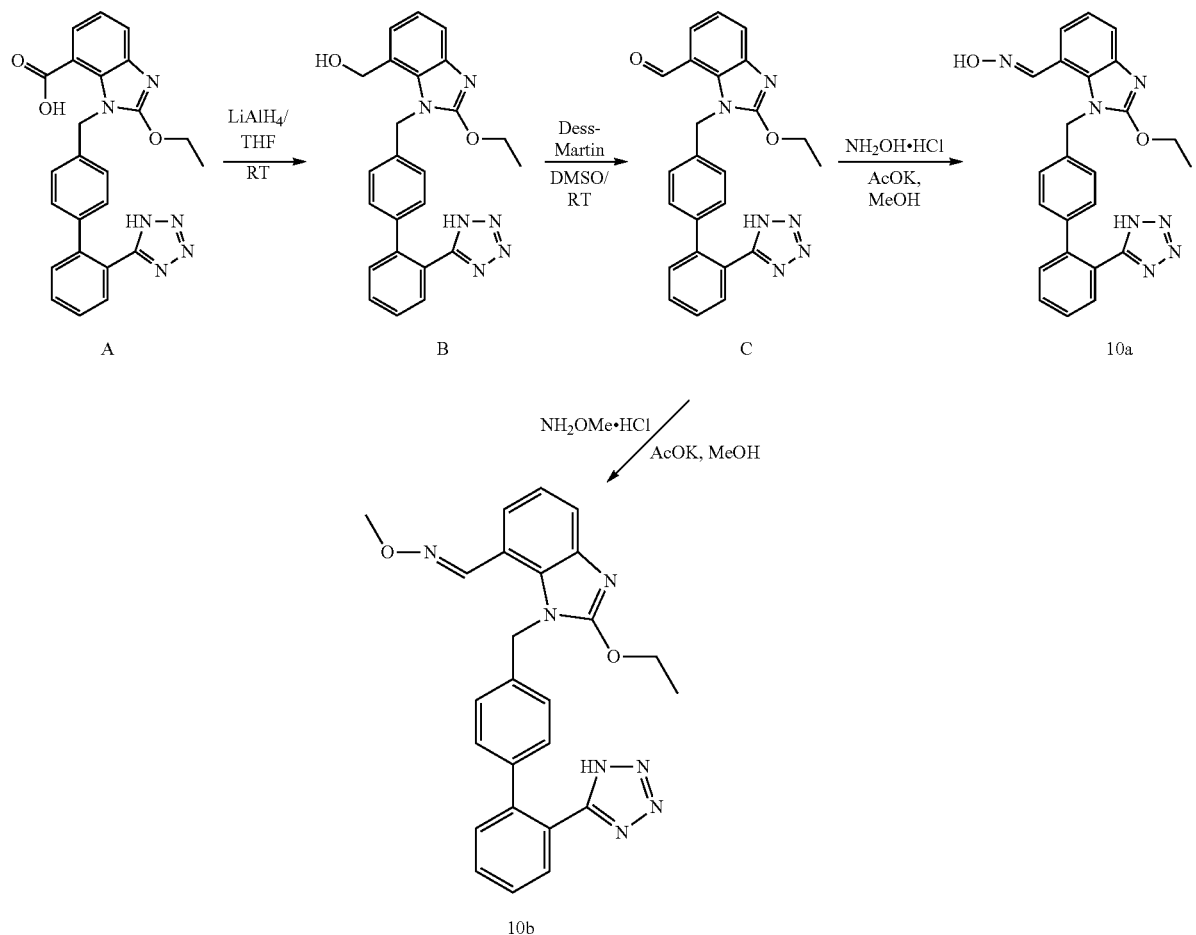

Intermediate B: (1-((2'-(1H-Tetrazol-5-yl)-[1,1'-biphenyl]-4-yl)methyl)-2-ethoxy-1H-benzo[d]imidazol-7-yl)methanol To a solution of compound A (2.0 g, 4.54 mmol) in dry THF (50 mL) at room temperature was added LAH (345 mg, 9.1 mmol) in five portions. The mixture was stirred at room temperature overnight then cooled to 0° C. and quenched with water (100 mL) and stirred for an additional 30 min. The reaction mixture was filtered and the filtrate was acidified slowly with a 1M aqueous HCl solution. The resulting crystalline precipitate was collected by suction filtration and washed with a saturated aqueous solution of NaHCO$_3$ (3×50 mL) to give (1-((2'-(1H-tetrazol-5-yl)-[1,1'-biphenyl]-4-yl)methyl)-2-ethoxy-1H-benzo[d]imidazol-7-yl)methanol (1.5 g, 77%) as a white solid.

LC-MS (Agilent): $R_t$ 3.15 min; m/z calculated for $C_{24}H_{22}N_6O_2$ [M+H]$^+$ 427.18, [M+Na]$^+$ 449.18, found [M+H]$^+$ 427.2, [M+Na]$^+$ 449.2.

Intermediate C: 1-((2'-(1H-Tetrazol-5-yl)-[1,1-biphenyl]-4-yl)methyl)-2-ethoxy-1H-benzo[d]imidazole-7-carbaldehyde To a stirred solution of intermediate B (1.5 g, 3.5 mmol) in DMSO (50 mL) was added Dess-Martin Periodinane (2.2 g, 5.25 mmol). The mixture was stirred at room temperature for 6 h then poured into a saturated aqueous solution of NaHSO$_3$ (300 mL). The precipitate formed was collected by filtration and washed with a saturated aqueous solution of NaHCO$_3$ (50 mL×3) to give 1-((2'-(1H-tetrazol-5-yl)-[1,1'-biphenyl]-4-yl)methyl)-2-ethoxy-1H-benzo[d]imidazole-7-carbaldehyde (0.8 g, 54%) as a white solid.

LC-MS (Agilent): $R_t$ 3.26 min; m/z calculated for $C_{24}H_{20}N_6O_2$ [M+H]$^+$ 425.16, [M+Na]$^+$ 447.16, found [M+H]$^+$ 425.2, [M+Na]$^+$ 447.1.

Example 10a 1-((2'-(1H-Tetrazol-5-yl)-[1,1'-biphenyl]-4-yl)methyl)-2-ethoxy-1H-benzo[d]imidazole-7-carbaldehyde oxime A mixture of intermediate C (100 mg, 0.24 mmol), AcOK (46 mg, 0.47 mmol) and hydroxylamine hydrochloride (33 mg, 0.47 mmol) in MeOH (5 mL) was stirred at room temperature for 20 min. The solvent was removed under reduced pressure at room temperature and the residue was poured into water and the mixture was stirred at room temperature for 10 min. The solid formed was filtered, washed with water (10 mL×3) and dried under vacuum at 50° C. for 3 h to give 1-((2'-(1H-tetrazol-5-yl)-[1,1'-biphenyl]-4-yl)methyl)-2-ethoxy-1H-benzo[d]imidazole-7-carbaldehyde oxime (80 mg, 77%) as a white solid.

LC-MS (Agilent): $R_t$ 3.23 min; m/z calculated for $C_{24}H_{21}N_7O_2$ [M+H]$^+$ 440.47, [M+Na]$^+$ 462.47, found [M+H]$^+$ 440.2, [M+Na]$^+$ 462.2.

$^1$H NMR: (400 MHz, DMSO-$d_6$) δ (ppm): 11.3 (br s, 1H), 8.30 (s, 1H), 7.47-7.63 (m, 5H), 7.29 (d, J=7.6 Hz, 1H), 7.12 (t, J=8.0 Hz, 1H), 7.03 (d, J=8.0 Hz, 2H), 6.95 (d, J=8.0 Hz, 2H), 5.48 (s, 2H), 4.58 (q, J=7.2 Hz, 2H), 1.38 (t, J=7.2 Hz, 3H).

Example 10b 1-((2%(1H-Tetrazol-5-yl)-[1,1'-biphenyl]-4-yl)methyl)-2-ethoxy-1H-benzo[d]imidazole-7-carbaldehyde O-methyl oxime A mixture of intermediate C (150 mg, 0.35 mmol), AcOK (69 mg, 0.71 mmol) and O-methylhydroxylamine hydrochloride (59 mg, 0.71 mmol) in MeOH (5 mL) was stirred at room temperature for 20 min. The solvent was removed under reduced pressure at room temperature and the residue was poured into water and the mixture was stirred at room temperature for 10 min. The solid formed was filtered and washed with water (10 mL×3). The solid was collected and dried under reduced pressure at 50° C. for 3 h to give 1-((2'-(1H-tetrazol-5-yl)-[1,1'-biphenyl]-4-yl)methyl)-2-ethoxy-1H-benzo[d]imidazole-7-carbaldehyde O-methyl oxime (95 mg, 59%) as a white solid.

LC-MS (Agilent): $R_t$ 3.30 min; m/z calculated for $C_{26}H_{23}N_7O_2$ [M+H]$^+$ 454.50, [M+Na]$^+$ 476.50, found [M+H]$^+$ 454.2, [M+Na]$^+$ 476.2.

$^1$H NMR: (400 MHz, DMSO-$d_6$) δ (ppm): 8.36 (s, 1H), 7.48-7.64 (m, 5H), 7.30 (d, J=8.0 Hz, 1H), 7.15 (t, J=8.0 Hz, 1H), 7.04 (d, J=8.0 Hz, 2H), 6.92 (d, J=8.0 Hz, 2H), 5.49 (s, 2H), 4.58 (q, J=7.2 Hz, 2H), 3.81 (s, 3H), 1.38 (t, J=7.2 Hz, 3H).

Example 11

Formula 147—Compound 11a

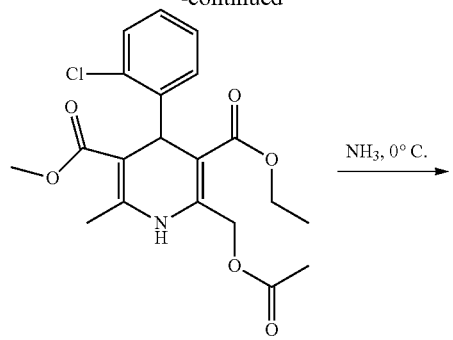

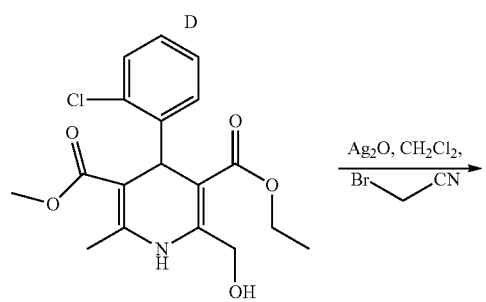

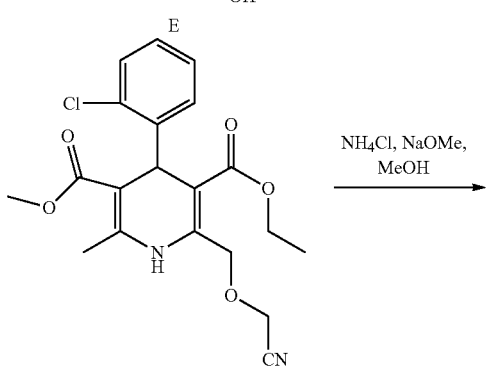

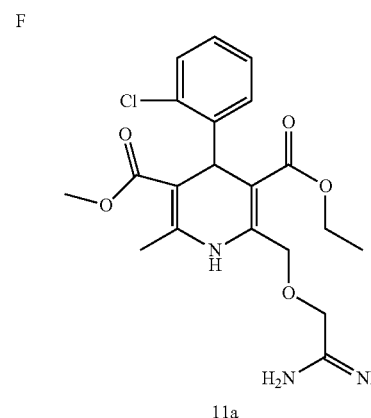

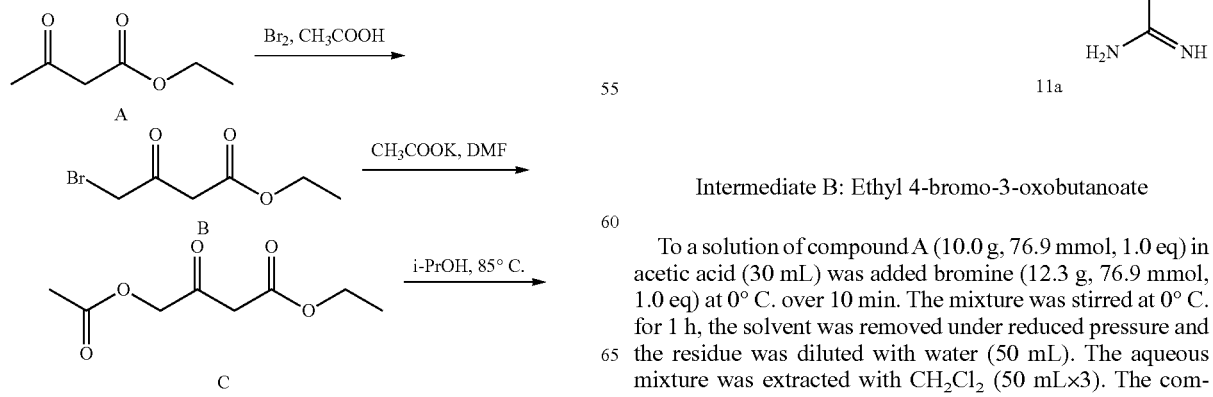

Intermediate B: Ethyl 4-bromo-3-oxobutanoate

To a solution of compound A (10.0 g, 76.9 mmol, 1.0 eq) in acetic acid (30 mL) was added bromine (12.3 g, 76.9 mmol, 1.0 eq) at 0° C. over 10 min. The mixture was stirred at 0° C. for 1 h, the solvent was removed under reduced pressure and the residue was diluted with water (50 mL). The aqueous mixture was extracted with $CH_2Cl_2$ (50 mL×3). The combined organic layers were washed with brine (60 mL×2), dried over MgSO₄ and concentrated under reduced pressure to give ethyl 4-bromo-3-oxobutanoate (14.3 g, 85%) as a yellow oil.

LC-MS (Agilent): $R_t$ 3.06 min; m/z calculated for $C_6H_9BrO_3$ [M+H]⁺ 208.97. found 209.1.

Intermediate C: Ethyl 4-acetoxy-3-oxobutanoate

To a solution of intermediate B (10.0 g, 47.4 mmol, 1.0 eq) in dry DMF (60 mL) was added potassium acetate (13.9 g, 142.2 mmol, 3.0 eq) at room temperature. The mixture was heated at 80° C. for 16 h then allowed to cool to room temperature, diluted with EtOAc (150 mL) and washed with water (120 mL×3). The organic layer was washed with brine (60 mL×2), dried over Na₂SO₄ and concentrated under reduced pressure. The residue was purified by flash chromatography (Pet. ether/EtOAc, 1/10 to 1/2, v/v) to give ethyl 4-acetoxy-3-oxobutanoate (1.44 g, 16%) as a yellow oil.

LC-MS (Agilent): $R_t$ 3.12 min; m/z calculated for $C_9H_{12}O_5$ [M+H]⁺ 189.07. found 189.1

Intermediate D: 3-Ethyl 5-methyl 2-(acetoxymethyl)-4-(2-chlorophenyl)-1,4-dihydro-6-methylpyridine-3,5-dicarboxylate To a solution of intermediate C (1.2 g, 6.4 mmol, 1.0 eq) and 2-chlorobenzaldehyde (890 mg, 6.4 mmol, 1.0 eq) in isopropanol (30 mL) was added (Z)-methyl 3-aminobut-2-enoate (736 mg, 6.4 mmol, 1.0 eq) and the mixture was heated at reflux for 16 h. The mixture was concentrated under reduced pressure and the residue was diluted with water (50 mL). The aqueous mixture was extracted with EtOAc (60 mL×3) and the combined organic layers were washed with brine, dried over Na₂SO₄ and concentrated under reduced pressure to give 3-ethyl 5-methyl 2-(acetoxymethyl)-4-(2-chlorophenyl)-1,4-dihydro-6-methylpyridine-3,5-dicarboxylate (1.2 g, 53%) as a light yellow solid.

LC-MS (Agilent): $R_t$ 3.20 min; m/z calculated for $C_{20}H_{22}ClNO_6$ [M+H]⁺ 408.11. found 408.1.

Intermediate E: 3-Ethyl 5-methyl 4-(2-chlorophenyl)-2-(hydroxymethyl)-6-methyl-1,4-dihydropyridine-3,5-dicarboxylate To a solution of intermediate D (1.2 g, 2.9 mmol, 1.0 eq) in methanol (20 mL) was added a methanolic ammonia solution (1.0 M, 15 mL, 15 mmol). The mixture was stirred at 0° C. for 2 h then the solvent was removed under reduced pressure and the residue was diluted with water (50 mL). The aqueous mixture was extracted with CH₂Cl₂ (50 mL×3) and the combined organic layers were washed with brine (60 mL×2), dried over MgSO₄ and concentrated under reduced pressure. The residue was purified by flash chromatography (Pet. ether/EtOAc, 1/10 to 1/2, v/v) to give 3-ethyl 5-methyl 4-(2-chlorophenyl)-2-(hydroxymethyl)-6-methyl-1,4-dihydropyridine-3,5-dicarboxylate (0.70 g, 65%) as a yellow solid.

LC-MS (Agilent): $R_t$ 3.28 min; m/z calculated for $C_{18}H_{20}ClNO_5$ [M+H]⁺ 366.1, [M+Na]⁺ 388.1, found [M+H]⁺ 366.1, [M+Na]⁺ 388.1.

¹H NMR: (400 MHz, CDCl₃) δ (ppm): 7.39 (m, 1H), 7.25 (m, 1H), 7.13 (m, 1H), 7.05 (m, 1H), 5.41 (s, 1H), 4.75 (d, J=4.4 Hz, 2H), 4.06 (m, 2H), 3.63 (s, 3H), 2.33 (s, 3H), 1.20 (t, J=7.2 Hz, 3H).

Intermediate F: 3-Ethyl 5-methyl 4-(2-chlorophenyl)-2-((cyanomethoxy)methyl)-6-methyl-1,4-dihydropyridine-3,5-dicarboxylate To a solution of intermediate E (0.6 g, 1.6 mmol, 1.0 eq) in CH₂Cl₂ (20 mL) was added 2-bromoacetonitrile (0.59 g, 4.8 mmol, 3.0 eq) at room temperature. The mixture was stirred at room temperature for 1 h before addition of Ag₂O (1.1 g, 4.8 mmol, 3.0 eq) and n-Bu₄NI (586 mg, 1.6 mmol, 1.0 eq). Stirring was continued at room temperature for an additional 16 h in the dark. The solids were removed by filtration through Celite and the filtrate was concentrated under reduced pressure. The residue was purified by flash chromatography (Pet. ether/EtOAc, 1/10 to 1/2, v/v) to give 3-ethyl 5-methyl 4-(2-chlorophenyl)-2-((cyanomethoxy)methyl)-6-methyl-1,4-dihydropyridine-3,5-dicarboxylate (0.40 g, 60%) as a yellow solid.

LC-MS (Agilent): $R_t$ 3.30 min; m/z calculated for $C_{20}H_{21}ClN_2O_5$ [M+H]⁺ 405.1, [M+Na]⁺ 427.1, found [M+H]⁺ 405.1, [M+Na]⁺ 427.1.

¹H NMR: (400 MHz, CDCl₃) δ (ppm): 7.38 (m, 1H), 7.25 (m, 1H), 7.16 (m, 1H), 7.10 (m, 1H), 6.71 (br s, 1H), 5.43 (s, 1H), 4.95 (d, J=16.0 Hz, 1H), 4.88 (d, J=14.8 Hz, 1H), 4.41 (s, 2H), 4.08 (m, 2H), 3.64 (s, 3H), 2.36 (s, 3H), 1.21 (t, J=7.2 Hz, 3H).

11a: 3-Ethyl 5-methyl 2-((amidinomethoxy)methyl)-4-(2-chlorophenyl)-1,4-dihydro-6-methylpyridine-3,5-dicarboxylate To a solution of intermediate F (380 mg, 0.940 mmol) and NH₄Cl (127 mg, 2.35 mmol, 2.5 eq) in toluene (35 mL) was added NaOMe (127 mg, 2.35 mmol, 2.5 eq) and the resulting mixture was stirred at 80° C. for 40 min. After cooling to room temperature, the mixture was treated with a methanolic ammonia solution (1.0 M, 10 mL, 10 mmol) and stirred for an additional 2 h. The solvent was removed under reduced pressure and the residue was diluted with water (50 mL) and extracted with CH₂Cl₂ (50 mL×3). The combined organic layers were washed with brine (60 mL×2), dried over MgSO₄ and concentrated under reduced pressure. The residue was purified by flash chromatography (Pet. ether/EtOAc, 1:10 to 1:2, v/v) to give 3-ethyl 5-methyl 2-((amidinomethoxy)methyl)-4-(2-chlorophenyl)-1,4-dihydro-6-methylpyridine-3,5-dicarboxylate (210 mg, 53%) as a light yellow solid.

LC-MS (Agilent): $R_t$ 3.00 min; m/z calculated for $C_{20}H_{24}ClN_3O_5$ [M+H]⁺ 422.1. found 422.1.

¹H NMR: (400 MHz, CDCl₃), δ (ppm): 8.38 (br s, 3H), 8.21 (s, 1H), 7.36-7.39 (m, 1H), 7.21 (d, J=8.0 Hz, 1H), 7.11 (t, J=7.6 Hz, 1H), 7.00 (t, J=7.2 Hz, 1H), 5.38 (s, 1H), 4.56-4.84 (m, 4H), 3.93-4.06 (m, 2H), 3.58 (s, 3H), 2.37 (s, 3H), 1.14 (t, J=6.8 Hz, 3H).

Example 12

Formula 139—Compounds 12a & 12b

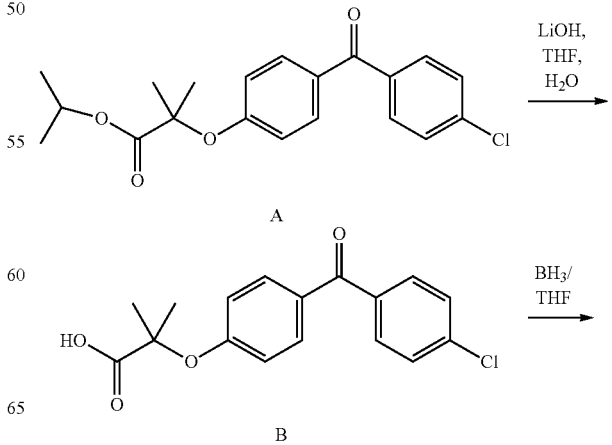

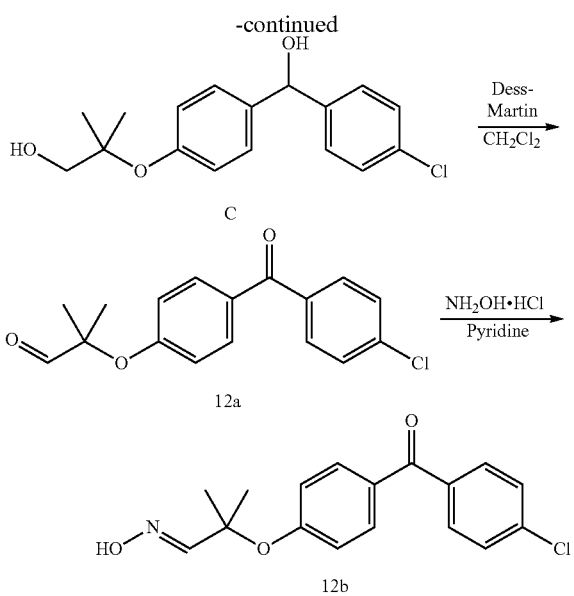

Intermediate B: 2-(4-(4-chlorobenzoyl)phenoxy)-2-methylpropanoic acid

To a stirred solution of compound A (1.0 g, 2.77 mmol) in THF (10 mL) was added LiOH.H$_2$O (0.7 g, 16.6 mmol) and H$_2$O (10 mL). The resulting mixture was heated at reflux overnight then quenched with a 1M aqueous HCl solution and extracted with EtOAc (10 mL×3). The combined organic layers were washed with brine, dried over MgSO$_4$ and concentrated under reduced pressure. The residue was purified by flash chromatography (CH$_2$Cl$_2$/MeOH, 15/1, v/v) to give 2-(4-(4-chlorobenzoyl)phenoxy)-2-methylpropanoic acid (130 mg, 15%) as a white solid.

LC-MS (Agilent): R$_t$ 3.00 min; m/z calculated for C$_{17}$H$_{15}$ClO$_4$ [M+H]$^+$ 319.07. found 319.1.

Intermediate C: 2-(4-((4-Chlorophenyl)(hydroxy)methyl)phenoxy)-2-methylpropan-1-ol To a stirred solution of intermediate B (500 mg, 1.57 mmol) in dry THF (10 mL) at 0° C. under nitrogen was added a solution of borane in THF (1M, 4.7 mL, 4.7 mmol) dropwise. The resulting mixture was heated at 50° C. for 3 h then cooled to 0° C., quenched with MeOH and extracted with EtOAc (10 mL×3). The combined organic layers were washed with brine, dried over MgSO$_4$ and the solvent was removed under reduced pressure. The residue was purified by flash chromatography (Pet. ether/EtOAc, 5/1 to 2/1, v/v) to give 2-(4-((4-chlorophenyl)(hydroxy)methyl)phenoxy)-2-methylpropan-1-ol (452 mg, 94%) as a white solid.

LC-MS (Agilent): R$_t$ 3.00 min; m/z calculated for C$_{17}$H$_{19}$ClO$_3$ [M+Na]$^+$ 329.1. found 329.0.

12a: 2-(4-(4-Chlorobenzoyl)phenoxy)-2-methylpropanal

To a stirred solution of intermediate C (453 mg, 1.4 mmol) in CH$_2$Cl$_2$ (10 mL) at room temperature was added Dess-Martin Periodinane (1.8 g, 4.3 mmol) and the resulting mixture was stirred overnight. The reaction was quenched with water and the mixture was extracted with CH$_2$Cl$_2$ (10 mL×3) and the combined organic layers were washed with brine and dried over MgSO$_4$. The solvent was removed under reduced pressure and the residue was purified by flash chromatography (Pet. ether/EtOAc, 5/1 to 2/1, v/v) to give 2-(4-(4-chlorobenzoyl)phenoxy)-2-methylpropanal (284 mg, 66%) as a white solid.

LC-MS (Agilent): R$_t$ 3.37 min; m/z calculated for C$_{17}$H$_{15}$ClO$_3$[M+MeOH+H]$^+$ 335.1. found 335.1.
$^1$H-NMR: (400 MHz, CDCl$_3$) δ (ppm): 9.82 (s, 1H), 7.74 (d, J=9.2 Hz, 2H), 7.71 (d, J=8.4 Hz, 2H), 7.45 (d, J=8.4 Hz, 2H), 6.89 (d, J=8.8 Hz, 2H), 1.52 (s, 6H).

12b: (E)-2-(4-(4-Chlorobenzoyl)phenoxy)-2-methylpropanal oxime

A solution of example 11a (80 mg, 0.26 mmol) and hydroxylamine hydrochloride (18 mg, 0.26 mmol) in pyridine (2.5 mL) was stirred at 10° C. for 90 min. The solvent was removed under reduced pressure the residue was purified by flash chromatography (Pet. ether/EtOAc, 10/1 to 5/1, v/v) to give (E)-2-(4-(4-chlorobenzoyl)phenoxy)-2-methylpropanal oxime (52 mg, 62%) as a white solid.

LC-MS (Agilent): R$_t$ 3.32 min; m/z calculated for C$_{17}$H$_{16}$ClNO$_3$[M+H]$^+$ 318.08, [M+Na]$^+$ 340.1, found [M+H]$^+$ 318.1, [M+Na]$^+$ 340.1.
$^1$H-NMR: (400 MHz, DMSO-d$_6$) δ (ppm): 11.1 (s, 1H), 7.70 (m, 4H), 7.62-7.59 (m, 3H), 7.06 (d, J=8.8 Hz, 2H), 1.53 (s, 6H).

Example 13

Formula 102—Compounds 13a & 13b

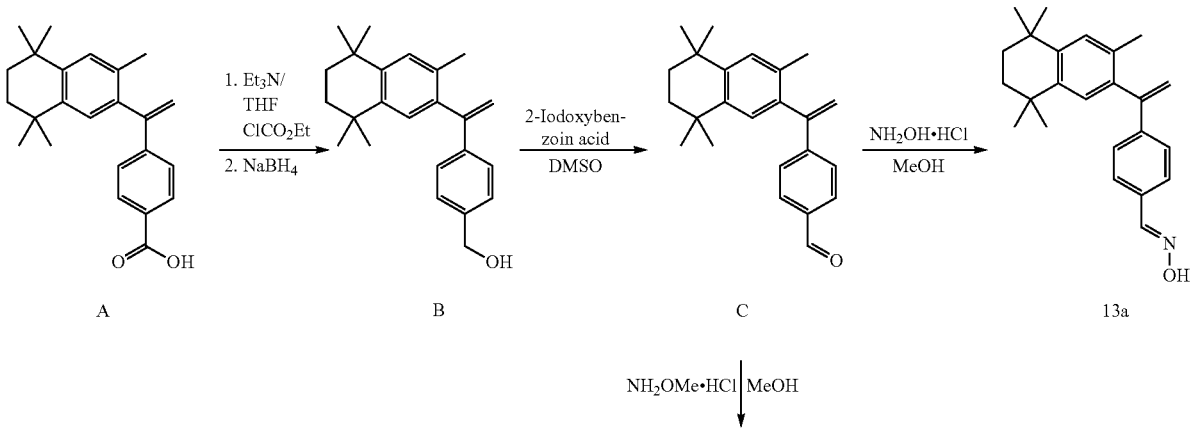

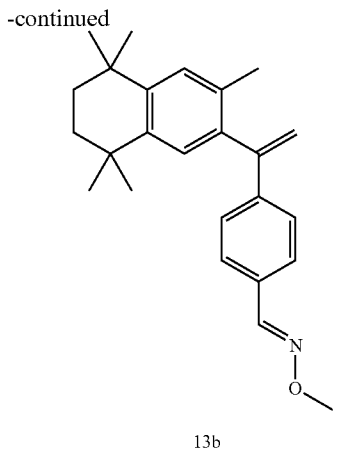

13b

Intermediate B: (4-(1-(3,5,5,8,8-Pentamethyl-5,6,7,8-tetrahydronaphthalen-2-yl)vinyl)phenyl)methanol To a stirred solution of compound A (4.0 g, 11.5 mmol) in THF (100 mL) at room temperature was added ethyl chloroformate (1.43 mL, 14.3 mmol) and triethylamine (2.26 mL). The mixture was stirred at room temperature for 30 min and then filtered. The filtrate was diluted with water and the solvent was removed under reduced pressure. To the residue was added ice water (200 mL) and $NaBH_4$ (15 g, 38 mmol). The resulting mixture was stirred at 0° C. for 1 h then water (100 mL) and methyl t-butyl ether (300 mL) was added. The organic layer was separated, washed with brine, dried over $Na_2SO_4$ and concentrated under reduced pressure to give (4-(1-(3,5,5,8,8-pentamethyl-5,6,7,8-tetrahydronaphthalen-2-yl)vinyl)phenyl)methanol (3.6 g, 93%) as a white solid.

LC-MS (Agilent): $R_t$ 3.77 min; m/z calculated for $C_{24}H_{30}O$ [M+Na]$^+$ 357.2. found 357.2.

Intermediate C: 4-(1-(3,5,5,8,8-Pentamethyl-5,6,7,8-tetrahydronaphthalen-2-yl)vinyl)benzaldehyde To a stirred solution of intermediate B (0.5 g, 1.50 mmol) in DMSO (20 mL) was added 2-iodoxybenzoic acid (0.84 g, 3.0 mmol) and the mixture was stirred at room temperature for 2 h. The reaction was quenched with $NaHSO_3$ and the mixture was diluted with EtOAc (400 mL) and washed with water (400 mL×4). The organic layer was dried over $Na_2SO_4$ and the solvent was removed under reduced pressure to give 4-(1-(3,5,5,8,8-pentamethyl-5,6,7,8-tetrahydronaphthalen-2-yl) vinyl)benzaldehyde (0.48 g, 97%) as a white solid.

LC-MS (Agilent): $R_t$ 3.93 min; m/z calculated for $C_{20}H_{28}O$ [M+H]$^+$ 333.5, [M+Na]$^+$ 355.5. found [M+H]$^+$ 333.2, [M+Na]$^+$ 355.2.

13a: 4-(1-(3,5,5,8,8-Pentamethyl-5,6,7,8-tetrahydronaphthalen-2-yl)vinyl)benzaldehyde oxime To a stirred solution of intermediate C (150 mg, 0.45 mmol) in methanol (10 mL) at room temperature was added hydroxylamine hydrochloride (94 mg, 1.35 mmol) and the mixture was stirred at room temperature overnight. The methanol was removed under reduced pressure and the residue was partitioned between EtOAc (300 mL) and water (300 mL). The layers were separated and the aqueous phase was extracted with EtOAc (200 mL×2). The combined organic layers were dried over $Na_2SO_4$ and the solvent was removed under reduced pressure to give 4-(1-(3,5,5,8,8-pentamethyl-5,6,7,8-tetrahydronaphthalen-2-yl)vinyl)benzaldehyde oxime (160 mg, 100%) as a white solid.

LC-MS (Agilent): $R_t$ 3.93 min; m/z calculated for $C_{24}H_{29}NO$ [M+H]$^+$ 348.2, [M+Na]$^+$ 370.5. found [M+H]$^+$ 348.2, [M+Na]$^+$ 370.2.

$^1$H NMR: (400 MHz, CDCl$_3$) δ (ppm): 8.12 (s, 1H), 7.51 (d, J=8.4 Hz, 2H), 7.31 (d, J=8.4 Hz, 2H), 7.12 (s, 1H), 7.07 (s, 1H), 5.77 (d, J=1.2 Hz, 1H), 5.25 (d, J=1.2 Hz, 1H), 1.96 (s, 3H), 1.70 (s, 4H), 1.30 (s, 6H), 1.27 (s, 6H).

13b: 4-(1-(3,5,5,8,8-Pentamethyl-5,6,7,8-tetrahydronaphthalen-2-yl)vinyl)benzaldehyde O-methyl oxime To a stirred solution of intermediate C (100 mg, 0.3 mmol) in methanol (5 mL) was added O-methylhydroxylamine hydrochloride (75 mg, 0.9 mmol) and the mixture was stirred at room temperature overnight. The methanol was removed under reduced pressure and the residue was partitioned between EtOAc (200 mL) and water (200 mL). The layers were separated and the aqueous phase was extracted with EtOAc (150 mL×2). The combined organic layers were dried over $Na_2SO_4$ and the solvent was removed under reduced pressure to give 4-(1-(3,5,5,8,8-pentamethyl-5,6,7,8-tetrahydronaphthalen-2-yl)vinyl)benzaldehyde O-methyl oxime (70 mg, 64%) as a white solid.

LC-MS (Agilent): $R_t$ 4.42 min; m/z calculated for $C_{25}H_{31}NO$ [M+H]$^+$ 362.2, [M+Na]$^+$ 384.5. found [M+H]$^+$ 362.3, [M+Na]$^+$ 384.2.

$^1$H NMR: (400 MHz, CDCl$_3$) δ (ppm): 8.04 (s, 1H), 7.51 (d, J=8.4 Hz, 2H), 7.29 (d, J=10.8 Hz, 2H), 7.12 (s, 1H), 7.07 (s, 1H), 5.76 (s, 1H), 2.25 (s, 1H), 3.97 (s, 3H), 1.95 (s, 3H), 1.69 (s, 4H), 1.30 (s, 6H), 1.27 (s, 6H).

Example 14

Formula 151—Compounds 14a & 14b

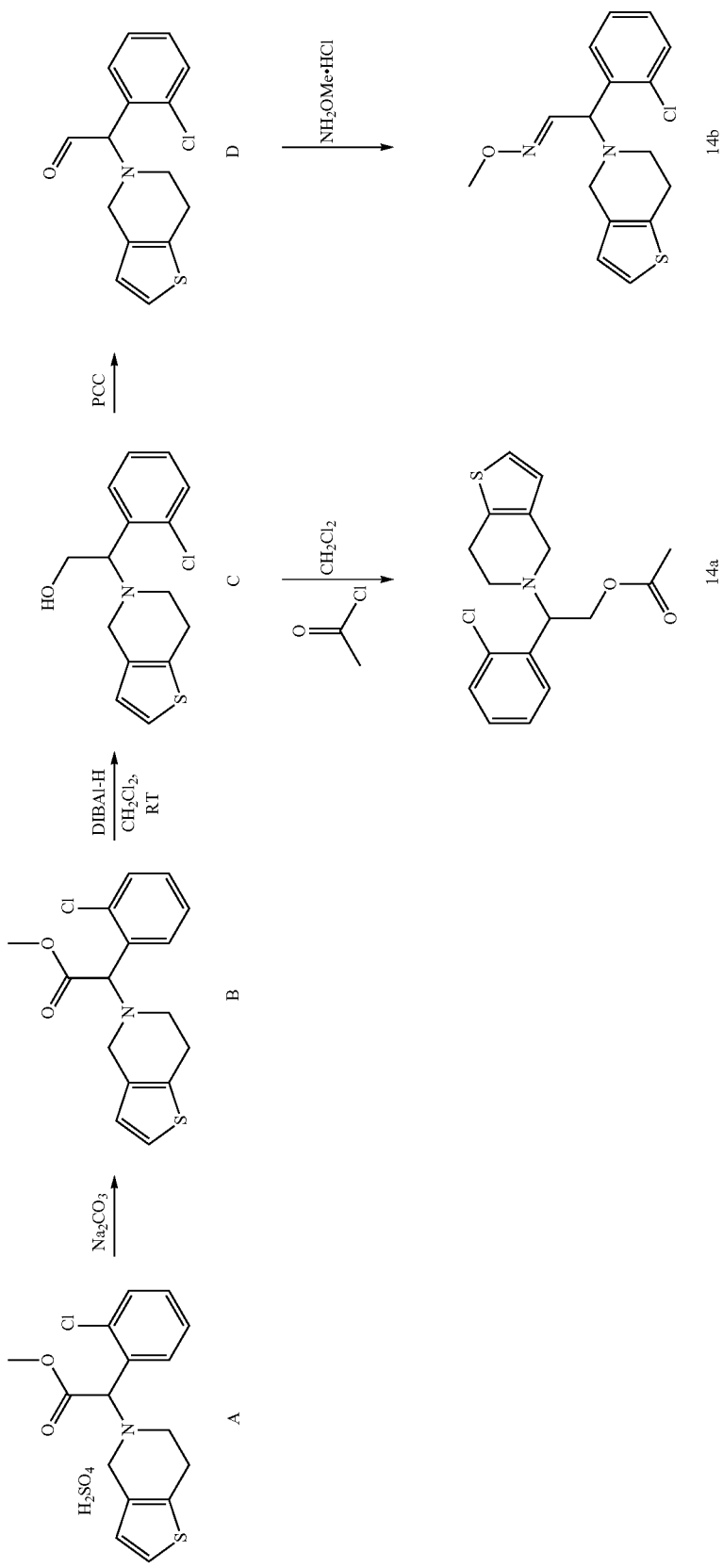

Intermediate B: Methyl 2-(2-chlorophenyl)-2-(6,7-dihydrothieno[3,2-c]pyridin-5(4H)-yl)acetate Compound A (1.25 g, 0.03 mol) was treated with a saturated aqueous $Na_2CO_3$ solution (10 mL) and the mixture was extracted with $CH_2Cl_2$ (30 mL×2). The combined organic layers were dried over $Na_2SO_4$ and the solvent was removed under reduced pressure to give methyl 2-(2-chlorophenyl)-2-(6,7-dihydrothieno[3,2-c]pyridin-5(4H)-yl)acetate (0.96 g, 99%) as a yellow oil.

Intermediate C: 2-(2-Chlorophenyl)-2-(6,7-dihydrothieno[3,2-c]pyridin-5(4H)-yl)ethanol To a stirred solution of intermediate B (960 mg, 3.0 mmol, 1.0 eq) in $CH_2Cl_2$ (15 mL) at 0° C. was added a 1.0 M solution of DIBAl-H in hexanes (9 mL, 9.0 mmol, 3.0 eq) dropwise and the mixture was stirred at room temperature for 1 h. The reaction was quenched with water (10 mL) and the mixture was extracted with $CH_2Cl_2$ (25 mL×2). The combined organic layers were washed with brine, dried over $Na_2SO_4$ and the solvent was removed under reduced pressure to give 2-(2-chlorophenyl)-2-(6,7-dihydrothieno[3,2-c]pyridin-5(4H)-yl)ethanol (850 mg, 95%) as a yellow oil.

LC-MS (Agilent): $R_t$ 2.88 min; m/z calculated for $C_{15}H_{16}ClNOS$ [M+H]$^+$ 294.06. found 294.1.

$^1$H NMR: (400 MHz, CDCl$_3$) δ (ppm): 7.49 (m, 2H), 7.28 (m, 2H), 7.10 (d, J=5.2 Hz, 1H), 6.75 (d, J=5.2 Hz, 1H), 4.55 (dd, J=4.8, 4.4 Hz, 1H), 4.00 (dd, J=11.2, 7.6 Hz, 1H), 3.84 (dd, J=11.2, 4.8 Hz, 1H), 3.80 (d, J=14.4 Hz, 1H), 3.68 (d, J=14.4 Hz, 1H), 3.06 (m, 1H), 2.90 (m, 2H), 2.80 (m, 1H).

Intermediate D: 2-(2-Chlorophenyl)-2-(6,7-dihydrothieno[3,2-c]pyridin-5(4H)-yl)acetaldehyde To a stirred solution of intermediate C (440 mg, 1.5 mmol, 1.0 eq) in $CH_2Cl_2$ (10 mL) at room temperature was added PCC (645 mg, 3 mmol) and Celite (~0.5 g). The mixture was stirred at room temperature for 3 h, additional PCC (645 mg, 3 mmol) was added and stirring was continued for an additional 5 h at 40° C. The mixture was filtered and the filtrate was washed with water, dried over $Na_2SO_4$ and the solvent was removed under reduced pressure. The residue was purified by column chromatography (Pet. ether/EtOAc, 20/1, v/v) to give 2-(2-chlorophenyl)-2-(6,7-dihydrothieno[3,2-c]pyridin-5(4H)-yl)acetaldehyde (80 mg) as a light yellow oil, which was used directly in the next step.

14a: 2-(2-Chlorophenyl)-2-(6,7-dihydrothieno[3,2-c]pyridin-5(4H)-yl)ethyl acetate To a stirred solution of intermediate C (270 mg, 0.9 mmol) in $CH_2Cl_2$ (20 mL) at room temperature was added acetyl chloride (235 mg, 3 mmol, 3.0 eq) and the resulting mixture was stirred at this temperature overnight. The mixture was concentrated under reduced pressure and the residue was purified by column chromatography (Pet. ether/EtOAc, 5/1, v/v) to give 2-(2-chlorophenyl)-2-(6,7-dihydrothieno[3,2-c]pyridin-5(4H)-yl)ethyl acetate (80 mg, 35%) as a light yellow oil.

LC-MS (Agilent): $R_t$ 3.15 min; m/z calculated for $C_{17}H_{18}ClNO_2S$ [M+H]$^+$ 336.07. found 336.1.

$^1$H NMR: (400 MHz, CDCl$_3$) δ (ppm): 7.61 (m, 1H), 7.38 (m, 1H), 7.26 (m, 2H), 7.09 (d, J=4.8 Hz, 1H), 6.97 (d, J=4.8 Hz, 1H), 4.55 (m, 1H), 4.41 (t, J=5.6 Hz, 1H), 4.37 (m, 1H), 3.83 (d, J=14.4 Hz, 1H), 3.62 (d, J=14.8 Hz, 1H), 2.76-2.93 (m, 4H), 2.00 (s, 3H).

14b: (E)-2-(2-Chlorophenyl)-2-(6,7-dihydrothieno[3,2-c]pyridin-5(4H)-yl)acetaldehyde O-methyl oxime To a solution of intermediate D (70 mg, 0.24 mmol) in methanol (2 mL) at room temperature was added O-methylhydroxylamine hydrochloride (40 mg, 0.48 mmol, 2.0 eq). The resulting mixture was heated at 70° C. for 2 h and the reaction was quenched by addition of a saturated aqueous $Na_2CO_3$ solution until pH a' 8. The mixture was extracted with EtOAc and the combined organic layers were washed with brine, dried over $Na_2SO_4$ and the solvent was removed under reduced pressure to give (E)-2-(2-chlorophenyl)-2-(6,7-dihydrothieno[3,2-c]pyridin-5(4H)-yl)acetaldehyde O-methyl oxime (50 mg, 40%) as a light yellow solid.

LC-MS (Agilent): $R_t$ 2.88 min; m/z calculated for $C_{16}H_{17}ClN_2OS$ [M+H$_2$O+H]$^+$ 339.08. found 339.1

$^1$H NMR: (400 MHz, CDCl$_3$) δ (ppm): 8.15 (s, 1H), 7.22-7.39 (m, 5H), 7.14 (d, J=5.2 Hz, 1H), 4.35 (dd, J=8.4, 4.0 Hz, 1H), 3.95 (s, 3H), 3.79 (dd, J=10.8, 4.0 Hz, 1H), 3.50 (dd, J=10.8, 8.4 Hz, 1H), 3.08 (m, 2H), 2.83 (m, 2H).

Example 15

Formula 121—Compounds 15a and 15b

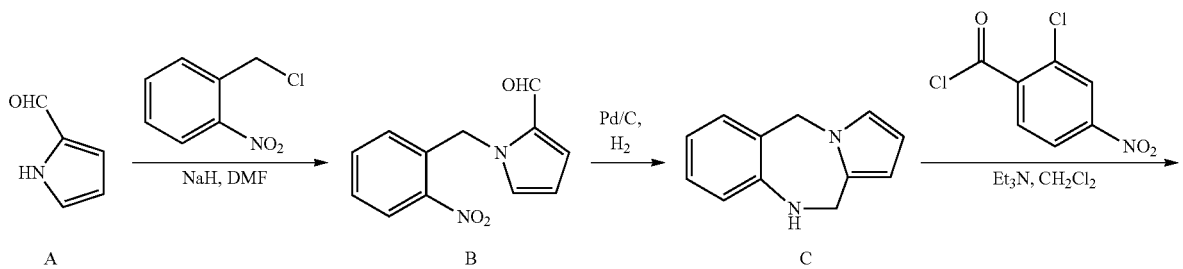

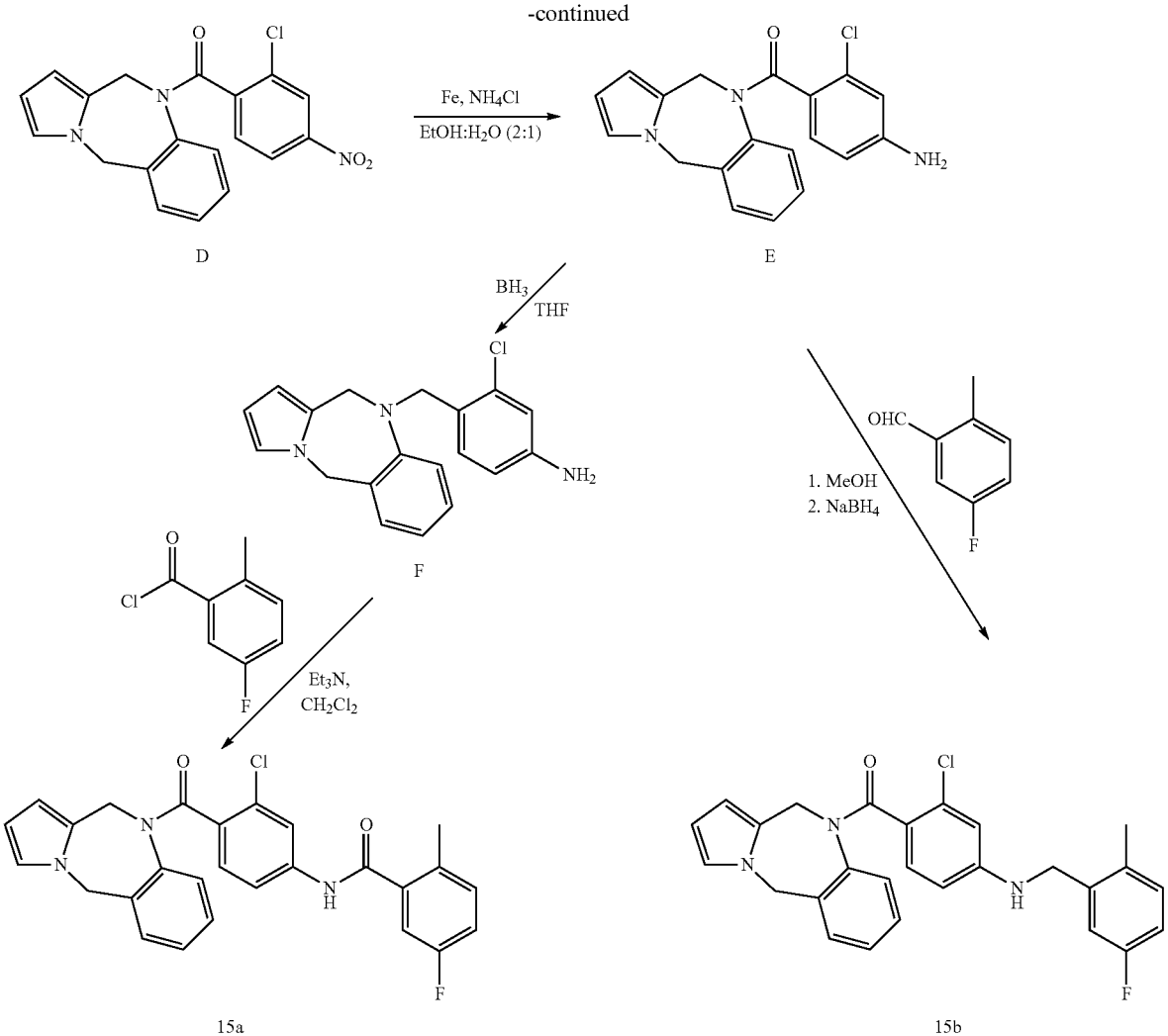

Intermediate E: (4-Amino-2-chlorophenyl)(5H-benzo[e]pyrrolo[1,2-a][1,4]diazepin-10(11H)-yl)methanone (4-Amino-2-chlorophenyl)(5H-benzo[e]pyrrolo[1,2-a][1,4]diazepin-10(11H)-yl)methanone was obtained from compound A in four steps and 27% overall yield according to the procedures described in *J. Med. Chem.* 1998, 41, 2442-2444 and *J. Med. Chem.* 1980, 23, 462-465.

Intermediate F: 4-((5H-Benzo[e]pyrrolo[1,2-a][1,4]diazepin-10(11H)-yl)methyl)-3-chloroaniline To a solution of intermediate E (600 mg, 1.8 mmol, 1.0 eq) in dry THF (20 mL) was added a 1.0 M solution of $BH_3$ in THF (4.5 mL, 4.5 mmol, 2.5 eq) and the resulting mixture was stirred at room temperature for 18 h. Water (20 mL) was added and mixture was stirred for 15 minutes then extracted with EtOAc. The combined organic layers were dried over $Na_2SO_4$ and concentrated under reduced pressure to give a solid which was purified by flash chromatography (Pet. ether/EtOAc, 10/1, v/v) to give 4-((5H-benzo[e]pyrrolo[1,2-a][1,4]diazepin-10(11H)-yl)methyl)-3-chloroaniline (110 mg, 19%) as a white solid.

LC-MS (Agilent): $R_t$ 3.41 min; m/z calculated for $C_{19}H_{18}ClN_3$ [M+H]$^+$ 324.12. found 324.1.

15a: N-(4-((5H-Benzo[e]pyrrolo[1,2-a][1,4]diazepin-10(11H)-yl)methyl)-3-chlorophenyl)-5-fluoro-2-methylbenzamide To a solution of intermediate F (100 mg, 0.3 mmol, 1.0 eq) in $CH_2Cl_2$ (15 mL) was added triethylamine (1.0 g, 0.9 mmol, 3.0 eq) at room temperature and the resulting mixture was stirred for 30 min. A solution of 5-fluoro-2-methylbenzoyl chloride (50.0 mg, 0.36 mmol, 1.2 eq) in $CH_2Cl_2$ (5 mL) was then added and stirring was continued for a further 18 h. The solvent was evaporated under reduced pressure to give a solid, which was purified by flash chromatography (Pet. ether/EtOAc, 5/1, v/v) to give N-(4-((5H-benzo[e]pyrrolo[1,2-a][1,4]diazepin-10(11H)-yl)methyl)-3-chlorophenyl)-5-fluoro-2-methylbenzamide (72 mg, 51%) as a white solid.

LC-MS (Agilent): $R_t$ 3.69 min; m/z calculated for $C_{27}H_{23}ClFN_3O$ [M+H]$^+$ 460.15. found 460.1.

$^1$H NMR: (400 MHz, DMSO-$d_6$) δ (ppm): 10.5 (s, 1H), 8.01 (d, J=2.0 Hz, 1H), 7.57 (dd, J=8.4, 2.0 Hz, 1H), 7.37-7.31 (m, 3H), 7.25 (m, 1H), 7.15 (dd, J=7.6, 1.6 Hz, 1H), 7.08 (m, 1H), 6.82 (m, 1H), 6.70 (m, 1H), 6.63 (d, J=8.4 Hz, 1H), 5.89-5.92 (m, 2H), 5.29 (s, 2H), 4.48 (d, J=3.6 Hz, 4H), 2.35 (s, 3H).

15b: (5H-Benzo[e]pyrrolo[1,2-a][1,4]diazepin-10 (11H)-yl)(2-chloro-4-(5-fluoro-2-methylbenzylamino)phenyl)methanone A solution of intermediate E (200 mg, 0.6 mmol, 1.0 eq) and 5-fluoro-2-methyl-benzaldehyde (124 mg, 0.9 mmol, 1.5 eq) in MeOH (20 mL) was heated at reflux for 18 h then cooled to room temperature. NaBH$_4$ (45 mg, 1.2 mmol, 2.0 eq) was then added and the mixture was stirred at room temperature for 4 h. The solvent was removed under reduced pressure to give a solid, which was purified by flash chromatography (Pet. ether/EtOAc, 5/1, v/v) to give (5H-benzo[e]pyrrolo[1,2-a][1,4]diazepin-10(11H)-yl)(2-chloro-4-(5-fluoro-2-methylbenzylamino)phenyl)methanone (50 mg, 18%) as a white solid.

LC-MS (Agilent): R$_t$ 3.49 min; m/z calculated for C$_{27}$H$_{23}$ClFN$_3$O [M+H]$^+$ 460.15. found 460.1.

$^1$H NMR: (400 MHz, CDCl$_3$) δ (ppm): 7.25 (m, 1H), 7.19-6.79 (m, 7H), 6.65 (m, 1H), 6.43 (m, 1H), 6.24 (m, 1H), 6.10-5.98 (m, 2H), 5.38-4.77 (m, 4H), 4.17 (m, 2H), 2.26 (s, 3H).

Example 16

Formula 158—Compounds 16a & 16b

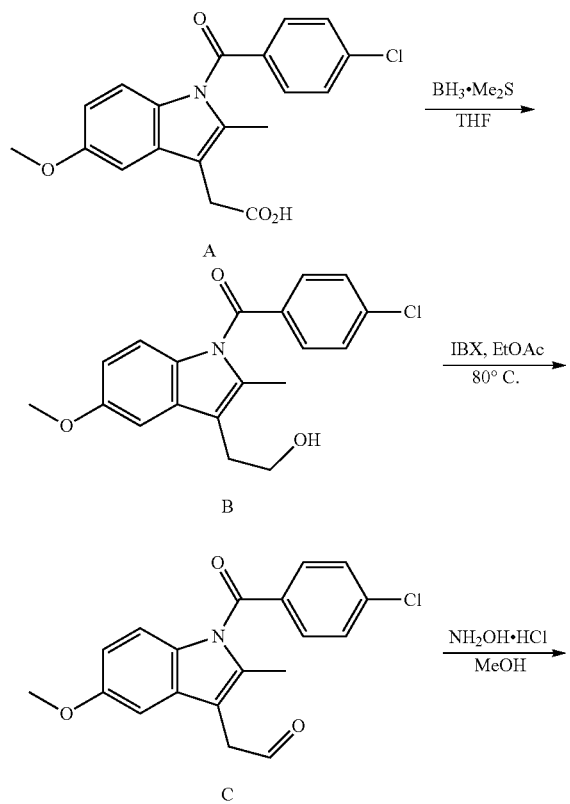

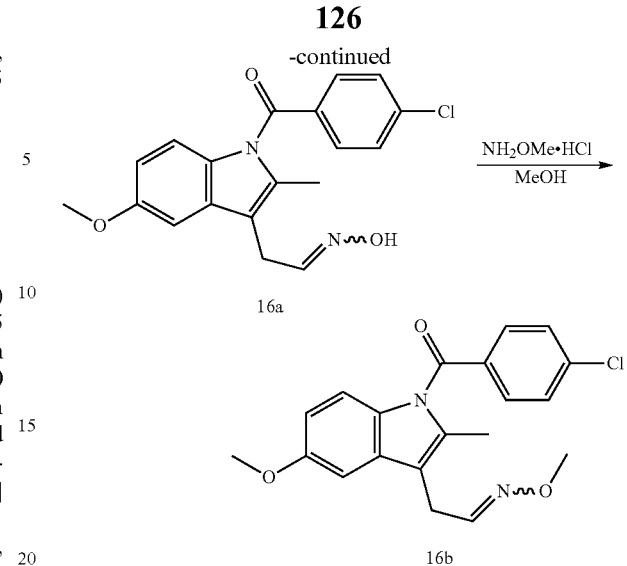

Intermediate B: (4-Chlorophenyl)(3-(hydroxymethyl)-5-methoxy-2-methyl-1H-indol-1-yl)methanone To a stirred solution of compound A (200 mg, 0.559 mmol) in THF (2 mL) was added a 2 M solution of BH$_3$.Me$_2$S in THF (0.31 mL, 0.615 mmol) at −20° C. The mixture was allowed to warm to room temperature and stirred for 18 h. The solvent was removed under reduced pressure and the residue was purified by silica gel column chromatography (CH$_2$Cl$_2$/MeOH, 50/1, v/v) to give (4-chlorophenyl)(3-(hydroxymethyl)-5-methoxy-2-methyl-1H-indol-1-yl)methanone (150 mg, 83%) as a yellow solid.

LC-MS (Agilent): R$_t$ 3.45 min; m/z calculated for C$_{19}$H$_{18}$ClNO$_3$ [M+Na]$^+$ 366.1. found 366.1.

$^1$H NMR: (400 MHz, CDCl$_3$) δ (ppm): 7.66 (dd, J=6.8, 2.0 Hz, 2H), 7.48 (dd, J=6.8, 2.0 Hz, 2H), 6.97 (d, J=2.4 Hz, 1H), 6.89 (d, J=8.8 Hz, 1H), 6.68 (dd, J=8.8 Hz, 2.4 Hz, 1H), 3.88 (t, J=6.8 Hz, 2H), 3.87 (s, 3H), 2.96 (t, J=6.8 Hz, 2H), 2.39 (s, 3H).

Intermediate C: 2-(1-(4-Chlorobenzoyl)-5-methoxy-2-methyl-1H-indol-3-yl)acetaldehyde To a solution of intermediate B (150 mg, 0.44 mmol) in EtOAc (1.5 mL) was added IBX (0.31 g, 1.1 mmol) at room temperature and the resulting mixture was heated at 80° C. for 2 h. The mixture was filtered and the filtrate was concentrated under reduced pressure to give 2-(1-(4-chlorobenzoyl)-5-methoxy-2-methyl-1H-indol-3-yl)acetaldehyde (100 mg, 67%) as a powder.

LC-MS (Agilent): R$_t$ 3.47 min; m/z calculated for C$_{19}$H$_{16}$ClNO$_3$ [M+MeOH+Na]$^+$ 396.08. found 369.1.

$^1$H NMR: (400 MHz, CDCl$_3$) δ (ppm): 9.73 (s, 1H), 7.70 (d, J=8.4 Hz, 2H), 7.50 (d, J=8.4 Hz, 2H), 7.29 (s, 1H), 6.87 (m, 1H), 6.71 (m, 1H), 3.85 (s, 3H), 3.75 (d, J=1.6 Hz, 2H), 2.40 (s, 3H).

16a: 2-(1-(4-Chlorobenzoyl)-5-methoxy-2-methyl-1H-indol-3-yl)acetaldehyde oxime

To a solution of intermediate C (200 mg, 0.6 mmol) in MeOH (2 mL) and pyridine (0.2 mL) was added NH$_2$OH.HCl (48 mg, 0.7 mmol) at room temperature and the resulting mixture was stirred for 2 h. The solvent was removed under reduced pressure and the residue was purified by silica gel column chromatography (Pet. ether/EtOAc, 3/1, v/v) to give 2-(1-(4-chlorobenzoyl)-5-methoxy-2-methyl-1H-indol-3-yl)acetaldehyde oxime (150 mg, 72%) as a white solid, $^1$H-NMR spectroscopy revealed a 1:1 mixture of isomers.

LC-MS (Agilent): $R_t$ 3.40 min; m/z calculated for $C_{19}H_{17}ClN_2O_3$ [M+H]$^+$ 357.09, [M+Na]$^+$ 379.09, found [M+H]$^+$ 357.1, [M+Na]$^+$ 379.1.

$^1$H NMR: (400 MHz, DMSO-$d_6$) δ (ppm): 11.2 (s, 0.5H), 10.6 (s, 0.5H), 7.70-7.63 (m, 4H), 7.38 (t, J=6.0 Hz, 0.5H), 7.08 (m, 1H), 6.94 (dd, J=9.2, 4.8 Hz, 1H), 6.73-6.70 (m, 1.5H), 3.77 (s, 3H), 3.67 (d, J=5.6 Hz, 1H), 3.54 (d, J=6.0 Hz, 1H), 2.23 (s, 3H).

16b: 2-(1-(4-Chlorobenzoyl)-5-methoxy-2-methyl-1H-indol-3-yl)acetaldehyde O-methyl oxime To a solution of intermediate C (200 mg, 0.6 mmol) in MeOH (2 mL) and pyridine (0.2 mL) was added NH$_2$OMe.HCl (56 mg, 0.68 mmol) at room temperature and the resulting mixture was stirred for 2 h. The solvent was removed under reduced pressure and the residue was purified by silica gel column chromatography (Pet. ether/EtOAc, 3/1, v/v) to give 2-(1-(4-chlorobenzoyl)-5-methoxy-2-methyl-1H-indol-3-yl)acetaldehyde O-methyl oxime (150 mg, 71%) as a white solid, $^1$H-NMR spectroscopy revealed a 1:1 mixture of isomers.

LC-MS (Agilent): $R_t$ 3.55 min; m/z calculated for $C_{20}H_{19}ClN_2O_3$ [M+H]$^+$ 371.11, [M+Na]$^+$ 393.11, found [M+H]$^+$ 371.1, [M+Na]$^+$ 393.1.

$^1$H NMR: (400 MHz, DMSO-$d_6$) δ (ppm): 7.69 (AB, J=8.4 Hz, 2H), 7.65 (AB, J=8.8 Hz, 2H), 7.45 (t, J=6.4 Hz, 0.5H), 7.10 (d, J=2.8 Hz, 0.5H), 7.05 (d, J=2.4 Hz, 0.5H), 6.94 (dd, J=9.2, 2.8 Hz, 1H), 6.82 (t, J=5.6 Hz, 0.5H), 6.73 (dd, J=9.2, 2.4 Hz, 1H), 3.89 (s, 1.5H), 3.77 (s, 3H), 3.74 (s, 1.5H), 3.66 (d, J=5.6 Hz, 1H), 3.56 (d, J=6.0 Hz, 1H), 2.24 (s, 1.5H), 2.22 (s, 1.5H).

Example 17

Formula 154—Compound 17a

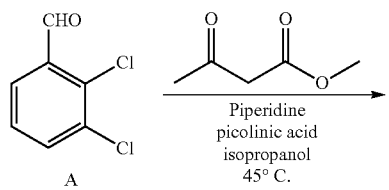
A

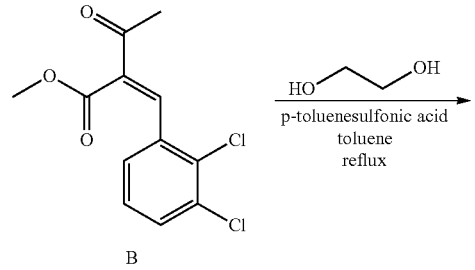
B

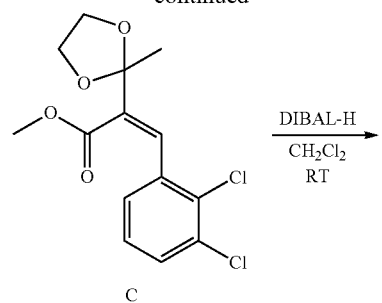
C

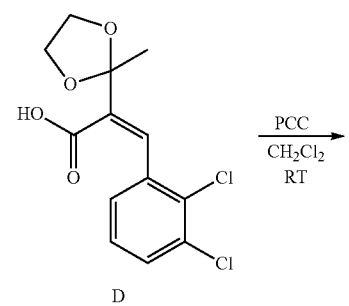
D

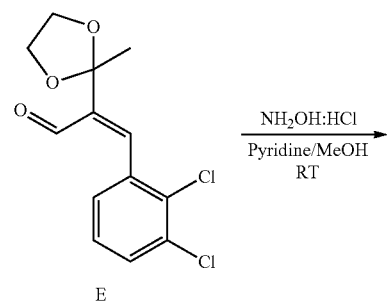
E

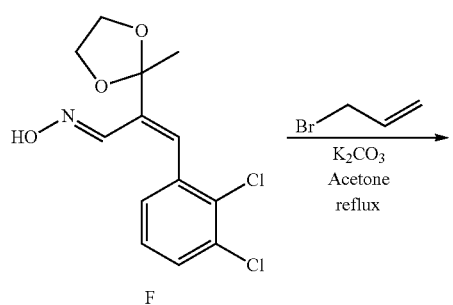
F

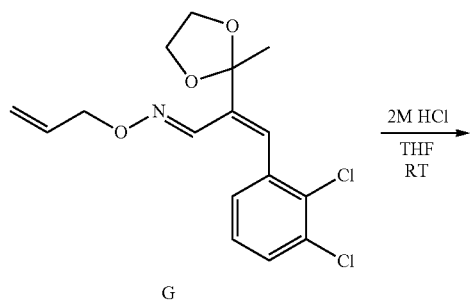
G

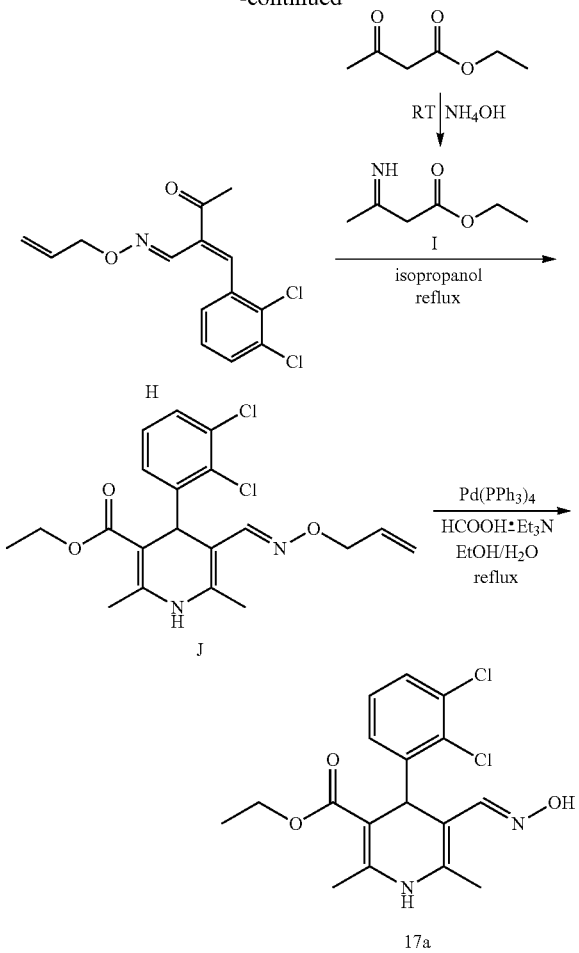

Intermediate B: (Z)-Methyl 2-(2,3-dichlorobenzylidene)-3-oxobutanoate

To a solution of compound A (10.1 g, 57 mmol, 1.0 eq) and methyl 3-oxobutanoate (8.60 g, 74 mmol, 1.3 eq) in isopropanol (100 mL) was added piperidine (0.24 g, 2.8 mmol, 0.05 eq) and picolinic acid (0.35 g, 2.8 mmol, 0.05 eq) at room temperature. The resulting mixture was heated at 45° C. overnight then cooled to 0° C. and the crystalline solid was collected by suction filtration, washed with isopropanol (20 mL) and dried under vacuum to give (Z)-methyl 2-(2,3-dichlorobenzylidene)-3-oxobutanoate (4.00 g, 25%) as a white solid.

LC-MS (Agilent): $R_t$ 3.62 min; m/z calculated for $C_{12}H_{10}Cl_2O_3$ [M+H]$^+$ 273.1, [M+Na]$^+$ 295.0, found [M+H]$^+$ 273.0, [M+Na]$^+$ 294.9.

Intermediate C: (Z)-Methyl 3-(2,3-Dichlorophenyl)-2-(2-methyl-1,3-dioxolan-2-yl)acrylate To a solution of intermediate B (2.0 g, 7.3 mmol, 1.0 eq) in toluene (50 mL) was added ethylene glycol (0.9 g, 14.6 mmol, 2.0 eq) and p-toluenesulfonic acid (126 mg, 0.7 mmol, 0.1 eq) and the resulting mixture was heated at reflux for 6 h in a Dean-Stark apparatus. The mixture was cooled to room temperature, water (50 mL) was added and the organic layer was separated and dried over $Na_2SO_4$. The solvent was removed under reduced pressure and the residue was purified by column chromatography (Pet. ether/EtOAc, 10/1, v/v) to give (Z)-methyl 3-(2,3-dichlorophenyl)-2-(2-methyl-1,3-dioxolan-2-yl)acrylate (1.0 g, 43%) as a white solid.

LC-MS (Waters): $R_t$ 7.46 min; m/z calculated for $C_{14}H_4O_2O_4$ [M+Na]$^+$ 339.03. found 338.9

Intermediate D: (E)-3-(2,3-Dichlorophenyl)-2-(2-methyl-1,3-dioxolan-2-yl)prop-2-en-1-ol To a solution of intermediate C (500 mg, 1.6 mmol, 1.0 eq) in $CH_2Cl_2$ (10 mL) was added a 1.0 M solution of DIBAl-H in hexanes (6.3 mL, 6.3 mmol, 4.0 eq) dropwise at −78° C. The resulting mixture was warmed to room temperature and stirred overnight. Water (0.24 mL), 15% aqueous NaOH (0.24 mL) and water (0.72 mL) were added to the reaction mixture in that order and stirring was continued for 15 min at room temperature. $MgSO_4$ was then added and stirring was continued for a further 15 min. The mixture was filtered, the filtrate was concentrated under reduced pressure and the residue was purified by column chromatography (Pet. ether/EtOAc, 10/1, v/v) to give (E)-3-(2,3-dichlorophenyl)-2-(2-methyl-1,3-dioxolan-2-yl)prop-2-en-1-ol (250 mg, 55%) as a colourless oil.

LC-MS (Waters): $R_t$ 6.88 min; m/z calculated for $C_{13}H_{14}Cl_2O_3$ [M+Na]$^+$ 311.03. found 311.0.

Intermediate E: (E)-3-(2,3-Dichlorophenyl)-2-(2-methyl-1,3-dioxolan-2-yl)acrylaldehyde To a solution of intermediate D (1.3 g, 4.5 mmol, 1.0 eq) in $CH_2Cl_2$ (20 mL) was added PCC (1.9 g, 9.0 mmol, 2.0 eq). The resulting mixture was stirred at room temperature for 2 h and then filtered through Celite. The filtrate was concentrated under reduced pressure to give (E)-3-(2,3-dichlorophenyl)-2-(2-methyl-1,3-dioxolan-2-yl)acrylaldehyde (1.3 g, 100%) as a brown oil, which was used directly in the next step.

Intermediate F: (1E,2E)-3-(2,3-Dichlorophenyl)-2-(2-methyl-1,3-dioxolan-2-yl)acrylaldehyde oxime To a solution of intermediate E (1.3 g, 4.5 mmol, 1.0 eq) in pyridine (2.5 mL) and methanol (25 mL) was added hydroxylamine hydrochloride (310 mg, 4.5 mmol, 1.0 eq) and the resulting mixture was stirred at room temperature overnight. The mixture was concentrated under reduced pressure and the residue was treated with a 1M aqueous HCl solution (10 mL) and EtOAc (10 mL). The organic layer was separated, dried over $Na_2SO_4$ and the solvent was removed under reduced pressure to give (1E,2E)-3-(2,3-dichlorophenyl)-2-(2-methyl-1,3-dioxolan-2-yl)acrylaldehyde oxime (1.3 g, 96%) as a light green solid.

LC-MS (Waters): $R_t$ 8.03 min; m/z calculated for $C_{13}H_{13}Cl_2NO_3$ [M+H]$^+$ 302.03, [M+Na]$^+$ 324.03, found [M+H]$^+$ 302.0, [M+Na]$^+$ 324.0.

Intermediate G: (1E,2E)-3-(2,3-Dichlorophenyl)-2-(2-methyl-1,3-dioxolan-2-yl)acrylaldehyde O-allyl oxime To a solution of intermediate F (1.3 g, 4.3 mmol, 1.0 eq) in acetone (30 mL) was added $K_2CO_3$ (1.2 g, 8.6 mmol, 2.0 eq) and 3-bromoprop-1-ene (1.6 g, 12.9 mmol, 3.0 eq) and the resulting mixture was heated at reflux overnight. The mixture was concentrated under reduced pressure the residue was partitioned between water (20 mL) and EtOAc (20 mL). The organic layer was separated, dried over $Na_2SO_4$ and the solvent was removed under reduced pressure to give (1E,2E)-3-(2,3-dichlorophenyl)-2-(2-methyl-1,3-dioxolan-2-yl)acrylaldehyde O-allyl oxime (1.3 g, 88%) as a brown oil, which was used directly in the next step.

Intermediate H: (1E,2E)-2-(2,3-Dichlorobenzylidene)-3-oxobutanal O-allyl oxime To a solution of intermediate G (1.3 g, 3.8 mmol, 1.0 eq) in THF (30 mL) was added 2 M aqueous HCl solution (60 mL) and the resulting mixture was stirred at room temperature overnight. EtOAc (50 mL) was added to the mixture and the organic layer was separated, dried over $Na_2SO_4$ and the solvent was removed under reduced pressure to give (1E,2E)-2-(2,3-dichlorobenzylidene)-3-oxobutanal O-allyl oxime (1.0 g, 91%) as a yellow oil.

LC-MS (Waters): $R_t$ 4.28 min; m/z calculated for $C_{14}H_{13}Cl_2NO_2$ [M+H]$^+$ 298.03, [M+Na]$^+$ 320.03, found [M+H]$^+$ 297.9, [M+Na]$^+$ 319.9.

Intermediate I: Ethyl 3-iminobutanoate

A solution of ethyl acetoacetate (50 g, 385 mmol, 1.0 eq) in 25% aqueous ammonia (300 mL) was stirred at room temperature for 1 h then extracted with EtOAc (2×300 mL). The combined organic layers were dried over $Na_2SO_4$ and the solvent was removed under reduced pressure to give ethyl 3-iminobutanoate (42 g, 85%) as a yellow oil, which was used directly in the next step.

Intermediate J: (E)-Ethyl 5-((allyloxyimino)methyl)-4-(2,3-dichlorophenyl)-2,6-dimethyl-1,4-dihydropyridine-3-carboxylate To a solution of intermediate H (1.0 g, 3.4 mmol, 1.0 eq) in isopropanol (20 mL) was added intermediate I (432 mg, 3.4 mmol, 1.0 eq) and the resulting mixture was stirred at reflux overnight. The solvent was removed under reduced pressure and the residue was purified by column chromatography (Pet. ether/EtOAc, 5/1, v/v) to give (E)-ethyl 5-((allyloxyimino)methyl)-4-(2,3-dichlorophenyl)-2,6-dimethyl-1,4-dihydropyridine-3-carboxylate (0.8 g, 58%) as a yellow solid.

LC-MS (Waters): $R_t$ 6.67 min; m/z calculated for $C_{20}H_{22}Cl_2N_2O_3$ [M+H]$^+$ 409.1. found 409.0.

17a: (E)-Ethyl 4-(2,3-dichlorophenyl)-5-((hydroxyimino)methyl)-2,6-dimethyl-1,4-dihydropyridine-3-carboxylate To a solution of intermediate J (400 mg, 0.98 mmol, 1.0 eq) in EtOH (20 mL) and $H_2O$ (5 mL) was added HCOOH.NEt$_3$ (431 mg, 2.93 mmol, 3 eq) and Pd[PPh$_3$]$_4$ (113 mg, 0.10 mmol, 0.1 eq) and the resulting mixture was heated at reflux for 3 h. The solvent was removed under reduced pressure and the residue was purified by column chromatography (Pet. ether/EtOAc, 5/1, v/v) to give (E)-ethyl 4-(2,3-dichlorophenyl)-5-((hydroxyimino)methyl)-2,6-dimethyl-1,4-dihydropyridine-3-carboxylate (100 mg, 28%) as a yellow solid.

LC-MS (Agilent): $R_t$ 3.35 min; m/z calculated for $C_{17}H_{18}Cl_2N_2O_3$ [M+H]$^+$ 369.07. found 369.1.

$^1$H NMR: (400 MHz, DMSO-d$_6$) δ (ppm): 10.3 (s, 1H), 8.74 (s, 1H), 7.84 (s, 1H), 7.35 (dd, J=7.6, 1.6 Hz, 1H), 7.27 (dd, J=8.0, 1.6 Hz, 1H), 7.22 (m, 1H), 5.28 (s, 1H), 3.94 (qd, J=7.2, 1.2 Hz, 2H), 2.22 (s, 3H), 1.99 (s, 3H), 1.09 (t, J=7.2 Hz, 3H).

Example 18

Formula 98—Compounds 18a & 18b

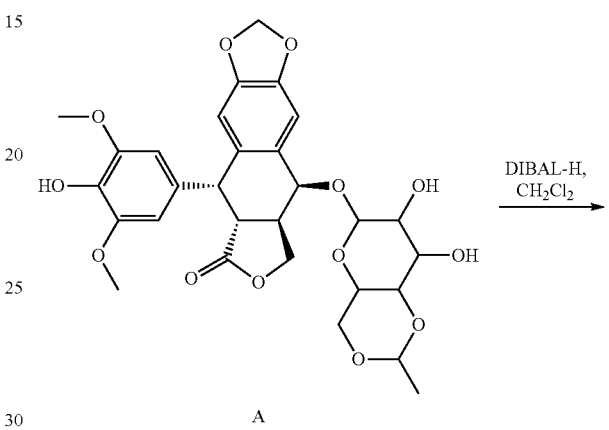

A

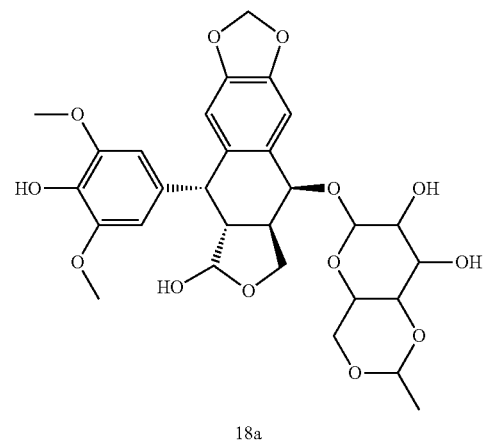

18a

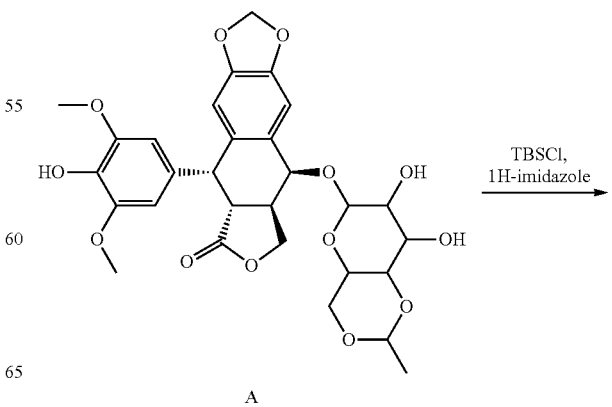

A

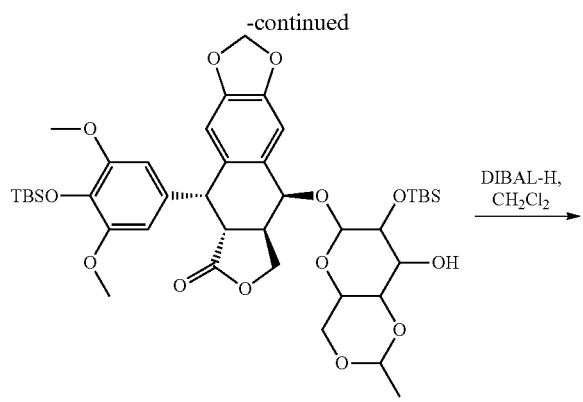

B

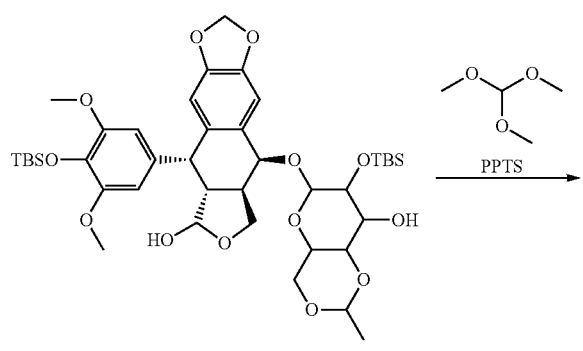

C

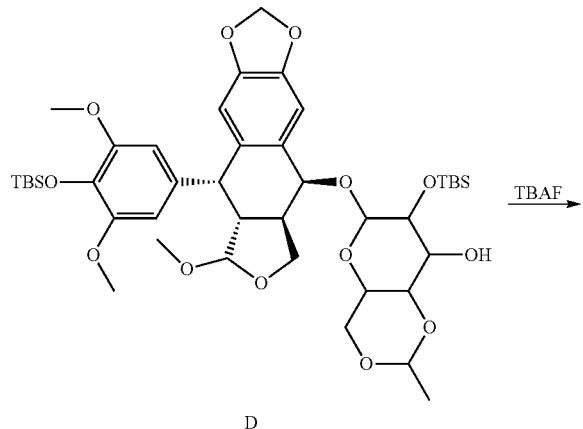

D

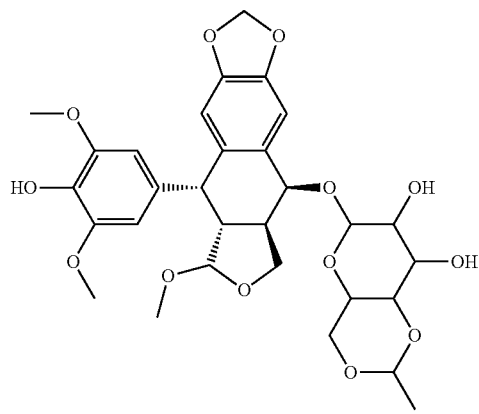

18b

18a: 6-(((5S,5aR,8R,8aR,9R)-8-Hydroxy-9-(4-hydroxy-3,5-dimethoxyphenyl)-5,5a,6,8,8a,9-hexahydrofuro[3',4':6,7]naphtho[2,3-d][1,3]dioxol-5-yl)oxy)-2-methylhexahydropyrano[3,2-d][1,3]dioxine-7,8-diol To a stirred solution of compound A (300 mg, 0.51 mmol, 1.0 eq) in $CH_2Cl_2$ (30 mL) was added a 1.0 M solution of DIBAl-H in hexanes (1.5 mL, 1.5 mmol, 3.0 eq) at −78° C. and the resulting mixture was stirred at this temperature for 40 min. A saturated aqueous ammonium chloride solution was slowly added and the mixture was extracted with $CH_2Cl_2$ (60 mL×3). The combined organic layers were washed with brine (50 mL×2), dried over $Na_2SO_4$ and concentrated under reduced pressure. The residue was purified by flash chromatography (MeOH/$CH_2Cl_2$, 1/100 to 1/10, v/v) to give 6-(((5S,5aR,8R,8aR,9R)-8-hydroxy-9-(4-hydroxy-3,5-dimethoxyphenyl)-5,5a,6,8,8a,9-hexahydrofuro[3',4':6,7]naphtho[2,3-d][1,3]dioxol-5-yl)oxy)-2-methylhexahydropyrano[3,2-d][1,3]dioxine-7,8-diol (40 mg, 13%) as a light yellow solid.

LC-MS (Agilent): $R_t$ 3.07 min; m/z calculated for $C_{29}H_{34}O_{13}$ $[M+Na]^+$ 613.2. found 613.1.

$^1$H NMR: (400 MHz, $CDCl_3$) δ (ppm): 6.76 (s, 1H), 6.51 (s, 1H), 6.09 (s, 2H), 5.98 (d, J=3.6 Hz, 2H), 5.50 (s, 1H), 4.95 (d, J=2.8 Hz, 1H), 4.70 (m, 2H), 4.32 (m, 2H), 4.20 (m, 2H), 3.82 (t, J=7.6 Hz, 1H), 3.77 (s, 6H), 3.60 (m, 2H), 3.41 (m, 1H), 3.31-3.21 (m, 2H), 2.75 (m, 1H), 2.53 (m, 1H), 1.39 (d, J=4.8 Hz, 3H).

Intermediate B: (5R,5aR,8aR,9S)-5-(4-((tert-Butyldimethylsilyl)oxy)-3,5-dimethoxyphenyl)-9-((7-((tert-butyldimethylsilyl)oxy)-8-hydroxy-2-methylhexahydro pyrano[3,2-d][1,3]dioxin-6-yl)oxy)-5,5a,8a,9-tetrahydrofuro[3',4':6,7]naphtho[2,3-d][1,3]dioxol-6(8H)-one To a solution of compound A (300 mg, 0.51 mmol, 1.0 eq) and TBSCl (375 mg, 2.5 mmol, 5.0 eq) in DMF (40 mL) was added 1H-imidazole (347 mg, 5.1 mmol, 10 eq) and the resulting mixture was stirred at 80° C. for 1 h. The mixture was then diluted with EtOAc (100 mL) and washed with water (60 mL×3) and brine (50 mL×2) and dried over $Na_2SO_4$. The solvent was removed under reduced pressure and the residue was purified by flash chromatography (EtOAc/hexane, 1/10 to 1/1, v/v) to give (5R,5aR,8aR,9S)-5-(4-((tert-butyldimethylsilyl)oxy)-3,5-dimethoxyphenyl)-9-((7-((tert-butyldimethylsilyl)oxy)-8-hydroxy-2-methylhexahydropyrano[3,2-d][1,3]dioxin-6-yl)oxy)-5,5a,8a,9-tetrahydrofuro[3',4':6,7]naphtho[2,3-d][1,3]dioxol-6(8H)-one (310 mg, 73%) as a white solid.

LC-MS (Agilent): $R_t$ 3.99 min; m/z calculated for $C_{41}H_{60}O_{13}Si_2$ $[M+Na]^+$ 839.36. found 840.0.

$^1$H NMR: (400 MHz, $CDCl_3$) δ (ppm): 6.85 (s, 1H), 6.58 (s, 1H), 6.22 (s, 2H), 6.01 (dd, J=10.8, 1.2 Hz, 2H), 4.91 (d, J=3.6 Hz, 1H), 4.69 (m, 1H), 4.63 (d, J=8.0 Hz, 1H), 4.59 (d, J=5.2 Hz, 1H), 4.41 (dd, J=10.4, 8.8 Hz, 1H), 4.22-4.13 (m, 2H), 3.67 (s, 6H), 3.66 (t, J=8.4 Hz, 1H), 3.56 (t, J=6.0 Hz, 1H), 3.40 (t, J=8.0 Hz, 1H), 3.30-3.20 (m, 3H), 2.87 (m, 1H), 1.36 (d, J=4.8 Hz, 3H), 0.99 (s, 9H), 0.90 (s, 9H), 0.11 (m, 12H).

Intermediate C: (5R,5aR,6R,8aR,9S)-5-(4-((tert-Butyldimethylsilyl)oxy)-3,5-dimethoxyphenyl)-9-((7-((tert-butyldimethylsilyl)oxy)-8-hydroxy-2-methylhexahydro pyrano[3,2-d][1,3]dioxin-6-yl)oxy)-5,5a,6,8,8a,9-hexahydrofuro[3',4':6,7]naphtho[2,3-d][1,3]dioxol-6-ol To a stirred solution of intermediate B (310 mg, 0.38 mmol, 1.0 eq) in $CH_2Cl_2$ (30 mL) was added a 1.0 M solution of DIBAl-H in hexanes (1.1 mL, 1.1 mmol, 3.0 eq) at −78° C. and the resulting mixture was stirred at this temperature for 40 min. A saturated aqueous ammonium chloride solution was slowly added and the mixture was extracted with $CH_2Cl_2$ (60 mL×3). The combined organic layers were washed with brine (50 mL×2), dried over $Na_2SO_4$ and concentrated under reduced pressure. The residue was purified by flash chromatography ($CH_2Cl_2$/MeOH, 100/1 to 10/1, v/v) to give (5R, 5aR,6R,8aR,9S)-5-(4-((tert-butyldimethylsilyl)oxy)-3,5-dimethoxyphenyl)-9-((7-((tert-butyldimethylsilyl)oxy)-8-hydroxy-2-methylhexahydropyrano[3,2-d][1,3]dioxin-6-yl)oxy)-5,5a,6,8,8a,9-hexahydrofuro[3',4':6,7]naphtho[2,3-d][1,3]dioxol-6-ol (120 mg, 39%) as a light yellow solid, which was used directly in the next step.

Intermediate D: 7-((tert-Butyldimethylsilyl)oxy)-6-(((5S,5aR,8R,8aR,9R)-9-(4-((tert-butyldimethylsilyl)oxy)-3,5-dimethoxyphenyl)-8-methoxy-5,5a,6,8,8a,9-hexahydro furo[3',4':6,7]naphtho[2,3-d][1,3]dioxol-5-yl)oxy)-2-methylhexahydropyrano[3,2-d][1,3]dioxin-8-ol To a solution of intermediate C (120 mg, 0.14 mmol, 1.0 eq) in trimethoxymethane (10 mL) was added PPTS (2.5 mg, 0.01 mmol, 0.1 eq) and the mixture was stirred at room temperature for 40 min. The solvent was removed under reduced pressure and the residue was diluted with $CH_2Cl_2$ (60 mL), washed with water (30 mL×2) and dried over $MgSO_4$. The solvent was removed under reduced pressure to give 7-((tert-butyldimethylsilyl)oxy)-6-(((5S,5aR,8R,8aR,9R)-9-(4-((tert-butyldimethylsilyl)oxy)-3,5-dimethoxyphenyl)-8-methoxy-5,5a,6,8,8a,9-hexahydrofuro[3',4':6,7]naphtho[2,3-d][1,3]dioxol-5-yl)oxy)-2-methylhexahydro pyrano[3,2-d][1,3]dioxin-8-ol (110 mg, 92%), which was used in the next step without further purification.

LC-MS (Waters): $R_t$ 3.43 min; m/z calculated for $C_{42}H_{64}O_{13}Si_2$ [M−2TBS+Na]$^+$ 627.22. found 627.1.

18b: 6-(((5S,5aR,8R,8aR,9R)-9-(4-Hydroxy-3,5-dimethoxyphenyl)-8-methoxy-5,5a,6,8,8a,9-hexahydrofuro[3',4':6,7]naphtho[2,3-d][1,3]dioxol-5-yl)oxy)-2-methylhexahydro pyrano[3,2-d][1,3]dioxine-7,8-diol To a stirred solution of intermediate D (110 mg, 0.13 mmol, 1.0 eq) in THF (20 mL) was added TBAF (34 mg, 0.13 mmol, 1.0 eq) at room temperature and the mixture was stirred for 1 h. The solvent was removed under reduced pressure and the residue was diluted with EtOAc (80 mL), washed with water (60 mL×2) and dried over $MgSO_4$. The solvent was removed under reduced pressure and the residue was purified by flash chromatography ($CH_2Cl_2$/MeOH, 100/1 to 10/1, v/v) to give 6-(((5S,5aR,8R,8aR,9R)-9-(4-hydroxy-3,5-dimethoxyphenyl)-8-methoxy-5,5a,6,8,8a,9-hexahydrofuro[3',4':6,7]naphtho[2,3-d][1,3]dioxol-5-yl)oxy)-2-methylhexa hydropyrano[3,2-d][1,3]dioxine-7,8-diol (40 mg, 50%) as a white solid.

LC-MS (Agilent): $R_t$ 3.26 min; m/z calculated for $C_{30}H_{36}O_{13}$[M+Na]$^+$ 627.22. found 627.3.

$^1$H NMR: (400 MHz, CDCl$_3$) δ (ppm): 6.75 (s, 1H), 6.52 (s, 1H), 6.12 (s, 2H), 5.98 (d, J=10.0 Hz, 2H), 5.47 (s, 1H), 4.90 (d, J=3.2 Hz, 1H), 4.75 (m, 1H), 4.52 (d, J=7.6 Hz, 1H), 4.33 (m, 2H), 4.18 (m, 1H), 4.11 (m, 1H), 3.88 (t, J=7.6 Hz, 1H), 3.78 (s, 6H), 3.72 (m, 1H), 3.59 (m, 1H), 3.42 (m, 1H), 3.40 (s, 3H), 3.36 (m, 2H), 2.80-2.75 (m, 1H), 2.55-2.47 (m, 1H), 1.40 (d, J=4.8 Hz, 3H).

Example 19

Formula 57—Compound 19a

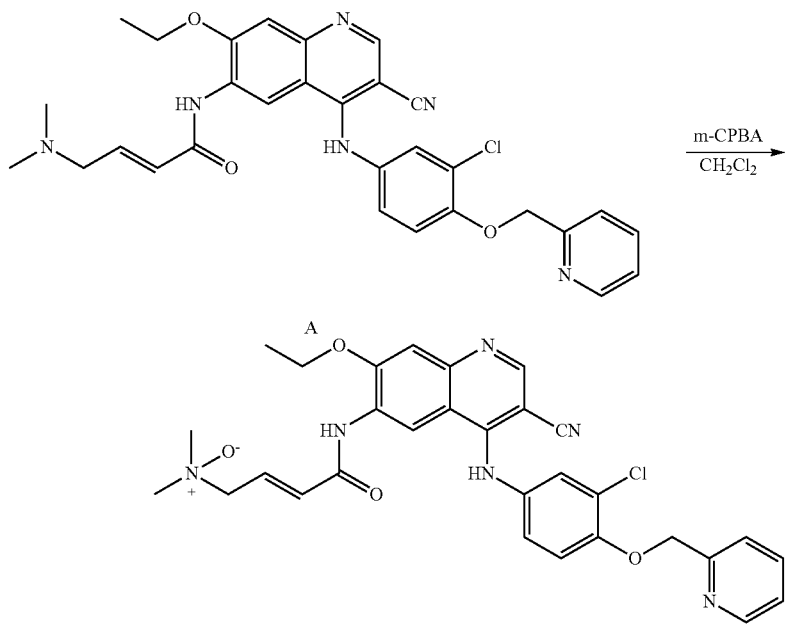

19a

19a: (E)-4-((4-((3-Chloro-4-(pyridin-2-ylmethoxy)phenyl)amino)-3-cyano-7-ethoxyquinolin-6-yl)amino)-N,N-dimethyl-4-oxobut-2-en-1-amine oxide To a solution of compound A (200 mg, 0.36 mmol, 1.0 eq) in $CH_2Cl_2$ (20 mL) was added m-CPBA (74 mg, 0.43 mmol, 1.2 eq) and the resulting mixture was stirred at room temperature for 4 h. A saturated aqueous solution of $NaHCO_3$ (20 mL) was then added and the organic layer was separated, dried over $Na_2SO_4$ and concentrated under reduced pressure. The residue was purified by preparative TLC ($CH_2Cl_2$/MeOH, 10/1, v/v) to give (E)-4-((4-((3-chloro-4-(pyridin-2-ylmethoxy)phenyl)amino)-3-cyano-7-ethoxyquinolin-6-yl)amino)-N,N-dimethyl-4-oxobut-2-en-1-amine oxide (20 mg, 10%) as a yellow solid.

LC-MS (Agilent): $R_t$ 3.03 min; m/z calculated for $C_{30}H_{29}ClN_6O_4[M+H]^+$ 573.19. found 573.2.

$^1$H NMR: (400 MHz, $CD_3OD$) δ (ppm): 8.98 (s, 1H), 8.57 (m, 1H), 8.39 (s, 1H), 7.92 (td, J=7.2, 1.6 Hz, 1H), 7.72 (d, J=8.0 Hz, 1H), 7.39 (m, 1H), 7.36 (d, J=2.4 Hz, 1H), 7.28 (s, 1H), 7.24-7.13 (m, 3H), 6.74 (d, J=15.6 Hz, 1H), 5.29 (s, 2H), 4.32 (q, J=6.8 Hz, 2H), 4.20 (d, J=7.2 Hz, 2H), 3.28 (s, 6H), 1.57 (t, J=6.8 Hz, 3H).

Example 20

Formula 153—Compounds 20a & 20b

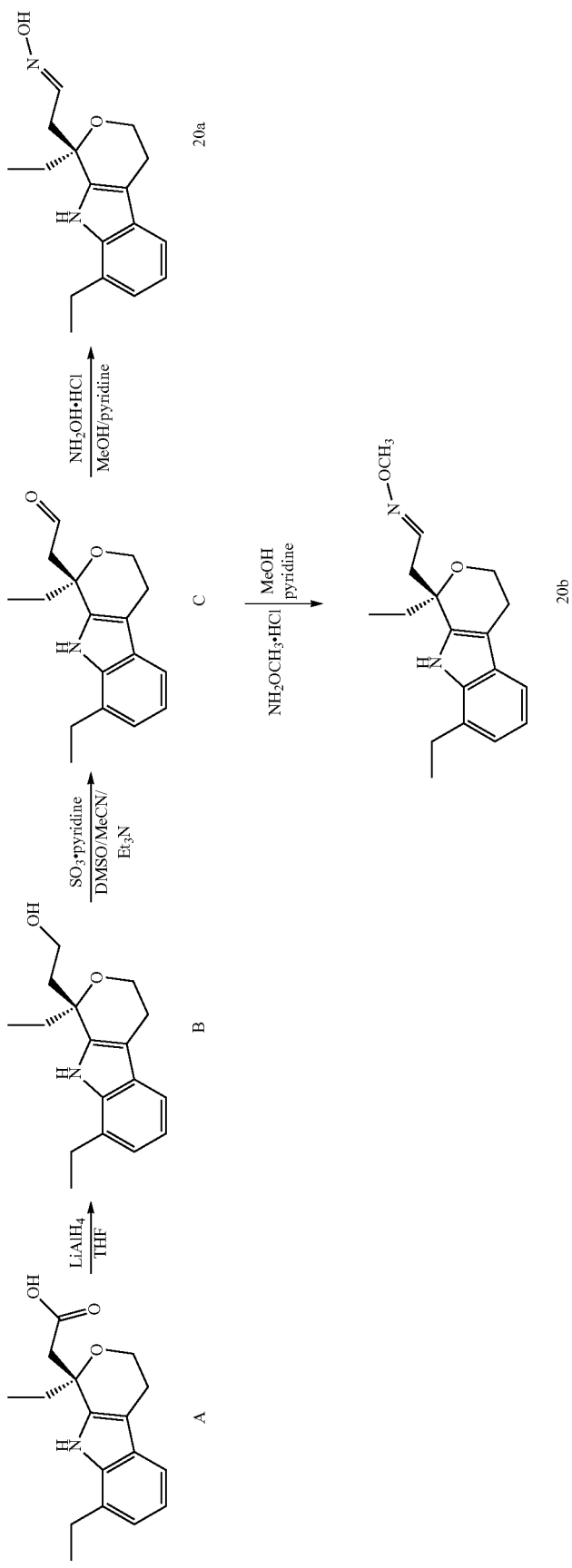

Intermediate B: (R)-2-(1,8-Diethyl-1,3,4,9-tetrahydropyrano[3,4-b]indol-1-yl)ethanol To a solution of compound A (2.0 g, 6.97 mmol, 1.0 eq) in dry THF (15.5 mL) under nitrogen was added a solution of LiAlH$_4$ (0.4 g, 10.5 mmol, 1.5 eq) in dry THF (10.5 mL) dropwise and the resulting mixture was stirred at room temperature overnight. The reaction was slowly quenched with EtOAc (15 mL) and poured into water. The resulting emulsion was filtered and the filtrate was extracted twice with EtOAc (30 mL×2). The combined organic layers were washed with brine, dried over Na$_2$SO$_4$ and concentrated under reduced pressure. Purification by column chromatography (CH$_2$Cl$_2$/MeOH, 50/1 to 20/1) gave (R)-2-(1,8-diethyl-1,3,4,9-tetrahydropyrano[3,4-b]indol-1-yl)ethanol (835 mg, 44%) as a yellow oil.

LC-MS (Waters): R$_t$ 5.89 min; m/z calculated for C$_{17}$H$_{23}$NO$_2$[M+Na]$^+$ 296.17. found 296.1.

Intermediate C: (R)-2-(1,8-Diethyl-1,3,4,9-tetrahydropyrano[3,4-b]indol-1-yl)acetaldehyde To a solution of intermediate B (530 mg, 1.94 mmol, 1.0 eq) in acetonitrile (2.5 mL), DMSO (2.5 mL) and Et$_3$N (2.5 mL) was added SO$_3$.pyridine (1.85 g, 11.6 mmol, 6.0 eq) and the resulting mixture was stirred at room temperature for 40 min. The mixture was poured into water and extracted with EtOAc (20 mL×2). The combined organic layers were washed with 3% aqueous HCl solution (20 mL), saturated aqueous NaHCO$_3$ solution (20 mL) and brine (20 mL) then dried over MgSO$_4$ and concentrated under reduced pressure. The residue was purified by column chromatography (Pet. ether/EtOAc, 50/1 to 30/1, v/v) to give (R)-2-(1,8-diethyl-1,3,4,9-tetrahydropyrano[3,4-b]indol-1-yl)acetaldehyde (292 mg, 58%) as a yellow oil.

LC-MS (Waters): R$_t$ 6.03 min; m/z calculated for C$_{17}$H$_{21}$NO$_2$[M+MeOH+Na]$^+$ 326.3. found 326.1.

20a: (R)-2-(1,8-diethyl-1,3,4,9-tetrahydropyrano[3,4-b]indol-1-yl)acetaldehyde oxime To a solution of intermediate C (50 mg, 0.184 mmol, 1.0 eq) in methanol (10 mL) and pyridine (1 mL) was added hydroxylamine hydrochloride (38.4 mg, 0.552 mmol, 3.0 eq) and the resulting mixture was stirred at room temperature for 4 h. The solvent was removed under reduced pressure and the residue was purified by column chromatography (Pet. ether/EtOAc, 50/1 to 30/1, v/v) to give (R)-2-(1,8-diethyl-1,3,4,9-tetrahydropyrano[3,4-b]indol-1-yl)acetaldehyde oxime (40 mg, 76%) as a yellow oil, $^1$H NMR spectroscopy revealed a ~1:1 mixture of isomers.

LC-MS (Agilent): R$_t$ 3.48 min; m/z calculated for C$_{17}$H$_{22}$N$_2$O$_2$[M+H]$^+$ 287.17. found 287.2.

$^1$H-NMR: (400 MHz, DMSO-d$_6$) δ (ppm): 10.8 (s, 0.5H), 10.5 (s, 1H), 10.4 (s, 0.5H), 7.25-7.22 (m, 1H), 7.16 (dd, J=6.8, 5.2 Hz, 0.5H), 6.94-6.87 (m, 2H), 6.58 (app t, J=4.4 Hz, 0.5H), 3.92 (m, 2H), 2.96-2.81 (m, 3.5H), 2.70-2.62 (m, 2.5H), 2.0 (m, 1H), 1.83 (m, 1H), 1.25 (m, 3H), 0.75 (t, J=7.2 Hz, 1.5H), 0.71 (t, J=7.2 Hz, 1.5H).

20b: (R)-2-(1,8-diethyl-1,3,4,9-tetrahydropyrano[3,4-b]indol-1-yl)acetaldehyde O-methyl oxime To a solution of intermediate C (50 mg, 0.184 mmol, 1.0 eq) in methanol (10 mL) and pyridine (1 mL) was added methylhydroxylamine hydrochloride (18.5 mg, 0.22 mmol, 1.2 eq) and the resulting mixture was stirred at room temperature for 4 h. The solvent was removed under reduced pressure and the residue was purified by column chromatography (Pet. ether/EtOAc, 50/1 to 30/1, v/v) to give (R)-2-(1,8-diethyl-1,3,4,9-tetrahydropyrano[3,4-b]indol-1-yl)acetaldehyde O-methyl oxime (50 mg, 91%) as a yellow solid, $^1$H NMR spectroscopy revealed a ~1:1 mixture of isomers.

LC-MS (Agilent): R$_t$ 3.52 min; m/z calculated for C$_{18}$H$_{24}$N$_2$O$_2$[M+H]$^+$ 301.18, [M+Na]$^+$ 323.4, found [M+H]$^+$ 301.2, [M+Na]$^+$ 323.2.

$^1$H-NMR (400 MHz, DMSO-d$_6$) δ (ppm): 10.5 (m, 1H), 7.25-7.20 (m, 1.5H), 6.94-6.88 (m, 2H), 6.62 (t, J=4.8 Hz, 0.5H), 3.91 (m, 2H), 3.77 (s, 1.5H), 3.67 (s, 1.5H), 2.96-2.82 (m, 3.5H), 2.73-2.63 (m, 2.5H), 1.96-2.05 (m, 1H), 1.90-1.75 (m, 1H), 1.25 (m, 3H), 0.75 (t, J=7.2 Hz, 1.5H), 0.71 (t, J=7.2 Hz, 1.5H).

Example 21

Formula 123—Compounds 21a & 21b

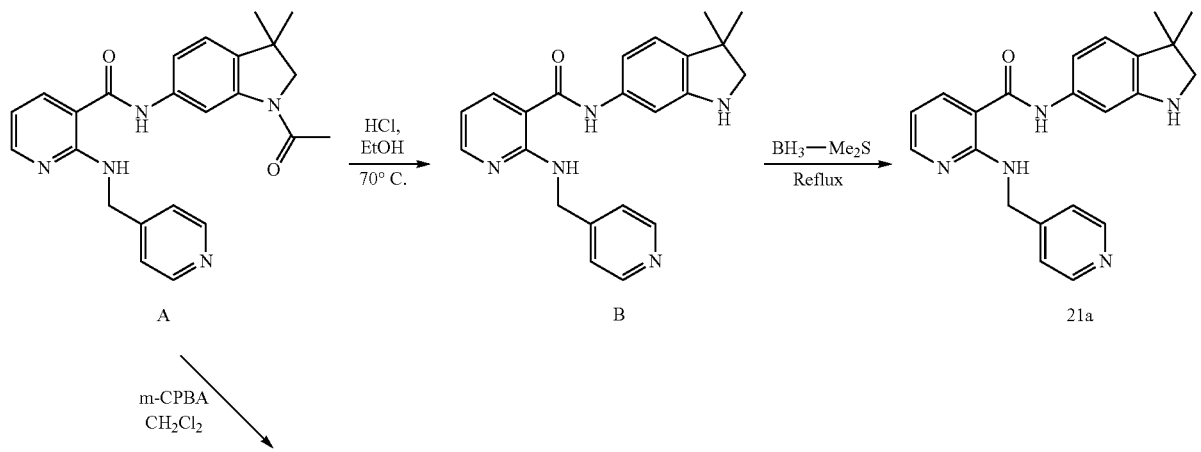

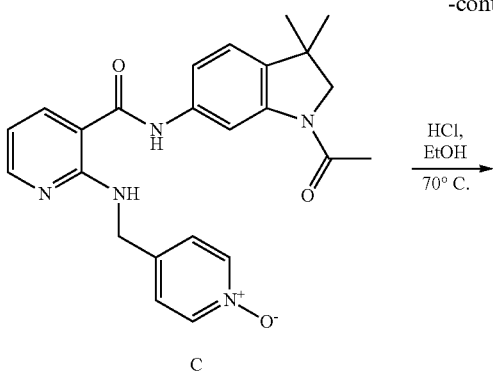
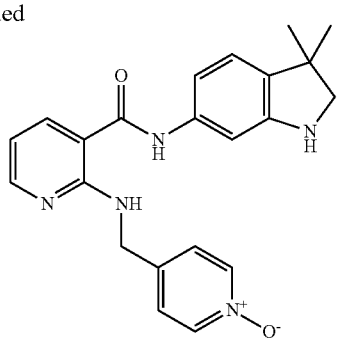

Compounds A and B can be synthesised according to the procedures described in US20030125339.

Intermediate C: 4-(((3-((1-Acetyl-3,3-dimethylindolin-6-yl)carbamoyl)pyridin-2-yl)amino)methyl)pyridine 1-oxide To a solution of compound A (200 mg, 0.48 mmol) in dry CH$_2$Cl$_2$ (10 mL) at 0° C. was added m-CPBA (166 mg, 0.96 mmol) in three portions and the mixture was allowed to warm to room temperature and stirred for 30 min. A 5% aqueous Na$_2$S$_2$O$_4$ solution was added and the mixture was extracted with EtOAc (3×20 mL). The combined organic layers were washed with a saturated aqueous solution of NaHCO$_3$, brine and dried over Na$_2$SO$_4$. The solvent was removed under reduced pressure and the residue was washed with ether to give 4-(((3-((1-acetyl-3,3-dimethylindolin-6-yl)carbamoyl)pyridin-2-yl)amino)methyl)pyridine 1-oxide (130 mg, 63%) as a pale yellow solid.

LC-MS (Agilent): R$_t$ 3.24 min; m/z calculated for C$_{24}$H$_{25}$N$_5$O$_3$ [M+H]$^+$ 432.49. found 432.2.2.

$^1$H NMR: (400 MHz, DMSO-d$_6$) δ (ppm): 10.3 (s, 1H), 8.48 (t, J=6.0 Hz, 1H), 8.35 (s 1H), 8.16-8.08 (m, 4H), 7.45 (dd, J=8.0, 1.2 Hz, 1H), 7.33 (d, J=6.8 Hz, 2H), 7.20 (d, J=8.0 Hz, 1H), 6.70 (m, 1H), 4.62 (d, J=6.0 Hz, 2H), 3.87 (s, 2H), 2.17 (s, 3H), 1.30 (s, 6H).

21a: 3,3-Dimethyl-N-((2-(pyridin-4-ylmethylamino)pyridin-3-yl)methyl)indolin-6-amine To a solution of BH$_3$.Me$_2$S (1M in THF, 10 mL, 10 mmol, 12.5 eq) was added intermediate B (300 mg, 0.8 mmol, 1.0 eq) at 0° C. under nitrogen. The mixture was allowed to warm to room temperature, stirred for 1 h then heated at reflux for 48 h. After cooling to 0° C., a 2 M aqueous HCl solution (20 mL) was added dropwise and the mixture was heated at 70° C. for 3 h then cooled to room temperature and washed with EtOAc (15 mL×3). The aqueous layer was basified to pH 8-9 with a 3 M aqueous NaOH solution and extracted with EtOAc (20 mL×3). The combined organic layers were washed with brine, dried over Na$_2$SO$_4$ and the solvent was removed under reduced pressure. The residue was purified by column chromatography (EtOAc/Pet. ether, 1/100 to 1/5, v/v) to give a light yellow sticky oil, which was further purified by preparative TLC (EtOAc/Pet. ether, 1/2, v/v) to give 3,3-dimethyl-N-((2-(pyridin-4-ylmethylamino)pyridin-3-yl)methyl)indolin-6-amine (22 mg, 8%) as a pale yellow solid.

LC-MS (Agilent): R$_t$ 3.19 min; m/z calculated for C$_{22}$H$_{25}$N$_5$ [M+H]$^+$ 360.47. found 360.2.

$^1$H NMR: (400 MHz, DMSO-d$_5$) δ (ppm): 8.93 (br s, 3H), 8.09 (br s, 2H), 7.84 (m, 2H), 7.14 (d, J=8.0 Hz, 1H), 6.91 (m, 1H), 6.69 (d, J=8.0 Hz, 1H), 6.61 (s, 1H), 5.18 (s, 2H), 4.37 (s, 2H), 3.38 (s, 3H), 3.17 (s, 1H), 1.29 (s, 6H).

21b: 4-(((3-((3,3-Dimethylindolin-6-yl)carbamoyl)pyridin-2-yl)amino)methyl)pyridine 1-oxide A mixture of intermediate C (120 mg, 0.28 mmol), concentrated HCl (5 mL) and ethanol (5 mL) was heated at 70° C. overnight and then allowed to cool to room temperature. The solvent was removed under reduced pressure and the residue was diluted with water and washed with EtOAc (3×10 mL). The aqueous phase was basified to pH 7-8 with a 3 M aqueous NaOH solution and extracted with EtOAc (3×20 mL). The combined organic layers were washed with brine and dried over Na$_2$SO$_4$. The solvent was removed under reduced pressure and the residue was washed with ether to give 4-(((3-((3,3-dimethylindolin-6-yl)carbamoyl)pyridin-2-yl)amino)methyl)pyridine 1-oxide (80 mg, 74%) a pale yellow solid.

LC-MS (Agilent): R$_t$ 2.85 min; m/z calculated for C$_{22}$H$_{23}$N$_5$O$_2$ [M+H]$^+$ 390.45. found 390.2.

$^1$H NMR: (400 MHz, DMSO-d$_6$) δ (ppm): 9.98 (s, 1H), 8.42 (t, J=6.0 Hz, 1H), 8.14 (m, 3H), 8.03 (d, J=6.8 Hz, 1H), 7.31 (d, J=6.4 Hz, 2H), 6.97-6.87 (m, 3H), 6.68 (dd J=4.8, 2.4 Hz, 1H), 5.55 (s, 1H), 4.62 (d, J=6.0 Hz, 2H), 3.19 (s, 2H), 1.22 (s, 6H).

Example 22

Formula 152—Compound 22a

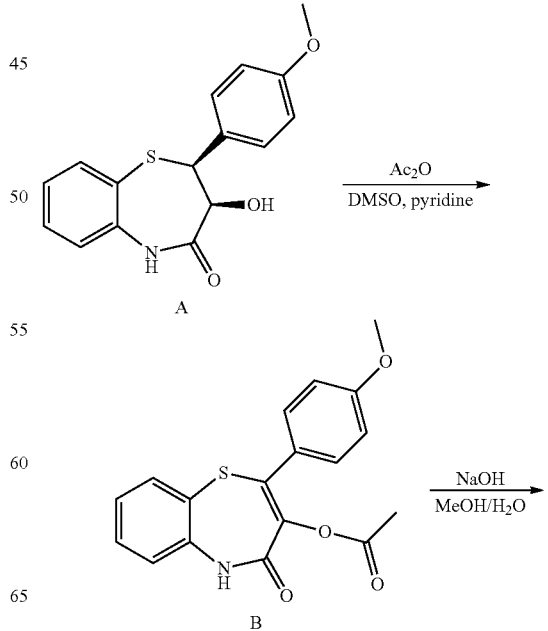

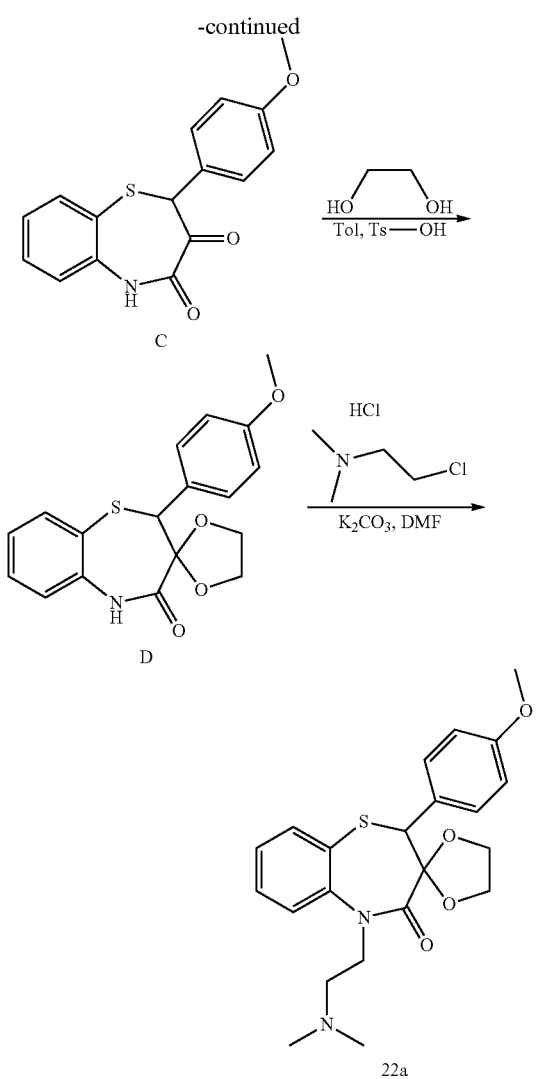

Intermediate C: 2-(4-Methoxyphenyl)benzo[b][1,4]thiazepine-3,4(2H,5H)-dione

Compound A was converted to 2-(4-methoxyphenyl)benzo[b][1,4]thiazepine-3,4(2H,5H)-dione in two steps using the procedure described in *Journal of Organic Chemistry*, 1996, 61, 8586.

Intermediate D: 2-(4-Methoxyphenyl)-2H-spiro[benzo[b][1,4]thiazepine-3,2'-[1,3]dioxolan]-4(5H)-one A mixture of intermediate C (798 mg, 2.7 mmol), ethane-1,2-diol (661 mg, 10.7 mmol) and Ts-OH (184 mg, 1.1 mmol) in toluene (40 mL) was heated at reflux in a Dean-Stark apparatus for 3 h. The mixture was poured into water and the aqueous solution was extracted with EtOAc. The organic layer was washed with brine, dried over $Na_2SO_4$ and concentrated under reduced pressure. The residue was purified by flash chromatography (Pet. ether/EtOAc, 4/1, v/v) to give 2-(4-methoxyphenyl)-2H-spiro[benzo[b][1,4]thiazepine-3,2'-[1,3]dioxolan]-4(5H)-one (390 mg, 43%) as a light yellow solid.

LC-MS (Agilent): $R_t$ 2.83 min; m/z calculated for $C_{18}H_{17}NO_4S$ [M+H]$^+$ 344.09. found 344.1.

22a: 5-(2-(Dimethylamino)ethyl)-2-(4-methoxyphenyl)-2H-spiro[benzo[b][1,4]thiazepine-3,2'-[1,3]dioxolan]-4(5H)-one To a mixture of intermediate D (200 mg, 0.6 mmol) and $K_2CO_3$ (241 mg, 1.7 mmol) in DMF (5 mL) was added 2-chloro-N,N-dimethylethanamine hydrochloride (101 mg, 0.7 mmol). The mixture was stirred at 60° C. for 6 h then cooled to room temperature and poured into water. The aqueous mixture was extracted with EtOAc and the organic layer was washed with brine, dried over $Na_2SO_4$ and concentrated under reduced pressure. The residue was purified by flash chromatography ($CH_2Cl_2$/MeOH, 20:1, v/v) to give 5-(2-(dimethylamino)ethyl)-2-(4-methoxyphenyl)-2H-spiro[benzo[b][1,4]thiazepine-3,2'-[1,3]dioxolan]-4(5H)-one (120 mg, 50%) as a white solid.

LC-MS (Agilent): $R_t$ 2.91 min; m/z calculated for $C_{22}H_{26}N_2O_4S$ [M+H]$^+$ 415.16. found 415.2.

$^1$H NMR: (400 MHz, DMSO-$d_6$) δ (ppm): 7.51 (d, J=8.8 Hz, 2H), 7.44 (d, J=7.2 Hz, 1H), 7.33 (m, 2H), 7.07 (m, 1H), 6.88 (d, J=8.8 Hz, 2H), 5.41 (s, 1H), 3.82-4.13 (m, 6H), 3.70 (s, 3H), 2.30-2.46 (m, 2H), 2.17 (s, 6H).

Example 23

Formula 104—Compounds 23a & 23b

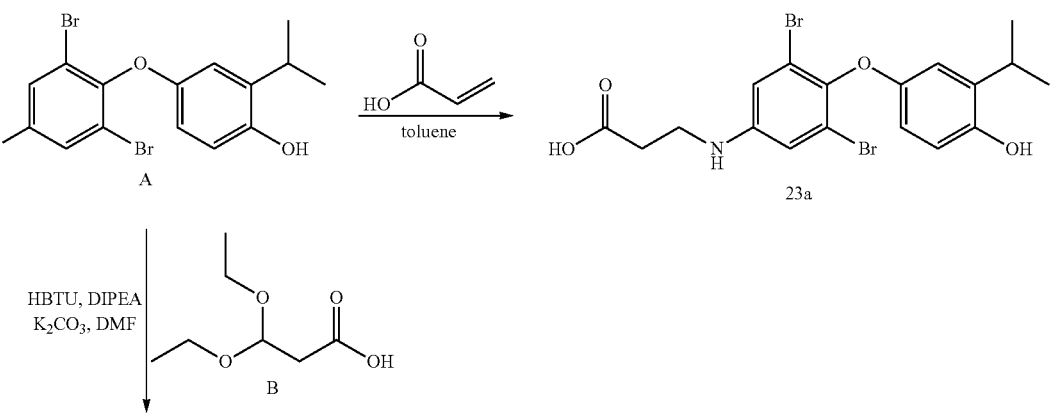

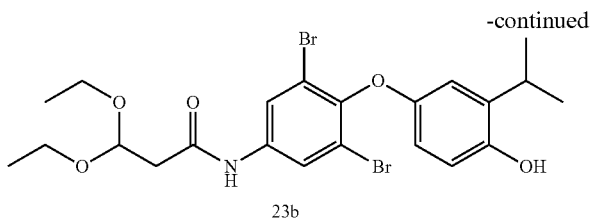
23b

Compound A can be synthesised according to the procedure described in WO2003039456. Compound B can be synthesised according to the procedure described in *J. Med. Chem.* 2005, 48, 306.

23a: 3-(3,5-Dibromo-4-(4-hydroxy-3 isopropylphenoxy)phenylamino) propanoic acid A solution of compound A (200 mg, 0.5 mmol, 1.0 eq) and acrylic acid (54 mg, 0.75 mmol, 1.5 eq) in toluene (2 mL) was heated at 100° C. in a sealed steel tube overnight. The reaction mixture was cooled to room temperature and concentrated under reduced pressure. The residue was purified by column chromatography (CH$_2$Cl$_2$/MeOH, 20/1, v/v) to give 3-(3,5-dibromo-4-(4-hydroxy-3-isopropylphenoxy)phenylamino) propanoic acid (60 mg, 25%) as a white solid.

LC-MS (Agilent): R$_t$ 3.40 min; m/z calculated for C$_{18}$H$_{19}$Br$_2$NO$_4$ [M+H]$^+$ 473.97. found 474.0.

$^1$H NMR: (400 MHz, DMSO-d$_6$) δ (ppm): 8.95 (s, 1H), 6.88 (s, 2H), 6.65-6.62 (m, 2H), 6.26-6.23 (dd, J=8.4, 2.8 Hz, 1H), 6.16-6.13 (m, 1H), 3.24 (m, 2H), 3.17 (sept, J=7.2 Hz, 1H), 2.49 (t, J=6.8 Hz, 2H), 1.10 (d, J=7.2 Hz, 6H).

23b: N-(4-(4-Hydroxy-3-isopropylphenoxy)-3,5-dibromophenyl)-3,3-diethoxypropanamide To a solution of compound A (202 mg, 1.25 mmol, 1.0 eq) in DMF (20 mL) was added HBTU (592 mg, 1.56 mmol, 1.25 eq) and DIPEA (323 mg, 2.50 mmol, 2.0 eq) and the mixture was stirred at room temperature for 30 min. Compound B (500 mg, 1.25 mmol, 1.0 eq) and K$_2$CO$_3$ (172 mg, 1.25 mmol, 1.0 eq) were then added and stirring was continued at room temperature overnight. Water (30 mL) was added and the mixture was extracted with EtOAc (20 mL×3). The combined organic layers were washed with water (50 mL), a saturated aqueous solution of Na$_2$CO$_3$ (50 mL), brine (50 mL) then dried over Na$_2$SO$_4$. The solvent was removed under reduced pressure and the residue was purified by column chromatography (Pet. ether/EtOAc, 7/1, v/v) to give N-(4-(4-hydroxy-3-isopropylphenoxy)-3,5-dibromophenyl)-3,3-diethoxypropanamide (72 mg, 15%) as a yellow solid.

LC-MS (Agilent): R$_t$ 3.69 min; m/z calculated for C$_{22}$H$_{27}$Br$_2$NO$_5$ [M+Na]$^+$ 566.0, 568.0. found 566.0, 568.0.

$^1$H NMR: (400 MHz, DMSO-d$_6$) δ (ppm): 10.3 (s, 1H), 9.05 (s, 1H), 7.98 (s, 2H), 6.66 (m, 2H), 6.27 (dd, J=8.8, 3.2 Hz, 1H), 4.92 (t, J=5.6 Hz, 1H), 3.66-3.59 (m, 2H), 3.54-3.46 (m, 2H), 3.15 (pent, J=7.2 Hz, 1H), 2.65-2.64 (d, J=5.6 Hz, 2H), 1.13-1.10 (m, 12H).

Example 24

Formula 3—Compounds 24a & 24b

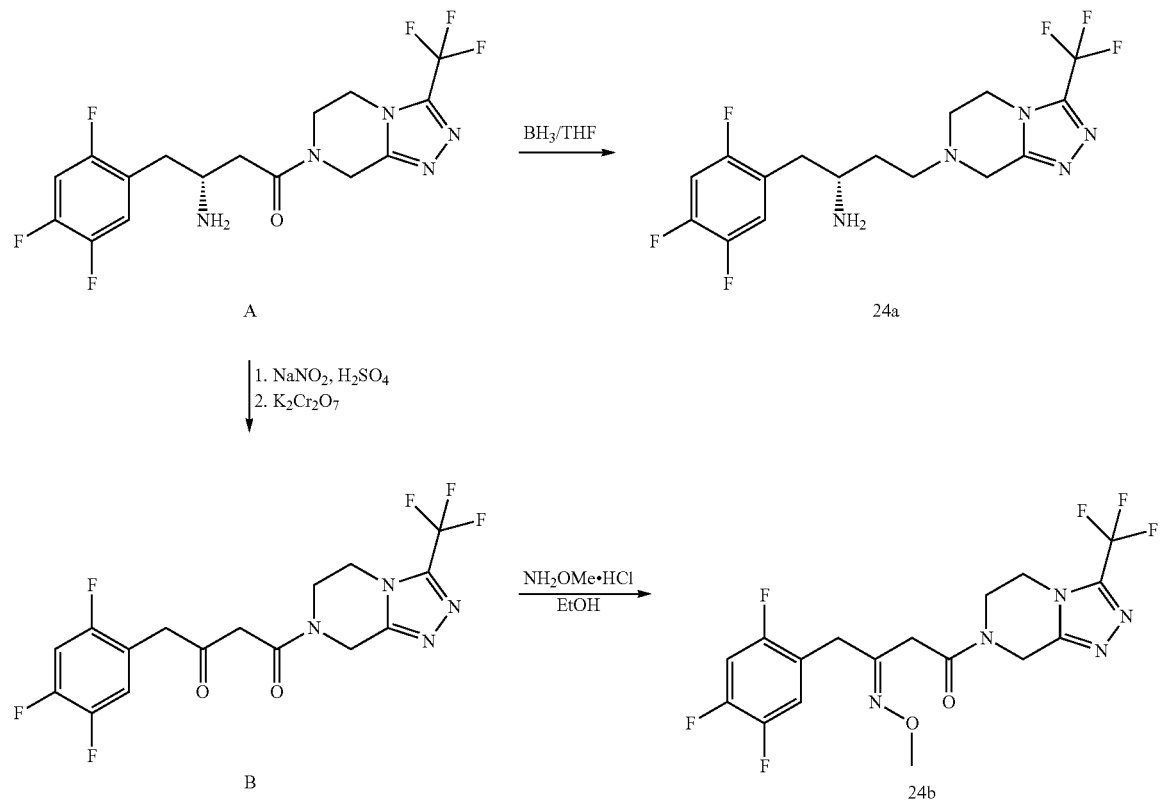

Intermediate B: 1-(3-(Trifluoromethyl)-5,6-dihydro-[1,2,4]triazolo[4,3-a]pyrazin-7(8H)-yl)-4-(2,4,5-trifluorophenyl)butane-1,3-dione Intermediate B can be obtained in two steps from compound A according to the procedure described in WO2010122578.

24a: (R)-4-(3-(Trifluoromethyl)-5,6-dihydro-[1,2,4]triazolo[4,3-a]pyrazin-7(8H)-yl)-1-(2,4,5-trifluorophenyl)butan-2-amine To a stirred solution of compound A (500 mg, 1.25 mmol) in THF (50 mL) at room temperature was added a 1.0 M solution of $BH_3 \cdot THF$ in THF (5.75 mL, 5.75 mmol) and the resulting mixture was stirred at room temperature overnight. The reaction was slowly quenched by dropwise addition of methanol (10 mL) followed by addition of a 0.5 M aqueous HCl solution (5 mL). The mixture was extracted with EtOAc (50 mL×3) and the combined organic layers were dried over $Na_2SO_4$ and concentrated under reduced pressure to give a solid. The crude product was washed with $CH_2Cl_2$ and THF to give (R)-4-(3-(trifluoromethyl)-5,6-dihydro-[1,2,4]triazolo[4,3-a]pyrazin-7(8H)-yl)-1-(2,4,5-trifluorophenyl)butan-2-amine (68 mg, 14%) as a white solid.

LC-MS (Agilent): $R_t$ 2.98 min; m/z calculated for $C_{16}H_{17}F_6N_5[M+H]^+$ 394.14. found 394.1.

$^1H$ NMR: (400 MHz, $CD_3OD$) δ (ppm): 7.35 (m, 1H), 7.24 (m, 1H), 4.26 (t, J=5.6 Hz, 2H), 3.94 (AB, J=15.2 Hz, 1H), 3.87 (AB, J=15.6 Hz, 1H), 3.68 (m, 1H), 3.12-2.93 (m, 4H), 2.82 (m, 2H), 1.89 (m, 2H).

24b: 3-(Methoxyimino)-1-(3-(trifluoromethyl)-5,6-dihydro-[1,2,4]triazolo[4,3-a]pyrazin-7(8H)-yl)-4-(2,4,5-trifluorophenyl)butan-1-one To a stirred solution of intermediate B (93 mg, 0.23 mmol) in ethanol (5 mL) and pyridine (5 mL) was added O-methylhydroxylamine hydrochloride (30 mg, 0.35 mmol) and the resulting mixture was stirred at room temperature for 4 h. The solvent was removed under reduced pressure and the residue was dissolved in THF (5 mL) and $CH_2Cl_2$ (5 mL) then washed with a 2 M aqueous HCl solution and dried over $Na_2SO_4$. The solvent was removed under reduced pressure and the residue was purified by column chromatography ($CH_2Cl_2$/MeOH, 50/1 to 25/1, v/v) to give 3-(methoxyimino)-1-(3-(trifluoromethyl)-5,6-dihydro-[1,2,4]triazolo[4,3-a]pyrazin-7(8H)-yl)-4-(2,4,5-trifluorophenyl)butan-1-one (20 mg, 20%) as a white solid, HPLC analysis revealed a ~1:1 mixture of isomers.

LC-MS (Agilent): $R_t$ 3.36 min; m/z calculated for $C_{17}H_{15}F_6N_5O_2$ $[M+H]^+$ 436.11, $[M+Na]^+$ 458.1, found $[M+H]^+$ 436.1, $[M+Na]^+$ 458.1

$^1H$ NMR: (400 MHz, $CDCl_3$) δ (ppm): 7.14-7.07 (m, 1H), 6.94-6.90 (m, 1H), 5.04-4.90 (m, 2H), 4.18 (m, 2H), 4.12-3.94 (m, 2H), 3.91 (br s, 1H), 3.82 (br s, 1H), 3.78-3.70 (m, 1H), 3.65 (m, 2H), 3.49-3.40 (m, 1H), 3.37-3.31 (m, 1H).

Example 25

Formula 2—Compound 25a

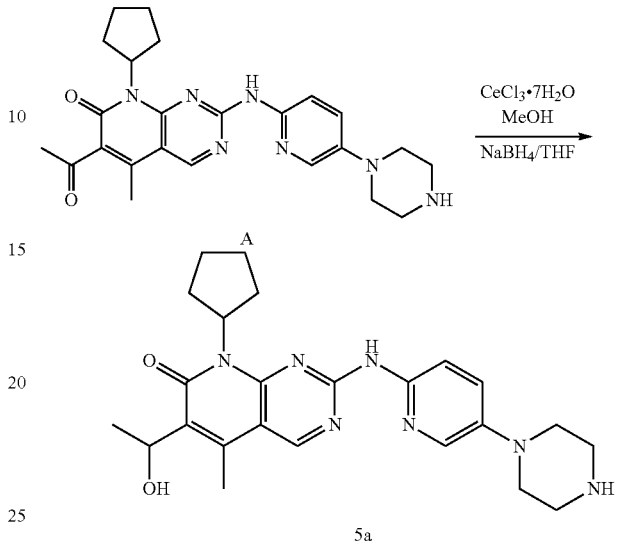

25a: 8-cyclopentyl-6-(1-hydroxyethyl)-5-methyl-2-(5-(piperazin-1-yl)pyridin-2-ylamino)pyrido[2,3-d]pyrimidin-7(8H)-one To a stirred solution of compound A (100 mg, 0.22 mmol, 1.0 eq) in MeOH (50 mL) and THF (20 mL) was added $CeCl_3 \cdot 7H_2O$ (164 mg, 0.44 mmol, 2.0 eq) then $NaBH_4$ (16.3 mg, 0.44 mmol, 2.0 eq). The resulting mixture was stirred at room temperature for 48 h and then quenched with a saturated aqueous solution of $NH_4Cl$ (10 mL). The aqueous layer was extracted with $CH_2Cl_2$ (10 mL×2) and the combined organic layers were washed with brine and dried over $MgSO_4$. The solvents were removed under reduced pressure and the residue was purified by flash chromatography ($CH_2Cl_2$/MeOH, 10/1, v/v) to give 8-cyclopentyl-6-(1-hydroxyethyl)-5-methyl-2-(5-(piperazin-1-yl)pyridin-2-ylamino)pyrido[2,3-d]pyrimidin-7(8H)-one (31 mg, 30%) as a yellow solid.

LC-MS (Agilent): $R_t$ 3.02 min; m/z calculated for $C_{24}H_{31}N_7O_2$ $[M+H]^+$ 450.25. found 450.3.

$^1H$ NMR: (400 MHz, DMSO-$d_6$) δ (ppm): 9.86 (s, 1H), 8.91 (s, 1H), 8.02 (d, J=2.8 Hz, 1H), 7.87 (d, J=9.2 Hz, 1H), 7.44 (dd, J=8.8, 2.8 Hz, 1H), 5.86 (m, 1H), 5.23 (m, 1H), 5.15 (d, J=5.6 Hz, 1H), 3.06 (m, 4H), 2.86 (m, 4H), 2.55 (s, 3H), 2.25 (m, 2H), 1.91 (m, 2H), 1.75 (m, 2H), 1.59 (m, 2H), 1.35 (d, J=6.4 Hz, 3H).

Example 26

Formula 142—Compounds 26a and 26b

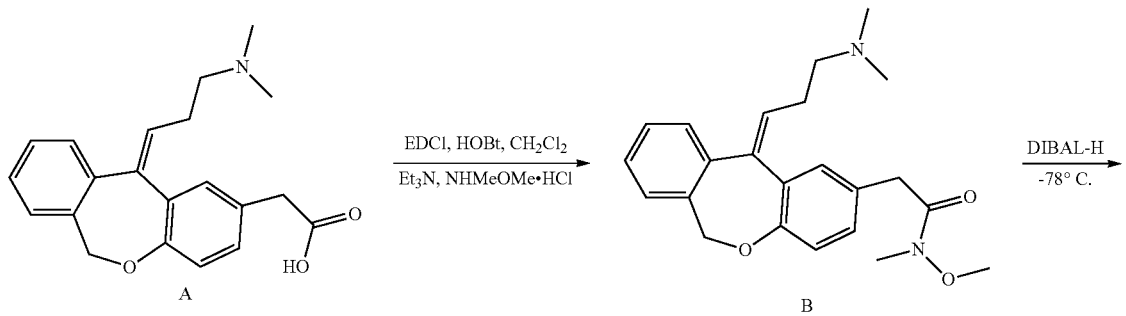

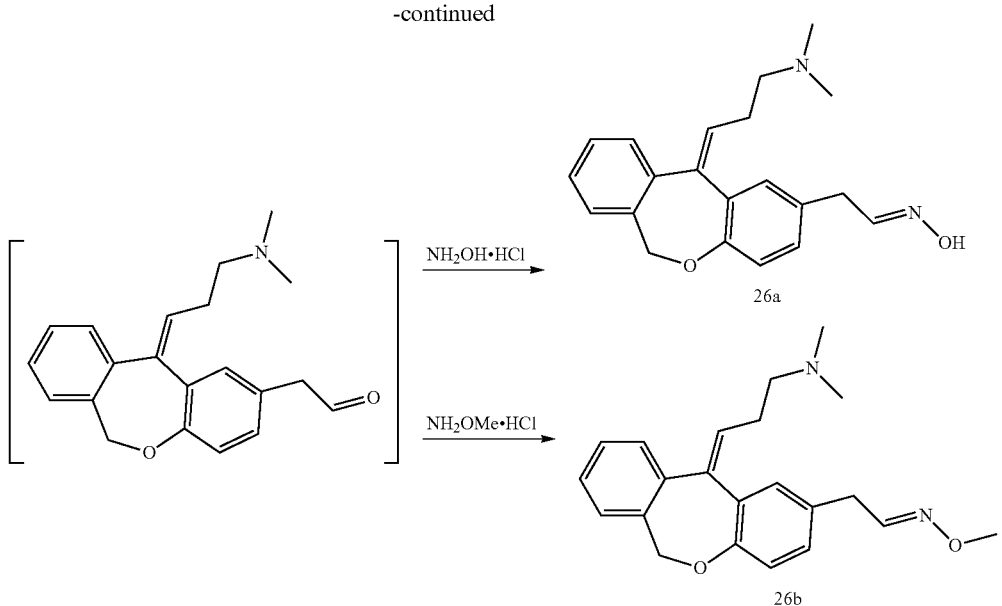

Intermediate B: (Z)-2-(11-(3-(Dimethylamino)propylidene)-6,1'-dihydrodibenzo[b,e]oxepin-2-yl)-N-methoxy-N-methylacetamide To a stirred solution of compound A (2.0 g, 5.9 mmol, 1.0 eq), EDCl (1.7 g, 8.9 mmol, 1.5 eq), HOBt (1.2 g, 8.9 mmol, 1.5 eq) and Et$_3$N (1.7 g, 17.7 mmol, 3.0 eq) in dry CH$_2$Cl$_2$ (100 mL) was added O, N-dimethylhydroxylamine hydrochloride (1.1 g, 11.8 mmol, 2.0 eq). The resulting mixture was stirred at room temperature for 16 h, diluted with CH$_2$Cl$_2$ (100 mL), washed with water (100 mL×2) and dried over MgSO$_4$. The solvent was removed under reduced pressure and the residue was purified by flash chromatography (CH$_2$Cl$_2$/MeOH, 100/1 to 10/1, v/v) to give (Z)-2-(11-(3-(dimethylamino)propylidene)-6,11-dihydrodibenzo[b,e]oxepin-2-yl)-N-methoxy-N-methylacetamide (800 mg, 37%) as a light yellow solid.

LC-MS (Waters): R$_t$ 4.57 min; m/z calculated for C$_{23}$H$_{28}$N$_2$O$_3$[M+H]$^+$ 381.21. found 381.1.

26a: (Z)-2-(11-(3-(Dimethylamino)propylidene)-6,1'-dihydrodibenzo[b,e]oxepin-2-yl)acetaldehyde oxime To a stirred solution of intermediate B (800 mg, 2.1 mmol, 1.0 eq) in dry CH$_2$Cl$_2$ (50 mL) was added a 1.0 M solution of DIBAl-H in hexanes (4.2 mL, 4.2 mmol, 2.0 eq) dropwise at −78° C. and the mixture was stirred at this temperature for 1 h. The reaction was quenched with MeOH, hydroxylamine hydrochloride (292 mg, 4.2 mmol, 2.0 eq) and Et$_3$N (636 mg, 6.3 mmol, 3.0 eq) were added and stirring was continued at room temperature for a further 5 h. The solvent was removed under reduced pressure and the residue was dissolved in CH$_2$Cl$_2$ (100 mL), washed with water (60 mL×2), brine (50 mL×2) and dried over Na$_2$SO$_4$. The solvent was removed under reduced pressure and the residue was purified by flash chromatography (CH$_2$Cl$_2$/MeOH, 100/1 to 10/1, v/v) to give (Z)-2-(11-(3-(dimethylamino)propylidene)-6,11-dihydrodibenzo[b,e]oxepin-2-yl)acetaldehyde oxime (95 mg, 13%) as a white solid, $^1$H-NMR spectroscopy revealed a ~1:1 mixture of isomers.

LC-MS (Agilent): R$_t$ 3.04 min; m/z calculated for C$_{21}$H$_{24}$N$_2$O$_2$ [M+H]$^+$ 337.18. found 337.2.

$^1$H NMR: (400 MHz, DMSO-d$_6$) δ (ppm): 11.0 (s, 0.5H), 10.6 (s, 0.5H), 7.40-7.25 (m, 4.5H), 7.04 (m, 2H), 6.78 (m, 1.5H), 5.68 (t, J=6.8 Hz, 1H), 5.20 (m, 2H), 3.53 (d, J=5.2 Hz, 1H), 3.18 (d, J=4.4 Hz, 0.5H), 2.48-2.39 (m, 4H), 2.11 (s, 6H).

26b: (Z)-2-(11-(3-(Dimethylamino)propylidene)-6,1'-dihydrodibenzo[b,e]oxepin-2-yl)acetaldehyde O-methyl oxime To a stirred solution of intermediate B (800 mg, 2.1 mmol, 1.0 eq) in dry CH$_2$Cl$_2$ (50 mL) was added a 1.0 M solution of DIBAl-H in hexanes (4.2 mL, 4.2 mmol, 2.0 eq) dropwise at −78° C. and the mixture was stirred at this temperature for 1 h. The reaction was quenched with MeOH, methoxylamine hydrochloride (359 mg, 4.2 mmol, 2.0 eq) and Et$_3$N (636 mg, 6.3 mmol, 3.0 eq) were added and stirring was continued at room temperature for a further 5 h. The solvent was removed under reduced pressure and the residue was dissolved in CH$_2$Cl$_2$ (100 mL), washed with water (60 mL×2), brine (50 mL×2) and dried over Na$_2$SO$_4$. The solvent was removed under reduced pressure and the residue was purified by flash chromatography (CH$_2$Cl$_2$/MeOH, 100/1 to 10/1, v/v) to give (Z)-2-(11-(3-(dimethylamino)propylidene)-6,11-dihydrodibenzo[b,e]oxepin-2-yl)acetaldehyde O-methyl oxime (68 mg, 9%) as a white solid, $^1$H-NMR spectroscopy revealed a ~1:1 mixture of isomers.

LC-MS (Agilent): R$_t$ 3.22 min; m/z calculated for C$_{22}$H$_{26}$N$_2$O$_2$ [M+H]$^+$ 351.2. found 351.2.

$^1$H NMR: (400 MHz, DMSO-d$_6$) δ (ppm): 7.49 (t, J=6.4 Hz, 0.5H), 7.38-7.25 (m, 4H), 7.02 (m, 2H), 6.87 (t, J=5.6 Hz, 0.5H), 6.80 (dd, J=8.0, 2.4 Hz, 1H), 5.67 (t, J=6.4 Hz, 1H), 5.15 (br s, 2H), 3.83 (s, 1.3H), 3.73 (s, 1.7H), 3.55 (d, J=5.6 Hz, 1H), 3.41 (d, J=6.4 Hz, 1H), 2.54 (m, 4H), 2.23 (s, 6H).

Example 27

Formula 29—Compound 27a

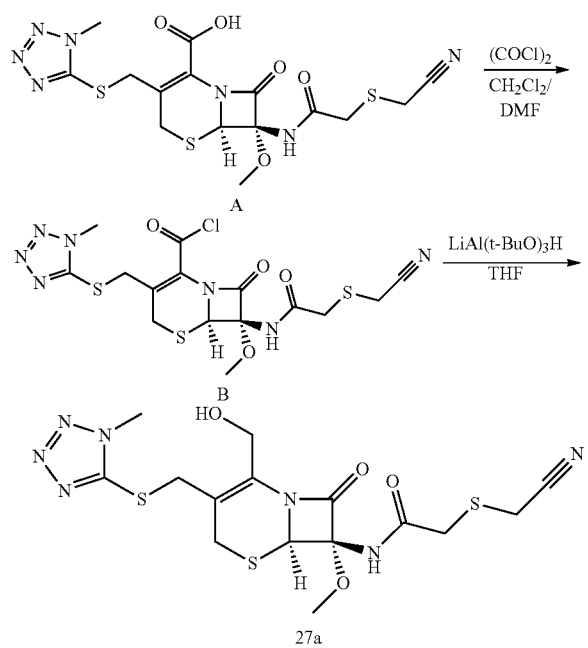

Intermediate B: (6R,7S)-7-(2-(Cyanomethylthio) acetamido)-7-methoxy-3-((1-methyl-1H-tetrazol-5-ylthio)methyl)-8-oxo-5-thia-1-aza-bicyclo[4.2.0]oct-2-ene-2-carbonyl chloride To a stirred suspension of compound A (10.0 g, 21.2 mmol, 1.0 eq) and DMF (0.5 mL) in dry $CH_2Cl_2$ (120 mL) at 0° C. under nitrogen was added a solution of oxalyl chloride (5.2 mL, 42.5 mmol) in $CH_2Cl_2$ (20 mL) over 20 min. The resulting mixture was stirred at 0° C. for 1 h to give a clear solution and stirring was continued for a further 3 h. The solvent was removed under reduced pressure keeping the temperature below 10° C. to give crude (6R,7S)-7-(2-(cyanomethylthio) acetamido)-7-methoxy-3-((1-methyl-1H-tetrazol-5-ylthio) methyl)-8-oxo-5-thia-1-aza-bicyclo[4.2.0]oct-2-ene-2-carbonyl chloride (12.4 g) as a yellow solid, which was used directly in the next step without purification.

LC-MS (Agilent): $R_t$ 1.25 min; m/z calculated for $C_{22}H_{27}Br_2NO_5$ $[M-Cl^-+HOCH_3]^+$ 486.06. found 485.9.

Example 27a 2-(Cyanomethylthio)-N-((6R,7S)-2-(hydroxymethyl)-7-methoxy-3-((1-methyl-1H-tetrazol-5-ylthio) methyl)-8-oxo-5-thia-1-aza-bicyclo[4.2.0]oct-2-en-7-yl)acetamide To a solution of intermediate B (12.4 g, 21.2 mmol, 1.0 eq) in THF (160 mL) at 0° C. under nitrogen was added a solution of $LiAl(O-tBu)_3H$ (10.3 g, 42.5 mmol, 2.0 eq) in THF (50 mL) over 30 min. The resulting mixture was stirred at 0° C. for 4 h and then poured into a cold 0.1M aqueous HCl solution (300 mL). The pH of the solution was adjusted to 2 with a saturated aqueous $NaHCO_3$ solution and the mixture was extracted with EtOAc (50 mL×3). The combined organic layers were washed with brine, dried over $Na_2SO_4$ and the solvent was removed under reduced pressure. The residue was purified by flash chromatography ($CH_2Cl_2$/MeOH, 50/1, v/v) to give 2-(cyanomethylthio)-N-((6R,7S)-2-(hydroxymethyl)-7-methoxy-3-((1-methyl-1H-tetrazol-5-ylthio)methyl)-8-oxo-5-thia-1-aza-bicyclo[4.2.0]oct-2-en-7-yl)acetamide (2.10 g, 22%) as a yellow solid.

LC-MS (Agilent): $R_t$ 0.91 min; m/z calculated for $C_{16}H_{13}N_7O_4S_3$ $[M+Na]^+$ 480.07. found 479.9.

$^1$H NMR: (400 MHz, DMSO-$d_6$) δ (ppm): 9.52 (s, 1H), 5.15 (t, J=5.6 Hz, 1H), 5.09 (s, 1H), 4.30 (m, 2H), 4.25 (d, J=13.6 Hz, 1H), 4.04 (d, J=13.6 Hz, 1H), 3.93 (s, 3H), 3.76 (m, 2H), 3.63 (d, J=17.6 Hz, 1H), 3.48 (br s, 2H), 3.42 (s, 3H), 3.31 (d, J=17.6 Hz, 1H).

Example 28

Formula 125—Compound 28a

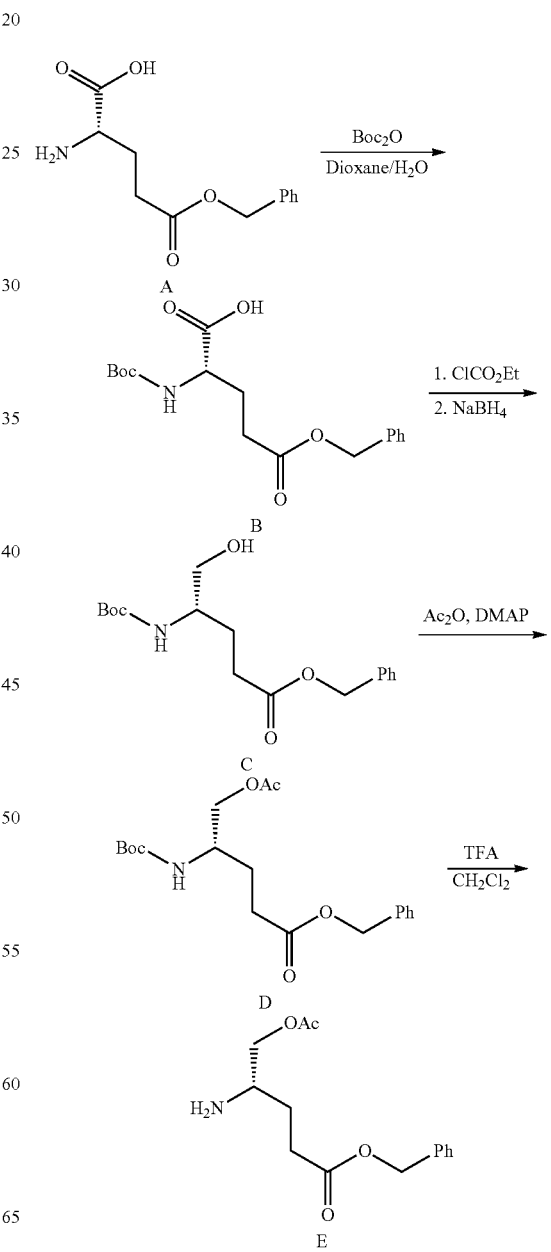

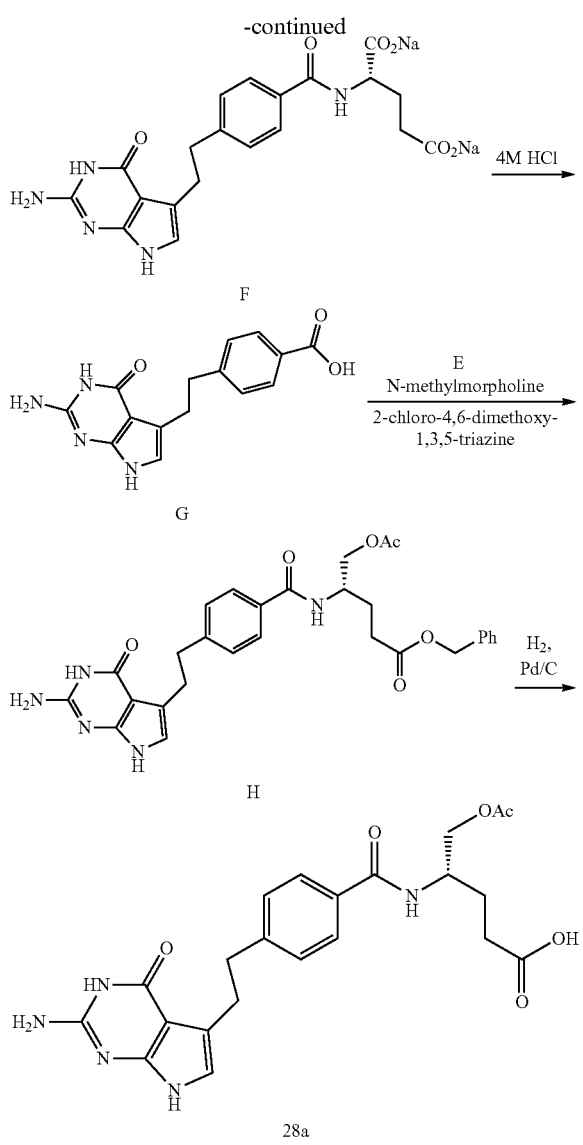

Intermediate B: (S)-5-(Benzyloxy)-2-(tert-butoxycarbonyl)-5-oxopentanoic acid To a solution of compound A (5.0 g, 21.1 mmol) in dixoane and water (1:1, 40 mL) at 0° C. was added Boc₂O (5.06 g, 23.1 mmol) and the mixture was stirred overnight. The solvent was removed under reduced pressure and the residue was diluted with water (30 mL), basified with Na₂CO₃ (0.7 g) and washed with EtOAc (3×20 mL). The aqueous layer was adjusted to pH 2-3 with a 5 M aqueous HCl solution and extracted with EtOAc (4×50 mL). The combined organic extracts were washed with brine, dried over Na₂SO₄ and the solvent was removed under reduced pressure to afford (S)-5-(benzyloxy)-2-(tert-butoxycarbonyl)-5-oxopentanoic acid (7.1 g, 100%) as a viscous colourless oil.

LC-MS (Agilent): $R_t$ 3.40 min; m/z calculated for $C_{17}H_{23}NO_6$ [M+Na]⁺ 360.15. found 360.1.

Intermediate C: (S)-Benzyl 4-(tert-butoxycarbonyl)-5-hydroxypentanoate

To a solution of intermediate B (6.5 g, 20 mmol) in THF (20 mL) under nitrogen at −10° C. was added N-methylmorphline (2.0 g, 20 mmol) and ethyl chloroformate (2.3 g, 20 mmol) and the mixture was stirred at −10° C. for 25 min. Sodium borohydride (2.2 g, 60 mmol) was then added to the mixture followed by a slow addition of MeOH (60 mL) over a period of 1 h at 0° C. The mixture was stirred at 0° C. for an additional 10 min and then quenched with a 1M aqueous HCl solution (20 mL). The organic solvents were removed under reduced pressure and the aqueous mixture was extracted with EtOAc. The combined organic extracts were washed with a 1M aqueous HCl solution, water and a 5% aqueous NaHCO₃ solution, dried over Na₂SO₄ and the solvent was removed under reduced pressure. The residue was purified by column chromatography (Pet. ether/EtOAc, 5/1, 2/1, 1/1, v/v) to give (S)-benzyl 4-(tert-butoxycarbonyl)-5-hydroxypentanoate (3.7 g, 60%) as a yellow oil.

LC-MS (Waters): $R_t$ 5.54 min; m/z calculated for $C_{17}H_{25}NO_5$ [M+Na]⁺ 346.17. found 346.0.

Intermediate D: (S)-Benzyl 5-acetoxy-4-(tert-butoxycarbonyl)pentanoate

To a stirred solution of intermediate C (3.6 g, 11 mmol) and DMAP (2.0 g, 14 mmol) in CH₂Cl₂ (15 mL) at room temperature was added acetic anhydride (1.7 g, 16 mmol) and the mixture was stirred for 1 h. The mixture was diluted with CH₂Cl₂ (20 mL), washed with a 2 M aqueous HCl solution and a 5% aqueous NaHCO₃ solution then dried over Na₂SO₄. The solvent was removed under reduced pressure to give (S)-benzyl 5-acetoxy-4-(tert-butoxycarbonyl)pentanoate (4.0 g, 98%) as a yellow oil, which was used without further purification.

LC-MS (Waters): $R_t$ 5.72 min; m/z calculated for $C_{19}H_{27}NO_6$ [M+Na]⁺ 388.17. found 388.0.

¹H NMR: (400 MHz, CDCl₃) δ (ppm): 7.38 (m, 5H), 5.15 (s, 2H), 4.61 (d, J=8.4 Hz, 1H), 4.09 (m, 2H), 3.92 (m, 1H), 2.49 (t, J=7.6 Hz, 2H), 2.09 (s, 3H), 1.94 (m, 1H), 1.73 (m, 1H), 1.45 (s, 9H).

Intermediate E: (S)-Benzyl 5-acetoxy-4-aminopentanoate

To a stirred solution of intermediate D (950 mg, 2.60 mmol) in CH₂Cl₂ (14 mL) at 0° C. was added TFA (14 mL) and the resulting mixture was stirred at 0° C. for 15 min, then at room temperature for a further 2 h. The solvent was removed under reduced pressure and the residue was co-evaporated with toluene to remove residual TFA to afford (S)-benzyl 5-acetoxy-4-aminopentanoate, which was used directly in the next step.

Intermediate G: 4-(2-(2-Amino-4-oxo-4,7-dihydro-3H-pyrrolo[2,3-d]pyrimidin-5-yl)ethyl)benzoic acid Compound F (1.40 g, 2.97 mmol) was suspended in a 4 M aqueous HCl solution (18 mL) and the mixture was heated at 100° C. for 5 days and then allowed to cool to room temperature. The precipitate was filtered and washed with hot water (30 mL) and EtOH (30 mL), dried in vacuo, then slurried with hot EtOH/H₂O (10:1, 30 mL×2). The solid was collected by filtration and dried in vacuo to afford 4-(2-(2-amino-4-oxo-4,7-dihydro-3H-pyrrolo[2,3-d]pyrimidin-5-yl)ethyl)benzoic acid (0.326 g, 37%) as a green solid.

LC-MS (Waters): $R_t$ 5.10 min; m/z calculated for $C_{15}H_{14}N_4O_3$ [M+H]⁺ 299.11. found 299.1.

H-NMR: (400 MHz, DMSO-d₆) δ (ppm): 11.6 (br s, 1H), 11.5 (s, 1H), 7.84 (d, J=8.0 Hz, 2H), 7.30 (d, J=8.0 Hz, 2H), 6.49 (s, 1H), 2.85-2.97 (m, 4H).

Intermediate H: (S)-Benzyl 5-acetoxy-4-(4-(2-(2-amino-4-oxo-4,7-dihydro-3H-pyrrolo[2,3-d]pyrimidin-5-yl)ethyl)benzamido)pentanoate To a suspension of intermediate G (0.50 g, 1.68 mmol) in dry DMF (10 mL) was added 2-chloro-4,6-dimethoxy-1,3,5-triazine (0.35 g, 2.01 mmol) and N-methylmorpholine (0.37 mL, 3.4 mmol) and the resulting mixture was stirred at room temperature for 3 h. A solution of intermediate E (assumed 2.5 mmol) and N-methylmorpholine (0.37 mL, 3.4 mmol) in DMF (5 mL) was added and stirring was continued at room temperature overnight. The solvent was removed under reduced pressure and the residue was purified by silica gel column chromatography (CH$_2$Cl$_2$/MeOH, 15/1 to 5/1) to afford (S)-benzyl 5-acetoxy-4-(4-(2-(2-amino-4-oxo-4,7-dihydro-3H-pyrrolo[2,3-d]pyrimidin-5-yl)ethyl)benzamido)pentanoate (0.70 g, 77%).

LC-MS (Waters): R$_t$ 6.14 min; m/z calculated for C$_{29}$H$_{31}$N$_6$O$_6$ [M+H]$^+$ 546.23. found 546.0.

Example 28a (S)-5-Acetoxy-4-(4-(2-(2-amino-4-oxo-4,7-dihydro-3H-pyrrolo[2,3-d]pyrimidin-5-yl)ethyl)benzamido)pentanoic acid A mixture of intermediate H (100 mg, 0.183 mmol) and 10% Pd/C (10 mg) in DMF and THF (1:1, 6 mL) was stirred under a hydrogen atmosphere (1 atm) overnight. The mixture was filtered through Celite and the filtrate was concentrated under reduced pressure. The residue was purified by preparative HPLC to give (S)-5-acetoxy-4-(4-(2-(2-amino-4-oxo-4,7-dihydro-3H-pyrrolo[2,3-d]pyrimidin-5-yl)ethyl)benzamido)pentanoic acid as a light green solid (4.9 mg, 6%).

LC-MS (Waters): R$_t$ 4.13 min; m/z calculated for C$_{22}$H$_{26}$N$_6$O$_6$ [M+H]$^+$ 456.18. found 456.0.

$^1$H NMR: (400 MHz, DMSO-d$_6$) δ (ppm): 10.9 (s, 1H), 10.6 (br s, 1H), 8.17 (d, J=8.4 Hz, 1H), 7.74 (d, J=8.0 Hz, 2H), 7.29 (d, J=8.0 Hz, 2H), 6.57 (br s, 2H), 6.40 (s, 1H), 4.24-3.90 (m, 3H), 2.97 (m, 2H), 2.86 (m, 2H), 2.28 (m, 2H), 2.0 (s, 3H), 1.91-1.65 (m, 2H).

Example 29

Formula 101—Compounds 29a & 29b

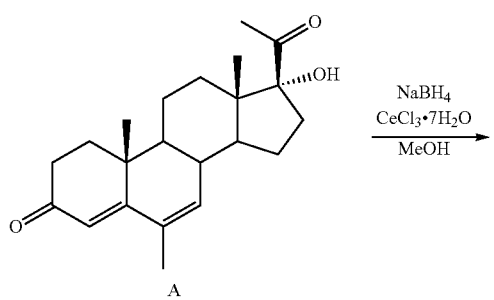

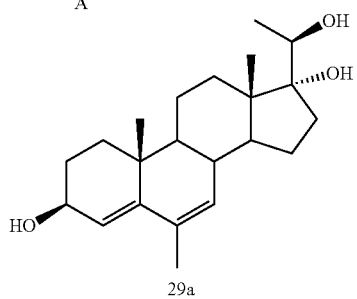

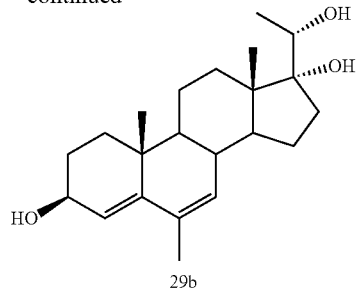

29a: (3S,10R,13S,17R)-17-((R)-1-hydroxyethyl)-6,10,13-trimethyl-2,3,8,9,10,11,12,13,14,15,16,17-dodecahydro-1H-cyclopenta[a]phenanthrene-3,17-diol 29b: (3S,10R,13S,17R)-17-((S)-1-hydroxyethyl)-6,10,13-trimethyl-2,3,8,9,10,11,12,13,14,15,16,17-dodecahydro-1H-cyclopenta[a]phenanthrene-3,17-diol To a solution of compound A (200 mg, 0.58 mmol, 1.0 eq) and cerium(w) chloride heptahydrate (653 mg, 1.75 mmol, 3.0 eq) in methanol (20 mL) at 0° C. was added sodium borohydride (66 mg, 1.75 mmol, 3.0 eq). The mixture was stirred for 5 min then diluted with water (50 mL) and extracted with CH$_2$Cl$_2$ (2×50 mL). The combined organic layers were dried over Na$_2$SO$_4$ and the solvent was removed under reduced pressure. The residue was purified by preparative HPLC to give two isomeric products. One isomer (40 mg, 20%) was obtained as a white solid and assigned as (3S,10R,13S,17R)-17-((R)-1-hydroxyethyl)-6,10,13-trimethyl-2,3,8,9,10,11,12,13,14,15,16,17-dodecahydro-1H-cyclopenta[a]phenanthrene-3,17-diol.

LC-MS (Agilent): R$_t$ 3.69 min; m/z calculated for C$_{22}$H$_{34}$O$_3$ [M+Na]$^+$ 369.25. found 369.2.

$^1$H NMR: (400 MHz, DMSO-d$_5$) δ (ppm): 5.47 (s, 1H), 5.43 (s, 1H), 4.72 (d, J=5.6 Hz, 1H), 4.12 (d, J=6.4 Hz, 1H), 4.07 (m, 1H), 3.61 (m, 1H), 3.54 (s, 1H), 1.96 (m, 2H), 1.90-1.65 (m, 6H), 1.65-1.35 (m, 6H), 1.20 (m, 3H), 1.02 (d, J=6.4 Hz, 3H), 0.89 (s, 3H), 0.85 (m, 1H), 0.69 (s, 3H).

The other isomer (40 mg, 20%) was obtained as a white solid and assigned as (3S,10R,13S,17R)-17-((S)-1-hydroxyethyl)-6,10,13-trimethyl-2,3,8,9,10,11,12,13,14,15,16,17-dodecahydro-1H-cyclopenta[a]phenanthrene-3,17-diol.

LC-MS (Agilent): R$_t$ 3.66 min; m/z calculated for C$_{22}$H$_{34}$O$_3$ [M+Na]$^+$ 369.25. found 369.2.

$^1$H NMR: (400 MHz, DMSO-d$_6$) δ (ppm): 5.46 (s, 1H), 5.43 (s, 1H), 4.72 (d, J=5.6 Hz, 1H), 4.07 (m, 1H), 4.01 (d, J=6.8 Hz, 1H), 3.75 (quint, J=6.8 Hz, 1H), 3.43 (s, 1H), 2.01 (m, 1H), 1.85 (m, 1H), 1.75-1.65 (m, 6H), 1.60-1.40 (m, 5H), 1.40-1.10 (m, 4H), 1.01 (d, J=6.0 Hz, 3H), 0.90 (s, 3H), 0.86 (m, 1H), 0.78 (s, 3H).

Example 30

Formula 93—Compound 30a

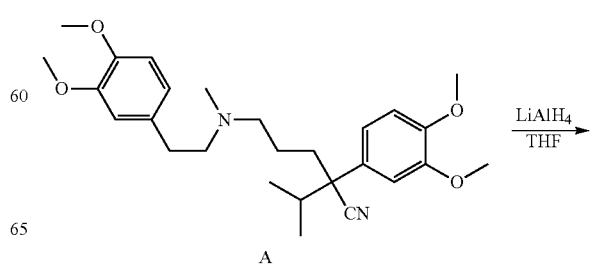

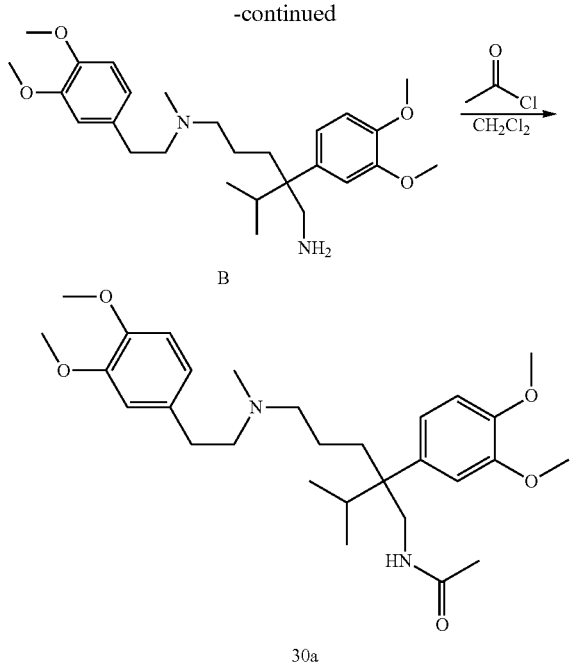

Intermediate B: N1-(3,4-Dimethoxyphenethyl)-4-(3,4-dimethoxyphenyl)-4-isopropyl-N1-methylpentane-1,5-diamine To a solution of compound A (300 mg, 0.66 mmol) in THF (30 mL) at room temperature was added LiAlH$_4$ (606 mg, 16 mmol) and the resulting mixture was heated at reflux for 10 h. The mixture was cooled to 0° C., diluted with Et$_2$O (150 mL) and the excess LiAlH$_4$ was quenched with a 2 M aqueous KOH solution (6 mL). The mixture was stirred for 30 min and extracted with EtOAc (3×20 mL). The combined organic extracts were dried over Na$_2$SO$_4$ and the solvent was removed under reduced pressure to give N1-(3,4-dimethoxyphenethyl)-4-(3,4-dimethoxyphenyl)-4-isopropyl-N1-methylpentane-1,5-diamine (284 mg, 100%), which was used without further purification.

LC-MS (Agilent): R$_t$ 3.24 min; m/z calculated for C$_{27}$H$_{42}$N$_2$O$_4$ [M+H]$^+$ 459.31. found 459.3.

30a: N-(5-((3,4-Dimethoxyphenethyl)(methyl)amino)-2-(3,4-dimethoxyphenyl)-2-isopropylpentyl) acetamide To a solution of intermediate B (284 mg, 0.62 mmol) and Et$_3$N (68.7 mg, 0.68 mmol) in anhydrous CH$_2$Cl$_2$ (20 mL) at 0° C. was added acetyl chloride (53.5 mg, 0.68 mmol). The mixture was stirred at room temperature for 1 h, washed with water and the organic layer was dried over Na$_2$SO$_4$. The solvent was removed under reduced pressure and the reside was purified by flash chromatography (Pet. ether/EtOAc, 1/1, v/v) to give N-(5-((3,4-dimethoxyphenethyl)(methyl)amino)-2-(3,4-dimethoxyphenyl)-2-isopropylpentyl)acetamide (21 mg, 7%) as a colourless oil.

LC-MS (Agilent): R$_t$ 3.24 min; m/z calculated for C$_{29}$H$_{44}$N$_2$O$_5$ [M+H]$^+$ 501.33. found 501.3.

$^1$H NMR: (400 MHz, CDCl$_3$) δ (ppm): 6.84-6.73 (m, 6H), 6.07 (m, 1H), 3.88 (s, 3H), 3.87 (s, 3H), 3.86 (s, 3H), 3.85 (s, 3H), 3.60 (dd, J=13.6, 4.4 Hz, 1H), 2.75 (m, 2H), 2.63 (m, 2H), 2.43 (m, 2H), 2.31 (s, 3H), 1.91 (s, 3H), 1.83 (m, 2H), 1.45-1.28 (m, 4H), 0.80 (d, J=6.8 Hz, 3H), 0.76 (d, J=6.8 Hz, 3H).

Example 31

Formula 127—Compounds 31a & 31b

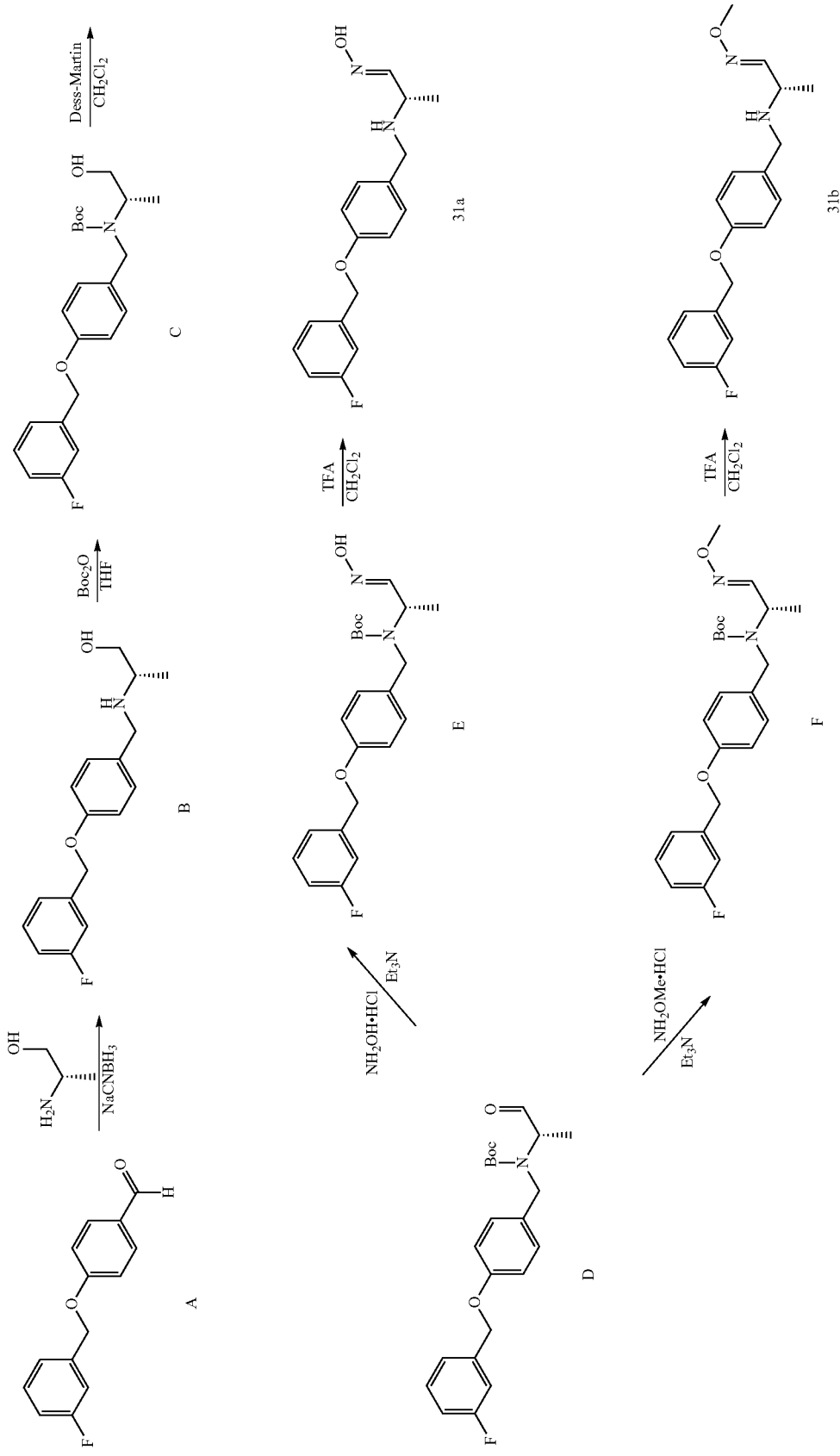

Compound A can be synthesised according to the procedure described in WO2009074478.

Intermediate B: (S)-2-(4-(3-Fluorobenzyloxy)benzylamino)propan-1-ol

To a solution of compound A (3.36 g, 15 mmol) in methanol (30 mL) was added (S)-2-aminopropan-1-ol (1.29 mL, 16.5 mmol) and the resulting mixture was stirred at room temperature overnight. To the mixture was added NaCNBH$_3$ (3.78 g, 60 mmol) and stirring was continued at room temperature for 3 h. The solvent was removed under reduced pressure and the residue was dissolved with EtOAc (300 mL) and washed with water (3×200 mL) then dried over Na$_2$SO$_4$. The solvent was removed under reduced pressure and the residue was purified by flash chromatography (CH$_2$Cl$_2$/MeOH, 25/1, v/v) to give (S)-2-(4-(3-fluorobenzyloxy)benzylamino)propan-1-ol (3.13 g, 72%) as an oil.
LC-MS (Agilent): R$_t$ 3.04 min; m/z calculated for C$_{17}$H$_{20}$FNO$_2$ [M+H]$^+$ 290.15. found 290.1.

Intermediate C: (S)-tert-Butyl 4-(3-fluorobenzyloxy)benzyl(1-hydroxypropan-2-yl)carbamate To a solution of intermediate B (3.13 g, 10.8 mmol) in anhydrous THF (30 mL) was added Boc$_2$O (3.46 mL, 16.2 mmol) and Et$_3$N (2.34 mL, 16.2 mmol) and the resulting mixture was stirred at room temperature for 4 h. The solvent was removed under reduced pressure and the residue was purified by flash chromatography (Pet. ether/EtOAc, 6/1, v/v) to give (S)-tert-butyl 4-(3-fluorobenzyloxy)benzyl(1-hydroxypropan-2-yl)carbamate (3.7 g, 80%) as an oil.
LC-MS (Agilent): R$_t$ 3.74 min; m/z calculated for C$_{22}$H$_{28}$FNO$_4$ [M+Na]$^+$ 412.2. found 412.2.

Intermediate D: (S)-tert-Butyl 4-(3-fluorobenzyloxy)benzyl(1-oxopropan-2-yl)carbamate To a solution of intermediate C (3.2 g, 8.22 mmol) in CH$_2$Cl$_2$ (50 mL) at room temperature was added Dess-Martin Periodinane (13.9 g, 32.9 mmol) and the resulting mixture was stirred for 2 h. The solvent was removed under reduced pressure and the residue was purified by flash chromatography (Pet. ether/EtOAc, 10/1, v/v) to give (S)-tert-butyl 4-(3-fluorobenzyloxy)benzyl(1-oxopropan-2-yl)carbamate (1.2 g, 38%) as a yellow solid.

Intermediate E: (S)-tert-Butyl 4-(3-fluorobenzyloxy)benzyl(1-(hydroxyimino)propan-2-yl)carbamate To a solution of intermediate D (550 mg, 1.42 mmol) in methanol (28 mL) at room temperature was added hydroxylamine hydrochloride (197 mg, 2.84 mmol) and Et$_3$N (0.41 mL, 2.94 mmol) and the resulting mixture was stirred for 2 h. The solvent was removed under reduced pressure and the residue was purified by flash chromatography (Pet. ether/EtOAc, 10/1, v/v) to give (S)-tert-butyl 4-(3-fluorobenzyloxy)benzyl(1-(hydroxyimino)propan-2-yl)carbamate (421 mg, 74%) as an oil.
LC-MS (Agilent): R$_t$ 3.85 min; m/z calculated for C$_{22}$H$_{27}$FN$_2$O$_4$ [M+Na]$^+$ 425.2. found 425.2.

31a: (S)-2-(4-(3-Fluorobenzyloxy)benzylamino)propanal oxime

Intermediate E (380 mg, 0.94 mmol) was dissolved in a 1M solution of TFA in CH$_2$Cl$_2$ (8.5 mL, 8.5 mmol) and the mixture was stirred at room temperature for 2 h. The solvent was removed under reduced pressure and the residue was purified by prepararative silica gel TLC (Pet. Ether/EtOAc, 3/2, v/v) to give (S)-2-(4-(3-fluorobenzyloxy)benzylamino)propanal oxime (27 mg, 10%) as a light yellow solid.
LC-MS (Agilent): R$_t$ 3.24 min; m/z calculated for C$_{17}$H$_{19}$FN$_2$O$_2$ [M+H]$^+$ 303.14. found 303.1.
$^1$H NMR: (400 MHz, CDCl$_3$) δ (ppm): 7.33 (m, 2H), 7.24 (m, 2H), 7.18-7.12 (m, 2H), 7.03 (m, 1H), 6.91 (m, 2H), 5.05 (s, 2H), 3.82 (dd, J=12.8, 4.8 Hz, 1H), 3.75 (m, 1H), 3.53 (quint, J=6.4 Hz, 1H), 1.27 (d, J=6.8 Hz, 3H).

Intermediate F: (S)-tert-Butyl 4-(3-fluorobenzyloxy)benzyl(1-(methoxyimino)propan-2-yl)carbamate To a solution of intermediate D (550 mg, 1.42 mmol) in methanol (28 mL) at room temperature was added methylhydroxylamine hydrochloride (197 mg, 2.36 mmol) and Et$_3$N (0.41 mL, 2.94 mmol) and the resulting mixture was stirred for 2 h. The solvent was removed under reduced pressure and the residue was purified by flash chromatography (Pet. ether/EtOAc, 10/1, v/v) to give (S)-tert-butyl 4-(3-fluorobenzyloxy)benzyl(1-(methoxyimino)propan-2-yl)carbamate (421 mg, 74%) as an oil.
LC-MS (Agilent): R$_t$ 3.97 min; m/z calculated for C$_{23}$H$_{29}$FN$_2$O$_4$ [M+Na]$^+$ 439.21. found 439.2.

31b: (S)-2-(4-(3-Fluorobenzyloxy)benzylamino)propanal O-methyl oxime

Intermediate F (450 mg, 1.08 mmol) was dissolved in a 1M solution of TFA in CH$_2$Cl$_2$ (9.72 mL, 9.72 mmol) and the mixture was stirred at room temperature for 2 h. The solvent was removed under reduced pressure and the residue was purified by preparative silica gel TLC (Pet. Ether/EtOAc, 4/1, v/v) to give (S)-2-(4-(3-fluorobenzyloxy)benzylamino)propanal O-methyl oxime (8 mg, 2%) as a light yellow solid.
LC-MS (Agilent): R$_t$ 3.21 min; m/z calculated for C$_{18}$H$_{21}$FN$_2$O$_2$ [M+Na]$^+$ 317.16. found 317.2.
$^1$H NMR: (400 MHz, CDCl$_3$) δ (ppm): 7.40-7.28 (m, 4H), 7.21-7.10 (m, 2H), 7.03 (m, 1H), 6.93 (m, 2H), 5.06 (s, 2H), 3.88 (s, 3H), 3.83-3.71 (m, 2H), 3.51 (quint, J=6.4 Hz, 1H), 1.31 (d, J=6.8 Hz, 3H).

Example 32

Formula 122—Compound 32a

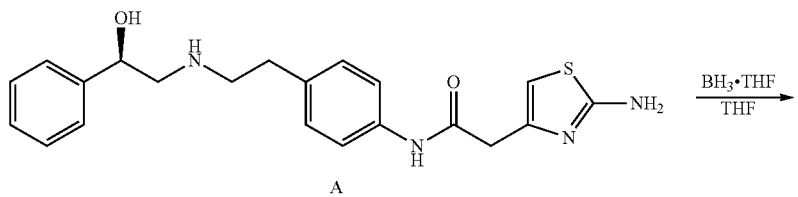

A

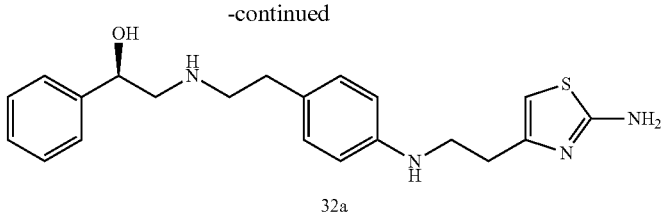

32a

32a: (R)-2-(4-(2-(2-Aminothiazol-4-yl)ethylamino)phenethylamino)-1-phenylethanol To a solution of compound A (300 mg, 0.76 mmol) in dry THF (15 mL) was added a 1M solution of BH$_3$.THF in THF (2.27 mL, 2.27 mmol) dropwise at 0° C. The mixture was stirred at 50° C. for 2 h and then allowed to cool to room temperature and stirring was continued overnight. The reaction was quenched with a 1M aqueous HCl solution (5 mL) and diluted with water (20 mL). Most of the THF was removed under reduced pressure and the aqueous mixture was adjusted to pH 10 with a 1M aqueous NaOH solution and extracted with CH$_2$Cl$_2$. The combined organic extracts were washed with brine, dried over Na$_2$SO$_4$ and the solvent was removed under reduced pressure. The residue was purified by column chromatography (CH$_2$Cl$_2$/MeOH/conc.NH$_4$OH, 10/1/0.05, v/v) followed by preparative HPLC to afford the product as a TFA salt (62 mg). An aliquot of the salt (25 mg) was free-based by dissolving in a saturated aqueous Na$_2$CO$_3$ solution (5 mL) and extracting with CH$_2$Cl$_2$. The organic layer was dried over Na$_2$SO$_4$ and concentrated under reduced pressure to give (R)-2-(4-(2-(2-aminothiazol-4-yl)ethylamino)phenethylamino)-1-phenylethanol (10 mg, 9%) as a white foam.

LC-MS (Agilent): R$_t$ 3.07 min; m/z calculated for C$_{21}$H$_{26}$N$_4$OS [M+H]$^+$ 383.18. found 383.2.

$^1$HNMR: (400 MHz, CDCl$_3$/CD$_3$OD, ~20:1) δ (ppm): 7.29 (m, 4H), 7.22 (m, 1H), 6.95 (d, J=8.4 Hz, 2H), 6.53 (d, J=8.4 Hz, 2H), 6.10 (s, 1H), 4.66 (dd, J=9.2, 4.0 Hz, 1H), 3.32 (t, J=6.8 Hz, 2H), 2.80-2.61 (m, 8H).

Example 33

Formula 131—Compound 33a

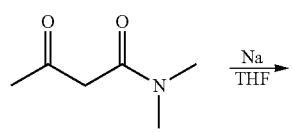

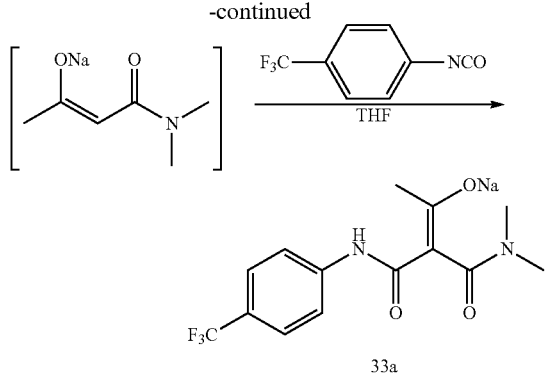

33a

33a: Sodium 3-(dimethylcarbamoyl)-4-oxo-4-(4-(trifluoromethyl)phenylamino)but-2-en-2-olate To a stirred suspension of sodium metal (0.25 g, 11 mmol, 1.1 eq) in dry THF (50 mL) was added N,N-dimethyl-3-oxobutanamide (1.3 g, 10 mmol, 1.0 eq) and the mixture was stirred overnight. To the resulting white suspension was added 4-(trifluoromethyl)phenyl isocyanate (1.8 g, 10 mmol, 1.0 eq) dropwise at room temperature. The mixture was then heated at reflux for 4 h, cooled to room temperature and diluted with MTBE (80 mL). The solid in the mixture was collected by filtration, washed with EtOAc (20 mL) and CH$_2$Cl$_2$ (20 mL) and dried under vacuum to give sodium 3-(dimethylcarbamoyl)-4-oxo-4-(4-(trifluoromethyl)phenylamino)but-2-en-2-olate (40 mg, 1%) as a yellow solid.

LC-MS (Agilent): R$_t$ 3.40 min; m/z calculated for C$_{14}$H$_{14}$F$_3$N$_2$NaO$_3$ [M+H]$^+$ 339.09. found 339.1.

$^1$H NMR: (400 MHz, DMSO-d$_6$) δ (ppm): 13.5 (s, 1H), 7.65 (d, J=8.8 Hz, 2H), 7.45 (d, J=8.4 Hz, 2H), 2.90 (s, 3H), 2.85 (s, 3H), 1.69 (s, 3H).

Semagacestat Example 34

Formula 130—Compounds 34a, 34b and 34c

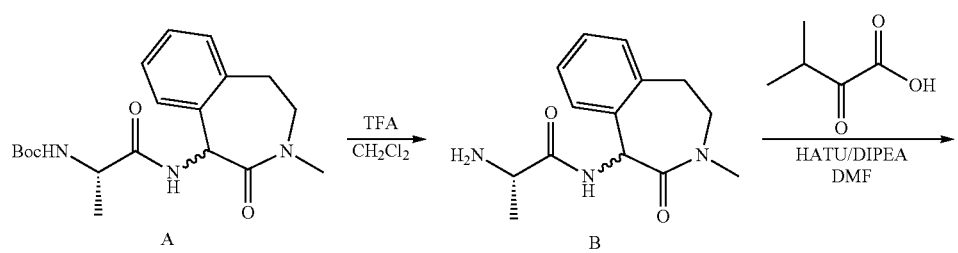

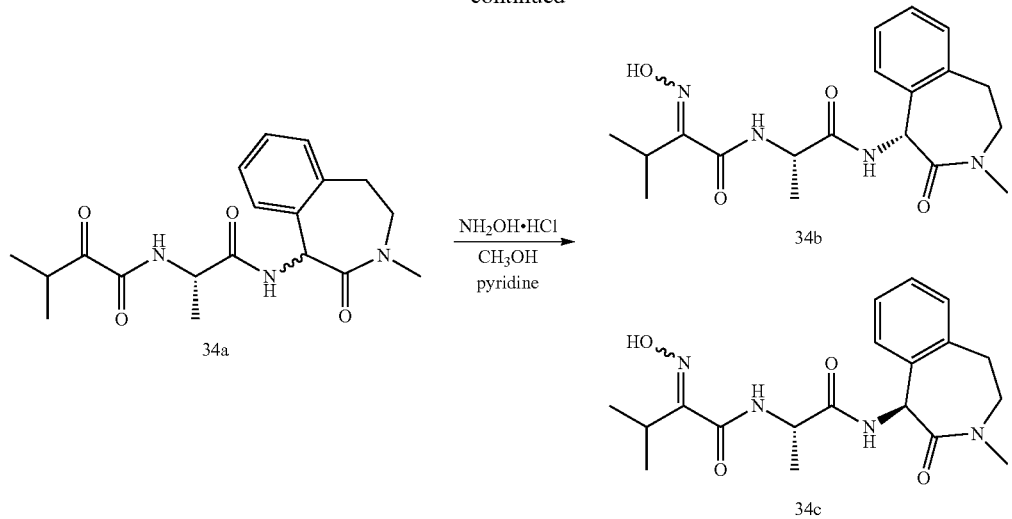

Compound A can be synthesised according to the procedure described in U.S. Pat. No. 7,468,365. It can be obtained as a ~1.5:1 mixture of diastereoisomers, determined by integration of the NMR spectrum.

Intermediate B: (S)-2-Amino-N-(3-methyl-2-oxo-2,3,4,5-tetrahydro-1H-benzo[d]azepin-1-yl)propanamide To a 1M solution of TFA in CH$_2$Cl$_2$ (30 mL, 30 mmol) at room temperature was added compound A (600 mg, 1.66 mmol) and the resulting mixture was stirred overnight. A saturated aqueous solution of Na$_2$CO$_3$ was slowly added to adjust the pH to 8-9. The organic layer was separated and the aqueous layer was extracted with CH$_2$Cl$_2$ (2×30 mL). The combined organic extracts were washed with brine, dried over Na$_2$SO$_4$ and the solvent was removed under reduced pressure to give (S)-2-amino-N-(3-methyl-2-oxo-2,3,4,5-tetrahydro-1H-benzo[d]azepin-1-yl)propanamide (278 mg, 64%) as a yellow solid.

LC-MS (Agilent): R$_t$ 3.90 min; m/z calculated for C$_{14}$H$_{19}$N$_3$O$_2$ [M+H]$^+$ 262.15. found 262.1.

34a: (S)-3-Methyl-N-(1-(3-methyl-2-oxo-2,3,4,5-tetrahydro-1H-benzo[d]azepin-1-ylamino)-1-oxopropan-2-yl)-2-oxobutanamide To a solution of 3-methyl-2-oxobutanoic acid (100 mg, 0.87 mmol, 1.0 eq) in dry DMF (25 mL) at room temperature was added HATU (413 mg, 0.87 mmol, 1.0 eq) and DIPEA (561 mg, 1.09 mmol, 1.25 eq) and the resulting mixture was stirred at room temperature for 30 min. Intermediate B (227 mg, 0.87 mmol, 1.0 eq) was then added and the mixture was stirred at room temperature overnight. The mixture was diluted with water (30 mL) and extracted with EtOAc (3×20 mL). The combined organic extracts were washed with water (50 mL), a saturated aqueous Na$_2$CO$_3$ solution (50 mL) and brine (50 mL) then dried over Na$_2$SO$_4$. The solvent was removed under reduced pressure and the residue was purified by column chromatography (CH$_2$Cl$_2$/MeOH, 50/1 to 15/1, v/v) to give (S)-3-Methyl-N-(1-(3-methyl-2-oxo-2,3,4,5-tetrahydro-1H-benzo[d]azepin-1-ylamino)-1-oxopropan-2-yl)-2-oxobutanamide (150 mg, 48%) as a white solid, $^1$H-NMR spectroscopy revealed the diastereoisomeric ratio to be ~2:1.

LC-MS (Agilent): R$_t$ 3.40 min; m/z calculated for C$_{13}$H$_{26}$N$_3$O$_4$ [M+H]$^+$ 360.18. found 360.2.

$^1$H-NMR: (400 MHz, DMSO-d$_6$) δ (ppm): 8.88 (d, J=8.0 Hz, 0.66H), 8.82 (d, J=8.0 Hz, 0.33H), 8.44 (d, J=7.6 Hz, 0.33H), 8.36 (d, J=7.6 Hz, 0.66H), 7.26-7.13 (m, 4H), 6.26-6.21 (m, 1H), 4.60 (m, 1H), 4.25 (m, 1H), 3.39 (m, 1H), 3.22-3.15 (m, 2H), 2.93 (m, 1H), 2.92 (m, 3H), 1.40 (m, 3H), 1.06 (d, J=6.8 Hz, 6H).

34b: 2-(Hydroxyimino)-3-methyl-N—((S)-1-((R)-3-methyl-2-oxo-2,3,4,5-tetrahydro-1H-benzo[d]azepin-1-ylamino)-1-oxopropan-2-yl)butanamide and 34c: 2-(Hydroxyimino)-3-methyl-N—((S)-1-((S)-3-methyl-2-oxo-2,3,4,5-tetrahydro-1H-benzo[d]azepin-1-ylamino)-1-oxopropan-2-yl)butanamide To a solution of example 33a (100 mg, 0.28 mmol, 1.0 eq) in methanol (20 mL) and pyridine (2 mL) was added hydroxylamine hydrochloride (23 mg, 0.33 mmol, 1.2 eq) and the resulting mixture was stirred at room temperature for 4 h. The solvent was removed under reduced pressure and the residue was purified by column chromatography (CH$_2$Cl$_2$/MeOH, 50/1 to 30/1, v/v) to separate the diastereoisomers. The minor diastereoisomer (25 mg, 24%) was obtained as a colourless oil and was assigned as 2-(hydroxyimino)-3-methyl-N—((S)-1-((R)-3-methyl-2-oxo-2,3,4,5-tetrahydro-1H-benzo[d]azepin-1-ylamino)-1-oxopropan-2-yl)butanamide, $^1$H-NMR spectroscopy revealed a ~1:1 mixture of oxime isomers.

LC-MS (Agilent): R$_t$ 3.43 min; m/z calculated for C$_{19}$H$_{26}$N$_4$O$_4$ [M+H]$^+$ 375.2. found 375.2.

$^1$H-NMR: (400 MHz, DMSO-d$_6$) δ (ppm): 11.6 (s, 0.5H), 11.5 (s, 0.5H), 8.30 (m, 1H), 8.22 (m, 1H), 7.25-7.13 (m, 4H), 6.21 (m, 1H), 4.55 (m, 1H), 4.24 (m, 1H), 3.42-3.38 (m, 1H), 3.32-3.28 (m, 1H), 3.22-3.16 (m, 2H), 2.91 (s, 1.5H), 2.90 (s, 1.5H), 1.37 (m, 3H), 1.15 (m, 6H).

The major diastereoisomer (45 mg, 43%) was obtained as a colourless oil and was assigned as 2-(hydroxyimino)-3-methyl-N—((S)-1-((S)-3-methyl-2-oxo-2,3,4,5-tetrahydro-1H-benzo[d]azepin-1-ylamino)-1-oxopropan-2-yl)butanamide, $^1$H-NMR spectroscopy revealed a ~1:1 mixture of oxime isomers.

LC-MS (Agilent): R$_t$ 3.41 min; m/z calculated for C$_{19}$H$_{26}$N$_4$O$_4$ [M+H]$^+$ 375.2. found 375.2.

¹H-NMR: (400 MHz, DMSO-d₆) δ (ppm): 11.1 (s, 0.5H), 11.06 (s, 0.5H), 8.80 (d, J=6.8 Hz, 0.5H), 8.68 (d, J=7.6 Hz, 0.5H), 8.27 (d, J=7.2 Hz, 0.5H), 8.23 (d, J=7.6 Hz, 0.5H), 7.31-7.11 (m, 4H), 6.23 (m, 1H), 4.62 (m, 0.5H), 4.50 (m, 0.5H), 4.24 (m, 1H), 3.41-3.36 (m, 1H), 3.18 (m, 2H), 2.92 (s, 3H), 2.68 (m, 1H), 1.33 (m, 3H), 1.15 (m, 6H).

Example 35

Formula 95—Comparative Compound 35a

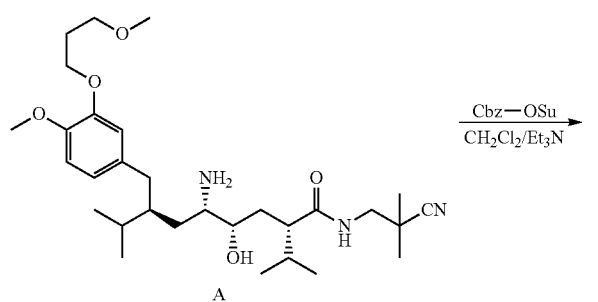

Intermediate B: Benzyl (3S,5S,6S,8S)-3-(4-methoxy-3-(3-methoxypropoxy)benzyl)-8-((3-amino-2,2-dimethyl-3-oxopropyl)carbamoyl)-6-hydroxy-2,9-dimethyldecan-5-ylcarbamate To a solution of compound A (0.99 g, 1.8 mmol) in CH₂Cl₂ (15 mL) was added Et₃N (364 mg, 3.6 mmol) and Cbz-OSu (673 mg, 2.7 mmol) and the resulting mixture was stirred at room temperature for 1 h. The mixture was diluted with EtOAc, washed with water and brine, dried over MgSO₄ and the solvent was removed under reduced pressure to give benzyl (3S,5S,6S,8S)-3-(4-methoxy-3-(3-methoxypropoxy)benzyl)-8-((3-amino-2,2-dimethyl-3-oxopropyl)carbamoyl)-6-hydroxy-2,9-dimethyldecan-5-ylcarbamate (1.1 g, 100%) as a colourless oil.

Intermediate C: (3S,5S,6S,8S)-8-(4-methoxy-3-(3-methoxypropoxy)benzyl)-3-((3-amino-2,2-dimethyl-3-oxopropyl)carbamoyl)-6-(benzyloxycarbonyl)-2,9-dimethyldecan-5-yl acetate To a solution of intermediate B (1.05 g, 1.8 mmol) in CH₂Cl₂ (15 mL) was added Et₃N (364 mg, 3.6 mmol) and acetic anhydride (364 mg, 2.7 mmol) and the resulting mixture was stirred at room temperature for 1 h. The mixture was diluted with EtOAc, washed with water and brine, dried over MgSO₄ and the solvent was removed under reduced pressure to give (3S,5S,6S,8S)-8-(4-methoxy-3-(3-methoxypropoxy)benzyl)-3-((3-amino-2,2-dimethyl-3-oxopropyl)carbamoyl)-6-(benzyloxycarbonyl)-2,9-dimethyldecan-5-yl acetate (1.3 g, 99%) as a colourless oil.

Intermediate D: (3S,5S,6S,8S)-8-(4-methoxy-3-(3-methoxypropoxy)benzyl)-6-(benzyloxycarbonyl)-3-((2-cyano-2-methylpropyl)carbamoyl)-2,9-dimethyldecan-5-yl acetate To a solution of intermediate C (1.3 g, 1.8 mmol) and Et₃N (546 mg, 5.4 mmol) in MeCN (10 mL) was added POCl₃ (364 mg, 2.7 mmol) at 0° C. The resulting mixture was stirred at room temperature for 30 min and poured onto ice. The mixture was extracted with EtOAc and the combined organic extracts were washed with water, brine and dried over MgSO₄. The solvent was removed under reduced pressure and the residue was purified by column chromatography (hexanes/EtOAc, 3/1, v/v) to give (3S,5S,6S,8S)-8-(4-methoxy-3-(3-methoxypropoxy)benzyl)-6-(benzyloxycarbonyl)-3-((2-cyano-2-methylpropyl)carbamoyl)-2,9-dimethyldecan-5-yl acetate (0.62 g, 49%) as a colourless oil.

LC-MS (Waters): $R_t$ 6.52 min; m/z calculated for $C_{40}H_{69}N_3O_8$ [M+H]⁺ 710.43. found 710.5.

Example 35a (S)-2-(((4S,5S)-4-((S)-2-(4-methoxy-3-(3-methoxypropoxy)benzyl)-3-methylbutyl)-2-oxooxazolidin-5-yl)methyl)-N-(2-cyano-2-methylpropyl)-3-methylbutanamide To a solution of intermediate D (25 mg, 0.035 mmol) in ethanol (10 mL) was added a 1M aqueous NaOH solution (5 mL) and the resulting mixture was heated at reflux for 3 h. The mixture was extracted with EtOAc and the combined organic extracts were washed with water, brine and dried over $MgSO_4$. The solvent was removed under reduced pressure and the residue was purified by preparative TLC (hexanes/EtOAc, 3/1, v/v) to give (S)-2-(((4S,5S)-4-((S)-2-(4-methoxy-3-(3-methoxypropoxy)benzyl)-3-methylbutyl)-2-oxooxazolidin-5-yl)methyl)-N-(2-cyano-2-methylpropyl)-3-methylbutanamide (12 mg, 61%) as a colourless oil.

LC-MS (Agilent): $R_t$ 3.55 min; m/z calculated for $C_{31}H_{49}N_3O_6$ $[M+H]^+$ 560.36. found 560.4.

$^1$H NMR: (400 MHz, DMSO-$d_6$) δ (ppm): 6.80 (d, J=1.6 Hz, 1H), 6.77 (d, J=8.4 Hz, 1H), 6.68 (dd, J=8.0, 1.6 Hz, 1H), 6.56 (app t, J=6.4 Hz, 1H), 6.36 (br s, 1H), 4.18 (t, J=6.4 Hz, 2H), 3.94 (ddd, J=11.6, 6.0, 2.0 Hz, 1H), 3.86 (s, 3H), 3.65 (t, J=6.4 Hz, 2H), 3.54 (dd, J=14.0, 7.2 Hz, 1H), 3.41 (s, 3H), 3.36 (dd, J=13.6, 6.0 Hz, 1H), 3.22 (m, 1H), 2.49 (m, 2H), 2.26 (m, 1H), 2.13 (m, 2H), 1.95-1.73 (m, 4H), 1.71-1.48 (m, 3H), 1.35 (s, 3H), 1.34 (s, 3H), 0.97-0.93 (m, 6H), 0.85-0.82 (m, 6H).

Example 36

Formula 117—Compounds 36a & 36b

Intermediate B: 2-((2S,6aS,6bR,7S,8aS,8bS,11aR,12aS,12bS)-2,6b-Difluoro-7-hydroxy-6a,8a,10,10-tetramethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoacetaldehyde To a solution of compound A (2.7 g, 6.0 mmol) in MeOH (60 mL) was added $Cu(OAc)_2$ (1.3 g, 7.2 mmol) and the mixture was stirred at room temperature overnight. The solids were removed by filtration and washed with EtOAc. The filtrate was concentrated under reduced pressure and the residue was dissolved in EtOAc (100 mL), washed with water (40 mL×2) then dried over $Na_2SO_4$. The solvent was removed under reduced pressure to give 2-((2S,6aS,6bR,7S,8aS,8bS,11aR,12aS,12bS)-2,6b-difluoro-7-hydroxy-6a,8a,10,10-tetramethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoacetaldehyde (2.8 g, 98%) as a white solid.

LC-MS (Agilent): $R_t$ 3.11 min; m/z calculated for $C_{24}H_{29}O_6$ $[M+MeOH+H]^+$ 483.2. found 483.2.

36a: 2-((2S,6aS,6bR,7S,8aS,8bS,11aR,12aS,12bS)-2,6b-Difluoro-7-hydroxy-6a,8a,10,10-tetramethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoacetaldehyde oxime A solution of intermediate B (450 mg, 1 mmol, 1.0 eq), hydroxylamine hydrochloride (80 mg, 1.1 mmol, 1.1 eq) and triethylamine (110 mg, 1.1 mmol, 1.1 eq) in MeOH (10 mL) was stirred at room temperature overnight. The reaction was

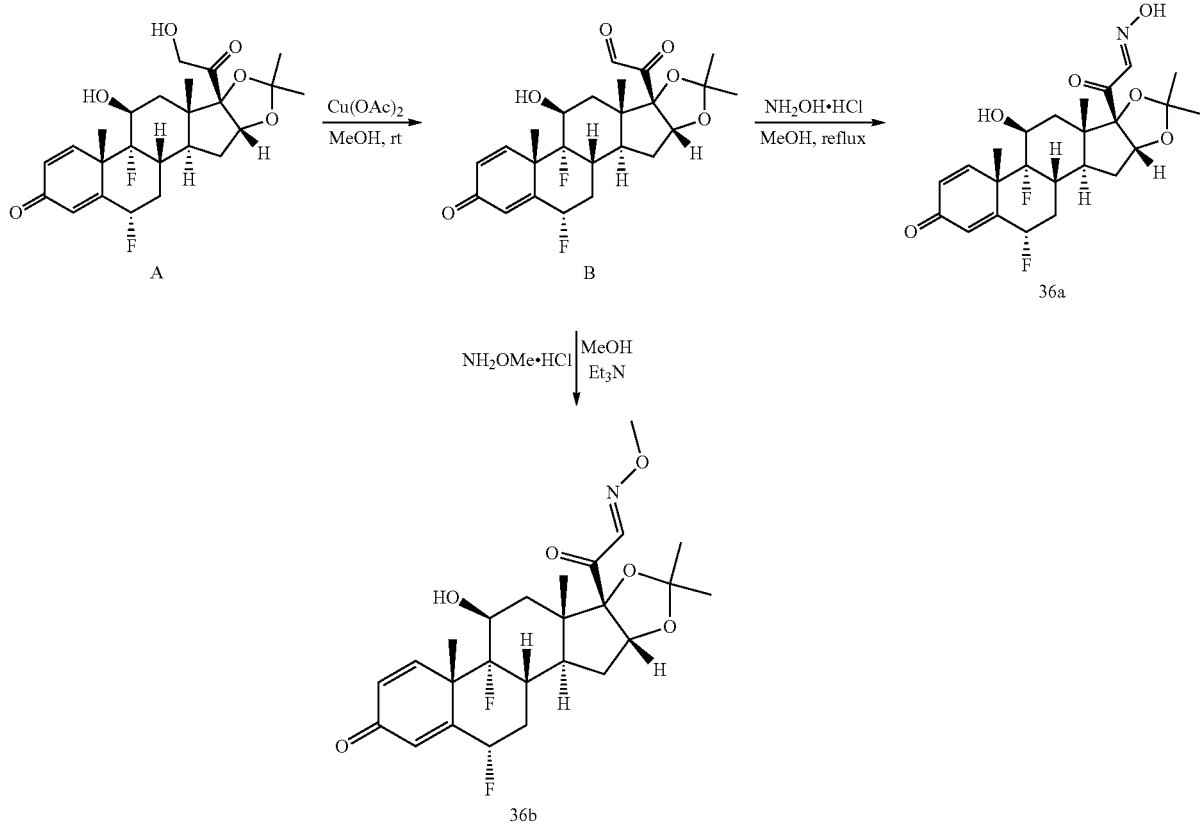

quenched with water (5 mL) and the solvent was removed under reduced pressure. The crude product was purified by preparative TLC (Pet. ether/EtOAc, 1/2, v/v) to give 2-((2S,6aS,6bR,7S,8aS,8bS,11aR,12aS,12bS)-2,6b-difluoro-7-hydroxy-6a,8a,10,10-tetramethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoacetaldehyde oxime (70 mg, 15%) as a white powder.

LC-MS (Agilent): $R_t$ 3.22 min; m/z calculated for $C_{24}H_{29}NO_6$ $[M+H]^+$ 466.2. found 466.1.

$^1$H NMR: (400 MHz, $CD_3OD$) δ (ppm): 8.02 (s, 1H), 7.33 (d, J=10.0 Hz, 1H), 6.39 (d, J=10.0 Hz, 1H), 6.32 (s, 1H), 5.51 (m, 1H), 5.15 (d, J=3.6 Hz, 1H), 4.32 (d, J=8.8 Hz, 1H), 2.71 (m, 1H), 2.26 (m, 3H), 1.69 (m, 4H), 1.59 (s, 3H), 1.45 (s, 3H), 1.14 (s, 3H), 0.95 (s, 3H).

36b: 2-((2S,6aS,6bR,7S,8aS,8bS,11aR,12aS,12bS)-2,6b-Difluoro-7-hydroxy-6a,8a,10,10-tetramethyl-4-oxo-2,4,6a,6b,7,8,8a,8b,11a,12,12a,12b-dodecahydro-1H-naphtho[2',1':4,5]indeno[1,2-d][1,3]-dioxol-8b-yl)-2-oxoacetaldehyde O-methyl oxime A solution of intermediate B (450 mg, 1 mmol, 1.0 eq), O-methylhydroxylamine hydrochloride (92 mg, 1.1 mmol, 1.1 eq) and triethylamine (110 mg, 1.1 mmol, 1.1 eq) in MeOH (10 mL) was stirred at room temperature overnight. The reaction was quenched with water (5 mL) and the MeOH was removed under reduced pressure. The crude product was collected by filtration and washed with water (5 mL). Purification by preparative TLC (Pet. ether/EtOAc, 1/1, v/v) then gave 2-((2S,6aS,6bR,7S,8aS,8bS,11aR,12aS,12bS)-2,6b-difluoro-7-hydroxy-6a,8a,10,10-tetramethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoacetaldehyde O-methyl oxime (70 mg, 15%) as a white powder.

LC-MS (Agilent): $R_t$ 3.31 min; m/z calculated for $C_{25}H_{31}NO_6$ $[M+H]^+$ 480.2. found 480.2.

$^1$H NMR: (400 MHz, $CD_3OD$) δ (ppm): 8.00 (s, 1H), 7.35 (d, J=10.0 Hz, 1H), 6.36 (d, J=10.0 Hz, 1H), 6.32 (s, 1H), 5.51 (m, 1H), 5.13 (d, J=4.8 Hz, 1H), 4.31 (d, J=9.2 Hz, 1H), 4.08 (s, 3H), 2.64 (m, 1H), 2.36 (m, 1H), 2.29 (m, 2H), 1.71 (m, 4H), 1.59 (s, 3H), 1.45 (s, 3H), 1.14 (s, 3H), 0.95 (s, 3H).

Methodology—Cresset

The compounds were analysed for field similarity to the parent. This was determined based on the conformation of the parent when the parent is in the active site. In some cases the conformation was determined using crystal structures of the parent in the active site. In some cases the conformation of the parent in the active site was a predicted conformation based on what information was available. In some cases the binding energies of the compounds were also calculated. The methodology used for these analyses are described in more detail below:

| Step | Details | Methodology | Output(s) |
|---|---|---|---|
| 1. | Background research: literature searching to identify key information regarding mechanism of action for the parent molecule and related therapeutics. | a) Journal papers and web-based information<br>b) Search of PDB database for relevant protein crystal structure(s) | c) X-ray crystal structure(s) of relevant proteins and small molecule ligands<br>d) Set of known actives with the same mechanism of action |
| 2. | Templating: identification of a key set of active molecules from within the therapeutic class, generation model for protein/ligand binding | a) Import the chemical structures of a set of known actives into FieldTemplater, generate a consensus template containing as many of the actives as possible<br>b) Output the template (set of proposed active conformations) and the individual active conformation of the parent structure. | c) Field Template - alignment of e.g. 5 known active molecules, to give hypothesis for interaction with protein<br>d) Active conformation for parent molecule - either from crystal structure or from Field Template<br>e) Docking model - model protein structure which can be used for calculation of interaction energies |
| 3. | FieldAlign analysis: calculation of Field-based similarity scores between analogues and template/parent | a) Load the template files from Step 2 a) into FieldAlign, load analogue structures, calculate best alignment and associated similarity score for each analogue.<br>b) Repeat with the single structure of the parent compound from Step 2 b) | c) Ranked scores for the proposed analogues based on the Field similarity score<br>d) Aligned best conformation for each analogue |

-continued

| Step | Details | Methodology | Output(s) |
|---|---|---|---|
| 4. | Prediction of binding energies: docking of poses from step 3 into crystal structure, calculation of interaction energies. | a) Take aligned analogues from Step 3 b) and load into Accelrys Discovery Studio.<br>b) Load protein crystal structure as found in 1 c), and prepare for docking (apply CHARMm force field, remove ligand from active site, define active site sphere<br>c) Calculate binding energies for analogues using flexible ligand optimisation under the CHARMm force field | d) Aligned conformations from step 3 b) docked into crystal structure with calculated energies<br>e) Ranking of analogues relative to parent structure |
| 5. | Assessment and ranking of analogues: generation of a consensus score based on similarities and binding energies. | a) Calculation of consensus score based on sum of ranks for each of the two alignments and the binding energy calculations | b) Ranked priority list for the proposed analogues |

The stereoisomeric identity (R vs S or E vs Z) of any group described in the following examples is that of the parent active unless otherwise indicated.

The compounds analysed in the following examples have been organised into bands depending on the results obtained in analysis of that compound. In an embodiment, of the invention the compound is any which falls with band A for a specific analysis for a specific formula. In another embodiment, the compound is anywhich falls within band A or band B for a specific analysis for a specific formula. In a further embodiment, the compound is anywhich falls within band A, band B or band C for a specific analysis for a specific formula.

Example 37

A range of structures have been assessed for their potential as analogues of oseltamivir. Oseltamivir is a neuraminidase used to treat flu. It acts by blocking the action of neuraminidase in releasing new virus particles from the surface of an infected cell. There are many x-ray crystal structures of neuraminidase, including several with bound inhibitors. The template for analysis was based on the 2HU4 structure of oseltamivir bound to viral neuraminidase.

For field similarity: A is over 80% similarity; B is 60-79% similarity and C is 30-59% similarity.

| Formula | Parent | Structure | Field similarity to parent |
|---|---|---|---|
| 162 | oseltamivir | V is $H(NH_2)$; L is N═CHMe; Z is CH-ethylene glycol acetal | B |
| 162 | oseltamivir | V is $H(NH_2)$; L is NHAc; Z is $CH_2OH$ | A |
| 162 | oseltamivir | V is $H(NH_2)$; L is N═CHMe; Z is $CH(OEt)_2$ | B |
| 162 | oseltamivir | V is $H(NH_2)$; L is N═CHMe; Z is CH═NOH | B |
| 162 | oseltamivir | V is $H(NH_2)$; L is N═CHMe; Z is C(O)H | B |
| 162 | oseltamivir | V is $H(NH_2)$; L is NHAc; Z is C(O)H | A |
| 162 | oseltamivir | V is $H(NH_2)$; L is NHAc; Z is CH-ethylene glycol acetal | B |
| 162 | oseltamivir | V is $H(NH_2)$; L is NHAc; Z is $CH(OEt)_2$ | B |
| 162 | oseltamivir | V is $H(NH_2)$; L is NHAc; Z is CH═NOH | A |
| 162 | oseltamivir | V is $H(NH_2)$; L is N═CHMe; Z is $CO_2Et$ | C |
| 162 | oseltamivir | V is $H(NH_2)$; L is N═CHMe; Z is $CO_2H$ | A |
| | oseltamivir | Comparative example: Formula 162 in which V is $NH_2$; L is NHAc; Z is CH═NOBn | B |

Example 38

A range of structures were tested for their potential as analogues of the fluoroquinolone antibitotics, such as ciprofloxacin. The fluoroquinolone antibitotics are active due to their ability to interact with bacterial DNA gyrase and/or topoisomerase II. DNA gyrase (or 'gyrase' for short) is an important protein involved in DNA replication within bacteria; mechanistically the gyrase is involved in relaxing 'supercoils' within the DNA strand which form ahead of the point of replication (by DNA polymerase). The fluoroquinolones intercalate the DNA and prevent decatenation of the replicated DNA from the gyrase.

Based on the 2XCT structure, we can see the complex of interactions which are made by the fluoroquinolone ligand: it is intercalating into the DNA strand, fitting in between two of the nucleosides, as well as chelating to a Manganese ion and interacting with the DNA binding site on the gyrase itself.

The complexity of these interactions meant that it was difficult to draw exact conclusions or make quantitative predictions of likely binding activity.

One driving factor for these compounds will be the ability to chelate the Manganese, which is the catalytic metal ion sitting in the active site of the gyrase. This ability was assessed by looking at the intensity of the negative electrostatic field at the Mananganese position; a proxy for this was to inspect the magnitude of the negative Field point being generated by any given analogue. The negative field point on the ring carbonyl for several known fluoroquinolone antibiotics are as follows:

| Antibiotic | Negative field point on ring carbonyl |
|---|---|
| Ciprofloxacin | −14.15 |
| Moxifloxacin | −16.80 |
| Gatifloxacin | −16.77 |
| Pefloxacin | −16.53 |

For the analogues, the values are as follows: A if the negative field point is between −20 and −15; B if the negative field point is between −10 and −15; and C if the negative field point is between −5 and −10.

| Formula | Parent | Structure | Negative field point on ring carbonyl or equivalent |
|---|---|---|---|
| 90 | Ciprofloxacin | G is =O; Z is $CO_2Me$ | A |
| 90 | Ciprofloxacin | G is =O; Z is CH=NOMe | C |
| 90 | Ciprofloxacin | G is =NOMe; Z is CH=NOMe | A |
| 90 | Ciprofloxacin | G is =O; Z is C(O)H | A |
| 90 | Ciprofloxacin | G is =O; Z is C(O)Et | A |

Example 39

A range of structures have been assessed for their potential as analogues of pregabalin. Pregabalin is a primary neuronal signalling molecule which mediates a number of processes within neuronal synapses. Its principle activity is as an inhibitory neurotramsitter and it appears to act through binding to a specific $Ca^{2+}$ ion channel in the central nervous system. There is no relevant structural biology information as pregabalin binds to an extracellular domain of the ion channel which has not been characterised by x-ray studies. Analysis was based on both looking at the quantitative field similarity of the analogues to a set of known active compounds, and also a more qualitative assessment of the field patterns shown by the molecules.

For field similarity: Field similarity A means a similarity of 80-85%; and B means a similarity of 70-79%.

| Formula | Parent | Structure | Field similarity to parent |
|---|---|---|---|
| 163 | pregabalin | W is $CH_2NH_2$; Z is $CH_2OH$ | A |
| 163 | pregabalin | W is $CH_2NH_2$; Z is C(O)H | B |

Example 40

Report 4

Penicillin Binding Proteins (named for their propensity for binding to penicillin and related compounds) are critical proteins involved in the final stages of the assembly of bacterial cell walls, where they catalyse the cross-linking of peptidoglycan units. Interfering with this process leads to irregularities in cell wall construction, with concomitant bactericidal effect. Penicillin Binding Protein 3 ("PBP-3") is a well characterised member of the group of PBP's and is the target for a variety of antibiotic agents. The β-lactam antibiotics (penicillins, penems, carbapenems, cephalosporins, etc) inactivate PBP's by covalently bonding to the catalytic serine residue within the PBP active site.

There are several examples in the PDB of compounds bound to PBP-3, including Aztreonam (PDB code: 3PBS), meropenem (PDB code: 3PBR), imipenem (3PBQ), ceftazidime (3PBO) and cefotaxime (2XD1). The analogues of meropenem were aligned with a template based on the (open ring) configuration of meropenem in 3PBR. The analogues of faropenem and imipenem were aligned with a template based on the (open ring) configuration of meropenem in 3PBQ. The analogues of cefmetazole and cefepime were aligned with a template based on the (open ring) configuration of cefotaxime in 2XD1.

For field similarity: A is over 90% similarity; B is 80-89% similarity; C is 70-79% similarity and D is 60-69% similarity.

For relative binding energy: A means binding energy is greater than the parent; B means binding energy is within 50 Kcal of the parent; C means the binding energy is within 100 Kcal and D means the binding energy is within 250 Kcal of the parent.

| Formula | Parent | Structure | Field similairt to parent (open ring) | Field similarity to parent (closed ring) | Binding energy relative to parent |
|---|---|---|---|---|---|
| 64 | Imipenem | Q is S; W is CH=NH; Z is $CO_2H$; G is =O | A | C | B |
| 64 | Imipenem | Q is S; W is CH=NH; Z is $CO_2H$; G is =NOH (2 isomers) | B/B | C/C | B/C |
| 64 | Imipenem | Q is S; W is CH=NH; Z is $CO_2H$; G is =NOMe (2 isomers) | B/B | C/C | C/C |
| 64 | Imipenem | Q is S; W is CH=NH; Z is $CO_2H$; G is $(OMe)_2$ | C | D | D |
| 64 | Imipenem | Q is S; W is CH=NH; Z is $CO_2H$; G is ethylene glycol acetal | B | C | D |
| 64 | Imipenem | Q is S; W is CH=NH; Z is C(O)H; G is H(OH) | B | C | D |
| 64 | Imipenem | Q is S; W is CH=NH; Z is $CH_2OH$; G is H(OH) | C | D | D |

| For-mula | Parent | Structure | Field similairt to parent (open ring) | Field similarity to parent (closed ring) | Binding energy relative to parent |
|---|---|---|---|---|---|
| 64 | Imipenem | Q is S; W is CH=NH; Z is CH$_2$OAc; G is H(OH) | C | D | D |
| 64 | Imipenem | Q is S; W is CH=NH; Z is CH=NOH; G is H(OH) (2 isomers) | B/B | D/C | D/D |
| 64 | Imipenem | Q is S; W is CH=NH; Z is CH=NOMe; G is H(OH) (2 isomers) | C/C | D/D | D/D |
| 64 | Imipenem | Q is S; W is CH=NH; Z is CH(OMe)$_2$; G is H(OH) | C | D | D |
| 64 | Imipenem | Q is S; W is CH=NH; Z is CH-ethylene glycol acetal; G is H(OH) | C | D | D |
| 64 | Imipenem | Q is SO; W is CH=NH; Z is CO$_2$H; G is H(OH) | A | C | A |
| 64 | Imipenem | Q is SO$_2$; W is CH=NH; Z is CO$_2$H; G is H(OH) | B | C | A |
| 60 | Faropenem | Z is CO$_2$H; G is =O | A | A | B |
| 60 | Faropenem | Z is CO$_2$H; G is =NOH | B/A E/Z | B/B E/Z | C/B E/Z |
| 60 | Faropenem | Z is CO$_2$H; G is =NOMe | B/C E/Z | C/C E/Z | C/C E/Z |
| 60 | Faropenem | Z is CO$_2$H; G is (OMe)$_2$ | B | B | D |
| 60 | Faropenem | Z is CO$_2$H; G is ethylene glycol acetal | B | B | D |
| 60 | Faropenem | Z is C(O)H; G is H(OH) | B | C | D |
| 60 | Faropenem | Z is CH$_2$OH; G is H(OH) | A | B | D |
| 60 | Faropenem | Z is CH$_2$OAc; G is H(OH) | C | B | D |
| 60 | Faropenem | Z is CH=NOH; G is H(OH) | B/B E/Z | B/B E/Z | D/D E/Z |
| 60 | Faropenem | Z is CH=NOMe; G is H(OH) | B/B E/Z | C/B E/Z | D/D E/Z |
| 60 | Faropenem | Z is CH(OMe)$_2$; G is H(OH) | B | B | D |
| 60 | Faropenem | Z is CH-ethylene glycol acetal; G is H(OH) | B | C | D |
| 65 | Meropenem | Q is S; W is C(O)NMe$_2$; G is H(OH); Z is C(O)H | C | C | D |
| 65 | Meropenem | Q is S; W is C(O)NMe$_2$; G is H(OH); Z is CH$_2$OH | C | C | D |
| 65 | Meropenem | Q is S; W is C(O)NMe$_2$; G is H(OH); Z is CH$_2$OAc | D | D | D |
| 65 | Meropenem | Q is S; W is C(O)NMe$_2$; G is H(OH); Z is CH=NOH | B | D | D |
| 65 | Meropenem | Q is S; W is C(O)NMe$_2$; G is H(OH); Z is CH=NOMe | D | D | D |
| 65 | Meropenem | Q is S; W is C(O)NMe$_2$; G is H(OH); Z is CH(OMe)$_2$ | D | D | D |
| 65 | Meropenem | Q is S; W is C(O)NMe$_2$; G is H(OH); Z is CH-ethylene glycol acetal | C | D | D |
| 65 | Meropenem | Q is SO; W is C(O)NMe$_2$; G is H(OH); Z is CO$_2$H | C | D | B |
| 65 | Meropenem | Q is SO$_2$; W is C(O)NMe$_2$; G is =O; Z is CO$_2$H | C | D | B |
| 65 | Meropenem | Q is S; W is C(O)NMe$_2$; G is =NOH; Z is CO$_2$H | C | D | A |
| 65 | Meropenem | Q is S; W is C(O)NMe$_2$; G is =NOMe; Z is CO$_2$H | C | C | B |
| 65 | Meropenem | Q is S; W is C(O)NMe$_2$; G is ethylene glycol acetal; Z is CO$_2$H | C | C | B |
| 65 | Meropenem | Q is S; W is C(O)NMe$_2$; G is (OMe)$_2$; Z is CO$_2$H | C | D | B |
| 65 | Meropenem | Q is S; W is CH$_2$NMe$_2$; G is H(OH); Z is CO$_2$H | D | C | C |
| 51 | Cefepime | Y is =O; Z is C(O)H; V is =NOMe | B | D | D |
| 51 | Cefepime | Y is =O; Z is CH=NOH (2 isomers); V is =NOMe | B/B | D/D | D/D |
| 51 | Cefepime | Y is =O; Z is CH=NOMe (2 isomers); V is =NOMe | B/B | D/D | D/D |
| 51 | Cefepime | Y is =O; Z is CH(OMe)$_2$; V is =NOMe | B | D | D |
| 51 | Cefepime | Y is =O; Z is CH-ethylene glycol acetal; V is =NOMe | B | D | D |
| 51 | Cefepime | Y is =O; Z is CH$_2$OH; V is =NOMe | B | D | D |

-continued

| Formula | Parent | Structure | Field similairt to parent (open ring) | Field similarity to parent (closed ring) | Binding energy relative to parent |
|---|---|---|---|---|---|
| 51 | Cefepime | Y is =O; Z is CH$_2$OAc; V is =NOMe | C | D | D |
| 51 | Cefepime | Y is H$_2$; Z is CO$_2$H; V is =NOMe | B | D | D |
| 51 | Cefepime | Y is =O; Z is CO$_2$H; V is H(NH$_2$) | B | D | A |
| 51 | Cefepime | Y is =O; Z is CO$_2$H; V is H(NHAc) | C | D | A |
| 29 | Cefmetazole | Q$_1$ is S; Q$_2$ is S; Z is C(O)H; Y is =O; W is CN | C | D | C |
| 29 | Cefmetazole | Q$_1$ is S; Q$_2$ is S; Z is CH=NOH (2 isomers); Y is =O; W is CN | C/C | D/D | C/C |
| 29 | Cefmetazole | Q$_1$ is S; Q$_2$ is S; Z is CH=NOMe (2 isomers); Y is =O; W is CN | D/C | D/D | C/C |
| 29 | Cefmetazole | Q$_1$ is S; Q$_2$ is S; Z is CH(OMe)$_2$; Y is =O; W is CN | C | D | C |
| 29 | Cefmetazole | Q$_1$ is S; Q$_2$ is S; Z is CH-ethylene glycol acetal; Y is =O; W is CN | C | D | C |
| 29 | Cefmetazole | Q$_1$ is S; Q$_2$ is S; Z is CH$_2$OH; Y is =O; W is CN | C | D | C |
| 29 | Cefmetazole | Q$_1$ is S; Q$_2$ is S; Z is CH$_2$OAc; Y is =O; W is CN | C | D | C |
| 29 | Cefmetazole | Q$_1$ is SO; Q$_2$ is S; Z is CO$_2$H; Y is =O; W is CN | C | D | A |
| 29 | Cefmetazole | Q$_1$ is SO$_2$; Q$_2$ is S; Z is CO$_2$H; Y is =O; W is CN | B | D | A |
| 29 | Cefmetazole | Q$_1$ is S; Q$_2$ is SO; Z is CO$_2$H; Y is =O; W is CN | C | D | A |
| 29 | Cefmetazole | Q$_1$ is S; Q$_2$ is SO$_2$; Z is CO$_2$H; Y is =O; W is CN | C | D | A |
| 29 | Cefmetazole | Q$_1$ is S; Q$_2$ is S; Z is CO$_2$H; Y is H$_2$; W is CN | C | D | C |
| 29 | Cefmetazole | Q$_1$ is S; Q$_2$ is S; Z is CO$_2$H; Y is =O; W is CH$_2$NH$_2$ | C | D | A |
| 29 | Cefmetazole | Q$_1$ is S; Q$_2$ is S; Z is CO$_2$H; Y is =O; W is C(O)NH$_2$ | C | D | A |
| 29 | Cefmetazole | Q$_1$ is S; Q$_2$ is S; Z is CO$_2$H; Y is =O; W is C(O)NHMe | C | D | A |
| 29 | Cefmetazole | Q$_1$ is S; Q$_2$ is S; Z is CO$_2$H; Y is =O; W is C(O)NMe$_2$ | C | D | A |
| 29 | Cefmetazole | Q$_1$ is S; Q$_2$ is S; Z is CO$_2$H; Y is =O; W is C(NH)NH$_2$ | D | D | B |
| 29 | Cefmetazole | Q$_1$ is S; Q$_2$ is S; Z is CO$_2$H; Y is =O; W is C(NH)NHMe | D | D | A |
| 29 | Cefmetazole | Q$_1$ is S; Q$_2$ is S; Z is CO$_2$H; Y is =O; W is C(NH)NMe$_2$ | D | D | A |
| 29 | Cefmetazole | Q$_1$ is S; Q$_2$ is S; Z is CO$_2$H; Y is =O; W is CH=NOH (2 isomers) | C/C | D/D | A |
| 29 | Cefmetazole | Q$_1$ is S; Q$_2$ is S; Z is CO$_2$H; Y is =O; W is CH=NOMe (2 isomers) | C/C | D/D | A |
| 160 | Aztreonam | Y is H$_2$; Z is CO$_2$H | B | C | A |
| 160 | Aztreonam | Y is =O; Z is C(O)H | B | B | A |
| 160 | Aztreonam | Y is =O; Z is CH$_2$OH | C | C | A |
| 160 | Aztreonam | Y is =O; Z is CH$_2$OAc | C | C | A |
| 160 | Aztreonam | Y is =O; Z is CH=NOH | C | D | B |
| 160 | Aztreonam | Y is =O; Z is CH=NOMe | C | C | A |
| 160 | Aztreonam | Y is =O; Z is CH(OMe)$_2$ | C | C | A |
| 160 | Aztreonam | Y is =O; Z is CH-ethylene glycol acetal | C | D | A |

Example 41

A range of structures have been assessed for their potential as analogues of metronidazole. Metronidazole is an antibiotic used to treat anaerobic bacterial and parasitic infections. The mechanism of action involves reductive activation of the nitroaromtatic system. There is no directly relevant structural biology information. Metronidazole has been docked into a crystal structure (1 L5P) of Trichomans ferredoxin and there is a crystal structure of metronidazole in complex with the NimA protein, which is implicated in resistance to nitroimidazoles by 2-electron reduction). The template used for the analysis derives from a combination of drugs: dimetridazole; nimorazole; metronidazole; ornidazole; secnidazole and tinidazole. Field similarity A means a similarity of 80-85%; and B means a similarity of 75-79%.

| Formula | Parent | Structure | Field similarity |
|---|---|---|---|
| 1 | Metronidazole | J is $NO_2$; Z is C(O)H | A |
| 1 | Metronidazole | J is $NO_2$; Z is $CO_2H$ | A |
| 1 | Metronidazole | J is $NO_2$; Z is $CO_2Et$ | A |
| 1 | Metronidazole | J is $NO_2$; Z is CH-ethylene glycol acetal | B |
| 1 | Metronidazole | J is $NO_2$; Z is $CH(OMe)_2$ | A |
| 1 | Metronidazole | J is $NO_2$; Z is CH=NOH | A |
| 1 | Metronidazole | J is $NO_2$; Z is CH=NOMe | A |

Example 42

A range of structures have been assessed for their activity at the angiotensin receptor. Angiotensin is a peptidic hormone which is critical in controlling vascular dilation/contraction. Angiotensin receptor blockers lower the blood pressure by blockading the angiotensin 1 receptor. A first field similarity assessment was based on aligning the structures to the angiotensin II molecule extracted from the model in PDB code 1ZV0 (the alignment being carried out in the presence of the model receptor structure). A second field similarity assessment is based on a simple field-based alignment of the structures against a template derived from the structures of a series of known Angiotensin Receptor Blockers, including candesartan. A binding energy for docking to the angiotensin receptor was also calculated.

For candesartan analogues field similarity: A is over 80% similarity; B is 60-79% similarity and C is 30-59% similarity.

For losartan analogues field similarity: A is over 75% similarity; B is 60-74% similarity and C is 30-59% similarity.

For relative binding energy: A means binding energy is greater than the parent; B means binding energy is within 50 Kcal of the parent; C means the binding energy is within 100 Kcal and D means the binding energy is within 250 Kcal of the parent.

| Formula | Parent | Structure | Field Similarity to Angiotensin II | Field Similarity to Template | Binding Energy compared to parent. |
|---|---|---|---|---|---|
| 137 | Candesartan | Z is C(O)H | C | B | B |
| 137 | Candesartan | Z is CH=NOH | C | A | B |
| 137 | Candesartan | Z is CH=NOMe | C | A | B |
| 137 | Candesartan | Z is $CH(OMe)_2$ | C | B | C |
| 137 | Candesartan | Z is CH-ethylene glycol acetal | C | B | B |
| 137 | Candesartan | Z is $CH_2OH$ | C | B | B |
| 141 | Losartan | Z is C(O)H | C | A | B |
| 141 | Losartan | Z is CH=NOH | C | A | B |
| 141 | Losartan | Z is CH=NOMe | C | A | B |
| 141 | Losartan | Z is $CH(OMe)_2$ | C | C | B |
| 141 | Losartan | Z is CH-ethylene glycol acetal | C | B | B |
| 141 | Losartan | Z is $CO_2H$ | C | A | A |

Example 43

A range of structures have been assessed for their activity as Calcium Channel blockers. Calcium channel blockers are a therapy of choice for various applications in which vasodilation plays a key role, such as angina pectoris, migraine, hypertension and cardiac arrhythmia. There are three classes of Calcium channel blockers which bind to different binding sites on the L-type calcium channels: phenylalkylamines such as verapimil; benzothiazepines such as dilthiazem and 1,4-dihydropyridines such as amlodipine, felopidine and nifedipine. The assessment has been conducted by aligning the structures to the relevant parent molecule in a likely active confirmation. The likely active confirmation has been derived by comparison and analysis of the parent compound along with other known Ca channel actives from the same class. In the case of Verapamil the active conformation has been derived from prior knowledge of the binding modes, guided by the use of a homology model of the Ca channel.

For field similarity: A is over 90% similarity; B is 80-89% similarity; C is 60-79% similarity and D is 40-59% similarity.

| Formula | Parent | Structure | Similarity to parent |
|---|---|---|---|
| 147 | Amlodipine | $Z_1$ is $CO_2Me$; $Z_2$ is C(O)H; W is $CH_2NH_2$ | A |
| 147 | Amlodipine | $Z_1$ is $CO_2Me$; $Z_2$ is CH=NOH; W is $CH_2NH_2$ | A |

| Formula | Parent | Structure | Similarity to parent |
|---|---|---|---|
| 147 | Amlodipine | $Z_1$ is $CO_2Me$; $Z_2$ is CH=NOMe; W is $CH_2NH_2$ | A |
| 147 | Amlodipine | $Z_1$ is $CO_2Me$; $Z_2$ is $CH(OMe)_2$; W is $CH_2NH_2$ | B |
| 147 | Amlodipine | $Z_1$ is $CO_2Me$; $Z_2$ is CH-ethylene glycol acetal; W is $CH_2NH_2$ | B |
| 147 | Amlodipine | $Z_1$ is $CO_2Me$; $Z_2$ is $CH_2OH$; W is $CH_2NH_2$ | B |
| 147 | Amlodipine | $Z_1$ is $CO_2Me$; $Z_2$ is $CO_2Et$; W is CN | A |
| 147 | Amlodipine | $Z_1$ is $CO_2Me$; $Z_2$ is $CO_2Et$; W is $C(O)NH_2$ | A |
| 147 | Amlodipine | $Z_1$ is $CO_2Me$; $Z_2$ is $CO_2Et$; W is $C(NH)NH_2$ | A |
| 147 | Amlodipine | $Z_1$ is $CO_2Me$; $Z_2$ is $CO_2Et$; W is $CH_2NH_2$ | A |
| 147 | Amlodipine | $Z_1$ is C(O)H; $Z_2$ is $CO_2Et$; W is $CH_2NH_2$ | B |
| 147 | Amlodipine | $Z_1$ is CH=NOH; $Z_2$ is $CO_2Et$; W is $CH_2NH_2$ | B |
| 147 | Amlodipine | $Z_1$ is CH=NOMe; $Z_2$ is $CO_2Et$; W is $CH_2NH_2$ | B |
| 147 | Amlodipine | $Z_1$ is $CH(OMe)_2$; $Z_2$ is $CO_2Et$; W is $CH_2NH_2$ | B |
| 147 | Amlodipine | $Z_1$ is CH-ethylene glycol acetal; $Z_2$ is $CO_2Et$; W is $CH_2NH_2$ | B |
| 154 | Felodipine | $Z_1$ is $CO_2Et$; $Z_2$ is C(O)H | A |
| 154 | Felodipine | $Z_1$ is $CO_2Et$; $Z_2$ is CH=NOMe | C |
| 154 | Felodipine | $Z_1$ is $CO_2Et$; $Z_2$ is CH=NOH | A |
| 154 | Felodipine | $Z_1$ is $CO_2Et$; $Z_2$ is $CH(OMe)_2$ | B |
| 154 | Felodipine | $Z_1$ is $CO_2Et$; $Z_2$ is CH-ethylene glycol acetal | B |
| 154 | Felodipine | $Z_1$ is $CO_2Et$; $Z_2$ is $CH_2OH$ | A |
| 154 | Felodipine | $Z_1$ is C(O)Ht; $Z_2$ is $CO_2Me$ | A |
| 154 | Felodipine | $Z_1$ is CH=NOH; $Z_2$ is $CO_2Me$ | B |
| 154 | Felodipine | $Z_1$ is CH=NOMe; $Z_2$ is $CO_2Me$ | A |
| 154 | Felodipine | $Z_1$ is $CH(OMe)_2$; $Z_2$ is $CO_2Me$ | C |
| 154 | Felodipine | $Z_1$ is CH-ethylene glycol acetal; $Z_2$ is $CO_2Me$ | B |
| 154 | Felodipine | $Z_1$ is $CH_2OH$; $Z_2$ is $CO_2Me$ | B |
| 152 | Diltiazem | Y is =O; G is H(OH) | B |
| 152 | Diltiazem | Y is =O; G is =O | B |
| 152 | Diltiazem | Y is =O; G is =NHOH | B |
| 152 | Diltiazem | Y is =O; G is =NHOMe | B |
| 152 | Diltiazem | Y is =O; G is $(OMe)_2$ | B |
| 152 | Diltiazem | Y is =O; G is ethylene glycol acetal | B |
| 93 | Verapamil | W is $C(O)NMe_2$ | C |
| 93 | Verapamil | W is $C(O)NH_2$ | C |
| 93 | Verapamil | W is $CH_2NH_2$ | D |
| 93 | Verapamil | W is C(O)NHMe | C |
| 93 | Verapamil | W is $CH_2NHAc$ | C |
| 93 | Verapamil | W is CH=NOH | C |
| 93 | Verapamil | W is CH=NOMe | C |
| 93 | Verapamil | W is $C(NH)NH_2$ | D |
| 93 | Verapamil | W is C(NH)NHMe | D |
| 93 | Verapamil | W is $C(NH)NMe_2$ | D |
| 108 | Nifedipine | J is $NO_2$; $Z_1$ is $CO_2Me$; $Z_2$ is $CO_2Me$ | A |
| 108 | Nifedipine | J is $NH_2$; $Z_1$ is $CO_2Me$; $Z_2$ is $CO_2Me$ | B |
| 108 | Nifedipine | J is NHAc; $Z_1$ is $CO_2Me$; $Z_2$ is $CO_2Me$ | A |
| 108 | Nifedipine | J is $NO_2$; $Z_1$ is C(O)H; $Z_2$ is $CO_2Me$ | A |
| 108 | Nifedipine | J is $NO_2$; $Z_1$ is CH=NOH; $Z_2$ is $CO_2Me$ | A |
| 108 | Nifedipine | J is $NO_2$; $Z_1$ is CH=NOMe; $Z_2$ is $CO_2Me$ | A |
| 108 | Nifedipine | J is $NO_2$; $Z_1$ is $CH(OMe)_2$; $Z_2$ is $CO_2Me$ | A |
| 108 | Nifedipine | J is $NO_2$; $Z_1$ is CH-cyclic acetal; $Z_2$ is $CO_2Me$ | A |
| 108 | Nifedipine | J is $NO_2$; $Z_1$ is $CH_2OH$; $Z_2$ is $CO_2Me$ | A |
| 108 | Nifedipine | J is $NO_2$; $Z_1$ is $CH_2OAc$; $Z_2$ is $CO_2Me$ | B |

Example 43

A range of structures were tested for their potential as analogues of ezetimibe, which is believed to operate by blocking cholesterol absorption in the lower intestines. The mechanism of action is believed to be binding to the Niemann-Pick C1-Like (NPC1L1) protein which is expressed in the brush border cells lining the epithelium of the lower intestine. There are short-sequence x-ray structures available for the close analogue, NPC1 and for NPC1L1 itself but these were insufficiently accurate. Instead, a ligand based approach was adopted to generate a template of the active conformation of ezetimibe.

For field similarity: A is over 85% similarity; B is 80-84% similarity; and C is 75-80% similarity.

| Formula | Parent | Structure | Field similarity to parent |
|---|---|---|---|
| 138 | Ezetimibe | G is CH(OAc) | C |
| 138 | Ezetimibe | G is =O | A |
| 138 | Ezetimibe | G is =NOH | A |
| 138 | Ezetimibe | G is $(OMe)_2$ | A |
| 138 | Ezetimibe | G is =NOMe | B |
| 138 | Ezetimibe | G is ethylene glycol acetal | B |

Example 44

A range of structures were tested for their potential as analogues of otamixaban and apixaban. Otamixaban and apixaban are Factor Xa inhibitors used as anticoagulants.

Field analysis was performed on the otamixaban structures by aligning them to the active conformation extracted from the PDB structure of factor Xa, which has otamixaban in the active site (PDB code: 1KSN). Field analysis was performed on the apixaban structures by aligning them to the active conformation extracted from the PDB structure (PDB code: 2P16) of factor Xa, which has apixaban in the active site. Binding energies have also been calculated.

For otamixaban field similarity: A is over 80% similarity; and B is 70-80% similarity.

For otamixaban field similarity: A is over 90% similarity; and B is 85-89% similarity.

For relative binding energy: A means binding energy is greater than the parent; B means binding energy is within 50 Kcal of the parent; C means the binding energy is within 100 Kcal and D means the binding energy is within 750 Kcal of the parent.

alignment to both the active metabolite of clopidogrel and the anion of the active metabolite.

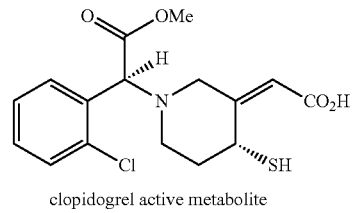 [SMILES: COC(=O)[C@H](c1ccccc1Cl)N1CC[C@@H](S)/C(=C\C(=O)O)C1]

clopidogrel active metabolite

For field similarity: A is over 90% similarity; B is 85-89% similarity and C is 80-84% similarity.

| Formula | Parent | Structure | Field similarity to parent | Binding energy relative to parent |
|---|---|---|---|---|
| 124 | Otamixaban | T is NO; Y is =O; W is C(O)NH$_2$; Z is CO$_2$Me | A | B |
| 124 | Otamixaban | T is NO; Y is =O; W is CH=NOH; Z is CO$_2$Me | B | B |
| 124 | Otamixaban | T is NO; Y is =O; W is CH=NOMe; Z is CO$_2$Me | B | D |
| 124 | Otamixaban | T is NO; Y is =O; W is CH$_2$NH$_2$; Z is CO$_2$Me | A | A |
| 124 | Otamixaban | T is NO; Y is =O; W is CN; Z is CO$_2$Me | A | C |
| 124 | Otamixaban | T is NO; Y is H$_2$; W is C(NH)NH$_2$; Z is CO$_2$Me | A | A |
| 124 | Otamixaban | T is NO; Y is =O; W is C(NH)NH$_2$; Z is CH$_2$OH | A | B |
| 124 | Otamixaban | T is NO; Y is =O; W is C(NH)NH$_2$; Z is C(O)H | A | B |
| 124 | Otamixaban | T is NO; Y is =O; W is C(NH)NH$_2$; Z is CH$_2$OAc | B | B |
| 124 | Otamixaban | T is N; Y is =O; W is C(NH)NH$_2$; Z is CO$_2$Me | A | B |
| 124 | Otamixaban | T is NO; Y is =O; W is C(NH)NH$_2$; Z is CH(OMe)$_2$ | B | C |
| 124 | Otamixaban | T is NO; Y is =O; W is C(NH)NH$_2$; Z is CH ethylene glycol acetal | B | B |
| 161 | Apixaban | Y$_1$ is H$_2$; Y$_2$ is =O; W is C(O)NH$_2$ | B | B |
| 161 | Apixaban | Y$_1$ is =O; Y$_2$ is H$_2$; W is C(O)NH$_2$ | B | A |
| 161 | Apixaban | Y$_1$ is =O; Y$_2$ is =O; W is CH$_2$NH$_2$ | B | A |
| 161 | Apixaban | Y$_1$ is =O; Y$_2$ is =O; W is CN | A | B |
| 161 | Apixaban | Y$_1$ is =O; Y$_2$ is =O; W is CH=NOH | A/A E/Z | A/A E/Z |
| 161 | Apixaban | Y$_1$ is =O; Y$_2$ is =O; W is CH=NOMe | B/B E/Z | B/A E/Z |

Example 45

A range of structures were tested for their potential as analogues of clopidogrel, an ADP-induced platelet aggregation inhibitor. The mechanism of action of clopidogrel requires oxidative activation resulting in opening of the thiophene ring to generate the active antithrombotic reagent, which is a reversible antagonist of the ADP receptor P2Y$_{12}$. There is no known crystal structure of the P2Y$_{12}$ receptor although homology modeals have been constructed. Alignment of the structures to clopidogrel was performed, as was

| Formula | Parent | Structure | Field similarity to parent | Field similarity to active metabolite | Field similarity to anion of active metabolite |
|---|---|---|---|---|---|
| 151 | Clopidogrel | Z is C(O)H | B | C | C |
| 151 | Clopidogrel | Z is CH(OMe)$_2$ | B | B | B |
| 151 | Clopidogrel | Z is CH-ethylene glycol acetal | C | A | B |
| 151 | Clopidogrel | Z is =NOH | A/B E/Z | C/C E/Z | A/C E/Z |
| 151 | Clopidogrel | Z is =NOMe | A/C E/Z | A/C E/Z | B/C E/Z |

-continued

| Formula | Parent | Structure | Field similarity to parent | Field similarity to active metabolite | Field similarity to anion of active metabolite |
|---|---|---|---|---|---|
| 151 | Clopidogrel | Z is $CH_2OH$ | A | A | B |
| 151 | Clopidogrel | Z is $CH_2OAc$ | C | C | B |

Example 46

A range of structures were tested for their potential as analogues of remikiren and aliskiren, which are inhibitors of the human target protein renin.

X-ray structures of human forms of Renin bound to both remikiren and aliskiren are available from the PDB as individual complexes (PDB entries: 2V0Z, 3D91). Analysis of each protein structure and interactions with ligands was achieved by overlaying other example complexes from the PDB. This information was used to derive the templates used in this study.

For aliskiren analogues field similarity: A is over 70% similarity; B is 66-69% similarity; C is 63-65% similarity and D is 55-62% similarity.

For remikiren analogues field similarity: A is over 70% similarity; B is 60-70% similarity; C is 55-59% similarity and D is 50-54% similarity

| Formula | Parent | Structure | Field similarity to parent |
|---|---|---|---|
| 95 | Aliskiren | V is $H(NH_2)$; G is H(OH); Y is =O; W is $C(O)NH_2$ | B |
| 95 | Aliskiren | V is $H(NH_2)$; G is =O; Y is =O; W is $C(O)NH_2$ | B |
| 95 | Aliskiren | V is $H(NH_2)$; G is H(OH); Y is $H_2$; W is $C(O)NH_2$ | C |
| 95 | Aliskiren | V is $H(NH_2)$; G is $(OMe)_2$; Y is =O; W is $C(O)NH_2$ | D |
| 95 | Aliskiren | V is $H(NH_2)$; G is ethylene glycol acetal Y is =O; W is $C(O)NH_2$ | C |
| 95 | Aliskiren | V is $H(NH_2)$; G is =NOH; Y is =O; W is $C(O)NH_2$ | C |
| 95 | Aliskiren | V is $H(NH_2)$; G is =NOMe; Y is =O; W is $C(O)NH_2$ | D |
| 95 | Aliskiren | V is =NOMe; G is H(OH); Y is =O; W is $C(O)NH_2$ | D |
| 95 | Aliskiren | V is =NOH; G is H(OH); Y is =O; W is $C(O)NH_2$ | B |
| 95 | Aliskiren | V is $H(NH_2)$; G is H(OH); Y is =O; W is $CH_2NH_2$ | B |
| 95 | Aliskiren | V is $H(NH_2)$; G is H(OH); Y is =O; W is $CH_2NHAc$ | A |
| 95 | Aliskiren | V is $H(NH_2)$; G is H(OH); Y is =O; W is CH=NOMe | B |
| 95 | Aliskiren | V is $H(NH_2)$; G is H(OH); Y is =O; W is CN | A |
| 95 | Aliskiren | V is $H(NH_2)$; G is H(OH); Y is =O; W is $CH_2OH$ | B |
| n/a | Aliskiren | Comparative compound 35a | D |
| 105 | Remikiren | Q is $S(O)_2$; $Y_1$ is $H_2$; $Y_2$ is =O; $G_1$ is H(OH); $G_2$ is H(OH) | D |
| 105 | Remikiren | Q is $S(O)_2$; $Y_1$ is =O; $Y_2$ is $H_2$; $G_1$ is H(OH); $G_2$ is H(OH) | D |
| 105 | Remikiren | Q is S; $Y_1$ is =O; $Y_2$ is =O; $G_1$ is H(OH); $G_2$ is H(OH) | A |
| 105 | Remikiren | Q is S(O); $Y_1$ is =O; $Y_2$ is =O; $G_1$ is H(OH); $G_2$ is H(OH) | A |
| 105 | Remikiren | Q is $S(O)_2$; $Y_1$ is =O; $Y_2$ is =O; $G_1$ is =O; $G_2$ is H(OH) | B |
| 105 | Remikiren | Q is $S(O)_2$; $Y_1$ is =O; $Y_2$ is =O; $G_1$ is H(OH); $G_2$ is =O | B |
| 105 | Remikiren | Q is $S(O)_2$; $Y_1$ is =O; $Y_2$ is =O; $G_1$ is =NOH; $G_2$ is H(OH) | C |
| 105 | Remikiren | Q is $S(O)_2$; $Y_1$ is =O; $Y_2$ is =O; $G_1$ is H(OH); $G_2$ is =NOH | D |
| 105 | Remikiren | Q is $S(O)_2$; $Y_1$ is =O; $Y_2$ is =O; $G_1$ is =NOMe; $G_2$ is H(OH) | C |
| 105 | Remikiren | Q is $S(O)_2$; $Y_1$ is =O; $Y_2$ is =O; $G_1$ is H(OH); $G_2$ is =NOMe | C |
| 105 | Remikiren | Q is $S(O)_2$; $Y_1$ is =O; $Y_2$ is =O; $G_1$ is $(OMe)_2$; $G_2$ is H(OH) | D |
| 105 | Remikiren | Q is $S(O)_2$; $Y_1$ is =O; $Y_2$ is =O; $G_1$ is H(OH); $G_2$ is $(OMe)_2$ | C |
| 105 | Remikiren | Q is $S(O)_2$; $Y_1$ is =O; $Y_2$ is =O; $G_1$ is ethylene glycol acetal; $G_2$ is H(OH) | D |

-continued

| For-mula | Parent | Structure | Field similarity to parent |
|---|---|---|---|
| 105 | Remikiren | Q is $S(O)_2$; $Y_1$ is =O; $Y_2$ is =O; $G_1$ is H(OH); $G_2$ is ethylene glycol acetal | D |

Example 47

A range of structures were tested for their potential as pemetrexed analogues. Folate derivatives have a host of enzymes which process and transport them for use inbiosymthetic pathways leading to DNA/RNA production and one carbon transfers. The mode of action of antifolates is complicated by their molecular similarity to folate such that they are consequently able to access the same active transport mechanisms and binding sites of the multiple folate related enzymes. The three main protein targets which are implicated in the action of these drugs are dihydrofolate reductase (DHFR), thymidylate synthase (TS) and glycinamide ribonucleotide formyl transferase (GARFT). The pharmacological activity of the proposed analogues of PMT will depend on the overall balance of interactions with these 4 targets and the various transporters. X-ray structures of human forms of DHFR, TS and GARFT are available from the PDB as complexes either of PMT itself or of close analogues

| Protein | Type | PDB code | Ligand/used | Template used |
|---|---|---|---|---|
| DHFR | Human | 2W3M | Folic acid/Y | Y |
| DHFR | Human | 2W3A | | |
| DHFR/TS | Bacterial | 3K2H | | |
| DHFR/TS | Bacterial | 3KJR | | |
| DHFR/TS | Bacterial | 3NRR | | |
| TS | Human | 1HVY | Tomudex/Y | Y |
| GARFT | Human | 1MEO | | |
| GARFT | Human | 1MEN | | |
| GARFT | Human | 1ZLX | | |
| GARFT | Human | 1ZLY | 10-formyl-5,8,dideaza-folate/Y | |
| GARFT | Human | 1RBY | 10-(trifluoroacetyl)-5,10-dideazaacyclic-5,6,7,8-tetrahydrofolic acid/Y | Y |
| GARFT | Bacterial | 1C2T | 10-formyl-5,8,10-tridiazafolic acid/Y | |
| FPGS | Bacterial | 1JBW | | |
| FPGS | Bacterial | 1JBV | | |
| FPGS | Bacterial | 3QCZ | Y (from 1RBY) | Y |

FPGS is not available as the human form, but bacterial examples are available. Analysis of the different forms of FPGS by alignment of the bacterial primary amino acid sequence with the human sequence shows that both the protein architecture and the key residues likely to contact PMT are conserved. It was thus deemed that the use of an appropriate bacterial form as a protein template for FPGS is a fair approximation. Thus, field similarity assessments were carried out for all four targets. Due to the conformational flexibility of the analogues they were assessed as the benzylglutamate core only.

For field similarity: A is over 70% similarity; B is 65-69% similarity; C is 60-64% similarity and D is 50-59% similarity.

| | | | Field Similarity to Parent | | | |
|---|---|---|---|---|---|---|
| Formula | Parent | Structure | DHFR | TS | GARFT | FGPS |
| 125 | Pemetrexed | Y is =O; $Z_1$ is $CH(OMe)_2$; $Z_2$ is $CO_2H$ | C | B | D | C |
| 125 | Pemetrexed | Y is =O; $Z_1$ is CH-ethylene glycol acetal; $Z_2$ is $CO_2H$ | D | B | C | C |
| 125 | Pemetrexed | Y is =O; $Z_1$ is CH=NOH; $Z_2$ is $CO_2H$ | C | B | C | C |
| 125 | Pemetrexed | Y is =O; $Z_1$ is CH=NOMe; $Z_2$ is $CO_2H$ | C | B | C | C |

-continued

| Formula | Parent | Structure | Field Similarity to Parent | | | |
|---|---|---|---|---|---|---|
| | | | DHFR | TS | GARFT | FGPS |
| 125 | Pemetrexed | Y is =O; $Z_1$ is $CH_2OH$; $Z_2$ is $CO_2H$ | C | A | C | B |
| 125 | Pemetrexed | Y is =O; $Z_1$ is $CH_2OAc$; $Z_2$ is $CO_2H$ | D | B | D | C |
| 125 | Pemetrexed | Y is =O; $Z_1$ is $CO_2H$; $Z_2$ is $CH(OMe)_2$ | C | B | C | C |
| 125 | Pemetrexed | Y is =O; $Z_1$ is $CO_2H$; $Z_2$ is CH-ethylene glycol acetal | C | B | C | C |
| 125 | Pemetrexed | Y is =O; $Z_1$ is $CO_2H$; $Z_2$ is CH=NOH | C | A | C | B |
| 125 | Pemetrexed | Y is =O; $Z_1$ is $CO_2H$; $Z_2$ is CH=NOMe | C | A | C | C |
| 125 | Pemetrexed | Y is =O; $Z_1$ is $CO_2H$; $Z_2$ is $CH_2OAc$ | D | C | D | C |
| 125 | Pemetrexed | Y is =O; $Z_1$ is $CO_2H$; $Z_2$ is C(O)H | C | A | C | B |
| 125 | Pemetrexed | Y is =O; $Z_1$ is $CO_2H$; $Z_2$ is $CH_2OH$ | B | A | C | B |
| 125 | Pemetrexed | Y is =O; $Z_1$ is C(O)H; $Z_2$ is $CO_2H$ | C | A | C | B |

Example 48

A range of structures were tested for their potential as analogues of bendamustine, which is a nitrogen mustard anti-cancer agent with clinical activity against a variety of cancers including non-Hodgkin's lymphoma, chronic lymphocytic leukemia, multiple myeloma and some solid tumours. It is presumed that as a nitrogen mustard bendamustine acts by alkylating DNA. In the absence of relevant structural information a low energy extended conformation was chosen for the butanoic acid side chain. The analysis was carried out on both the protonated and non-protonated forms of the benzimidazole group.

For field similarity: A is over 90% similarity; B is 85-89% similarity and C is 80-84% similarity.

| Formula | Parent | Structure | Field similarity to parent (neutral) | Field similarity to parent (protonated) |
|---|---|---|---|---|
| 113 | Bendamustine | Z is C(O)H | A | A |
| 113 | Bendamustine | Z is $CH(OMe)_2$ | C | B |
| 113 | Bendamustine | Z is CH-ethylene glycol acetal | B | B |
| 113 | Bendamustine | Z is CH=NOH | B/B E/Z | B/A E/Z |
| 113 | Bendamustine | Z is CH=NOMe | B/B E/Z | B/A E/Z |
| 113 | Bendamustine | Z is $CH_2OH$ | B | B |
| 113 | Bendamustine | Z is $CH_2OAc$ | C | C |

Example 49

A range of structures were tested for their potential as analogues of fluocinolone acetonide, a low- to medium-potency corticosteroid used for topical treatment of skin disorders and inflammatory conditions of the eye, ear and nose. The mechanism of action is complex but involves initial binsing to the cytostolic glucocorticoid receptor.

The fused ring system of fluocinolone acetonide provides a rigid skeleton with a side chain providing the only site of conformational flexibility. The side chain conformation of dexamethasone, a related corticosteroid, has been published in a number of crystal structures (3MNE, 3MNO, 3MNP, 3GN8, 1M2Z, 1P93). This conformation is very similar to the lowest energy fluocinolone acetonide side chain conformation found by molecular mechanics optimisation. This low energy structure was used as the template for field similarity analysis.

For field similarity: A is over 90% similarity; B is 87-88% similarity and C is 80-86% similarity.

| Formula | Parent | Structure | Field similarity to parent |
|---|---|---|---|
| 117 | Fluocinolone Acetonide | $G_1$ is H(OH); $G_2$ is H(OH); $G_3$ is =O; Z is $CH_2OH$ | A/B R/S |
| 117 | Fluocinolone Acetonide | $G_1$ is H(OAc); $G_2$ is H(OH); $G_3$ is =O; Z is $CH_2OH$ | C/C R/S |
| 117 | Fluocinolone Acetonide | $G_1$ is =O; $G_2$ is H(OH); $G_3$ is =O; Z is $CO_2H$ (anion) | C |
| 117 | Fluocinolone Acetonide | $G_1$ is =O; $G_2$ is H(OH); $G_3$ is =O; Z is $CO_2Me$ | B |
| 117 | Fluocinolone Acetonide | $G_1$ is =O; $G_2$ is H(OH); $G_3$ is =O; Z is $CH(OMe)_2$ | A |

| Formula | Parent | Structure | Field similarity to parent |
|---|---|---|---|
| 117 | Fluocinolone Acetonide | $G_1$ is =O; $G_2$ is H(OH); $G_3$ is =O; Z is CH-ethylene glycol acetal | B |
| 117 | Fluocinolone Acetonide | $G_1$ is =O; $G_2$ is H(OH); $G_3$ is =O; Z is CH=NOH | A/A E/Z |
| 117 | Fluocinolone Acetonide | $G_1$ is =O; $G_2$ is H(OH); $G_3$ is =O; Z is $CH_2OH$ | B/B E/Z |
| 117 | Fluocinolone Acetonide | $G_1$ is =O; $G_2$ is H(OH); $G_3$ is =O; Z is CH=NOMe | A |
| 117 | Fluocinolone Acetonide | $G_1$ is =O; $G_2$ is H(OH); $G_3$ is =O; Z is CH(O) | B |
| 117 | Fluocinolone Acetonide | $G_1$ is =O; $G_2$ is =O; $G_3$ is =O; Z is $CH_2OH$ | C/A E/Z |
| 117 | Fluocinolone Acetonide | $G_1$ is =O; $G_2$ is =NHOH; $G_3$ is =O; Z is $CH_2OH$ | C/C E/Z |
| 117 | Fluocinolone Acetonide | $G_1$ is =O; $G_2$ is =NHOMe; $G_3$ is =O; Z is $CH_2OH$ | C |
| 117 | Fluocinolone Acetonide | $G_1$ is =O; $G_2$ is $(OMe)_2$; $G_3$ is =O; Z is $CH_2OH$ | B |
| 117 | Fluocinolone Acetonide | $G_1$ is =O; $G_2$ is H(OH); $G_3$ is H(OH); Z is $CH_2OH$ | A/A E/Z |
| 117 | Fluocinolone Acetonide | $G_1$ is =O; $G_2$ is H(OH); $G_3$ is H(OAc); Z is $CH_2OH$ | C/A R/S |

Example 50

A range of structures were tested for their potential as analogues of neratinib, a tyrosine kinase inhibitor under investigation for the treatment of breast cancer and other solid tumors. It is a dual inhibitor of human epidermal growth factor receptor 2 (her2) and epidermal growth factor receptor (EGFR) kinases. The confirmation of neratinib in a covalent complex with the kinase domain of an epidermal growth factor mutant (T790M) is shown in a crystal structure (2JIV) and this confirmation has been used as the basis of the template for this analysis. In the case of the neratinib analogues which differed at the W site, the same exercise was repeated, this time using the neratinib core in the 2JIV binding site, rather than neratinib itself. To calculate the predicted binding energies the neratinib template was used.

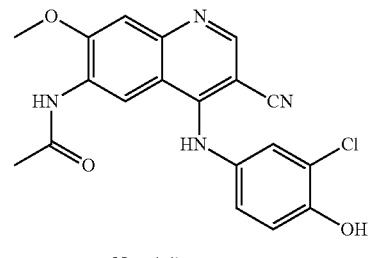

Neratinib core

For field similarity: A is over 95% similarity; B is 90-94% similarity; C is 85-89% similarity and D is 75-84% similarity.

For relative binding energy: A means binding energy is greater than the parent; B means binding energy is within 50 Kcal of the parent; C means the binding energy is within 100 Kcal and D means the binding energy is within 250 Kcal of the parent.

| Formula | Parent | Structure | Field similarity to parent | Field similarity to parent core | Binding energy relative to parent |
|---|---|---|---|---|---|
| 57 | Neratinib | $T_1$ is N; $T_2$ is N; Y is $H_2$; W is CN | B | n/a | B |
| 57 | Neratinib | $T_1$ is N; $T_2$ is NO; Y is =O; W is CN | B | n/a | B |
| 57 | Neratinib | $T_1$ is N; $T_2$ is N; Y is =O; W is $CH_2NH_2$ | B ($H^+$: B) | D ($H^+$: D) | A ($H^+$: B) |
| 57 | Neratinib | $T_1$ is N; $T_2$ is N; Y is =O; W is $C(O)NH_2$ | A | B | A |
| 57 | Neratinib | $T_1$ is N; $T_2$ is N; Y is =O; W is C(O)NHMe | B | C | B |
| 57 | Neratinib | $T_1$ is N; $T_2$ is N; Y is =O; W is $C(O)NMe_2$ | C | D | B |
| 57 | Neratinib | $T_1$ is N; $T_2$ is N; Y is =O; W is $C(NH)NH_2$ | B ($H^+$: C) | C ($H^+$: D) | A ($H^+$: B) |
| 57 | Neratinib | $T_1$ is N; $T_2$ is N; Y is =O; W is C(NH)NHMe | B ($H^+$: C) | C ($H^+$: D) | B ($H^+$: C)) |
| 57 | Neratinib | $T_1$ is N; $T_2$ is N; Y is =O; W is $C(NH)NMe_2$ | C ($H^+$: D) | D ($H^+$: D) | C ($H^+$: C) |

-continued

| Formula | Parent | Structure | Field similarity to parent | Field similarity to parent core | Binding energy relative to parent |
|---|---|---|---|---|---|
| 57 | Neratinib | $T_1$ is N; $T_2$ is N; Y is =O; W is CH=NOH | B/B E/Z | B/B E/Z | A/A E/Z |
| 57 | Neratinib | $T_1$ is N; $T_2$ is N; Y is =O; W is CH=NOMe | B/B E/Z | C/C E/Z | A/A E/Z |
| 57 | Neratinib | $T_1$ is NO; $T_2$ is N; Y is =O; W is CN | B | n/a | |

Example 51

A range of structures were tested for their potential as analogues of gemfibrozil, fenofibrate and aleglitazar. Gemfibrozil and fenofibrate are used in combination with HMG-CoA reductase inhibitors for the treatment of dyslipidemia and hypercholesterolemia in cardiovascular disorders such as atherosclerosis. The mode of action is to reduce levels of triglycerides and increase cholesterol excretion, which are effects mediated by the peroxisome proliferator-activated receptors (PPARs). The ligand binding domain of the alpha sub-type is the target for fibrates and many x-ray forms of the ligand binding domains of PPARs bound to compounds related to the fibrates are available. Field similarity was measured relative to the modelled conformation of the parent in the structure from PDB: 3DKT. Since fenofibrate is an ester prodrug and metabolised to the active fenofibric acid form, the acid variants of proposed ester analogues were also assessed.

Aleglitazar is also a fibrate which is an agonist for the ligand binding domain of the alpha sub-type of PPARs. Additionally, aleglitazar is an agonist for the gamma receptor and is therefore used as a dual active drug treatment for type II diabetes. X-ray structures of aleglitazar bound to the ligand binding domains of PPARα and PPARγ are available (3G8I and 3G9E). The field similarity of the aleglitazar analogues to aleglitazar was assessed using templates based on both receptors.

For field similarity: A is over 80% similarity; B is 70-79% similarity; C is 60-69% similarity and D is 40-59% similarity.

| Formula | Parent | Structure | Field similarity to parent (PParα) | Field similarity to parent (PPARγ) |
|---|---|---|---|---|
| 156 | Gemfibrozil | Z is C(O)H | A | n/a |
| 156 | Gemfibrozil | Z is CH(OMe)$_2$ | B | n/a |
| 156 | Gemfibrozil | Z is CH-ethylene glycol acetal | B | n/a |
| 156 | Gemfibrozil | Z is CH=NOH | B | n/a |
| 156 | Gemfibrozil | Z is CH=NOMe | B | n/a |
| 156 | Gemfibrozil | Z is CH$_2$OH | B | n/a |
| 156 | Gemfibrozil | Z is CH$_2$OAc | B | n/a |
| 139 | Fenofibrate | Z is C(O)H; G is =O | A | n/a |
| 139 | Fenofibrate | Z is CO$_2^i$Pr; G is H(OH) (S) | C | n/a |
| 139 | Fenofibrate | Z is CO$_2^i$Pr; G is H(OH) (R) | C | n/a |
| 139 | Fenofibrate | Z is CO$_2^i$Pr; G is H(OAc) (S) | D | n/a |
| 139 | Fenofibrate | Z is CO$_2^i$Pr; G is H(OAc) (R) | D | n/a |
| 139 | Fenofibrate | Z is CH=NOH; G is =O | A | n/a |
| 139 | Fenofibrate | Z is CH=NOMe; G is =O | C | n/a |
| 139 | Fenofibrate | Z is CH$_2$OH; G is =O | A | n/a |
| 139 | Fenofibrate | Z is CH$_2$OAc; G is =O | B | n/a |
| 139 | Fenofibrate | Z is CH(OMe)$_2$; G is =O | C | n/a |
| 139 | Fenofibrate | Z is CH-ethylene glycol acetal; G is =O | B | n/a |
| 139 | Fenofibrate | Z is CO$_2$H; G is =O | A | n/a |
| 139 | Fenofibrate | Z is CO$_2$H; G is H(OH) (S) | A | n/a |
| 139 | Fenofibrate | Z is CO$_2$H; G is H(OH) (R) | A | n/a |
| 139 | Fenofibrate | Z is CO$_2$H; G is H(OAc) (S) | A | n/a |
| 139 | Fenofibrate | Z is CO$_2$H; G is H(OAc) (R) | C | n/a |
| 107 | Aleglitazar | Z is C(O)H | A | A |
| 107 | Aleglitazar | Z is CH(OMe)$_2$ | B | C |
| 107 | Aleglitazar | Z is CH-ethylene glycol acetal | B | B |
| 107 | Aleglitazar | Z is CH=NOH | A/A E/Z | A/A E/Z |
| 107 | Aleglitazar | Z is CH=NOMe | A/C E/Z | B/C E/Z |
| 107 | Aleglitazar | Z is CH$_2$OH | A | A |
| 107 | Aleglitazar | Z is CH$_2$OAc | C | C |

Example 52

A range of structures were tested for their potential as analogues of sitagliptin, a DPP-4 inhibitor. There are a number of x-ray structures available which show the DPP-4 enzyme, both as the apo-protein and also with bound inhibitors. Analysis has been carried out by alignment of the analogues to the parent structure. A binding energy prediction for each of the structure into the DPP-4 crystal structure has also been carried out.

For field similarity: A is over 85% similarity; B is 80-85% similarity and C is 70-80% similarity.

For relative binding energy: A means binding energy is within 50 Kcal of the parent; and B means the binding energy is within 100 Kcal of the parent.

| Formula | Parent | Structure | Field similarity to parent | Binding energy relative to parent |
|---|---|---|---|---|
| 3 | Sitagliptin | V is =NOH (E); Y is =O | C | B |
| 3 | Sitagliptin | V is =NOH (Z); Y is =O | B | B |
| 3 | Sitagliptin | V is =NOMe (E); Y is =O | B | B |
| 3 | Sitagliptin | V is =NOMe (Z); Y is =O | C | B |
| 3 | Sitagliptin | V is H(NH$_2$); Y is H$_2$ | A | A |

Example 53

A range of structures were tested for their potential as analogues of adapalene, alitretinoin and bexatotene. Adapalene is a retinoid used for the topical treatment of acne. Its mode of action is not known. Alitretinoin is used for topical antiproliferative treatment of skin lesions in Kaposi's sarcoma and for oral treatment of chronic hand eczema. Alitretinoin can activate both the nuclear retinoic acid receptors and the retinoid X receptors (RXRs), which are involved in gene replication. Bexarotene is used as an oral antineoplastic agent for cutaneous T-cell lymphoma and is selective for RXRs. A number of crystal structures are available of alitretinoin in complexes with the RXR-alpha nuclear receptor. Of these the most promising is 3OAP. To generate a template of alitretinoin and adapalene, FieldTemplater was used to find possible alignments between alitretinoin and adapalene. One of the two highest scoring alignments has a conformation similar to that from PDB entry 3OAP and this was used for the field similarity analysis of alitretinoin and adapalene. An identical process, using bexarotene rather than adapalene was used to generate the template for bexarotene.

For adapalene analogues field similarity: A is over 90% similarity; B is 85-89% similarity; and C is 80-84% similarity.

For alitretinoin analogues field similarity: A is over 90% similarity; B is 85-89% similarity; and C is 80-84% similarity.

For bexarotene analogues field similarity: A is over 88% similarity; B is 84-87% similarity; and C is 80-84% similarity.

| Formula | Parent | Structure | Field similarity to parent |
|---|---|---|---|
| 135 | Adapalene | Z is C(O)H | A |
| 135 | Adapalene | Z is CH=NOH | A/A E/Z |
| 135 | Adapalene | Z is CH=NOMe | A/A E/Z |
| 135 | Adapalene | Z is CH(OMe)$_2$ | B |
| 135 | Adapalene | Z is CH-ethylene glycol acetal | B |
| 135 | Adapalene | Z is CH$_2$OH | A |
| 135 | Adapalene | Z is CH$_2$OAc | B |
| 94 | Alitretinoin | Z is C(O)H | A |
| 94 | Alitretinoin | Z is CH(OMe)$_2$ | B |
| 94 | Alitretinoin | Z is CH-ethylene glycol acetal | B |
| 94 | Alitretinoin | Z is CH=NOH | A/B E/Z |
| 94 | Alitretinoin | Z is CH=NOMe | A/A E/Z |
| 94 | Alitretinoin | Z is CH$_2$OH | A |
| 94 | Alitretinoin | Z is CH$_2$OAc | C |
| 102 | Bexarotene | Z is C(O)H | A |
| 102 | Bexarotene | Z is CH$_2$OH | A |
| 102 | Bexarotene | Z is CH$_2$OAc | B |
| 102 | Bexarotene | Z is CH(OMe)$_2$ | C |
| 102 | Bexarotene | Z is CH-ethylene glycol acetal | B |
| 102 | Bexarotene | Z is CH=NOH | A/A E/Z |
| 102 | Bexarotene | Z is CH=NOMe | A/A E/Z |

Example 54

A range of structures were tested for their potential as analogues of eprotirome. Eprotirome is a liver-selective agonist for the nuclear thyroid hormone receptor beta 1 (TRβ1) and has been shown to reduce serum total and LDL cholesterol as well as apolipoprotein B levels in humans. There are several crystal structures (eg 3JZC, 3IMY, 3GWX, 2PIN, SJ4A, 1R6G, 1Q4X, 1NAX, 1N46) of the ligand binding domain of TRβ1 in complex with agonists and antagonists. To generate a reference conformation of eprotirome, three ligands from crystal structures (rigid azauracil 1N46, propanoic acid 2J4A and oxyacetic acid 1Q4X) were aligned to each other, and eprotirome then aligned to this ensemble using the binding site of 1N46 as excluded volume.

For field similarity: A is over 90% similarity; B is 85-89% similarity and C is 80-85% similarity.

For relative binding energy: A means binding energy is greater than the parent; B means binding energy is within 50 Kcal of the parent; C means the binding energy is within 100 Kcal and D means the binding energy is within 250 Kcal of the parent.

| Formula | Parent | Structure | Field similarity to parent | Binding energy relative to parent |
|---|---|---|---|---|
| 104 | Eprotirome | Y is =O; Z is C(O)H | B | B |
| 104 | Eprotirome | Y is =O; Z is CH(OMe)$_2$ | C | C |
| 104 | Eprotirome | Y is =O; Z is CH-ethylene glycol acetal | B | B |
| 104 | Eprotirome | Y is =O; Z is CH=NOH | B/A E/Z | B |
| 104 | Eprotirome | Y is =O; Z is CH=NOMe | B/B E/Z | C |
| 104 | Eprotirome | Y is =O; Z is CH$_2$OH | A | B |
| 104 | Eprotirome | Y is =O; Z is CH$_2$OAc | C | B |
| 104 | Eprotirome | Y is H$_2$; Z is CO$_2$H | B | B |

Example 55

A range of structures were tested for their potential as analogues of omacetaxine mepesuccinate, an inducer of apoptosis by inhibition of protein synthesis (particularly Mcl-1 which inhibits apoptosis). The mechanism of action involves binding to the ribosomal A-site cleft in the peptidyl-tranferase centre. There is a published crystal structure (PDB entry 3G6E) of omacetaxine bound to the large ribosomal subunit of Haloarcula marismortui (an extreme halophillic archaeon). This conformation was used as the basis for the template structure used in the field similarity studies.

For field similarity: A is over 85% similarity; B is 80-84% similarity and C is 70-79% similarity.

| Formula | Parent | Structure | Field similarity to parent |
|---|---|---|---|
| 148 | Omacetaxine Mepesuccinate | Z is C(O)H; Y is =O | A |
| 148 | Omacetaxine Mepesuccinate | Z is CH(OMe)$_2$; Y is =O | A |
| 148 | Omacetaxine Mepesuccinate | Z is CH ethylene glycol acetal; Y is =O | B |
| 148 | Omacetaxine Mepesuccinate | Z is =NOH; Y is =O | B/B E/Z |
| 148 | Omacetaxine Mepesuccinate | Z is =NOMe; Y is =O | B/C E/Z |
| 148 | Omacetaxine Mepesuccinate | Z is CH$_2$OH; Y is =O | C |
| 148 | Omacetaxine Mepesuccinate | Z is CH$_2$OAc; Y is =O | C |
| 148 | Omacetaxine Mepesuccinate | Z is CO$_2$Me; Y is H$_2$ | B |

Example 56

A range of structures were tested for their potential as analogues of safinamide, a monoamine oxidase B inhibitor which also inhibits dopamine uptake, blocks voltage dependent Na channels, modulates Ca channels and inhibits glutamine release induced by abnormal neuronal activity. There is a published crystal structure of safinamide bound to human monoamine oxidase B (PDB entry 2V5Z). This conformation was used as the basis for the template structure used in the field similarity analyses. This crystal structure was also used to predict the binding energies relative to the parent.

For field similarity: A is over 85% similarity; B is 80-84% similarity and C is 70-79% similarity.

For relative binding energy: A means binding energy is within 15 Kcal of the parent; B means the binding energy is within 25 Kcal of the parent and C means the binding energy is within 50 Kcal of the parent.

| Formula | Parent | Structure | Field similarity to parent | Binding energy relative to parent |
|---|---|---|---|---|
| 127 | Safinamide | W is CH=NOH | A/A E/Z | A/C E/Z |
| 127 | Safinamide | W is CH=NOMe | B/A E/Z | B/A E/Z |
| 127 | Safinamide | W is CN | B | B |
| 127 | Safinamide | W is CH$_2$NH$_2$ | B (H$^+$: B) | B (H$^+$: A) |

Example 57

A range of structures were tested for their potential as analogues of etoposide and voreloxin, which are topoisomerase II inhibitors. A field similarity analysis of the etoposide analogues was carried out in the absence of any specific information on the way etoposide interferes with DNA ligation; for voreloxin the field similarity analysis was carried out based on an assessment of the mechanism of action of Voreloxin, i.e. DNA intercalation leading to interference with replication.

For field similarity: A is over 90% similarity; B is 85-89% similarity; C is 80-84% similarity and D is 70-79% similarity.

| Formula | Parent | Structure | Field similarity to parent |
|---|---|---|---|
| 98 | Etoposide | Y is H(OH); G$_1$ is H(OH); G$_2$ is H(OH) | D |
| 98 | Etoposide | Y is H(OMe); G$_1$ is H(OH); G$_2$ is H(OH) | C |
| 98 | Etoposide | Y is H(OMe); G$_1$ is H(OH); G$_2$ is =O | B |
| 98 | Etoposide | Y is H(OMe); G$_1$ is H(OH); G$_2$ is =NOH | A/B E/Z |
| 98 | Etoposide | Y is H(OMe); G$_1$ is H(OH); G$_2$ is =NOMe | A/C E/Z |
| 98 | Etoposide | Y is H(OMe); G$_1$ is H(OH); G$_2$ is (OMe)$_2$ | B |
| 98 | Etoposide | Y is H(OMe); G$_1$ is H(OH); G$_2$ is ethylene glycol acetal | D |
| 98 | Etoposide | Y is =O; G$_1$ is =O; G$_2$ is H(OH) | B |
| 98 | Etoposide | Y is =O; G$_1$ is =NOH; G$_2$ is H(OH) | C/B E/Z |
| 98 | Etoposide | Y is =O; G$_1$ is =NOMe; G$_2$ is H(OH) | B/C E/Z |
| 98 | Etoposide | Y is =O; G$_1$ is (OMe)$_2$; G$_2$ is H(OH) | D |
| 98 | Etoposide | Y is =O; G$_1$ is ethylene glycol acetal; G$_2$ is H(OH) | C |
| 98 | Etoposide | Y is H$_2$; G$_1$ is H(OH); G$_2$ is H(OH) | D |
| 149 | Voreloxin | G is =O; Z is C(O)H | A |
| 149 | Voreloxin | G is =O; Z is CH(OMe)$_2$ | A |
| 149 | Voreloxin | G is =O; Z is CH-ethylene glycol acetal | A |
| 149 | Voreloxin | G is =O; Z is =NOH | A/A |
| 149 | Voreloxin | G is =O; Z is =NOMe | A/B |
| 149 | Voreloxin | G is =O; Z is CH$_2$OH | A |
| 149 | Voreloxin | G is =O; Z is CH$_2$OAc | A |

Example 58

A range of structures were tested for their potential as analogues of doxorubicin, an antibiotic used in chemotherapy for a range of cancers. Its primary mode of action is by intercalating DNA. There are several crystal structures containing doxorubicin or doxorubicin analogues intercalated with DNA. The reference conformation of doxorubicin used in this analysis was based on 1P20. The analysis was performed twice, once comparing the whole structure with a rigid alignment of the whole molecule and with a flexible alignment of the corresponding core structure to the doxorubicin core template.

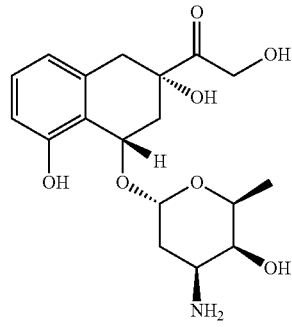

doxorubicin core

For field similarity: A is over 95% similarity; B is 90-94% similarity; and C is 84-89% similarity.

| Formula | Parent | Structure | Field similarity with parent | Field similarity of core with core of parent |
|---|---|---|---|---|
| 97 | Doxorubicin | $G_1$ is =O; Z is C(O)H; $G_2$ is H(OH); V is H($NH_2$) | B | B |
| 97 | Doxorubicin | $G_1$ is =O; Z is CH(OMe)$_2$; $G_2$ is H(OH); V is H($NH_2$) | B | B |
| 97 | Doxorubicin | $G_1$ is =O; Z is CH - ethylene glycol acetal; $G_2$ is H(OH); V is H($NH_2$) | A | B |
| 97 | Doxorubicin | $G_1$ is =O; Z is CH=NOH; $G_2$ is H(OH); V is H($NH_2$) | B/B E/Z | B/B E/Z |
| 97 | Doxorubicin | $G_1$ is =O; Z is CH=NOMe; $G_2$ is H(OH); V is H($NH_2$) | B/B E/Z | B/C E/Z |
| 97 | Doxorubicin | $G_1$ is =O; Z is $CO_2$H; $G_2$ is H(OH); V is H($NH_2$) | B | B |
| 97 | Doxorubicin | $G_1$ is =O; Z is $CO_2$Me; $G_2$ is H(OH); V is H($NH_2$) | B | C |
| 97 | Doxorubicin | $G_1$ is H(OH); Z is $CH_2$OH; $G_2$ is H(OH); V is H($NH_2$) | A/A R/S | A/B R/S |
| 97 | Doxorubicin | $G_1$ is H(OAc); Z is $CH_2$OH; $G_2$ is H(OH); V is H($NH_2$) | B/B R/S | C/C R/S |
| 97 | Doxorubicin | $G_1$ is =O; Z is $CH_2$OH; $G_2$ is =O; V is H($NH_2$) | B | B |
| 97 | Doxorubicin | $G_1$ is =O; Z is $CH_2$OH; $G_2$ is =NOH; V is H($NH_2$) | B/A E/Z | B/B E/Z |
| 97 | Doxorubicin | $G_1$ is =O; Z is $CH_2$OH; $G_2$ is =NOMe; V is H($NH_2$) | B/B E/Z | B/B E/Z |
| 97 | Doxorubicin | $G_1$ is =O; Z is $CH_2$OH; $G_2$ is (OMe)$_2$; V is H($NH_2$) | B | B |
| 97 | Doxorubicin | $G_1$ is =O; Z is $CH_2$OH; $G_2$ is ethylene glycol acetal; V is H($NH_2$) | B | B |

Example 59

A range of structures were tested for their potential as cladribine analogues. Cladribine is a 2-deoxyadenosine analogue used for treatment of hairy cell leukemia. Cladribine has potentially important interactions with both deoxycytidine kinase (as substrate/competitive inhibitor) and adenosine deaminase (as inhibitor). There are significant differences in the conformation of the deoxyribose ring in these two structures. Alignment of the analogues was determined against cladribine in deoxycytidine kinase template (based on 2ZIA; cladribine in C4S in complex with UDP) and against cladribine in adenosine deaminase template (based on 31AR; 2-deoxyadenosine in human adenosine deaminase).

For field similarity: A is over 90% similarity; B is 85-89% similarity and C is 80-84% similarity.

| Formula | Parent | Structure | Field similarity with parent (deoxycytidine kinase) | Field similarity with parent (adenosine deaminase) |
|---|---|---|---|---|
| 115 | Cladribine | G is H(OH); Z is C(O)H | B | A |
| 115 | Cladribine | G is H(OH); Z is CO$_2$H | B | A |
| 115 | Cladribine | G is H(OH); Z is CO$_2$Me | C | A |
| 115 | Cladribine | G is H(OH); Z is CH(OMe)$_2$ | B | A |
| 115 | Cladribine | G is H(OH); Z is CH-ethylene glycol acetal | C | B |
| 115 | Cladribine | G is H(OH); Z is CH=NOH | B/B E/Z | A/A E/Z |
| 115 | Cladribine | G is H(OH); Z is CH=NOMe | B/B E/Z | B/B E/Z |
| 115 | Cladribine | G is =O; Z is CH$_2$OH | B | A |
| 115 | Cladribine | G is =NOH; Z is CH$_2$OH | A/A E/Z | A/B E/Z |
| 115 | Cladribine | G is =NOMe; Z is CH$_2$OH | B/B E/Z | B/B E/Z |
| 115 | Cladribine | G is (OMe)$_2$; Z is CH$_2$OH | B | C |
| 115 | Cladribine | G is ethylene glycol acetal; Z is CH$_2$OH | B | C |

Example 60

A range of structures were tested for their potential as analogues of etodolac and indometacin, inhibitors of cyclooxygenase (COX). Etodolac is used in the treatment of inflammation and pain caused by osteoarthritis and rheumatoid arthritis. Indometacin is used for treatment of fever, pain, stiffness and swelling. There are no published crystal structures of etodolac bound to COX. In order to generate a template structure, alignments of etodolac to three of the published COX-2 inhibitors were performed. The template chosen was that created by alignment with PDB entry 3NTG. An indomethacin template was generated using the conformation of indomethacin extracted from PDB entry 4COX, in which indometacin is bound to the COX-2 isoform.

For field similarity: A is over 90% similarity; B is 85-89% similarity and C is 80-84% similarity.

| Formula | Parent | Structure | Field similarity with parent |
|---|---|---|---|
| 153 | Etodolac | Z is C(O)H | A |
| 153 | Etodolac | Z is CH=NOH | A/A E/Z |
| 153 | Etodolac | Z is CH=NOMe | A/A E/Z |
| 153 | Etodolac | Z is CH(OMe)$_2$ | B |
| 153 | Etodolac | Z is CH-ethylene glycol acetal | B |
| 153 | Etodolac | Z is CH$_2$OH | B |
| 153 | Etodolac | Z is CH$_2$OAc | B |
| 158 | Indometacin | Y is =O; Z is C(O)H | A |
| 158 | Indometacin | Y is =O; Z is CH=NOH | A/A E/Z |
| 158 | Indometacin | Y is =O; Z is CH=NOMe | B/B E/Z |
| 158 | Indometacin | Y is =O; Z is CH(OMe)$_2$ | B |
| 158 | Indometacin | Y is =O; Z is CH-ethylene glycol acetal | B |
| 158 | Indometacin | Y is =O; Z is CH$_2$OAc | B |
| 158 | Indometacin | Y is =O; Z is CH$_2$OH | A |
| 158 | Indometacin | Y is H$_2$; Z is CO$_2$H | B |

Example 61

A range of structures were tested for their potential as analogues of olopatadine, an inverse agonist of the histamine H1 receptor. An x-ray structure of olopatadine bound to the H$_1$ receptor (PDB entry: 3RZE) was used to generate the template for the field similarity assessment.

For field similarity: A is over 75% similarity; B is 70-74% similarity; and C is 64-69% similarity.

For relative binding energy: A means binding energy is greater than the parent; B means binding energy is within 50 Kcal of the parent; C means the binding energy is within 100 Kcal and D means the binding energy is within 250 Kcal of the parent.

| Formula | Parent | Structure | Field similarity to parent | Binding energy relative to parent |
|---|---|---|---|---|
| 142 | Olopatadine | Z is C(O)H | A | A |
| 142 | Olopatadine | Z is CH=NOH | A/A E/Z | A/A E/Z |
| 142 | Olopatadine | Z is CH=NOMe | B/B E/Z | A/C E/Z |
| 142 | Olopatadine | Z is CH(OMe)$_2$ | B | C |
| 142 | Olopatadine | Z is CH-ehtylene glycol acetal | C | B |
| 142 | Olopatadine | Z is CH$_2$OH | A | B |
| 142 | Olopatadine | Z is CH$_2$OAc | B | A |

Example 62

A range of structures were tested for their potential as analogues of dabigatran etexilate, an inhibitor of the human target thrombin. It is a prodrug, with the hexylcarbamate and ethyl ester being present to ensure bioavailability. An x-ray structure of the human form of thrombin bound to the 'free amidine' ethyl ester derivative of dabigatran is available (PDB: 1 KTS), and the template for field alignment studies was based on that. The dabigatran ester was truncated back to the methyl benzimidazole fragment, due to the inherent flexibility of dabigatran and the fact that the bound conformation appears to be unusual and problematic to reproduce. Predicted binding energies were also calculated, using the 1KTS PDB structure, and manually creating the analogues in the Xtal structure conformation, followed by docking into the protein and optimising the ligand structure.

For field similarity: A is over 90% similarity; B is 85-89% similarity and C is 75-84% similarity.

For relative binding energy: A means binding energy is greater than the parent; B means binding energy is within 50 Kcal of the parent; C means the binding energy is within 100 Kcal and D means the binding energy is within 250 Kcal of the parent.

| Formula | Parent | Structure | Field similarity to parent | Binding energy relative to parent |
|---|---|---|---|---|
| 116 | Dabigatran etexilate | Y is =O; Z is C(O)H | B | B |
| 116 | Dabigatran etexilate | Y is =O; Z is CH=NOH | B/B E/Z | B/A E/Z |
| 116 | Dabigatran etexilate | Y is =O; Z is CH=NOMe | B/C E/Z | B/B E/Z |
| 116 | Dabigatran etexilate | Y is =O; Z is CH(OMe)$_2$ | B | B |
| 116 | Dabigatran etexilate | Y is =O; Z is CH-ethylene glycol acetal | A | B |
| 116 | Dabigatran etexilate | Y is =O; Z is CH$_2$OH | A | A |
| 116 | Dabigatran etexilate | Y is =O; Z is CH$_2$OAc | B | A |
| 116 | Dabigatran etexilate | Y is H$_2$; Z is CO$_2$Et | C | A |

Example 63

A range of structures were tested for their potential as analogues of semagestat, an inhibitor of the human target gamma secretase. Gamma Secretase is a multiprotein complex consisting of a 1:1:1:1 ratio of nicastrin, pen-2, Presenilin and aph1, all of which contain multiple alpha helical domains. Presenilin is an aspartyl protease. Example aspartyl proteases were used to map the beta strand conformation likely to be formed by APP (amyloid beta precursor peptide), which is processed by Gamma Secretase. The resulting geometry modelled for the APP cleavage site was used to derive a root template for semagacestat. This conformation was consistant with a number of structurally related inhibitors from the literature.

For field similarity: A is over 85% similarity; B is 80-84% similarity and C is 75-79% similarity.

| Formula | Parent | Structure | Field similarity to parent |
|---|---|---|---|
| 130 | Semagacestat | Y$_1$ is =O; Y$_2$ is H$_2$; Y$_3$ is =O; G is H(OH) | B |
| 130 | Semagacestat | Y$_1$ is =O; Y$_2$ is =O; Y$_3$ is H$_2$; G is H(OH) | C |
| 130 | Semagacestat | Y$_1$ is H$_2$; Y$_2$ is =O; Y$_3$ is =O; G is H(OH) | B |
| 130 | Semagacestat | Y$_1$ is =O; Y$_2$ is =O; Y$_3$ is =O; G is =O | A |
| 130 | Semagacestat | Y$_1$ is =O; Y$_2$ is =O; Y$_3$ is =O; G is (OH)$_2$ | A |
| 130 | Semagacestat | Y$_1$ is =O; Y$_2$ is =O; Y$_3$ is =O; G is =NOH (E) | B |
| 130 | Semagacestat | Y$_1$ is =O; Y$_2$ is =O; Y$_3$ is =O; G is =NOH (Z) | B |
| 130 | Semagacestat | Y$_1$ is =O; Y$_2$ is =O; Y$_3$ is =O; G is =NOMe (E) | B |
| 130 | Semagacestat | Y$_1$ is =O; Y$_2$ is =O; Y$_3$ is =O; G is =NOMe (Z) | B |
| 130 | Semagacestat | Y$_1$ is =O; Y$_2$ is =O; Y$_3$ is =O; G is ethylene glycol acetal | B |
| 130 | Semagacestat | Y$_1$ is =O; Y$_2$ is =O; Y$_3$ is =O; G is (OMe)$_2$ | A |

Example 64

A range of structures were tested for their potential as analogues of megestrol. Megestrol acetate is a member of the steroid family of drugs and is structurally related to Progesterone and Cortisol.

The biological target of Megestrol is currently unknown, but the high structural similarity to both Progesterone and Cortisol suggests it will very likely share activity at many of the receptors and enzymes involved in both Cortisol and Progesterone recognition and metabolism. X-ray structures are available for a number of the human enzymes and receptors bound to steroids (PDB codes 1GWR, 1A28, 2Q1V) and these provided the template for aligning megestrol to the analogues.

For field similarity: A is over 85% similarity; B is 80-84% similarity and C is 75-79% similarity.

For relative binding energy: A means binding energy is greater than the parent; B means binding energy is within 20 Kcal of the parent; and C means the binding energy is within 50 Kcal.

| Formula | Parent | Structure | Field Similarity to Parent | Binding energy relative to parent |
|---|---|---|---|---|
| 101 | Megestrol | G$_1$ is H(OH) (R); G$_2$ is =O | A | A |
| 101 | Megestrol | G$_1$ is H(OH) (S); G$_2$ is =O | A | B |
| 101 | Megestrol | G$_1$ is H(OAc) (R); G$_2$ is =O | B | B |
| 101 | Megestrol | G$_1$ is H(OAc) (S); G$_2$ is =O | B | B |
| 101 | Megestrol | G$_1$ is =O; G$_2$ is H(OH) (R) | A | A |
| 101 | Megestrol | G$_1$ is =O; G$_2$ is H(OH) (S) | A | C |
| 101 | Megestrol | G$_1$ is =O; G$_2$ is H(OAc) (R) | B | B |
| 101 | Megestrol | G$_1$ is =O; G$_2$ is H(OAc) (S) | A | C |
| 101 | Megestrol | G$_1$ is H(OH) (R); G$_2$ is H(OH) (S) | B | B |
| 101 | Megestrol | G$_1$ is H(OH) (S); G$_2$ is H(OH) (S) | B | A |

-continued

| Formula | Parent | Structure | Field Similarity to Parent | Binding energy relative to parent |
|---|---|---|---|---|
| 101 | Megestrol | G₁ is H(OH) (R); G₂ is H(OH) (R) | B | B |
| 101 | Megestrol | G₁ is H(OH) (S); G₂ is H(OH) (R) | B | A |

Example 65

A range of structures were tested for their potential as analogues of ombrabulin, which is cytotoxic towards cancer cells, specifically by weakening tumours by targeting epithelial cells in the tumour vasculature. The mode of action is to inhibit tubulin polymerisation by binding to the colchicines site. Ombrabulin is a prodrug with the serine unit being hydrolysed in vivo to generate the active agent. The field similarity assessment was performed in relation to three different enzyme sites. Aspartyl aminopeptidase (APP; template derived from crystal structure 3L6S) and caspase1 (casp1; template derived from crystal structure 1RWV) were selected as the most representative protease candidates for removal of the serine residue. The colchicine binding site of tubulin (template derived from 1 SA1) was also used for the evaluation in the event that the serine residue is not removed in vivo from the ombrabulin analogue.

For field similarity: A is over 70% similarity; B is 60-70% similarity; C is 50-60% similarity and D is 40-50% similarity.

| Formula | Parent | Structure | Field similarity to parent (casp1) | Field similarity to parent (APP) | Field similarity to parent (tubulin) |
|---|---|---|---|---|---|
| 134 | Ombrabulin | Y is =O; V is H(NH₂); Z is C(O)H | A | C | B |
| 134 | Ombrabulin | Y is =O; V is H(NH₂); Z is CO₂H | A | D | B |
| 134 | Ombrabulin | Y is =O; V is H(NH₂); Z is CO₂Me | B | D | A |
| 134 | Ombrabulin | Y is =O; V is H(NH₂); Z is CH=NOH | B | C | B |
| 134 | Ombrabulin | Y is =O; V is H(NH₂); Z is CH=NOMe | B | D | B |
| 134 | Ombrabulin | Y is =O; V is H(NH₂); Z is CH(OMe)₂ | B | C | A |
| 134 | Ombrabulin | Y is =O; V is H(NH₂); Z is CH - ethylene glycol acetal | B | D | B |
| 134 | Ombrabulin | Y is H₂; V is H(NH₂); Z is CH₂OH | n/a | n/a | B |
| 134 | Ombrabulin | Y is =O; V is =NOH; Z is CH₂OH | A | D | A |
| 134 | Ombrabulin | Y is =O; V is =NOMe; Z is CH₂OH | B | C | B |

Example 66

A range of structures were tested for their potential as quetiapine analogues. Quetiapine is an antipsychotic which acts as an antagonist at a number of receptors, including dopamine (D1 and D2), adrenaline (Alpha1 and Alpha 2), serotonin (5-HT2) and histamine (H1). X-ray structures were available for a dopamine D3 and a histidine H1 receptor. These are reasonable surrogates to probe the activity of quetiapine analogues at the target receptors. Based on the binding of D2/D3 antagonist eticlopride and a structurally related H1 antagonists two template binding modes were derived.

For field similarity: A is over 86% similarity; B is 82-86% similarity and C is 75-82% similarity.

| Formula | Parent | Structure | Field similarity to parent (D3) | Field similarity to parent (H1) |
|---|---|---|---|---|
| 143 | Quetiapine | Z is C(O)H | A | A |
| 143 | Quetiapine | Z is CH=NOH | A/A E/Z | B/A E/Z |
| 143 | Quetiapine | Z is CH=NOMe | B/B E/Z | B/B E/Z |
| 143 | Quetiapine | Z is CH(OMe)₂ | B | C |
| 143 | Quetiapine | Z is CH-ethylene glycol acetal | B | C |
| 143 | Quetiapine | Z is CO₂H | A | A |
| 143 | Quetiapine | Z is CO₂Me | C | B |

Example 67

A range of structures were tested for their potential as mupirocin analogues. Mupiricin is an antibiotic which strongly inhibits both protein and RNA synthesis. Mupirocin activity appears to be via reversible inhibition of isoleucyl transfer RNA synthetase (IleRS). Crystal structures are available of IleRS both the apo form of the enzyme, and also with bound inhibitors. The mupirocin analogues were assessed based on both field similarity and predicted binding energy to the 1JZS IleRS structure. In the case of field alignments, the scores are expected to be relatively low due to the long flexible alkyl chain.

For field similarity: A is over 55% similarity; B is 50-54% similarity and C is 45-50% similarity.

For relative binding energy: A means binding energy is greater than the parent; B means binding energy is within 50 Kcal of the parent; C means the binding energy is within 200 Kcal and D means the binding energy is within 350 Kcal of the parent.

| Formula | Parent | Structure | Field similarity to parent | Binding energy compared to parent |
|---|---|---|---|---|
| 92 | Mupirocin | $G_1$ is H(OH); $G_2$ is H(OH); $G_3$ is =O; Z is $CO_2H$ | A | C |
| 92 | Mupirocin | $G_1$ is H(OH); $G_2$ is H(OH); $G_3$ is =NOH; Z is $CO_2H$ | B/A E/Z | B/B E/Z |
| 92 | Mupirocin | $G_1$ is H(OH); $G_2$ is H(OH); $G_3$ is =NOMe; Z is $CO_2H$ | B/B E/Z | B/D E/Z |
| 92 | Mupirocin | $G_1$ is H(OH); $G_2$ is H(OH); $G_3$ is $(OMe)_2$; Z is $CO_2H$ | C | D |
| 92 | Mupirocin | $G_1$ is H(OH); $G_2$ is H(OH); $G_3$ is ethylene glycol acetal; Z is $CO_2H$ | B | B |
| 92 | Mupirocin | $G_1$ is H(OH); $G_2$ is =O; $G_3$ is H(OH); Z is $CO_2H$ | A | B |
| 92 | Mupirocin | $G_1$ is H(OH); $G_2$ is =NOH; $G_3$ is H(OH); Z is $CO_2H$ | B/B E/Z | D/A E/Z |
| 92 | Mupirocin | $G_1$ is H(OH); $G_2$ is =NOMe; $G_3$ is H(OH); Z is $CO_2H$ | B/B E/Z | D/C E/Z |
| 92 | Mupirocin | $G_1$ is H(OH); $G_2$ is $(OMe)_2$; $G_3$ is H(OH); Z is $CO_2H$ | D | D |
| 92 | Mupirocin | $G_1$ is H(OH); $G_2$ is ethylene glycol acetal; $G_3$ is H(OH); Z is $CO_2H$ | D | C |
| 92 | Mupirocin | $G_1$ is =O; $G_2$ is H(OH); $G_3$ is H(OH); Z is $CO_2H$ | A | A |
| 92 | Mupirocin | $G_1$ is =NOH; $G_2$ is H(OH); $G_3$ is H(OH); Z is $CO_2H$ | B/B E/Z | B/C E/Z |
| 92 | Mupirocin | $G_1$ is =NOMe; $G_2$ is H(OH); $G_3$ is H(OH); Z is $CO_2H$ | B/B E/Z | B/D E/Z |
| 92 | Mupirocin | $G_1$ is $(OMe)_2$; $G_2$ is H(OH); $G_3$ is H(OH); Z is $CO_2H$ | A | C |
| 92 | Mupirocin | $G_1$ is ethylene glycol acetal; $G_2$ is H(OH); $G_3$ is H(OH); Z is $CO_2H$ | A | B |
| 92 | Mupirocin | $G_1$ is H(OH); $G_2$ is H(OH); $G_3$ is H(OH); Z is C(O)H | C | D |
| 92 | Mupirocin | $G_1$ is H(OH); $G_2$ is H(OH); $G_3$ is H(OH); Z is CH=NOH | B/B | D/D E/Z |
| 92 | Mupirocin | $G_1$ is H(OH); $G_2$ is H(OH); $G_3$ is H(OH); Z is CH=NOMe | A/B | D/C E/Z |
| 92 | Mupirocin | $G_1$ is H(OH); $G_2$ is H(OH); $G_3$ is H(OH); Z is $CH(OMe)_2$ | B | D |
| 92 | Mupirocin | $G_1$ is H(OH); $G_2$ is H(OH); $G_3$ is H(OH); Z is CH-ethylene glycol acetal | C | D |
| 92 | Mupirocin | $G_1$ is H(OH); $G_2$ is H(OH); $G_3$ is H(OH); Z is $CH_2OH$ | B | D |
| 92 | Mupirocin | $G_1$ is H(OH); $G_2$ is H(OH); $G_3$ is H(OH); Z is $CH_2OAc$ | C | D |

Example 68

A range of structures were tested for their potential as clindamycin analgogues. Clindamycin binds to a subunit of the bacterial ribosome and causes premature disassociation of the peoptidyl-tRNA from the ribosome. There are crystal structures available with clindamycin bound to the bacterial ribosome. The mupirocin analogues were assessed based on both field similarity and predicted binding energy to the 3OFZ structure.

For field similarity: A is over 80% similarity; B is 75-79% similarity and C is 65-74% similarity.

For relative binding energy: A means binding energy is greater than the parent; B means binding energy is within 50 Kcal of the parent; and C means the binding energy is within 750 Kcal of the parent.

| Formula | Parent | Structure | Field similarity to parent | Binding energy relative to parent |
|---|---|---|---|---|
| 91 | Clindamycin | Q is S; $G_1$ is H(OH); $G_2$ is H(OH); $G_3$ is H(OH); Y is $H_2$ | C | A |
| 91 | Clindamycin | Q is S(O); $G_1$ is H(OH); $G_2$ is H(OH); $G_3$ is H(OH); Y is =O | A | B |
| 91 | Clindamycin | Q is $S(O)_2$; $G_1$ is H(OH); $G_2$ is H(OH); $G_3$ is H(OH); Y is =O | A | A |
| 91 | Clindamycin | Q is S; $G_1$ is =O; $G_2$ is H(OH); $G_3$ is H(OH); Y is =O | B | B |
| 91 | Clindamycin | Q is S; $G_1$ is =NOH; $G_2$ is H(OH); $G_3$ is H(OH); Y is =O | A/A E/Z | B/B E/Z |
| 91 | Clindamycin | Q is S; $G_1$ is =NOMe; $G_2$ is H(OH); $G_3$ is H(OH); Y is =O | B/C E/Z | A/B E/Z |

-continued

| Formula | Parent | Structure | Field similarity to parent | Binding energy relative to parent |
|---|---|---|---|---|
| 91 | Clindamycin | Q is S; $G_1$ is (OMe)$_2$; $G_2$ is H(OH); $G_3$ is H(OH); Y is =O | B | A |
| 91 | Clindamycin | Q is S; $G_1$ is ethylene glycol acetal; $G_2$ is H(OH); $G_3$ is H(OH); Y is =O | B | B |
| 91 | Clindamycin | Q is S; $G_1$ is H(OH); $G_2$ is =O; $G_3$ is H(OH); Y is =O | B | B |
| 91 | Clindamycin | Q is S; $G_1$ is H(OH); $G_2$ is =NOH; $G_3$ is H(OH); Y is =O | B/B E/Z | B/B E/Z |
| 91 | Clindamycin | Q is S; $G_1$ is H(OH); $G_2$ is =NOMe; $G_3$ is H(OH); Y is =O | C/C E/Z | B/B E/Z |
| 91 | Clindamycin | Q is S; $G_1$ is H(OH); $G_2$ is (OMe)$_2$; $G_3$ is H(OH); Y is =O | A | B |
| 91 | Clindamycin | Q is S; $G_1$ is H(OH); $G_2$ is ethylene glycol acetal; $G_3$ is H(OH); Y is =O | B | A |
| 91 | Clindamycin | Q is S; $G_1$ is H(OH); $G_2$ is H(OH); $G_3$ is =O; Y is =O | A | C |
| 91 | Clindamycin | Q is S; $G_1$ is H(OH); $G_2$ is H(OH;) $G_3$ is =NOH; Y is =O | B/C E/Z | B/A E/Z |
| 91 | Clindamycin | Q is S; $G_1$ is H(OH); $G_2$ is H(OH); $G_3$ is =NOMe; Y is =O | C/B E/Z | C/B E/Z |
| 91 | Clindamycin | Q is S; $G_1$ is H(OH); $G_2$ is H(OH); $G_3$ is (OMe)$_2$; Y is =O | C | B |
| 91 | Clindamycin | Q is S; $G_1$ is H(OH); $G_2$ is H(OH); $G_3$ is ethylene glycol acetal; Y is =O | C | B |

Example 69

A range of structures were tested for their potential as canagliflozin anaglogues. Canagliflozin is an inhibitor of the subtype 2 sodium-glucose transport protein (SGLT2) which is responsible for most of the glucose reabsorption in the kidney. No crystal structures could be found with sufficient information to propose a binding mode with any confidence. Field alignment was carried out using the core structure with remote aromatic rings removed allowing the orientation of the polar groups to be sampled more effectively.

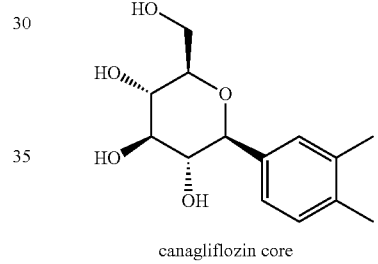

canagliflozin core

For field similarity: A is over 95% similarity; B is 90-94% similarity and C is 80-90% similarity.

| Formula | Parent | Structure | Field similarity to parent |
|---|---|---|---|
| 114 | Canagliflozin | Z is C(O)H; $G_1$ is H(OH); $G_2$ is H(OH); $G_3$ is H(OH) | A |
| 114 | Canagliflozin | Z is CO$_2$H; $G_1$ is H(OH); $G_2$ is H(OH); $G_3$ is H(OH) | A |
| 114 | Canagliflozin | Z is CO$_2$Me; $G_1$ is H(OH); $G_2$ is H(OH); $G_3$ is H(OH) | B |
| 114 | Canagliflozin | Z is CH=NOH; $G_1$ is H(OH); $G_2$ is H(OH); $G_3$ is H(OH) | B/B E/Z |
| 114 | Canagliflozin | Z is CH=NOMe; $G_1$ is H(OH); $G_2$ is H(OH); $G_3$ is H(OH) | B/B E/Z |
| 114 | Canagliflozin | Z is CH(OMe)$_2$; $G_1$ is H(OH); $G_2$ is H(OH); $G_3$ is H(OH) | B |
| 114 | Canagliflozin | Z is CH-ethylene glycol acetal; $G_1$ is H(OH); $G_2$ is H(OH); $G_3$ is H(OH) | B |
| 114 | Canagliflozin | Z is CH$_2$OH; $G_1$ is =O; $G_2$ is H(OH); $G_3$ is H(OH) | A |
| 114 | Canagliflozin | Z is CH$_2$OH; $G_1$ is =NOH; $G_2$ is H(OH); $G_3$ is H(OH) | B/B E/Z |
| 114 | Canagliflozin | Z is CH$_2$OH; $G_1$ is =NOMe; $G_2$ is H(OH); $G_3$ is H(OH) | B/C E/Z |
| 114 | Canagliflozni | Z is CH$_2$OH; $G_1$ is (OMe)$_2$; $G_2$ is H(OH); $G_3$ is H(OH) | C |
| 114 | Canagliflozin | Z is CH$_2$OH; $G_1$ is ethylene glycol acetal; $G_2$ is H(OH); $G_3$ is H(OH) | C |

-continued

| Formula | Parent | Structure | Field similarity to parent |
|---|---|---|---|
| 114 | Canagliflozin | Z is $CH_2OH$; $G_1$ is H(OH); $G_2$ is =O; $G_3$ is H(OH) | A |
| 114 | Canagliflozin | Z is $CH_2OH$; $G_1$ is H(OH); $G_2$ is =NOH; $G_3$ is H(OH) | B/B E/Z |
| 114 | Canagliflozin | Z is $CH_2OH$; $G_1$ is H(OH); $G_2$ is =NOMe; $G_3$ is H(OH) | C/B E/Z |
| 114 | Canagliflozin | Z is $CH_2OH$; $G_1$ is H(OH); $G_2$ is $(OMe)_2$; $G_3$ is H(OH) | C |
| 114 | Canagliflozin | Z is $CH_2OH$; $G_1$ is H(OH); $G_2$ is ethylene glycol acetal; $G_3$ is H(OH) | C |
| 114 | Canagliflozin | Z is $CH_2OH$; $G_1$ is H(OH); $G_2$ is H(OH); $G_3$ is =O | B |
| 114 | Canagliflozin | Z is $CH_2OH$; $G_1$ is H(OH); $G_2$ is H(OH); $G_3$ is =NOH | B/B E/Z |
| 114 | Canagliflozin | Z is $CH_2OH$; $G_1$ is H(OH); $G_2$ is H(OH); $G_3$ is =NOMe | C/C E/Z |
| 114 | Canagliflozin | Z is $CH_2OH$; $G_1$ is H(OH); $G_2$ is H(OH); $G_3$ is $(OMe)_2$ | C |
| 114 | Canagliflozin | Z is $CH_2OH$; $G_1$ is H(OH); $G_2$ is H(OH); $G_3$ is ethylene glycol acetal | C |

Example 70

A range of structures were tested for their potential as bimatoprost and latanoprost analogues. Bimatoprost and latanoprost are prostaglandin analogues used topically to control the progression of glaucoma and for the management of ocular hypertension. They are analogues of prostaglandin $F_{2\alpha}$ and they probably act as agonists of F-type prostaglandin (FP) receptors. There are no structures of prostaglandin F receptors, but there is a structure of bimatoprost bound to prostaglandin F synthetase (PDB entry 2F38). This structure was used to provide a reference conformation, by minimising the structure using the XED forcefield to provide a template for bimatoprost and latanoprost for the field similarity analysis.

For field similarity: A is over 95% similarity; B is 92-95% similarity; C is 90-91% similarity and C is 85-89% similarity.

| Formula | Parent | Structure | Field similarity to parent |
|---|---|---|---|
| 136 | Bimatoprost | $G_1$ is H(OH); $G_2$ is H(OH); $G_3$ is H(OH); Y is $H_2$ | B |
| 136 | Bimatoprost | $G_1$ is =O; $G_2$ is H(OH); $G_3$ is H(OH); Y is =O | A |
| 136 | Bimatoprost | $G_1$ is =NOH; $G_2$ is H(OH); $G_3$ is H(OH); Y is =O | B/B E/Z |
| 136 | Bimatoprost | $G_1$ is =NOMe; $G_2$ is H(OH); $G_3$ is H(OH); Y is =O | B/B E/Z |
| 136 | Bimatoprost | $G_1$ is $(OMe)_2$; $G_2$ is H(OH); $G_3$ is H(OH); Y is =O | C |
| 136 | Bimatoprost | $G_1$ is ethylene glycol acetal; $G_2$ is H(OH); $G_3$ is H(OH); Y is =O | C |
| 136 | Bimatoprost | $G_1$ is H(OH); $G_2$ is =O; $G_3$ is H(OH); Y is =O | A |
| 136 | Bimatoprost | $G_1$ is H(OH); $G_2$ is =NOH; $G_3$ is H(OH); Y is =O | A/B E/Z |
| 136 | Bimatoprost | $G_1$ is H(OH); $G_2$ is =NOMe; $G_3$ is H(OH); Y is =O | B/B E/Z |
| 136 | Bimatoprost | $G_1$ is H(OH); $G_2$ is $(OMe)_2$; $G_3$ is H(OH); Y is =O | C |
| 136 | Bimatoprost | $G_1$ is H(OH); $G_2$ is ethylene glycol acetal; $G_3$ is H(OH); Y is =O | C |
| 136 | Bimatoprost | $G_1$ is H(OH); $G_2$ is H(OH); $G_3$ is =O; Y is =O | A |
| 136 | Bimatoprost | $G_1$ is H(OH); $G_2$ is H(OH); $G_3$ is =NOH; Y is =O | B/B E/Z |
| 136 | Bimatoprost | $G_1$ is H(OH); $G_2$ is H(OH); $G_3$ is =NOMe; Y is =O | C/C E/Z |
| 136 | Bimatoprost | $G_1$ is H(OH); $G_2$ is H(OH); $G_3$ is $(OMe)_2$; Y is =O | C |
| 136 | Bimatoprost | $G_1$ is H(OH); $G_2$ is H(OH); $G_3$ is ethylene glycol acetal; Y is =O | C |
| 140 | Latanoprost | $G_1$ is H(OH); $G_2$ is H(OH); $G_3$ is H(OH); Y is C(O)H | C |
| 140 | Latanoprost | $G_1$ is H(OH); $G_2$ is H(OH); $G_3$ is H(OH); Y is CH=NOH | D/D E/Z |
| 140 | Latanoprost | $G_1$ is H(OH); $G_2$ is H(OH); $G_3$ is H(OH); Y is CH=NOMe | D/D E/Z |
| 140 | Latanoprost | $G_1$ is H(OH); $G_2$ is H(OH); $G_3$ is H(OH); Y is $CH(OMe)_2$ | D |

| Formula | Parent | Structure | Field similarity to parent |
|---|---|---|---|
| 140 | Latanoprost | $G_1$ is H(OH); $G_2$ is H(OH); $G_3$ is H(OH); Y is CH-ethylene glycol acetal | B |
| 140 | Latanoprost | $G_1$ is H(OH); $G_2$ is H(OH); $G_3$ is H(OH); Y is $CH_2OH$ | C |
| 140 | Latanoprost | $G_1$ is H(OH); $G_2$ is H(OH); $G_3$ is H(OH); Y is $CH_2OAc$ | B |
| 140 | Latanoprost | $G_1$ is =O; $G_2$ is H(OH); $G_3$ is H(OH); Y is $CO_2{}^iPr$ | A |
| 140 | Latanoprost | $G_1$ is =NOH; $G_2$ is H(OH); $G_3$ is H(OH); Y is $CO_2{}^iPr$ | B/B E/Z |
| 140 | Latanoprost | $G_1$ is =NOMe; $G_2$ is H(OH); $G_3$ is H(OH); Y is $CO_2{}^iPr$ | B/B E/Z |
| 140 | Latanoprost | $G_1$ is $(OMe)_2$; $G_2$ is H(OH); $G_3$ is H(OH); Y is $CO_2{}^iPr$ | C |
| 140 | Latanoprost | $G_1$ is ethylene glycol acetal; $G_2$ is H(OH); $G_3$ is H(OH); Y is $CO_2{}^iPr$ | C |
| 140 | Latanoprost | $G_1$ is H(OH); $G_2$ is =O; $G_3$ is H(OH); Y is $CO_2{}^iPr$ | A |
| 140 | Latanoprost | $G_1$ is H(OH); $G_2$ is =NOH; $G_3$ is H(OH); Y is $CO_2{}^iPr$ | B/B E/Z |
| 140 | Latanoprost | $G_1$ is H(OH); $G_2$ is =NOMe; $G_3$ is H(OH); Y is $CO_2{}^iPr$ | B/C E/Z |
| 140 | Latanoprost | $G_1$ is H(OH); $G_2$ is $(OMe)_2$; $G_3$ is H(OH); Y is $CO_2{}^iPr$ | C |
| 140 | Latanoprost | $G_1$ is H(OH); $G_2$ is ethylene glycol acetal; $G_3$ is H(OH); Y is $CO_2{}^iPr$ | C |
| 140 | Latanoprost | $G_1$ is H(OH); $G_2$ is H(OH); $G_3$ is =O; Y is $CO_2{}^iPr$ | A |
| 140 | Latanoprost | $G_1$ is H(OH); $G_2$ is H(OH); $G_3$ is =NOH; Y is $CO_2{}^iPr$ | B/B E/Z |
| 140 | Latanoprost | $G_1$ is H(OH); $G_2$ is H(OH); $G_3$ is =NOMe; Y is $CO_2{}^iPr$ | B/B E/Z |
| 140 | Latanoprost | $G_1$ is H(OH); $G_2$ is H(OH); $G_3$ is $(OMe)_2$; Y is $CO_2{}^iPr$ | C |
| 140 | Latanoprost | $G_1$ is H(OH); $G_2$ is H(OH); $G_3$ is ethylene glycol acetal; Y is $CO_2{}^iPr$ | C |

Example 71

A range of structures were tested for their potential as gemcitabine analogues. Gencitabine is used in chemotherapy against a number of cancers. Gemcitabine is a prodrug requiring activation by deoxycytidine kinase. There is a crystal structure of (PDB entry 2NO0) of gemcitabine bound to a mutant (C4S) human deoxycitidine kinase. The complex also includes bound ADP. The alignment to the gencitabine template was performed in the presence of the protein from this crystal structure.

For field similarity: A is over 90% similarity; B is 84-89% similarity; C is 80-84% similarity and D is 75-79% similarity.

| Formula | Parent | Structure | Field similarity to parent |
|---|---|---|---|
| 99 | Gemcitabine | Z is C(O)H; G is H(OH) | A |
| 99 | Gemcitabine | Z is $CH(OMe)_2$; G is H(OH) | D |
| 99 | Gemcitabine | Z is CH-ethylene glycol acetal; G is H(OH) | B |
| 99 | Gemcitabine | Z is CH=NOH; G is H(OH) | A/A E/Z |
| 99 | Gemcitabine | Z is CH=NOMe; G is H(OH) | B/C E/Z |
| 99 | Gemcitabine | Z is $CO_2H$; G is H(OH) | B |
| 99 | Gemcitabine | Z is $CO_2Me$; G is H(OH) | B |
| 99 | Gemcitabine | Z is $CH_2OH$; G is =O | C |
| 99 | Gemcitabine | Z is $CH_2OH$; G is =NOH | C/C E/Z |
| 99 | Gemcitabine | Z is $CH_2OH$; G is =NOMe | D/D E/Z |
| 99 | Gemcitabine | Z is $CH_2OH$; G is $(OMe)_2$ | D |
| 99 | Gemcitabine | Z is $CH_2OH$; G is ethylene glycol acetal | C |

Example 72

A range of structures were tested for their potential as analogues of darifenacin, which is an inverse agonist of the m3 muscaric receptor. Field analysis was performed by alignment to a consensus template constructed by modelling known m3 actives, tiotropium, darifenacin and two analogues of tiotropium.

For field similarity: A is over 85% similarity; B is 80-84% similarity and C is 70-79% similarity.

| Formula | Parent | Structure | Field similarity to parent |
|---|---|---|---|
| 164 | Darifenacin | W is CN | A |
| 164 | Darifenacin | W is CH=NOH | C/B E/Z |
| 164 | Darifenacin | W is CH=NOMe | C/B E/Z |
| 164 | Darifenacin | W is $CH_2NH_2$ | B |

Example 73

A range of structures were tested for their potential as analogues of acyclovir, an antiviral primarily used for the treatment of herper simplex, varicella zoster and herpes zoster infections. Acyclovir is a prodrug requiring activation by viral thymidine kinase. There is a crystal structure of acyclovir bound to herpes simplex type 1 thymidine kinase. The crystal structure shows two different orientations for the 'acyclosugar' fragment in the A subunit. The B subunit has only one orientation, similar to one of those in A. This was used as the basis of the template structure in this analysis.

For field similarity: A is over 88% similarity; and B is 85-87% similarity.

| Formula | Parent | Structure | Field similarity to parent |
|---|---|---|---|
| 159 | Acyclovir | Z is $CO_2H$ | A |
| 159 | Acyclovir | Z is $CO_2Me$ | B |
| 159 | Acyclovir | Z is CH=NOH | A/A E/Z |
| 159 | Acyclovir | Z is CH=NOMe | B/B E/Z |
| 159 | Acyclovir | Z is $CH(OMe)_2$ | B |
| 159 | Acyclovir | Z is CH-ethylene glycol acetal | A |
| 159 | Acyclovir | Z is C(O)H | A |

Example 74

A range of structures were tested for their potential as analogues of BIBF-1120, which is an inhibitor of vascular endothelial growth receptor (VEGFR), fibroblast growth factor receptor (FGFR) and platelet derived growth factor receptor (PDGFR). There is a crystal structure of BIBF-1120 bound to the kinase domain of human VEGFR2 (PDB entry 3C7Q). The structure of BIBF-1120 in PDB entry 3C7Q has some rather strained bond angles. A template conformation was therefore generated by flexible alignment of BIBF-1120 to the x-ray structure in the presence of the 3C7Q protein.

For field similarity: A is over 93% similarity; B is 90-92% similarity and C is 80-89% similarity.

| Formula | Parent | Structure | Field similarity to parent |
|---|---|---|---|
| 103 | BIBF-1120 | Z is C(O)H; $Y_1$ is =O; $Y_2$ is =O | A |
| 103 | BIBF-1120 | Z is $CH(OMe)_2$; $Y_1$ is =O; $Y_2$ is =O | A |
| 103 | BIBF-1120 | Z is CH-ethylene glycol acetal; $Y_1$ is =O; $Y_2$ is =O | A |
| 103 | BIBF-1120 | Z is CH=NOH; $Y_1$ is =O; $Y_2$ is =O | B/B E/Z |
| 103 | BIBF-1120 | Z is CH=NOMe; $Y_1$ is =O; $Y_2$ is =O | A/B E/Z |
| 103 | BIBF-1120 | Z is $CH_2OH$; $Y_1$ is =O; $Y_2$ is =O | A |
| 103 | BIBF-1120 | Z is $CH_2OAc$; $Y_1$ is =O; $Y_2$ is =O | C |
| 103 | BIBF-1120 | Z is $CO_2Me$; $Y_1$ is $H_2$; $Y_2$ is =O | C |
| 103 | BIBF-1120 | Z is $CO_2Me$; $Y_1$ is =O; $Y_2$ is $H_2$ | B |

Example 75

A range of structures were tested for their potential as analogues of ABT-263, which is an agonist of antiapoptotic members of the Bcl-2 proteins such as Bcl-2, Bcl-$x_L$ and Bcl-w as well as Mcl-1 and BclA1. There are no crystal structures containing ABT-263 itself, but structures containing the analogues ABT-737 (2YXJ) and W119542 (3INQ) bound to Bcl-$x_L$ have been published. Unsurprisingly for a protein-protein interaction inhibitor, ABT-263 is a large and flexible molecule. Consequently it is not possible to sample the conformational space of the whole molecule adequately. The field similarity analysis has therefore been carried out on analogues of the core structure. The corresponding template was created by manual alignment of the ABT-263 core to ABT-737 from PDB entry 2YXJ.

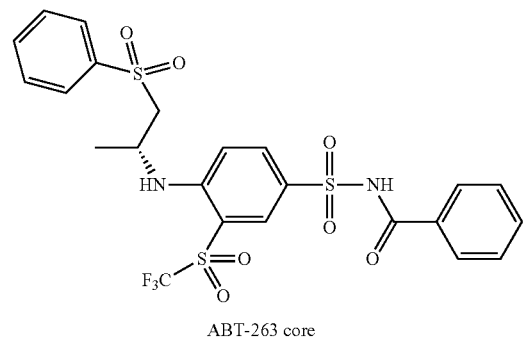 [SMILES: C[C@H](CS(=O)(=O)c1ccccc1)Nc1ccc(S(=O)(=O)NC(=O)c2ccccc2)cc1S(=O)(=O)C(F)(F)F]

ABT-263 core

For field similarity: A is over 95% similarity; B is 90-94% similarity and C is 80-89% similarity.

| Formula | Parent | Structure | Field similarity to core of parent |
|---|---|---|---|
| 150 | ABT-263 | $Q_1$ is S; $Q_2$ is $S(O)_2$; Y is $H_2$ | B |
| 150 | ABT-263 | $Q_1$ is S; $Q_2$ is S(O); Y is =O | C/C S/R |
| 150 | ABT-263 | $Q_1$ is S; $Q_2$ is S; Y is =O | C |
| 150 | ABT-263 | $Q_1$ is S(O); $Q_2$ is $S(O)_2$; Y is =O | A/B S/R |
| 150 | ABT-263 | $Q_1$ is $S(O)_2$; $Q_2$ is $S(O)_2$; Y is =O | B |

Example 76

A range of structures were tested for their potential as analogues of acadesine, an AMP-activated protein kinase activator. The templates for the field similarity analysis and determination of binding energies were derived from a crystal structure of acadesine in complex with the adenylate sensor of adenosine monophopsphate-activated protein kinase (PDB entry 2QRE).

For field similarity: A is over 90% similarity; B is 85-89% similarity and C is 80-84% similarity.

For relative binding energy: A means binding energy is greater than the parent; B means binding energy is within 50 Kcal of the parent; C means the binding energy is within 150 Kcal and D means the binding energy is within 1250 Kcal of the parent.

| Formula | Parent | Structure | Field similarity to parent | Binding energy relative to parent |
|---|---|---|---|---|
| 106 | Acadesine | Z is $CH_2OH$; $G_1$ is H(OH); $G_2$ is =O; W is $C(O)NH_2$ | A | C |
| 106 | Acadesine | Z is $CH_2OH$; $G_1$ is H(OH); $G_2$ is =NOH; W is $C(O)NH_2$ | B/B E/Z | A/B E/Z |
| 106 | Acadesine | Z is $CH_2OH$; $G_1$ is H(OH); $G_2$ is =NOMe; W is $C(O)NH_2$ | C/C E/Z | A/B E/Z |

-continued

| Formula | Parent | Structure | Field similarity to parent | Binding energy relative to parent |
|---|---|---|---|---|
| 106 | Acadesine | Z is $CH_2OH$; $G_1$ is H(OH); $G_2$ is $(OMe)_2$; W is $C(O)NH_2$ | B | B |
| 106 | Acadesine | Z is $CH_2OH$; $G_1$ is H(OH); $G_2$ is ethylene glycol acetal; W is $C(O)NH_2$ | B | B |
| 106 | Acadesine | Z is $CH_2OH$; $G_1$ is =O; $G_2$ is H(OH); W is $C(O)NH_2$ | A | B |
| 106 | Acadesine | Z is $CH_2OH$; $G_1$ is =NOH; $G_2$ is H(OH); W is $C(O)NH_2$ | B/A E/Z | A/B E/Z |
| 106 | Acadesine | Z is $CH_2OH$; $G_1$ is =NOMe; $G_2$ is H(OH); W is $C(O)NH_2$ | C/B E/Z | B/A E/Z |
| 106 | Acadesine | Z is $CH_2OH$; $G_1$ is $(OMe)_2$; $G_2$ is H(OH); W is $C(O)NH_2$ | B | A |
| 106 | Acadesine | Z is $CH_2OH$; $G_1$ is ethylene glycol acetal; $G_2$ is H(OH); W is $C(O)NH_2$ | B | C |
| 106 | Acadesine | Z is $CO_2H$; $G_1$ is H(OH); $G_2$ is H(OH); W is $C(O)NH_2$ | A | D |
| 106 | Acadesine | Z is $CO_2Me$; $G_1$ is H(OH); $G_2$ is H(OH); W is $C(O)NH_2$ | B | D |
| 106 | Acadesine | Z is C(O)H; $G_1$ is H(OH); $G_2$ is H(OH); W is $C(O)NH_2$ | B | D |
| 106 | Acadesine | Z is CH(OMe); $G_1$ is H(OH); $G_2$ is H(OH); W is $C(O)NH_2$ | B | D |
| 106 | Acadesine | Z is CH-ethylene glycol acetal; $G_1$ is H(OH); $G_2$ is H(OH); W is $C(O)NH_2$ | B | D |
| 106 | Acadesine | Z is CH=NOH; $G_1$ is H(OH); $G_2$ is H(OH); W is $C(O)NH_2$ | A/B E/Z | B/C E/Z |
| 106 | Acadesine | Z is CH=NOMe; $G_1$ is H(OH); $G_2$ is H(OH); W is $C(O)NH_2$ | B/B E/Z | D/D E/Z |
| 106 | Acadesine | Z is $CH_2OH$; $G_1$ is H(OH); $G_2$ is H(OH); W is CH=NOH | C/B E/Z | B/B E/Z |
| 106 | Acadesine | Z is $CH_2OH$; $G_1$ is H(OH); $G_2$ is H(OH); W is CH=NOMe | C/B E/Z | B/D E/Z |
| 106 | Acadesine | Z is $CH_2OH$; $G_1$ is H(OH); $G_2$ is H(OH); W is CN | B | B |
| 106 | Acadesine | Z is $CH_2OH$; $G_1$ is H(OH); $G_2$ is H(OH); W is $CH_2NH_2$ | B | B |

Example 77

A range of structures were tested for their potential as analogues of amrubicin, an inhibitor of topoisomerase II which acts by intercalation between base pairs of the DNA complex. There are no crystal structures containing amrubicin, but there are several containing other anthracycline antibiotics (e.g. daunomycin, doxorubicin and analogues) intercalated with DNA (PDB entries 1P20, 151D, 1DA9, 1D12). Structure 1P20 was used to provide a reference conformation of the anthracycline for this analysis. The alignment was carried out on core structures.

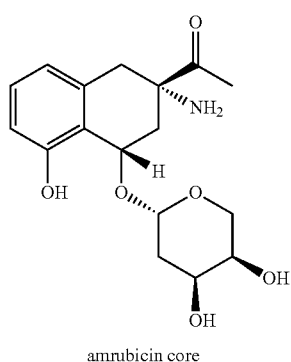 [SMILES: CC(=O)[C@]1(N)Cc2cccc(O)c2[C@@H](O[C@H]2C[C@H](O)[C@H](O)CO2)C1]

amrubicin core

For field similarity: A is over 90% similarity and B is 85-89% similarity

| Formula | Parent | Structure | Field Similarity to Parent |
|---|---|---|---|
| 110 | Amrubicin | $G_1$ is H(OH); $G_2$ is H(OH); $G_3$ is H(OH) | A/A R/S |
| 110 | Amrubicin | $G_1$ is H(OAc); $G_2$ is H(OH); $G_3$ is H(OH) | B/A R/S |
| 110 | Amrubicin | $G_1$ is =O; $G_2$ is H(OH); $G_3$ is =O | A |
| 110 | Amrubicin | $G_1$ is =O; $G_2$ is H(OH); $G_3$ is =NOH | A/A E/Z |
| 110 | Amrubicin | $G_1$ is =O; $G_2$ is H(OH); $G_3$ is =NOMe | B/B E/Z |
| 110 | Amrubicin | $G_1$ is =O; $G_2$ is H(OH); $G_3$ is $(OMe)_2$ | B |
| 110 | Amrubicin | $G_1$ is =O; $G_2$ is H(OH); $G_3$ is ethylene glycol acetal | B |
| 110 | Amrubicin | $G_1$ is =O; $G_2$ is =O; $G_3$ is H(OH) | A |
| 110 | Amrubicin | $G_1$ is =O; $G_2$ is =NOH; $G_3$ is H(OH) | B/A E/Z |
| 110 | Amrubicin | $G_1$ is =O; $G_2$ is =NOMe; $G_3$ is H(OH) | B/A E/Z |
| 110 | Amrubicin | $G_1$ is =O; $G_2$ is $(OMe)_2$; $G_3$ is H(OH) | B |
| 110 | Amrubicin | $G_1$ is =O; $G_2$ is ethylene glycol acetal; $G_3$ is H(OH) | B |

Example 78

A range of structures were tested for their potential as analogues of alvocidib, which shows dose-dependent inhibition of several phosphokinases and primarily cyclin dependent kinases cdk-1 to cdk9. There is a published crystal structure of alvocidib in human cdk-9 (PDB entry 3BLR). There are also three structures of alvocidib in glycogen phosphorylase. The template used for the field similarity analysis was generated from the structure of alvocidib PDB entry 3BLR, in which the piperidine nitrogen geometry has been amended to the protonated form.

For field similarity: A is over 95% similarity; B is 90-94% similarity; C is 85-89% similarity and D is 80-84% similarity.

| Formula | Parent | Structure | Field similarity to parent |
|---|---|---|---|
| 109 | alvocidib | $G_1$ is H(OH); $G_2$ is H(OH) | B/B R/S |
| 109 | alvocidib | $G_1$ is H(OAc); $G_2$ is H(OH) | C/C R/S |
| 109 | alvocidib | $G_1$ is =O; $G_2$ is =O | A |
| 109 | alvocidib | $G_1$ is =O; $G_2$ is =NOH | C/A E/Z |
| 109 | alvocidib | $G_1$ is =O; $G_2$ is =NOMe | D/B E/Z |
| 109 | alvocidib | $G_1$ is =O; $G_2$ is $(OMe)_2$ | C |
| 109 | alvocidib | $G_1$ is =O; $G_2$ is ethylene glycol acetal | C |

Example 79

A range of structures were tested for their potential as analogues of PD 0332991. PD 0332991 is a highly specific inhibitor of cyclin-dependent kinase 4 (cdk4) and cdk6, showing no activity against a panel of 36 other kinases. It has demonstrated antiproliferative activity in a variety of cell lines including retinoblastoma-positive, primary bone marrow myeloma and oestrogen receptor-positive breast cancer cells, and is being tested in human trials against a variety of cancers.

There is a published crystal structure of PD 0332991 in human cdk6 at moderate resolution (PDB entry 2EUF). The parent template structure was generated by flexible alignment to the geometry of the ligand excluded from PDB entry 2EUF, followed by adjustment of the torsion angle between the acetykl group and the pyridone ring, Binding energies for the analogueswirh the 2EUF crystal structure were also calculated.

For field similarity: A is over 85% similarity; B is 80-84% similarity; C is 75-79% similarity and D is 70-74% similarity.

For relative binding energy: A means binding energy is greater than the parent; B means binding energy is within 50 Kcal of the parent; and C means the binding energy is within 100 Kcal.

| Formula | Parent | Structure | Field similarity to parent | Binding energy relative to parent |
|---|---|---|---|---|
| 2 | PD 0332991 | G is H(OAc); Y is =O | C/C R/S | C/A R/S |
| 2 | PD 0332991 | G is H(OH); Y is =O | A/A R/S | B/B R/S |
| 2 | PD 0332991 | G is =O; Y is $H_2$ | B | B |

Example 80

A range of structures were tested for their potential as analogues of apaziquone. Apaziquone is an anticancer drug undergoing trials for treatment of superficial (non-invasive) bladder cancer. It shows no significant bone marrow toxicity, unlike other quinone drugs with a similar mechanism of action, such as mitomycin.

It is a prodrug, 2-electron reduction by NAD(P)H:quinone oxidoreductase (DT-diaphorase, which is overexpressed in many tumour cells) converting the quinone into the hydroquinone. The hydroxymethylpyrrole is inert in the quinone but a reactive alkylating agent in the hydroquinone, elimination of water leading to an electrophilic azafulvene species which alkylates DNA.

There is a crystal structure of apaziquone bound to DT-diaphorase (PDB entry 1GG5) and this was used to form a template for field similarity analysis.

For field similarity: A is over 93% similarity; B is 90-92% similarity; C is 85-89% similarity and D is 70-74% similarity.

| Formula | Parent | Structure | Field similarity to parent |
|---|---|---|---|
| 111 | Apaziquone | $Z_1$ is $CH_2OH$; $Z_2$ is C(O)H | A |
| 111 | Apaziquone | $Z_1$ is $CH_2OH$; $Z_2$ is CH=NOH | B/A E/Z |
| 111 | Apaziquone | $Z_1$ is $CH_2OH$; $Z_2$ is CH=NOMe | B/A E/Z |
| 111 | Apaziquone | $Z_1$ is $CH_2OH$; $Z_2$ is $CH(OMe)_2$ | C |
| 111 | Apaziquone | $Z_1$ is $CH_2OH$; $Z_2$ is CH-ethylene glycol acetal | C |
| 111 | Apaziquone | $Z_1$ is $CH_2OH$; $Z_2$ is $CO_2H$ | B |
| 111 | Apaziquone | $Z_1$ is $CH_2OH$; $Z_2$ is $CO_2Me$ | B |
| 111 | Apaziquone | $Z_1$ is C(O)H; $Z_2$ is $CH_2OH$ | A |
| 111 | Apaziquone | $Z_1$ is CH=NOH; $Z_2$ is $CH_2OH$ | B/A E/Z |
| 111 | Apaziquone | $Z_1$ is CH=NOMe; $Z_2$ is $CH_2OH$ | B/B E/Z |
| 111 | Apaziquone | $Z_1$ is $CH(OMe)_2$; $Z_2$ is $CH_2OH$ | C |
| 111 | Apaziquone | $Z_1$ is CH-ethylene glycol acetal; $Z_2$ is $CH_2OH$ | C |
| 111 | Apaziquone | $Z_1$ is $CO_2H$; $Z_2$ is $CH_2OH$ | B |
| 111 | Apaziquone | $Z_1$ is $CO_2Me$; $Z_2$ is $CH_2OH$ | B |

Example 81

A range of structures were tested for their potential as analogues of forodesine, an orally bioavailable inhibitor of purine nucleoside phosphorylase (PNPase) under development for the treatment of relapsed B-cell chronic lymphocytic leukaemia. There are several structures of forodesine in PNPase (2Q7O; 1PF7; IB80). The IB80 structure was used as the basis for the analysis. The template structure used was generated by simple minimisation of the structure of forodesine from IB80 using the XED forcefield.

For field similarity: A is over 95% similarity; B is 90-94% similarity; and C is 75-89% similarity.

For relative binding energy: A means binding energy is greater than the parent; B means binding energy is within 50 Kcal of the parent; C means binding energy is within 100 Kcal of the parent; and D means binding energy is within 250 Kcal of the parent.

| Formula | Parent | Structure | Field similarity to parent | Binding energy relative to parent |
|---|---|---|---|---|
| 118 | Forodesine | Z is C(O)H; $G_1$ is H(OH); $G_2$ is H(OH) | A | A |
| 118 | Forodesine | Z is $CO_2H$; $G_1$ is H(OH); $G_2$ is H(OH) | B | D |
| 118 | Forodesine | Z is $CO_2Me$; $G_1$ is H(OH); $G_2$ is H(OH) | B | A |
| 118 | Forodesine | Z is $CH(OMe)_2$; $G_1$ is H(OH); $G_2$ is H(OH) | C | B |

-continued

| Formula | Parent | Structure | Field similarity to parent | Binding energy relative to parent |
|---|---|---|---|---|
| 118 | Forodesine | Z is CH-ethylene glycol acetal; $G_1$ is H(OH); $G_2$ is H(OH) | B | B |
| 118 | Forodesine | Z is CH=NOH; $G_1$ is H(OH); $G_2$ is H(OH) | B/A E/Z | B/B E/Z |
| 118 | Forodesine | Z is CH=NOMe; $G_1$ is H(OH); $G_2$ is H(OH) | B/B E/Z | B/D E/Z |
| 118 | Forodesine | Z is $CH_2OH$; $G_1$ is =O; $G_2$ is H(OH) | A | C |
| 118 | Forodesine | Z is $CH_2OH$; $G_1$ is =NOH; $G_2$ is H(OH) | B/B E/Z | B/B E/Z |
| 118 | Forodesine | Z is $CH_2OH$; $G_1$ is =NOMe; $G_2$ is H(OH) | C/B E/Z | B/B E/Z |
| 118 | Forodesine | Z is $CH_2OH$; $G_1$ is $(OMe)_2$; $G_2$ is H(OH) | B | B |
| 118 | Forodesine | Z is $CH_2OH$; $G_1$ is ethylene glycol acetal; $G_2$ is H(OH) | B | B |
| 118 | Forodesine | Z is $CH_2OH$; $G_1$ is H(OH); $G_2$ is =O | B | B |
| 118 | Forodesine | Z is $CH_2OH$; $G_1$ is H(OH); $G_2$ is =NOH | B/B E/Z | A/A E/Z |
| 118 | Forodesine | Z is $CH_2OH$; $G_1$ is H(OH); $G_2$ is =NOMe | B/C E/Z | B/B E/Z |
| 118 | Forodesine | Z is $CH_2OH$; $G_1$ is H(OH); $G_2$ is $(OMe)_2$ | C | C |
| 118 | Forodesine | Z is $CH_2OH$; $G_1$ is H(OH); $G_2$ is ethylene glycol acetal | C | C |

Example 82

A range of structures were tested for their potential as analogues of teriflunomide, which has been developed as a treatment for sufferers of multiple sclerosis (MS). The mechanism of action is interference with pyrimidine synthesis, primarily by inhibiting dihydroorotate dehydrogenase (DHODH). There are a large number of high resolution x-ray structures known for DHODH, including a number with bound inhibitors. This analysis is based on the human enzyme with teriflunomide bound (PDB entry 1D3H). Field similarity analysis was carried out by alignment to the ligabnd conformation from the x-ray structure. Binding energy predictions were carried out by taking the top three scoring alignment poses from FieldAlign, and scoring against the 1D3H crystal structure using CHARMm, with flexible ligand optimisation on.

For field similarity: A is over 90% similarity; B is 85-89% similarity and C is 75-84% similarity.

For relative binding energy: A means binding energy is greater than the parent and B means binding energy is within 50 Kcal of the parent.

Example 83

A range of structures were tested for their potential as analogues of mirabegron, an orally active $\beta_3$ adrenoceptor agonist. There are no crystal structures of the $\beta_3$ adrenoceptor itself, but there are several structures of the homologous $\beta_2$ and $\beta_1$ receptors, some with bound ligands. The most relevant is PDB entry 3PDS of the $\beta_2$ with a bound ligand which is similar in size to mirabegron. A template based on this was used for field similarity analysis. The ethanolamine nitrogen was treated as protonated for all analogues. Binding energies were also calculated.

For field similarity: A is over 85% similarity; B is 80-84% similarity and C is 75-79% similarity.

For relative binding energy: A means binding energy is greater than the parent and B means binding energy is within 50 Kcal of the parent.

| Formula | Parent | Structure | Field similarity with parent | Binding energy relative to parent |
|---|---|---|---|---|
| 131 | Teriflunomide | Y is $H_2$; W is CN | B | B |
| 131 | Teriflunomide | Y is =O; W is $CH_2NHAc$ | C | B |
| 131 | Teriflunomide | Y is =O; W is $CH_2NH_2$ | C | B |
| 131 | Teriflunomide | Y is =O; W is CH=NOH | B/A E/Z | A/B E/Z |
| 131 | Teriflunomide | Y is =O; W is CH=NOMe | B/B E/Z | B/B E/Z |
| 131 | Teriflunomide | Y is =O; W is $C(O)NH_2$ | A | A |
| 131 | Teriflunomide | Y is =O; W is C(O)NHMe | B | A |
| 131 | Teriflunomide | Y is =O; W is $C(O)NMe_2$ | B | A |
| 131 | Teriflunomide | Y is =O; W is $C(NH)NH_2$ | C | A |
| 131 | Teriflunomide | Y is =O; W is C(NH)NHMe | C | A |
| 131 | Teriflunomide | Y is =O; W is $C(NH)NMe_2$ | C | A |

| Formula | Parent | Structure | Field similarity to parent | Binding energy relative to parent |
|---|---|---|---|---|
| 122 | mirabegron | G is H(OH); Y is H$_2$ | A | B |
| 122 | mirabegron | G is =O; Y is =O | A | B |
| 122 | mirabegron | G is =NOH; Y is =O | B/B E/Z | A/A E/Z |
| 122 | mirabegron | G is =NOMe; Y is =O | B/C E/Z | A/A E/Z |
| 122 | mirabegron | G is (OMe)$_2$; Y is =O | C | A |
| 122 | mirabegron | G is ethylene glycol acetal; Y is =O | B | A |

Example 84

A range of structures were tested for their potential as analogues of sapacitabine. Sapacitabine is a nucleoside analogue prodrug. It consists of an active warhead with a palmitoyl side chain which infers oral bioavailability. The palmitoyl group is removed by various amidases to reveal the active molecule CNDAC (2'-C-cyano-2'-deoxy-1-β-D-arabinopentofuranosylcytosine), albeit some studies have shown that sapacitabine itself also has anti-proliferative activity against certain tumours. The mechanism of action for CNDAC is multi-step: 1) as a nucleoside analogue it is phosphorylated (by deoxycytidine kinase-dCk) and then incorporated into DNA strands which are being synthesized, but after incorporation the molecule undergoes a beta-elimination, leading to a single-strand DNA break, 2) there is then a cascade of cell signalling actions which principally lead to apoptosis and a accumulation of cells in the G$_2$/M phase. Both of these outcomes lead to anti-proliferative activity either through cell death or arrest of cellular division.

In order to model the sapacitabine activity of this series of analogues, the focus rested principally on the CNDAC equivalents, i.e. by removing the palmitoyl group from the structures. Field analysis was carried out on the resulting species by alignment with the parent structure in the 1P62 crystal conformation. Binding energy predictions were also performed.

For field similarity: A is over 90% similarity; B is 85-89% similarity and C is 80-84% similarity.

For relative binding energy: A means binding energy is greater than the parent; B means binding energy is within 50 Kcal of the parent; C means the binding energy is within 100 Kcal of the parent and C means the binding energy is within 300 Kcal of the paren.

| Formula | Parent | Structure | Field similarity to parent | Binding energy relative to parent |
|---|---|---|---|---|
| 128 | Sapacitabine | Z is CH$_2$OH, G is H(OH), Y is =O; W is C(O)NH$_2$ | B | B |
| 128 | Sapacitabine | Z is CH$_2$OH, G is H(OH), Y is =O; W is C(O)NHMe | A | B |
| 128 | Sapacitabine | Z is CH$_2$OH, G is H(OH), Y is =O; W is C(O)NMe$_2$ | B | C |
| 128 | Sapacitabine | Z is CH$_2$OH, G is H(OH), Y is =O; W is C(NH)NH$_2$ | B | B |
| 128 | Sapacitabine | Z is CH$_2$OH, G is H(OH), Y is =O; W is C(NH)NHMe | B | B |
| 128 | Sapacitabine | Z is CH$_2$OH, G is H(OH), Y is =O; W is C(NH)NMe$_2$ | C | C |
| 128 | Sapacitabine | Z is CH$_2$OH, G is H(OH), Y is =O; W is CH=NOH | A/A E/Z | B/C E/Z |
| 128 | Sapacitabine | Z is CH$_2$OH, G is H(OH), Y is =O; W is CH=NOMe | B/B E/Z | D/C E/Z |

Example 85

A range of structures were tested for their potential as analogues of trabectedin. Trabectedin is used for treating cancer and its mode of action is believed to be through recognition and alkylation of specific nucleotide sequences in the DNA duplex. It blocks transcription of, and ultimately causes DNA damage in, specific oncogenes. The site of action is believed to be the minor groove of the DNA duplex, where the compound alkylates the guanine N2 atom via an intermediate iminium species. A reproduction of the literature models for the interaction of the target, along with the x-ray structure of a similar guanine alkylator (anthrmycin) was used to provide the template for the field similarity analyses of the analogues.

For field similarity: A is 85-90% similarity; B is 80-84% similarity; C is 75-79% similarity and D is 70-74% similarity.

| Formula | Parent | Structure | Field Similarity to Parent |
|---|---|---|---|
| 132 | Trabectedin | Q is S(O); Y$_2$ is =O; Y$_2$ is H(OH) | B |
| 132 | Trabectedin | Q is S(O)$_2$; Y$_1$ is =O; Y$_2$ is H(OH) | B |
| 132 | Trabectedin | Q is S; Y$_1$ is =O; Y$_2$ is =O | C |
| 132 | Trabectedin | Q is S; Y$_1$ is H(OH); Y$_2$ is H(OH) | B/A R/S |
| 132 | Trabectedin | Q is S; Y$_1$ is H(OMe); Y$_2$ is H(OH) | C/A R/S |
| 132 | Trabectedin | Q is S; Y$_1$ is H(OAc); Y$_2$ is H(OH) | C/D R/S |

Example 86

A range of structures were tested for their potential as analogues of motesanib, an orally bioavailable anticancer drug candidate. It inhibits vascular endothelial growth factor receptors 1, 2 and 3 (VEGFR1-3), platelet derived growth factor (PDGFR) and stem factor cell receptor (c-kit). There is a published crystal structure of motesanib in complex with the kinase domain of human VEGFR2 (PDB entry 3EFL) and the geometry of motesanib from this was used directly as the template structure for analysis.

For field similarity: A is over 95% similarity; B is 90-94% similarity and C is 85-89% similarity.

For relative binding energy: A means binding energy is greater than the parent and B means binding energy is within 50 Kcal of the parent.

| Formula | Parent | Structure | Field similarity to parent | Binding energy relative to parent |
|---|---|---|---|---|
| 123 | motesanib | $T_1$ is N; $T_2$ is N; Y is $H_2$ | B ($H^+$: C) | B ($H^+$: A) |
| 123 | motesanib | $T_1$ is N; $T_2$ is NO; Y is =O | A | A |
| 123 | motesanib | $T_1$ is NO; $T_2$ is N; Y is =O | A | A |

Example 87

A range of structures were tested for their potential as analogues of saredutant, an antidepressive and anti-anziolytic. Saredutant is an inhibitor of the NK2 receptor, the normal substrate for which is substance K (tachykinin A). There are no x-ray structures of the NK2 receptor available and so the analogues were assessed through field analysis alone.

For field similarity: A is 80-85% similarity and B is 75-79% similarity.

| Formula | Parent | Structure | Field similarity to parent |
|---|---|---|---|
| 129 | saredutant | Y is $H_2$; L is NHAc($H^+$) | B |
| 129 | saredutant | Y is =O; L is N=CHMe | A |

Example 88

A range of structures were tested for their potential as analogues of ramelteon, which is used for the treatment of insomnia, particularly delayed sleep onset. It is a selective agonist of melatonin $MT_1$ and $MT_2$ receptors. A reference conformation of ramelteon was generated from five melatonin $MT_1/MT_2$ agonists (agomelatine, LY-156,735), melatonin, ramelteon and tasimelteon) and this was used to determine the field similarity scores for the analogues.

For field similarity: A is 85-90% similarity.

| Formula | Parent | Structure | Field similarity to parent |
|---|---|---|---|
| 133 | ramelteon | Y is $H_2$ | A |

Example 89

A range of structures were tested for their potential as analogues of lixivaptan, a non-peptidic antagonist of the V2 subtype of vasopressin receptor which has been used as a treatment for hyponatremia (low blood sodiumlevels) common in heart failure. No x-ray structures are available for vasopressin specifically. The template for the field similarity analysis was based on an analysis of some larger derivatives and antagonists from the literature.

For field similarity: A is 90-95% similarity and B is 80-89% similarity.

| Formula | Parent | Structure | Field similarity to parent |
|---|---|---|---|
| 121 | lixivaptan | $Y_1$ is $H_2$; $Y_2$ is =O | A |
| 121 | lixivaptan | $Y_1$ is =O; $Y_2$ is $H_2$ | B |

Methodology for Examples 90-92

Cell Handling

PathHunter NHRPro cell lines were expanded from freezer stocks in T25 flasks according to standard procedures and maintained in selective growth media prior to assay.

Once it was established that the cells were healthy and growing normally, cells were passaged from flasks using cell dissociation reagent and seeded into white walled clear bottom 384-well microplates for compound profiling.

For profiling, cells were seeded at a density of 10000 cells per well in a total volume of 20 μL and were allowed to adhere and recover overnight prior to compound addition. Media contained charcoal-dextran filtered serum to reduce the level of hormones present.

Agonist Format

Intermediate dilution of compound stocks were generated such that 5 μL of 5× compound could be added to each well with a final DMSO concentration of 1% of total volume.

For profiling compound in agonist mode, the cells were incubated in the presence of compound at 37° C. for 5 hours.

Antagonist Format

Agonist dose curves were performed the morning of profiling to determine the EC80 value for the following antagonist testing with compounds. 5 μL of 5× agonist was added to each well with an equal concentration of vehicle present.

EC80 agonist concentration was determined directly from agonist dose curve.

For antagonist determination, cells were pre-incubated with antagonist followed by agonist challenge at the EC80 concentration.

5 μL of 5× compound added to cells and incubated at 37° C. for 30 minutes.

5 μL of 6× EC80 agonist added to cells and incubated at 37° C. for 90 minutes (180 minutes for EDG2 and EDG8).

Signal Detection

After appropriate compound incubation, assay signal was generated through a single addition of 15 μL (50% v/v) of PathHunter Detection reagent cocktail for agonist and antagonist assays respectively followed by one hour incubation at room temperature.

Microplates were read following signal generation with a PerkinElmer Envision™ instrument for chemiluminescent signal detection.

Data Analysis

Dose curves in the presence and absence of compound were plotted using GraphPad Prism or Activity Base.

For the agonist mode, percentage activity was calculated using the following formula:

% Activity=100%×(Mean RLU of test sample−mean RLU of vehicle control)/(mean MAX RLU control ligand−mean RLU of vehicle control).

Example 90

| Compound Name | Assay Name | Assay Format | Assay Target | Result Type | RC50 (µM) | Hill | Curve Bottom | Curve Top | Max Response |
|---|---|---|---|---|---|---|---|---|---|
| 9 Cis Retanoic acid | NHR Protein Interaction | Agonist | RARβ | EC50 | 0.005041 | 0.87 | 0 | 100 | 87.826 |
| Adapalene | NHR Protein Interaction | Agonist | RARβ | EC50 | 0.0017996 | 1.02 | 0 | 134.9 | 146.78 |
| Formula 135; Z is C(O)H | NHR Protein Interaction | Agonist | RARβ | EC50 | 0.14199 | 1.72 | 0 | 112.4 | 115.93 |
| Formula 135; Z is CH$_2$OH | NHR Protein Interaction | Agonist | RARβ | EC50 | 0.19864 | 1.16 | 0 | 127 | 131.9 |
| 9 Cis Retanoic acid | NHR Protein Interaction | Agonist | RARβ | EC50 | 0.0071358 | 1.21 | 0 | 108.3 | 98.978 |
| Formula 135; Z is CH=NOMe; compound 5a | NHR Protein Interaction | Agonist | RARβ | EC50 | 1.2746 | 0.71 | 6.5 | 45 | 45.098 |
| Formula 135; Z is CH=NOH; compound 5b | NHR Protein Interaction | Agonist | RARβ | EC50 | 0.82993 | 0.79 | 5.5 | 80 | 81.128 |

Example 91

| Compound Name | Assay Name | Assay Format | Assay Target | Result Type | RC50 (µM) | Hill | Curve Bottom | Curve Top | Max Response |
|---|---|---|---|---|---|---|---|---|---|
| Vasopressin | Arrestin | Agonist | AVPR2 | EC50 | 0.0007671 | 1.23 | −3.9 | 100.5 | 101.99 |
| Lixivaptan | Arrestin | Antagonist | AVPR2 | IC50 | 0.0012824 | 1.66 | 0 | 97.8 | 102.31 |
| Formula 121; Y$_1$ is =O; Y$_2$ is H$_2$; compound 15b | Arrestin | Antagonist | AVPR2 | IC50 | 2.367 | 1.59 | −14.1 | 100 | 79.39 |
| Formula 121; Y$_1$ is H$_2$; Y$_2$ is =O; compound 15a | Arrestin | Antagonist | AVPR2 | IC50 | 0.0037997 | 0.94 | −3.6 | 105.5 | 107.75 |
| 1-Adam-1,D-Tyr(Et)$_2$,Val4,Abu6,Arg8,9)VP | Arrestin | Antagonist | AVPR2 | IC50 | 0.074863 | 2.26 | −0.8 | 92.4 | 86.365 |

While both analogues of lixivaptan showed activity, the relative activities of two analogues compounds was as predicted by the in silico analysis (see Example 89)

Example 92

| Compound Name | Assay Name | Assay Format | Assay Target | Result Type | RC50 (µM) | Hill | Curve Bottom | Curve Top | Max Response |
|---|---|---|---|---|---|---|---|---|---|
| Angiotensin II | Arrestin | Agonist | AGTR1 | EC50 | 0.010236 | 1.7 | −1.7 | 101 | 101.02 |
| Candesartan | Arrestin | Antagonist | AGTR1 | IC50 | 0.0098746 | 0.9 | 10 | 101.3 | 100.69 |
| Losartan | Arrestin | Antagonist | AGTR1 | IC50 | 0.0082143 | 0.75 | 0 | 102.1 | 98.637 |
| Formula 141; Z is CH=NOH; compound 4a | Arrestin | Antagonist | AGTR1 | IC50 | 0.10941 | 1.39 | 12.3 | 97.2 | 96.652 |
| Formula 141; Z is CH=NOMe; compound 4b | Arrestin | Antagonist | AGTR1 | IC50 | 0.2479 | 1.19 | 6.4 | 99.9 | 97.383 |
| Formula 137; Z is CH=NOH; compound 10a | Arrestin | Antagonist | AGTR1 | IC50 | 0.046508 | 1.21 | 2.4 | 100.8 | 100.7 |
| Formula 137; Z is CH=NOMe; compound 10b | Arrestin | Antagonist | AGTR1 | IC50 | 0.048802 | 1.28 | 4.7 | 98.7 | 98.831 |
| Valsartan | Arrestin | Antagonist | AGTR1 | IC50 | 0.0017013 | 0.79 | 0 | 102.2 | 106.49 |

Methodology for Examples 93-95
A number of analogues were tested for their ability to kill cancer cells.
Protocol Summary
HepG2 cells were plated on 96-well tissue culture treated polystyrene plates at 0.5×10$^4$ cells in 100 µL per well. After 24 hr the cells are dosed with test compound at a range of concentrations and incubated for 72 hours. One hour prior to the end of the incubation period, the cells are loaded with MU [yellow; 3-(4,5-dimethyl-2-thiazolyl)-2,5-diphenyl-2H-tetrazolium bromide], the plates are dried and re-solubilised using DMSO. The plates are then scanned using SpectraFluor Plus (TECAN).

Assay Sensitivity

Cytotoxicity was assessed using MU. The assay provides a measurement of mitochondrial dehydrogenase activity and cell loss.

Cell Loss:

A decrease can indicate a loss of cells indicating toxicity due to necrosis, apoptosis or a reduction in cellular proliferation.

Mitochondrial Activity:

A decrease can also indicate an effect on mitochondrial function as mitochondrial dehydrogenasesreduce the MTT [yellow; 3-(4,5-dimethyl-2-thiazolyl)-2,5-diphenyl-2H-tetrazolium bromide] to formazan. The formazan is detected in this assay.

Example 93

The cells were dosed at concentrations of 0.04, 0.1, 0.4, 1, 4, 10, 40 and 100 μM. The assay was repeated three times at each concentration.

The results were as follows:

| Compound | Cell Health Parameter | MEC (μM) | AC50 (μM) |
|---|---|---|---|
| Bendamustine | Cell Loss | 40 | 92.3 |
| Formula 113; Z is C(O)H; compound 6a | Cell Loss | 4 | 5.83 |
| Formula 113; Z is CH=NOH; compound 6b | Cell Loss | 10 | 17.3 |

MEC = Minimum effective concentration that significantly crosses vehicle threshold.
AC50 = The concentration at which 50% maximum effect is observed for each cell health parameter.

Both compounds exhibited activity. Compound 6a, exhibited a higher activity than compound 6b. This corresponds to the predictions of the in silico analysis in example 48.

Example 94

The cells were dosed at concentrations of 0.02, 0.05, 0.2, 0.5, 2, 5, 20 and 50 μM. The assay was repeated three times at each concentration.

The results were as follows:

| Compound | Cell Health Parameter | MEC (μM) | AC50 (μM) |
|---|---|---|---|
| PD-0332991 | Cell Loss | 0.2 | 1.93 |
| Formula 2; G is H(OH); Y is =O; compound 2a | Cell Loss | 0.4 | 1.43 |

MEC = Minimum effective concentration that significantly crosses vehicle threshold.
AC50 = The concentration at which 50% maximum effect is observed for each cell health parameter.

Example 95

The cells were dosed at concentrations of 0.04, 0.1, 0.4, 1, 4, 10, 40 and 100 μM for bexarotene and the compound of formula 102 when Z is CH=NOH (compound 13a). The cells were dosed at concentrations of 0.02, 0.05, 0.2, 0.5, 2, 5, 20 and 50 μM for the compound of formula 102 when Z is CH=NOMe (compound 13b). The assay was repeated three times at each concentration.

The results were as follows:

| Compound | Cell Health Parameter | MEC (μM) | AC50 (μM) |
|---|---|---|---|
| Bexarotene | Cell Loss | 40 | 44.3 |
| Formula 102; Z is CH=NOH; compound 13a | Cell Loss | 40 | 15.8 |
| Formula 102; Z is CH=NOMe; compound 13b | Cell Loss | 50 | 45.6 |

MEC = Minimum effective concentration that significantly crosses vehicle threshold.
AC50 = The concentration at which 50% maximum effect is observed for each cell health parameter.

Example 96

The in vitro efficacy of a series of compounds was assessed for activity against a range of bacterial strains. All test articles were stored in the dark at 4° C. following delivery. Immediately prior to use, approximately 1 mg of each compound was accurately weighed and dissolved in the appropriate volume of DMSO to give a stock concentration of 1.28 g/L.

Strains

Susceptibility tests were performed against a range of anaerobic bacterial strains: Details of the strains used are as follows.

| SPECIES | STRAIN | COMMENTS |
|---|---|---|
| *Clostridium difficile* | BI1 | Human pathogenic strain |
| *Clostridium perfringens* | MU155 | Clinical strain |
| *Bacteroides fragilis* | ATCC 25293 | CLSI Control strain |
| *Prevotella melaninogenica* | ATCC 25845 | Type strain |

Revival and Growth of the Strains

All strains were recovered from long-term storage at −80° C. by sub-culturing onto fresh blood agar plates and incubating anaerobically at 37° C. for up to 4 days. Following visual checks to ensure purity and appropriate colony characteristics, isolates were deemed suitable for use.

Preparation of the Inoculum

The inocula for each bacterial strain were prepared by picking 5-10 distinct colonies from the culture plates (ensuring that the plates were not in an aerobic atmosphere for more than 30 minutes) and suspending them in 3 ml of reduced Wilkins-Chalgren broth. The inoculum was resuspended by vigorous shaking on a vortex mixer for 15s. The turbidity was then adjusted to McFarland standard 0.5 (1–5×10$^6$ CFU/ml). The inoculum was further diluted in reduced Wilkins-Chalgren broth with 5% lysed blood for MIC tests to give a final inoculum in each well of 2–8×10$^5$ CFU/ml.

MIC Assay Conditions

MICs were tested in Wilkins-Chalgren broth which had been reduced by rapid cooling following autoclaving and supplemented with 5% lysed horse blood in accordance with the appropriate CLSI guidelines (M11-A7).

Step 1: Addition of Test Article a. A stock solution was prepared at a concentration of 1.28 g/L in DMSO. The stock was further diluted in reduced Wilkins-Chalgren broth with 5% lysed blood to give a top starting concentration of 128 mg/L in the assay. 100

μL of reduced Wilkins-Chalgren broth with 5% lysed blood was dispensed into each well in columns 2-12. 200 μL of the appropriate test compound solution (at 256 mg/L) was dispensed into each well in column 1.

b. 100 μL aliquots were pipetted from column 1 wells and dispensed into column 2 with a multichannel pipette (±2% coefficient of variation) thus diluting two-fold. 100 μL samples were then pipetted from column 2 wells and dispensed into column 3. The process was repeated through to column 10. The final 100 μL of diluted drug from column 10 was then discarded. Row 11 acted as a positive control (no drug or test article, organisms added), Row 12 acted as a negative control (no drug or test article, and no organisms added).

Step 2: Addition of Bacterial Strains

100 μL of the appropriate inoculum suspension in reduced Wilkins-Chalgren broth with 5% lysed blood was added to the appropriate wells. This resulted in a well containing 200 μL final volume (made up of 100 μL diluted compound or diluents and 100 μL of inoculum or broth alone).

Step 3: Incubation of Assay Plates

All plates were incubated in the dark under anaerobic conditions at 37° C. for 48 hours.

Step 4: Reading of Plates

Plates were read visually 48 hours post inoculation. Endpoints of >90% inhibition were determined (CLSI interpretation endpoints following visual examination).

Results

| Compound | Clostridium difficile BI1 MIC μg/ml (>90%) | Clostridium perfringens MU155 MIC μg/ml (>90%) | Bacteroides fragilis ATCC 25293 MIC μg/ml (>90%) | Prevotella melaninogenica ATCC 25845 MIC μg/ml (>90%) |
|---|---|---|---|---|
| Metronidazole | ≤0.25 | 0.5 | 0.25 | 0.25 |
| Formula 1; J is $NO_2$; Z is $CH(OMe)_2$; compound 3a | ≤0.25 | 1 | 0.5 | 0.5 |
| Formula 1; J is $NO_2$; Z is CH=NOMe; compound 3b | ≤0.25 | 1 | 0.5 | 0.5 |

Methodology for Example 97 and Comparative Example 98

The solutions of the compounds to be tested were prepared in DMSO at a concentration of 10 mM, divided into aliquots and stored at −20° C. The stock solutions were further diluted with assay buffer to make final test solutions. All the final test solutions contained no more than 2.0% DMSO.

Method

Dilute test articles to desired concentration with assay buffer

Dilute protease with assay buffer

Add diluted test solution onto plate

Add diluted DPPIV protease component into plate

Pre-incubate for 10 minutes at 30° C., sealed with TopSeal-A 384, Clear Adhesive (PE)

Add substrate (Gly-Pro-AMC) to initiate reaction

Read absorption by using kinetics model with PHERAstarPLUS (BMG)

Data were recorded by PHEARstar$^{PLUS}$. Data acquisition and analyses were performed using Excel 2003 and GraphPad Prism 4.

Each assay was repeated for each compound 10 times.

Example 97

Sitagliptin analogues were tested for their ability as inhibitors of DPPIV.

Known inhibitor KR-62436 was also tested as a positive control.

The $IC_{50}$ values of the compounds tested were as follows:

| Compound | $IC_{50}$ |
|---|---|
| KR-62436 | 78.6 nM |
| Sitagliptin | 6 nM |
| Formula 3; V is =NOMe; Y is =O; Compound 24b | — |
| Formula 3; V is H($NH_2$); Y is $H_2$; Compound 24a | 81.3 nM |

Compound 24a showed an activity in this assay. Compound 24b did not exhibit significant activity in this assay. This corresponds to the predictions in the in silico analysis described in example 52 above.

Comparative Example 98

Compound 35a was tested for its ability as a renin inhibitor. Compound 35a was predicted to be a poor rennin inhibitor in the in silico analysis (see Example 46).

Known renin inhibitor Ac-HPFV-(Sta)-LF-$NH_2$ was used as a positive control.

The IC50 values of the compounds tested were as follows:

| Compound | $IC_{50}$ |
|---|---|
| Positive control | 8.4 nM |
| Aliskiren hemifumarate | 1.4 nM |
| Compound 35a | — |

Example 99

Eight test compound concentrations (0.001-10 μM; final DMSO concentration 0.5%) were incubated with recombinant human MAO-B (2 μg/mL) in the presence of the probe substrate kynuramine (25 μM) for 25 min at 37° C. Each test compound concentration was assessed in duplicate. The non-selective MAO inhibitor, tranylcypromine, was screened alongside the test compounds as a positive control. The reactions were terminated by addition of methanol containing internal standard for analytical quantification. The quenched samples were incubated at 4° C. for 10 min and centrifuged at 4° C. for 10 min. The supernatant was removed and analysed by LC-MS/MS for the probe metabolite 4-hydroxyquinoline. Generic Cyprotex LC-MS/MS analytical conditions were used.

A decrease in the formation of the metabolite compared to vehicle control was used to calculate an $IC_{50}$ value.

Inhibition of MAO-B Activity by Test Compounds and Positive Control ($IC_{50}$, Substrate=Kynuramine 25 μM)

| Compound | $IC_{50}$ (μM) |
|---|---|
| Safinamide | 0.165 |
| Formula 127; W is CH=NOH; compound 31a | 0.246 |
| Formula 127; W is CH=NOMe; compound 31b | 0.046 |
| Tranylcypromine | 0.031 |

MAO-B Percent Activity Remaining (Substrate = Kynuramine, 25 μM)

| Compound | Mean % Activity Remaining (n = 2) at Test Compound Concentration: | | | | | | | |
|---|---|---|---|---|---|---|---|---|
| | 0 μM | 0.001 μM | 0.010 μM | 0.04 μM | 0.1 μM | 0.4 μM | 1 μM | 10 μM |
| Safinamide | 100 | 101 | 95 | 79 | 62 | 31 | 13 | 2 |
| Formula 127; W is CH=NOH; compound 31a | 100 | 90 | 84 | 73 | 65 | 50 | 26 | 4 |
| Formula 127; W is CH=NOMe compound 31b | 100 | 90 | 75 | 57 | 34 | 15 | 6 | 1 |
| Tranylcypromine | 100 | 93 | 68 | 44 | 37 | 6 | 0 | 0 |

Example 100

Six compounds were evaluated for anti-influenza neuraminidase activity. Oseltamivir-sensitive influenza virus was incubated with compounds (8 concentrations, duplicate) in the presence of a chemiluminiscent substrate of neuraminidase (NA-XTD), Applied Biosystems). Reactions were monitored with a luminometer. As control, virus was incubated in the absence of compounds, and also in the presence of different concentrations of oseltamivir (oseltamivir carboxylic form). All test compounds and oseltamivir were assayed in parallel. $EC_{50}$ and $EC_{50}$ values were determined with GraphPad Prism.

The $EC_{50}$ and $EC_{50}$ values were as follows:

| Compound | EC50 (M) | EC90 (M) |
|---|---|---|
| Oseltamivir | $1.4 \times 10^{-10}$ | $1.3 \times 10^{-9}$ |
| Formula 162; V is $NH_2$; L is NHAc; Z is C(O)H | $3.2 \times 10^{-8}$ | $2.9 \times 10^{-7}$ |
| Formula 162; V is $NH_2$; L is NHAc; Z is CH=NOH | $7.6 \times 10^{-7}$ | $6.8 \times 10^{-6}$ |
| Formula 162; V is $NH_2$; L is NHAc; Z is $CH_2OH$ | $5.1 \times 10^{-8}$ | $4.6 \times 10^{-7}$ |
| Comparative example: Formula 162 in which V is $NH_2$; L is NHAc; Z is CH=NOBn | >10 μM | >10 μM |

No activity was observed for the comparative example. This compound was predicted to have poor activity by the in silico analysis (See Example 37).

The invention claimed is:

1. A compound according to formula 3 below:

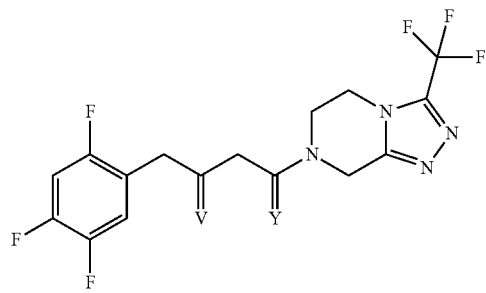

wherein:

(A)

is

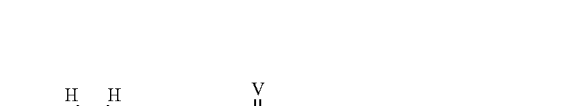
;

is independently selected from the group consisting of:

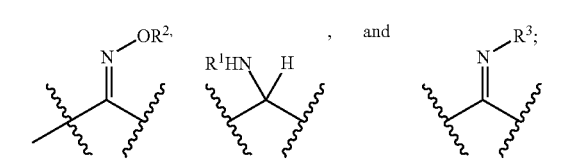

$R^1$ is independently at each occurrence H or $COCH_3$;

$R^2$ is independently at each occurrence $C_1$-$C_4$ alkyl; and $R^3$ is independently at each occurrence selected from the group consisting of: H and $C_{1-4}$ alkyl; or

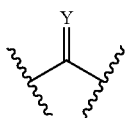

is independently selected from the group consisting of:

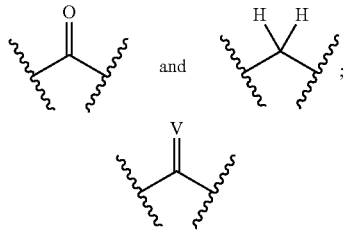

is independently selected from the group consisting of:

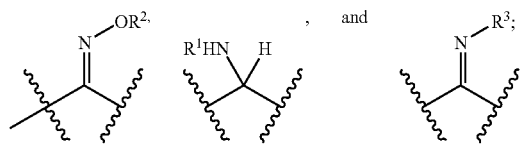

R[1] is independently at each occurrence COCH$_3$;
R[2] is independently at each occurrence C$_1$-C$_4$ alkyl; and
R[3] is independently at each occurrence selected from the group consisting of: H and C$_{1-4}$ alkyl.

2. The compound of claim 1, wherein

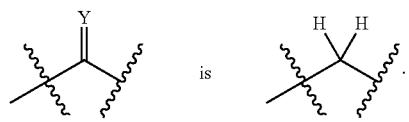

3. The compound of claim 1, wherein

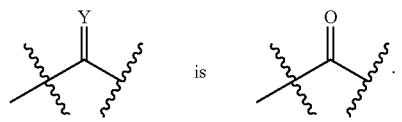

4. The compound of claim 1, wherein

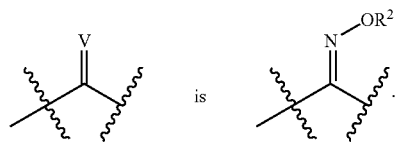

5. The compound of claim 4, wherein R[2] is methyl, ethyl, propyl, isopropyl, butyl, or tert-butyl.

6. The compound of claim 1, wherein

7. A pharmaceutical composition comprising: one or more pharmaceutical excipients; and a compound according to formula 3 below:

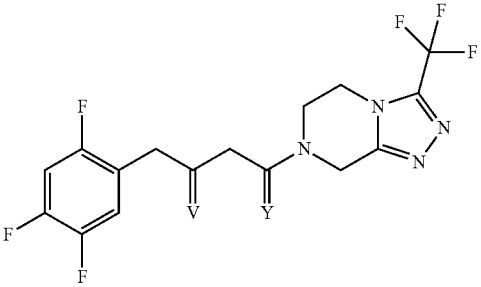

wherein:

is

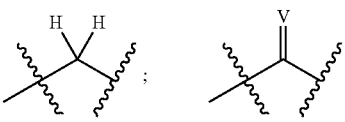

is independently selected from the group consisting of:

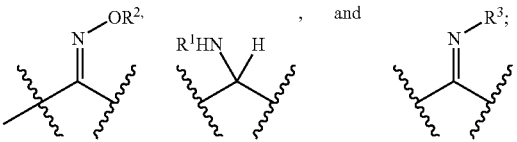

R[1] is independently at each occurrence H or COCH$_3$;
R[2] is independently at each occurrence H or C$_1$-C$_4$ alkyl; and
R[3] is independently at each occurrence selected from the group consisting of: H and C$_{1-4}$ alkyl; or

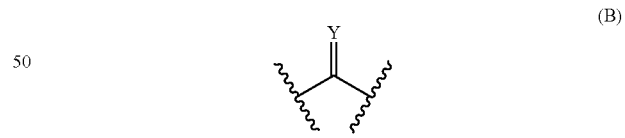

is independently selected from the group consisting of:

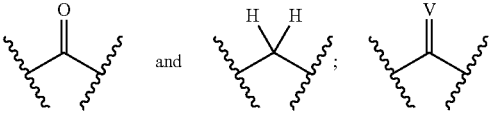

is independently selected from the group consisting of:

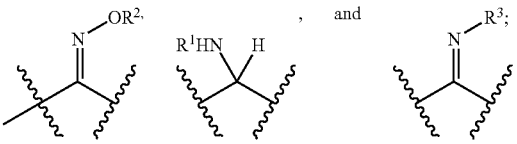

$R^1$ is independently at each occurrence $COCH_3$;
$R^2$ is independently at each occurrence H or $C_1$-$C_4$ alkyl; and
$R^3$ is independently at each occurrence selected from the group consisting of: H and $C_{1-4}$ alkyl.

8. The compound of claim 1, wherein the compound is

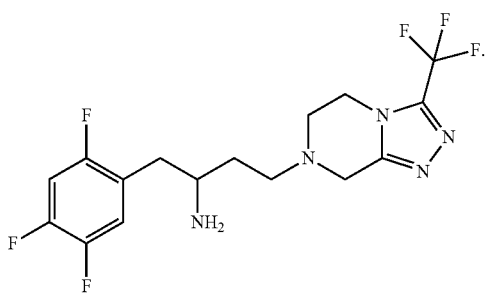 [SMILES: NC(CCN1CCn2c(nnc2C(F)(F)F)C1)Cc1cc(F)c(F)cc1F]

9. The pharmaceutical composition of claim 7, wherein the compound is

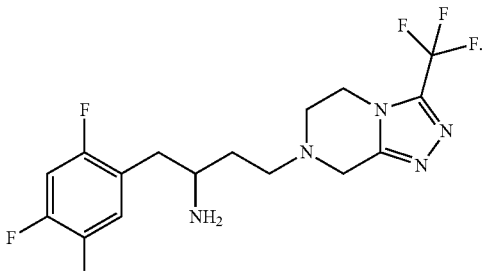

10. The pharmaceutical composition of claim 7, wherein $R^2$ is independently at each occurrence $C_1$-$C_4$ alkyl.

* * * * *